US006699703B1

(12) United States Patent
Doucette-Stamm et al.

(10) Patent No.: US 6,699,703 B1
(45) Date of Patent: Mar. 2, 2004

(54) **NUCLEIC ACID AND AMINO ACID SEQUENCES RELATING TO *STREPTOCOCCUS PNEUMONIAE* FOR DIAGNOSTICS AND THERAPEUTICS**

(75) Inventors: Lynn Doucette-Stamm, Framingham, MA (US); David Bush, Somerville, MA (US); Qiandong Zeng, Waltham, MA (US); Timothy Opperman, Somerville, MA (US); Chad Eric Houseweart, Waltham, MA (US)

(73) Assignee: Genome Therapeutics Corporation, Waltham, MA (US)

( * ) Notice: Subject to any disclaimer, the term of this patent is extended or adjusted under 35 U.S.C. 154(b) by 0 days.

(21) Appl. No.: 09/583,110

(22) Filed: May 26, 2000

Related U.S. Application Data

(63) Continuation-in-part of application No. 09/107,433, filed on Jun. 30, 1998.
(60) Provisional application No. 60/085,131, filed on May 12, 1998, and provisional application No. 60/051,553, filed on Jul. 2, 1997.

(51) Int. Cl.[7] .............................. C12Q 1/68; C12N 1/20; C12N 15/00; C12N 15/09; C12N 5/00; C07H 21/02; C07H 21/04
(52) U.S. Cl. ..................... 435/252.3; 435/6; 435/320.1; 435/325; 536/23.1; 536/24.1
(58) Field of Search ...................... 435/6, 252.3, 320.1, 435/325; 536/23.1, 24.1

(56) References Cited

U.S. PATENT DOCUMENTS

| 6,420,135 B1 | 7/2002 | Kunsch et al. ............. 435/69.1 |
| 6,573,082 B1 | 6/2003 | Choi et al. |

FOREIGN PATENT DOCUMENTS

| WO | WO 95/14712 | 6/1995 |
| WO | WO 95/31548 | 11/1995 |
| WO | WO 96/08582 | 3/1996 |
| WO | WO 98/18930 | 5/1998 |
| WO | WO 98/18931 | 5/1998 |
| WO | WO 98/26072 | 6/1998 |
| WO | WO 99/33871 | 7/1999 |
| WO | WO 00/37105 | 2/2000 |
| WO | WO 00/76540 | 2/2000 |
| WO | WO 00/14200 | 3/2000 |
| WO | WO 02/22168 A2 | 2/2002 |

OTHER PUBLICATIONS

US 6,159,469, 12/2000, Choi et al. (withdrawn)

*Primary Examiner*—John S. Brusca
*Assistant Examiner*—Shubo Zhou
(74) *Attorney, Agent, or Firm*—Genome Therapeutics Corporation

(57) ABSTRACT

The invention provides isolated polypeptide and nucleic acid sequences derived from *Streptococcus pneumoniae* that are useful in diagnosis and therapy of pathological conditions; antibodies against the polypeptides; and methods for the production of the polypeptides. The invention also provides methods for the detection, prevention and treatment of pathological conditions resulting from bacterial infection.

7 Claims, No Drawings

NUCLEIC ACID AND AMINO ACID SEQUENCES RELATING TO *STREPTOCOCCUS PNEUMONIAE* FOR DIAGNOSTICS AND THERAPEUTICS

RELATED APPLICATIONS

This application is a continuation-in-part of U.S. application Ser. No. 09/107,433, filed Jun. 30, 1998 which claims the benefit of U.S. provisional applications No. 60/085,131 filed May 12, 1998, and U.S. provisional application No. 60/051,553, filed Jul. 2, 1997, all of which are hereby incorporated herein by reference in their entirety.

FIELD OF THE INVENTION

The invention relates to isolated nucleic acids and polypeptides derived from *Streptococcus pneumoniae* that are useful as molecular targets for diagnostics, prophylaxis and treatment of pathological conditions, as well as materials and methods for the diagnosis, prevention, and amelioration of pathological conditions resulting from bacterial infection.

BACKGROUND OF THE INVENTION

*Streptococcus pneumoniae* (*S. pneumoniae*) is a common, spherical, gram-positive bacterium. Worldwide it is a leading cause of illness among children, the elderly, and individuals with debilitating medical conditions (Breiman, R. F. et al., 1994, JAMA 271: 1831). *S. pneumoniae* is estimated to be the causal agent in 3,000 cases of meningitis, 50,000 cases of bacteremia, 500,000 cases of pneumonia, and 7,000,000 cases of otitis media annnually in the United States alone (Reichler, M. R. et al., 1992, J. Infect. Dis. 166: 1346; Stool, S. E. and Field, M. J., 1989 Pediatr. Infect. Dis J. 8: S11). In the United States alone, 40,000 deaths result annually from *S. pneumoniae* infections (Williams, W. W. et al., 1988 Ann. Intern. Med. 108: 616) with a death rate approaching 30% from bacteremia (Butler, J. C. et al., 1993, JAMA 270: 1826). Pneumococcal pneumonia is a serious problem among the elderly of industrialized nations (Käyhty, H. and Eskola, J., 1996 Emerg. Infect. Dis. 2: 289) and is a leading cause of death among children in developing nations (Käyhty, H. and Eskola, J., 1996 Emerg. Infect. Dis. 2: 289; Stansfield, S. K., 1987 Pediatr. Infect. Dis. 6: 622).

Vaccines against *S. pneumoniae* have been available for a number of years. There are a large number of serotypes based on the polysaccharide capsule (van Dam, J. E., Fleer, A., and Snippe, H., 1990 Antonie van Leeuwenhoek 58: 1) although only a fraction of the serotypes seem to be associated with infections (Martin, D. R. and Brett, M. S., 1996 N. Z. Med. J. 109: 288). A multivalent vaccine against capsular polysaccharides of 23 serotypes (Smart, L. E., Dougall, A. J. and Gridwood, R. W., 1987 J. Infect. 14: 209) has provided protection for some groups but not for several groups at risk for pneumococcal infections, such as infants and the elderly (Mäkel, P. H. et al., 1980 Lancet 2: 547; Sankilampi, U., 1996 J. Infect. Dis. 173: 387). Conjugated pneumococcal capsular polysaccharide vaccines have somewhat improved efficacy, but are costly and, therefore, are not likely to be be in widespread use (Käyhty, H. and Eskola, J., 1996 Emerg. Infect. Dis. 2: 289).

At one time, *S. pneumoniae* strains were uniformly susceptible to penicillin. The report of a penicillin-resistant strain of (Hansman, D. and Bullen, M. M., 1967 Lancet 1: 264) was followed rapidly by many reports indicating the worldwide emergence of penicillin-resistant and penicillin non-susceptible strains (Klugman, K. P., 1990 Clin. Microbiol. Rev. 3: 171). *S. pneumoniae* strains which are resistant to multiple antibiotics (including penicillin) have also been observed recently within the United States (Welby, P. L., 1994 Pediatr. Infect. Dis. J. 13: 281; Ducin, J. S. et al., 1995 Pediatr. Infect. Dis. J. 14: 745; Butler, J. C., 1996 J. Infect. Dis. 174: 986) as well as internationally (Boswell, T. C. et al., 1996; J. Infect. 33: 17; Catchpole, C., Fraise, A., and Wise, R., 1996 Microb. Drug Resist. 2: 431; Tarasi, A. et al., 1997 Microb. Drug Resist. 3: 105).

A high incidence of morbidity is associated with invasive *S. pneumoniae* infections (Williams, W. W. et al., 1988 Ann. Intern. Med. 108: 616). Because of the incomplete effectiveness of currently available vaccines and antibiotics, the identification of new targets for antimicrobial therapies, including, but not limited to, the design of vaccines and antibiotics, which may help prevent infection or that may be useful in fighting existing infections, is highly desirable.

SUMMARY OF THE INVENTION

The present invention fulfills the needfor diagnostic tools and threapeutics by providing bacterial-specific compositions and methods for detecting, treating, and preventing bacterial infection, in particular *S. pneumoniae* infection.

The present invention encompasses isolated polypeptides and nucleic acids derived from *S. pneumoniae* that are useful as reagents for diagnosis of bacterial infection, components of effective antibacterial vaccines, and/or as targets for antibacterial drugs, including anti-*S. pneumoniae* drugs. The nucleic acids and peptides of the present invention also have utility for diagnostics and therapeutics for *S. pneumoniae* and other Streptococcus species. They can also be used to detect the presence of *S. pneumoniae* and other Streptococcus species in a sample; and in screening compounds for the ability to interfere with the *S. pneumoniae* life cycle or to inhibit *S. pneumoniae* infection. More specifically, this invention features compositions of nucleic acids corresponding to entire coding sequences of *S. pneumoniae* proteins, including surface or secreted proteins or parts thereof, nucleic acids capable of binding mRNA from *S. pneumoniae* proteins to block protein translation, and methods for producing *S. pneumoniae* proteins or parts thereof using peptide synthesis and recombinant DNA techniques. This invention also features antibodies and nucleic acids useful as probes to detect *S. pneumoniae* infection. In addition, vaccine compositions and methods for the protection or treatment of infection by *S. pneumoniae* are within the scope of this invention.

The nucleotide sequences provided in SEQ ID NO: 1–SEQ ID NO: 2661, a fragment thereof, or a nucleotide sequence at least 99.5% identical to a sequence contained within SEQ ID NO: 1–SEQ ID NO: 2661 may be "provided" in a variety of medias to facilitate use thereof. As used herein, "provided" refers to a manufacture, other than an isolated nucleic acid molecule, which contains a nucleotide sequence of the present invention, i.e., the nucleotide sequence provided in SEQ ID NO: 1–SEQ ID NO: 2661 , a fragment thereof, or a nucleotide sequence at least 99.5% identical to a sequence contained within SEQ ID NO: 1–SEQ ID NO: 2661. Uses for and methods for providing nucleotide sequences in a variety of media is well known in the art (see e.g., EPO Publication No. EP 0 756 006)

In one application of this embodiment, a nucleotide sequence of the present invention can be recorded on computer readable media. As used herein, "computer readable media" refers to any media which can be read and accessed directly by a computer. Such media include, but are not limited to: magnetic storage media, such as floppy discs, hard disc storage media, and magnetic tape; optical storage media such as CD-ROM; electrical storage media such as RAM and ROM; and hybrids of these categories such as magnetic/optical storage media. A person skilled in the art can readily appreciate how any of the presently known computer readable media can be used to create a manufacture comprising computer readable media having recorded thereon a nucleotide sequence of the present invention.

As used herein, "recorded" refers to a process for storing information on computer readable media. A person skilled in the art can readily adopt any of the presently known methods for recording information on computer readable media to generate manufactures comprising the nucleotide sequence information of the present invention.

A variety of data storage structures are available to a person skilled in the art for creating a computer readable media having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable media. The sequence information can be represented in a word processing text file, formatted in commercially-available software such as WordPerfect and Microsoft Word, or represented in the form of an ASCII file, stored in a database application, such as DB2, Sybase, Oracle, or the like. A person skilled in the art can readily adapt any number of data processor structuring formats (e.g. text file or database) in order to obtain computer readable media having recorded thereon the nucleotide sequence information of the present invention.

By providing the nucleotide sequence of SEQ ID NO: 1–SEQ ID NO: 2661, a fragment thereof, or a nucleotide sequence at least 99.5% identical to a sequence contained within SEQ ID NO: 1–SEQ ID NO: 2661 in computer readable form, a person skilled in the art can routinely access the sequence information for a variety of purposes. Computer software is publicly available which allows a person skilled in the art to access sequence information provided in a computer readable media. Examples of such computer software include programs of the "Staden Package", "DNA Star", "MacVector", GCG "Wisconsin Package" (Genetics Computer Group, Madison, Wis.) and "NCBI toolbox" (National Center for Biotechnology Information).

Computer algorithms enable the identification of S. pneumoniae open reading frames (ORFs) within SEQ ID NO: 1–SEQ ID NO: 2661 which contain homology to ORFs or proteins from other organisms. Examples of such similarity-search algorithms include the BLAST [Altschul et al., J. Mol. Biol. 215:403–410 (1990)] and Smith-Waterman [Smith and Waterman (1981) Advances in Applied Mathematics, 2:482–489] search algorithms. These algorithms are utilized on computer systems as exemplified below. The ORFs so identified represent protein encoding fragments within the S. pneumoniae genome and are useful in producing commercially important proteins such as enzymes used in fermentation reactions and in the production of commercially useful metabolites.

The present invention further provides systems, particularly computer-based systems, which contain the sequence information described herein. Such systems are designed to identify commercially important fragments of the S. pneumoniae genome. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A person skilled in the art can readily appreciate that any one of the currently available computer-based systems is suitable for use in the present invention. The computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of the S. pneumoniae genome which are similar to, or "match", a particular target sequence or target motif. A variety of known algorithms are known in the art and have been disclosed publicly, and a variety of commercially available software for conducting homology-based similarity searches are available and can be used in the computer-based systems of the present invention. Examples of such software includes, but is not limited to, FASTA (GCG Wisconsin Package), Bic_SW (Compugen Bioccelerator, BLASTN2, BLASTP2 and BLASTX2 (NCBI) and Motifs (GCG). BLASTN2, A person skilled in the art can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A person skilled in the art can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that many genes are longer than 500 amino acids, or 1.5 kb in length, and that commercially important fragments of the S. pneumoniae genome, such as sequence fragments involved in gene expression and protein processing, will often be shorter than 30 nucleotides.

As used herein, "a target structural motif," or "target motif," refers to any rationally selected sequence or combination of sequences in which the sequence(s) are chosen based on a specific functional domain or three-dimensional configuration which is formed upon the folding of the target polypeptide. There are a variety of target motifs known in the art. Protein target motifs include, but are not limited to, enzymatic active sites, membrane spanning regions, and signal sequences. Nucleic acid target motifs include, but are not limited to, promoter sequences, hairpin structures and inducible expression elements (protein binding sequences).

A variety of structural formats for the input and output means can be used to input and output the information in the computer-based systems of the present invention. A preferred format for an output means ranks fragments of the S. pneumoniae genome possessing varying degrees of homology to the target sequence or target motif. Such presentation provides aperson skilled in the art with a ranking of sequences which contain various amounts of the target sequence or target motif and identifies the degree of homology contained in the identified fragment.

A variety of comparing means can be used to compare a target sequence or target motif with the data storage means to identify sequence fragments of the S. pneumoniae genome. In the present examples, implementing software which implement the BLASTP2 and bic_SW algorithms (Altschul et al., J Mol. Biol. 215:403–410 (1990); Compugen Biocellerator) was used to identify open reading frames within the S. pneumoniae genome. A person skilled in the art can readily recognize that any one of the publicly available homology search programs can be used as the search means for the computer-based systems of the present invention.

The invention features S. pneumoniae polypeptides, preferably a substantially pure preparation of an S. pneumoniae polypeptide, or a recombinant S. pneumoniae polypeptide. In preferred embodiments: the polypeptide has biological activity; the polypeptide has an amino acid sequence at least 60%, 70%, 80%, 90%, 95%, 98%, or 99% identical to an amino acid sequence of the invention contained in the Sequence Listing, preferably it has about 65% sequence identity with an amino acid sequence of the invention contained in the Sequence Listing, and most preferably it has about 92% to about 99% sequence identity with an amino acid sequence of the invention contained in the Sequence Listing; the polypeptide has an amino acid sequence essentially the same as an amino acid sequence of the invention contained in the Sequence Listing; the polypeptide is at least 5, 10, 20, 50, 100, or 150 amino acid residues in length; the polypeptide includes at least 5, preferably at least 10, more preferably at least 20, more preferably at least 50, 100, or 150 contiguous amino acid residues of the invention contained in the Sequence Listing. In yet another preferred embodiment, the amino acid sequence which differs in sequence identity by about 7% to about 8% from the S. pneumoniae amino acid sequences of the invention contained in the Sequence Listing is also encompassed by the invention.

In preferred embodiments: the S. pneumoniae polypeptide is encoded by a nucleic acid of the invention contained in the Sequence Listing, or by a nucleic acid having at least 60%, 70%, 80%, 90%, 95%, 98%, or 99% homology with a nucleic acid of the invention contained in the Sequence Listing.

In a preferred embodiment, the subject S. pneumoniae polypeptide differs in amino acid sequence at 1, 2, 3, 5, 10 or more residues from a sequence of the invention contained in the Sequence Listing. The differences, however, are such that the S. pneumoniae polypeptide exhibits an S. pneumoniae biological activity, e.g., the S. pneumoniae polypeptide retains a biological activity of a naturally occurring S. pneumoniae enzyme.

In preferred embodiments, the polypeptide includes all or a fragment of an amino acid sequence of the invention contained in the Sequence Listing; fused, in reading frame, to additional amino acid residues, preferably to residues encoded by genomic DNA 5' or 3' to the genomic DNA which encodes a sequence of the invention contained in the Sequence Listing.

In yet other preferred embodiments, the S. pneumoniae polypeptide is a recombinant fusion protein having a first S. pneumoniae polypeptide portion and a second polypeptide portion, e.g., a second polypeptide portion having an amino acid sequence unrelated to S. pneumoniae. The second polypeptide portion can be, e.g., any of glutathione-S-transferase, a DNA binding domain, or a polymerase activating domain. In preferred embodiment the fusion protein can be used in a two-hybrid assay.

Polypeptides of the invention include those which arise as a result of alternative transcription events, alternative RNA splicing events, and alternative translational and postranslational events.

In a preferred embodiment, the encoded S. pneumoniae polypeptide differs (e.g., by amino acid substitution, addition or deletion of at least one amino acid residue) in amino acid sequence at 1, 2, 3, 5, 10 or more residues, from a sequence of the invention contained in the Sequence Listing. The differences, however, are such that: the S. pneumoniae encoded polypeptide exhibits a S. pneumoniae biological activity, e.g., the encoded S. pneumoniae enzyme retains a biological activity of a naturally occurring S. pneumoniae.

In preferred embodiments, the encoded polypeptide includes all or a fragment of an amino acid sequence of the invention contained in the Sequence Listing; fused, in reading frame, to additional amino acid residues, preferably to residues encoded by genomic DNA 5' or 3' to the genomic DNA which encodes a sequence of the invention contained in the Sequence Listing.

The S. pneumoniae strain, 14453, from which genomic sequences have been sequenced, has been deposited on Jun. 26, 1997 in the American Type Culture Collection and assigned the ATCC designation # 55987.

Included in the invention are: allelic variations; natural mutants; induced mutants; proteins encoded by DNA that hybridize under high or low stringency conditions to a nucleic acid which encodes a polypeptide of the invention contained in the Sequence Listing (for definitions of high and low stringency see Current Protocols in Molecular Biology, John Wiley & Sons, New York, 1989, 6.3.1–6.3.6, hereby incorporated by reference); and, polypeptides specifically bound by antisera to S. pneumoniae polypeptides, especially by antisera to an active site or binding domain of S. pneumoniae polypeptide. The invention also includes fragments, preferably biologically active fragments. These and other polypeptides are also referred to herein as S. pneumoniae polypeptide analogs or variants.

The invention further provides nucleic acids, e.g., RNA or DNA, encoding a polypeptide of the invention. This includes double stranded nucleic acids as well as coding and antisense single strands.

In preferred embodiments, the subject S. pneumoniae nucleic acid will include a transcriptional regulatory sequence, e.g. at least one of a transcriptional promoter or transcriptional enhancer sequence, operably linked to the S. pneumoniae gene sequence, e.g., to render the S. pneumoniae gene sequence suitable for expression in a recombinant host cell.

In yet a further preferred embodiment, the nucleic acid which encodes an S. pneumoniae polypeptide of the invention, hybridizes under stringent conditions to a nucleic acid probe corresponding to at least 8 consecutive nucleotides of the invention contained in the Sequence Listing; more preferably to at least 12 consecutive nucleotides of the invention contained in the Sequence Listing; more preferably to at least 20 consecutive nucleotides of the invention contained in the Sequence Listing; more preferably to at least 40 consecutive nucleotides of the invention contained in the Sequence Listing.

In another aspect, the invention provides a substantially pure nucleic acid having a nucleotide sequence which encodes an *S. pneumoniae* polypeptide. In preferred embodiments: the encoded polypeptide has biological activity; the encoded polypeptide has an amino acid sequence at least 60%, 70%, 80%, 90%, 95%, 98%, or 99% homologous to an amino acid sequence of the invention contained in the Sequence Listing; the encoded polypeptide has an amino acid sequence essentially the same as an amino acid sequence of the invention contained in the Sequence Listing; the encoded polypeptide is at least 5, 10, 20, 50, 100, or 150 amino acids in length; the encoded polypeptide comprises at least 5, preferably at least 10, more preferably at least 20', more preferably at least 50, 100, or 150 contiguous amino acids of the invention contained in the Sequence Listing.

In another aspect, the invention encompasses: a vector including a nucleic acid which encodes an *S. pneumoniae* polypeptide or an *S. pneumoniae* polypeptide variant as described herein; a host cell transfected with the vector; and a method of producing a recombinant *S. pneumoniae* polypeptide or *S. pneumoniae* polypeptide variant; including culturing the cell, e.g., in a cell culture medium, and isolating an *S. pneumoniae* polypeptide or an *S. pneumoniae* polypeptide variant, e.g., from the cell or from the cell culture medium.

In another series of embodiments, the invention provides isolated nucleic acids comprising sequences at least about 8 nucleotides in length, more preferably at least about 12 nucleotides in length, and most preferably at least about 15–20 nucleotides in length, that correspond to a subsequence of any one of SEQ ID NO: 1–SEQ ID NO: 2661 or complements thereof. Alternatively, the nucleic acids comprise sequences contained within any ORF (open reading frame), including a complete protein-coding sequence, of which any of SEQ ID NO: 1–SEQ ID NO: 2661 forms a part. The invention encompasses sequence-conservative variants and function-conservative variants of these sequences. The nucleic acids may be DNA, RNA, DNA/RNA duplexes, protein-nucleic acid (PNA), or derivatives thereof.

In another aspect, the invention features, a purified recombinant nucleic acid having at least 50%, 60%, 70%, 80%, 90%, 95%, 98%, or 99% homology with a sequence of the invention contained in the Sequence Listing.

In another aspect, the invention features nucleic acids capable of binding mRNA of *S. pneumoniae*. Such nucleic acid is capable of acting as antisense nucleic acid to control the translation of mRNA of *S. pneumoniae*. A further aspect features a nucleic acid which is capable of binding specifically to an *S. pneumoniae* nucleic acid. These nucleic acids are also referred to herein as complements and have utility as probes and as capture reagents.

In another aspect, the invention features an expression system comprising an open reading frame corresponding to *S. pneumoniae* nucleic acid. The nucleic acid further comprises a control sequence compatible with an intended host. The expression system is useful for making polypeptides corresponding to *S. pneumoniae* nucleic acid.

In another aspect, the invention features a cell transformed with the expression system to produce *S. pneumoniae* polypeptides.

In yet another embodiment, the invention encompasses reagents for detecting bacterial infection, including *S. pneumoniae* infection, which comprise at least one *S. pneumoniae*-derived nucleic acid defined by any one of SEQ ID NO: 1–SEQ ID NO: 2661, or sequence-conservative or function-conservative variants thereof. Alternatively, the diagnostic reagents comprise polypeptide sequences that are contained within any open reading frames (ORFs), including complete protein-coding sequences, contained within any of SEQ ID NO: 1–SEQ ID NO: 2661, or polypeptide sequences contained within any of SEQ ID NO: 2662–SEQ ID NO: 5322, or polypeptides of which any of the above sequences forms a part, or antibodies directed against any of the above peptide sequences or function-conservative variants and/or fragments thereof.

The invention further provides antibodies, preferably monoclonal antibodies, which specifically bind to the polypeptides of the invention. Methods are also provided for producing antibodies in a host animal. The methods of the invention comprise immunizing an animal with at least one *S. pneumoniae*-derived immunogenic component, wherein the immunogenic component comprises one or more of the polypeptides encoded by any one of SEQ ID NO: 1–SEQ ID NO: 2661 or sequence-conservative or function-conservative variants thereof, or polypeptides that are contained within any ORFs, including complete protein-coding sequences, of which any of SEQ ID NO: 1–SEQ ID NO: 2661 forms a part; or polypeptide sequences contained within any of SEQ ID NO: 2662–SEQ ID NO: 5322 or polypeptides of which any of SEQ ID NO: 2662–SEQ ID NO: 5322 forms a part. Host animals include any warm blooded animal, including without limitation mammals and birds. Such antibodies have utility as reagents for immunoassays to evaluate the abundance and distribution of *S. pneumoniae*-specific antigens.

In yet another aspect, the invention provides a method for detecting bacterial antigenic components in a sample, which comprises the steps of: (i) contacting a sample suspected to contain a bacterial antigenic component with a bacterial-specific antibody, under conditions in which a stable antigen-antibody complex can form between the antibody and bacterial antigenic components in the sample; and (ii) detecting any antigen-antibody complex formed in step (i), wherein detection of an antigen-antibody complex indicates the presence of at least one bacterial antigenic component in the sample. In different embodiments of this method, the antibodies used are directed against a sequence encoded by any of SEQ ID NO: 1–SEQ ID NO: 2661 or sequence-conservative or function-conservative variants thereof, or against a polypeptide sequence contained in any of SEQ ID NO: 2662–SEQ ID NO: 5322 or function-conservative variants thereof.

In yet another aspect, the invention provides a method for detecting antibacterial-specific antibodies in a sample, which comprises: (i) contacting a sample suspected to contain antibacterial-specific antibodies with a *S. pneumoniae* antigenic component, under conditions in which a stable antigen-antibody complex can form between the *S. pneumoniae* antigenic component and antibacterial antibodies in the sample; and (ii) detecting any antigen-antibody complex formed in step (i), wherein detection of an antigen-antibody complex indicates the presence of antibacterial antibodies in the sample. In different embodiments of this method, the antigenic component is encoded by a sequence contained in any of SEQ ID NO: 1–SEQ ID NO: 2661 or sequence-conservative and function-conservative variants thereof, or is a polypeptide sequence contained in any of SEQ ID NO: 2662–SEQ ID NO: 5322 or function-conservative variants thereof.

In another aspect, the invention features a method of generating vaccines for immunizing an individual against *S. pneumoniae*. The method includes: immunizing a subject with an *S. pneumoniae* polypeptide, e.g., a surface or secreted polypeptide, or active portion thereof, and a pharmaceutically acceptable carrier. Such vaccines have therapeutic and prophylactic utilities.

In another aspect, the invention features a method of evaluating a compound, e.g. a polypeptide, e.g., a fragment of a host cell polypeptide, for the ability to bind an *S. pneumoniae* polypeptide. The method includes: contacting the candidate compound with an *S. pneumoniae* polypeptide and determining if the compound binds or otherwise interacts with an *S. pneumoniae* polypeptide. Compounds which bind *S. pneumoniae* are candidates as activators or inhibitors of the bacterial life cycle. These assays can be performed in vitro or in vivo.

In another aspect, the invention features a method of evaluating a compound, e.g. a polypeptide, e.g., a fragment of a host cell polypeptide, for the ability to bind an *S. pneumoniae* nucleic acid, e.g., DNA or RNA. The method includes: contacting the candidate compound with an *S. pneumoniae* nucleic acid and determining if the compound binds or otherwise interacts with an *S. pneumoniae* polypeptide. Compounds which bind *S. pneumoniae* are candidates as activators or inhibitors of the bacterial life cycle. These assays can be performed in vitro or in vivo.

DETAILED DESCRIPTION OF THE INVENTION

The sequences of the present invention include the specific nucleic acid and amino acid sequences set forth in the Sequence Listing that forms a part of the present specification, and which are designated SEQ ID NO: 1–SEQ ID NO: 5322. Use of the terms "SEQ ID NO: 1–SEQ ID NO: 2661", "SEQ ID NO: 2662–SEQ ID NO: 5322", "the sequences depicted in Table 2", etc., is intended, for convenience, to refer to each individual SEQ ID NO individually, and is not intended to refer to the genus of these sequences. In other words, it is a shorthand for listing all of these sequences individually. The invention encompasses each sequence individually, as well as any combination thereof.

Definitions

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physico-chemical properties (such as, for example, acidic, basic, hydrophobic, and the like). "Function-conservative" variants also include any polypeptides that have the ability to elicit antibodies specific to a designated polypeptide.

An "*S. pneumoniae*-derived" nucleic acid or polypeptide sequence may or may not be present in other bacterial species, and may or may not be present in all *S. pneumoniae* strains. This term is intended to refer to the source from which the sequence was originally isolated. Thus, a *S. pneumoniae*-derived polypeptide, as used herein, may be used, e.g., as a target to screen for a broad spectrum antibacterial agent, to search for homologous proteins in other species of bacteria or in eukaryotic organisms such as fungi and humans, etc.

A purified or isolated polypeptide or a substantially pure preparation of a polypeptide are used interchangeably herein and, as used herein, mean a polypeptide that has been separated from other proteins, lipids, and nucleic acids with which it naturally occurs. Preferably, the polypeptide is also separated from substances, e.g., antibodies or gel matrix, e.g., polyacrylamide, which are used to purify it. Preferably, the polypeptide constitutes at least 10, 20, 50 70, 80 or 95% dry weight of the purified preparation. Preferably, the preparation contains: sufficient polypeptide to allow protein sequencing; at least 1, 10, or 100 mg of the polypeptide.

A purified preparation of cells refers to, in the case of plant or animal cells, an in vitro preparation of cells and not an entire intact plant or animal. In the case of cultured cells or microbial cells, it consists of a preparation of at least 10% and more preferably 50% of the subject cells.

A purified or isolated or a substantially pure nucleic acid, e.g., a substantially pure DNA, (are terms used interchangeably herein) is a nucleic acid which is one or both of the following: not immediately contiguous with both of the coding sequences with which it is immediately contiguous (i.e., one at the 5' end and one at the 3' end) in the naturally-occurring genome of the organism from which the nucleic acid is derived; or which is substantially free of a nucleic acid with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional *S. pneumoniae* DNA sequence.

A "contig" as used herein is a nucleic acid representing a continuous stretch of genomic sequence of an organism.

An "open reading frame", also referred to herein as ORF, is a region of nucleic acid which encodes a polypeptide. This region usually represents the total coding region for the polypeptide and can be determined from a stop to stop codon or from a start to stop codon.

As used herein, a "coding sequence" is a nucleic acid which is transcribed into messenger RNA and/or translated into a polypeptide when placed under the control of appropriate regulatory sequences. The boundaries of the coding sequence are determined by a translation start codon at the five prime terminus and a translation stop codon at the three prime terminus. A coding sequence can include but is not limited to messenger RNA, synthetic DNA, and recombinant nucleic acid sequences.

A "complement" of a nucleic acid as used herein refers to an anti-parallel or antisense sequence that participates in Watson-Crick base-pairing with the original sequence.

A "gene product" is a protein or structural RNA which is specifically encoded by a gene.

As used herein, the term "probe" refers to a nucleic acid, peptide or other chemical entity which specifically binds to a molecule of interest. Probes are often associated with or capable of associating with a label. A label is a chemical moiety capable of detection. Typical labels comprise dyes, radioisotopes, luminescent and chemiluminescent moieties, fluorophores, enzymes, precipitating agents, amplification sequences, and the like. Similarly, a nucleic acid, peptide or other chemical entity which specifically binds to a molecule of interest and immobilizes such molecule is referred herein as a "capture ligand". Capture ligands are typically associated with or capable of associating with a support such as nitro-cellulose, glass, nylon membranes, beads, particles and the like. The specificity of hybridization is dependent on conditions such as the base pair composition of the nucleotides, and the temperature and salt concentration of the reaction. These conditions are readily discernable to one of ordinary skill in the art using routine experimentation.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

Nucleic acids are hybridizable to each other when at least one strand of a nucleic acid can anneal to the other nucleic acid under defined stringency conditions. Stringency of hybridization is determined by: (a) the temperature at which hybridization and/or washing is performed; and (b) the ionic strength and polarity of the hybridization and washing solutions. Hybridization requires that the two nucleic acids contain complementary sequences; depending on the stringency of hybridization, however, mismatches may be tolerated. Typically, hybridization of two sequences at high stingency (such as, for example, in a solution of 0.5×SSC, at 65° C.) requires that the sequences be essentially completely homologous. Conditions of intermediate stringency (such as, for example, 2×SSC at 65° C.) and low stringency (such as, for example 2×SSC at 55° C.), require correspondingly less overall complementarity between the hybridizing sequences. (1×SSC is 0.15 M NaCl, 0.015 M Na citrate).

The terms peptides, proteins, and polypeptides are used interchangeably herein.

As used herein, the term "surface protein" refers to all surface accessible proteins, e.g. inner and outer membrane proteins, proteins adhering to the cell wall, and secreted proteins.

A polypeptide has S. pneumoniae biological activity if it has one, two and preferably more of the following properties: (1) if when expressed in the course of an S. pneumoniae infection, it can promote, or mediate the attachment of S. pneumoniae to a cell; (2) it has an enzymatic activity, structural or regulatory function characteristic of an S. pneumoniae protein; (3) or the gene which encodes it can rescue a lethal mutation in an S. pneumoniae gene. A polypeptide has biological activity if it is an antagonist, agonist, or super-agonist of a polypeptide having one of the above-listed properties.

A biologically active fragment or analog is one having an in vivo or in vitro activity which is characteristic of the S. pneumoniae polypeptides of the invention contained in the Sequence Listing, or of other naturally occurring S. pneumoniae polypeptides, e.g., one or more of the biological activities described herein. Especially preferred are fragments which exist in vivo, e.g., fragments which arise from post transcriptional processing or which arise from translation of alternatively spliced RNA's. Fragments include those expressed in native or endogenous cells as well as those made in expression systems, e.g., in CHO cells. Because peptides such as S. pneumoniae polypeptides often exhibit a range of physiological properties and because such properties may be attributable to different portions of the molecule, a useful S. pneumoniae fragment or S. pneumoniae analog is one which exhibits a biological activity in any biological assay for S. pneumoniae activity. Most preferably the fragment or analog possesses 10%, preferably 40%, more preferably 60%, 70%, 80% or 90% or greater of the activity of S. pneumoniae, in any in vivo or in vitro assay.

Analogs can differ from naturally occurring S. pneumoniae polypeptides in amino acid sequence or in ways that do not involve sequence, or both. Non-sequence modifications include changes in acetylation, methylation, phosphorylation, carboxylation, or glycosylation. Preferred analogs include S. pneumoniae polypeptides (or biologically active fragments thereof) whose sequences differ from the wild-type sequence by one or more conservative amino acid substitutions or by one or more non-conservative amino acid substitutions, deletions, or insertions which do not substantially diminish the biological activity of the S. pneumoniae polypeptide. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be made in view of the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3, 4, or 5-phenylproline, cis-3, 4, or 5-phenylproline |

TABLE 1-continued

CONSERVATIVE AMINO ACID REPLACEMENTS

| For Amino Acid | Code | Replace with any of |
| --- | --- | --- |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to an *S. pneumoniae* analog, will ordinarily be at least about 20 residues, more typically at least about 40 residues, preferably at least about 60 residues in length. Fragments of *S. pneumoniae* polypeptides can be generated by methods known to those skilled in the art. The ability of a candidate fragment to exhibit a biological activity of *S. pneumoniae* polypeptide can be assessed by methods known to those skilled in the art as described herein. Also included are *S. pneumoniae* polypeptides containing residues that are not required for biological activity of the peptide or that result from alternative mRNA splicing or alternative protein processing events.

An "immunogenic component" as used herein is a moiety, such as an *S. pneumoniae* polypeptide, analog or fragment thereof, that is capable of eliciting a humoral and/or cellular immune response in a host animal.

An "antigenic component" as used herein is a moiety, such as an *S. pneumoniae* polypeptide, analog or fragment thereof, that is capable of binding to a specific antibody with sufficiently high affinity to form a detectable antigen-antibody complex.

The term "antibody" as used herein is intended to include fragments thereof which are specifically reactive with *S. pneumoniae* polypeptides.

As used herein, the term "cell-specific promoter" means a DNA sequence that serves as a promoter, i.e., regulates expression of a selected DNA sequence operably linked to the promoter, and which effects expression of the selected DNA sequence in specific cells of a tissue. The term also covers so-called "leaky" promoters, which regulate expression of a selected DNA primarily in one tissue, but cause expression in other tissues as well.

Misexpression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-translational modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

As used herein, "host cells" and other such terms denoting microorganisms or higher eukaryotic cell lines cultured as unicellular entities refers to cells which can become or have been used as recipients for a recombinant vector or other transfer DNA, and include the progeny of the original cell which has been transfected. It is understood by individuals skilled in the art that the progeny of a single parental cell may not necessarily be completely identical in genomic or total DNA compliment to the original parent, due to accident or deliberate mutation.

As used herein, the term "control sequence" refers to a nucleic acid having a base sequence which is recognized by the host organism to effect the expression of encoded sequences to which they are ligated. The nature of such control sequences differs depending upon the host organism; in prokaryotes, such control sequences generally include a promoter, ribosomal binding site, terminators, and in some cases operators; in eukaryotes, generally such control sequences include promoters, terminators and in some instances, enhancers. The term control sequence is intended to include at a minimum, all components whose presence is necessary for expression, and may also include additional components whose presence is advantageous, for example, leader sequences.

As used herein, the term "operably linked" refers to sequences joined or ligated to function in their intended manner. For example, a control sequence is operably linked to coding sequence by ligation in such a way that expression of the coding sequence is achieved under conditions compatible with the control sequence and host cell.

The "metabolism" of a substance, as used herein, means any aspect of the expression, function, action, or regulation of the substance. The metabolism of a substance includes modifications, e.g., covalent or non-covalent modifications of the substance. The metabolism of a substance includes modifications, e.g., covalent or non-covalent modification, the substance induces in other substances. The metabolism of a substance also includes changes in the distribution of the substance. The metabolism of a substance includes changes the substance induces in the distribution of other substances.

A "sample" as used herein refers to a biological sample, such as, for example, tissue or fluid isloated from an individual (including without limitation plasma, serum, cerebrospinal fluid, lymph, tears, saliva and tissue sections) or from in vitro cell culture constituents, as well as samples from the environment.

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. The practice of the invention will employ, unless otherwise indicated, conventional techniques of chemistry, molecular biology, microbiology, recombinant DNA, and immunology, which are within the skill of the art. Such techniques are explained fully in the literature. See e.g., Sambrook, Fritsch, and Maniatis, *Molecular Cloning; Laboratory Manual* 2nd ed. (1989); *DNA Cloning*, Volumes I and II (D. N Glover ed. 1985); *Oligonucleotide Synthesis* (M. J. Gait ed, 1984); *Nucleic Acid Hybridization* (B. D. Hames & S. J. Higgins eds. 1984); the series, *Methods in Enzymoloqy* (Academic Press, Inc.), particularly Vol. 154 and Vol. 155 (Wu and Grossman, eds.); *PCR-A Practical Approach* (McPherson, Quirke, and Taylor, eds., 1991); *Immunology*, 2d Edition, 1989, Roitt et al., C. V. Mosby Company, and New York; *Advanced Immunology*, 2d Edition, 1991, Male et al., Grower Medical Publishing, New York.; *DNA Cloning: A Practical Approach*, Volumes I and II, 1985 (D. N. Glover ed.); *Oligonucleotide Synthesis*, 1984, (M. L. Gait ed); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; and *Gene Transfer Vectors for Mammalian Cells*, 1987 (J. H. Miller and M. P. Calos eds., Cold Spring Harbor Laboratory); Any suitable materials and/or methods known to those of skill can be utilized in carrying out the present invention: however preferred materials and/or methods are described. Materials, reagents and the like to which reference is made in the following description and examples are obtainable from commercial sources, unless otherwise noted.

S. pneumoniae Genomic Sequence

This invention provides nucleotide sequences of the genome of *S. pneumoniae* which thus comprises a DNA sequence library of *S. pneumoniae* genomic DNA. The detailed description that follows provides nucleotide sequences of *S. pneumoniae*, and also describes how the sequences were obtained and how ORFs and protein-coding sequences were identified. Also described are methods of using the disclosed *S. pneumoniae* sequences in methods including diagnostic and therapeutic applications. Furthermore, the library can be used as a database for identification and comparison of medically important sequences in this and other strains of *S. pneumoniae*.

To determine the genomic sequence of *S. pneumoniae*, DNA was isolated from strain 14453 of *S. pneumoniae* and mechanically sheared by nebulization to a median size of 2 kb. Following size fractionation by gel electrophoresis, the fragments were blunt-ended, ligated to adapter oligonucleotides, and cloned into each of 20 different pMPX vectors (Rice et al., abstracts of Meeting of Genome Mapping and Sequencing, Cold Spring Harbor, N.Y., 5/11–5/15, 1994, p. 225) and the PUC19 vector to construct a series of "shotgun" subclone libraries.

DNA sequencing was achieved using two sequencing methods. The first method used multiplex sequencing procedures essentially as disclosed in Church et al., 1988, *Science* 240:185; U.S. Pat. Nos. 4,942,124 and 5,149,625). DNA was extracted from pooled cultures and subjected to chemical or enzymatic sequencing. Sequencing reactions were resolved by electrophoresis, and the products were transferred and covalently bound to nylon membranes. Finally, the membranes were sequentially hybridized with a series of labelled oligonucleotides complimentary to "tag" sequences present in the different shotgun cloning vectors. In this manner, a large number of sequences could be obtained from a single set of sequencing reactions. The remainder of the sequencing was performed on ABI377 automated DNA sequencers. The cloning and sequencing procedures are described in more detail in the Exemplification.

Individual sequence reads were assembled using PHRAP (P. Green, Abstracts of DOE Human Genome Program Contractor-Grantee Workshop V, Jan. 1996, p.157). The average contig length was about 3–4 kb.

A variety of approaches are used to order the contigs so as to obtain a continuous sequence representing the entire *S. pneumoniae* genome. Synthetic oligonucleotides are designed that are complementary to sequences at the end of each contig. These oligonucleotides may be hybridized to libaries of *S. pneumoniae* genomic DNA in, for example, lambda phage vectors or plasmid vectors to identify clones that contain sequences corresponding to the junctional regions between individual contigs. Such clones are then used to isolate template DNA and the same oligonucleotides are used as primers in polymerase chain reaction (PCR) to amplify junctional fragments, the nucleotide sequence of which is then determined.

The *S. pneumoniae* sequences were analyzed for the presence of open reading frames (ORFs) comprising at least 180 nucleotides. As a result of the initial analysis of ORFs based on stop-to-stop codon reads, it should be understood that these ORFs may not correspond to the ORF of a naturally-occurring *S. pneumoniae* polypeptide. These ORFs may contain start codons which indicate the initiation of protein synthesis of a naturally-occurring *S. pneumoniae* polypeptide. Such start codons within the ORFs provided herein can be identified by those of ordinary skill in the relevant art, and the resulting ORF and the encoded *S. pneumoniae* polypeptide is within the scope of this invention. For example, within the ORFs a codon such as AUG or GUG (encoding methionine or valine) which is part of the initiation signal for protein synthesis can be identified and the portion of an ORF to corresponding to a naturally-occurring *S. pneumoniae* polypeptide can be recognized.

The second analysis of the ORFs included identifying the start codons and the predicted coding regions. These ORFs provided in this invention were defined by one or more of the following methods: evaluating the coding potential of such sequences with the program GENEMARK™ (Borodovsky and McIninch, 1993, *Comp.* 17:123), distinguishing the coding from noncoding regions using the program Glimmer (Fraser et al, *Nature*, 1997), determining codon usage (Staden et al., *Nucleic Acid Research* 10: 141), and each predicted ORF amino acid sequence was compared with all protein sequences found in current GENBANK, SWISS-PROT, and PIR databases using the BLAST algorithm. BLAST identifies local alignments occurring by chance between the ORF sequence and the sequence in the databank (Altschal et al., 1990, L Mol. Biol. 215:403–410). Homologous ORFs (probabilities less than $10^{-5}$ by chance) and ORF's that are probably non-homologous (probabilities greater than $10^{-5}$ by chance) but have good codon usage were identified. Both homologous, sequences and non-homologous sequences with good codon usage, are likely to encode proteins and are encompassed by the invention.

S. pneumoniae Nucleic Acids

The nucleic acids of this invention may be obtained directly from the DNA of the above referenced *S. pneumoniae* strain by using the polymerase chain reaction (PCR). See "*PCR, A Practical Approach*" (McPherson, Quirke, and Taylor, eds., IRL Press, Oxford, UK, 1991) for details about the PCR. High fidelity PCR can be used to ensure a faithful DNA copy prior to expression. In addition, the authenticity of amplified products can be verified by conventional sequencing methods. Clones carrying the desired sequences described in this invention may also be obtained by screening the libraries by means of the PCR or by hybridization of synthetic oligonucleotide probes to filter lifts of the library colonies or plaques as known in the art (see, e.g., Sambrook et al., *Molecular Cloning, A Laboratory Manual* 2nd edition, 1989, Cold Spring Harbor Press, NY).

It is also possible to obtain nucleic acids encoding *S. pneumoniae* polypeptides from a cDNA library in accordance with protocols herein described. A cDNA encoding an *S. pneumoniae* polypeptide can be obtained by isolating total mRNA from an appropriate strain. Double stranded cDNAs can then be prepared from the total mRNA. Subsequently, the cDNAs can be inserted into a suitable plasmid or viral (e.g., bacteriophage) vector using any one of a number of known techniques. Genes encoding *S. pneumoniae* polypeptides can also be cloned using established polymerase chain reaction techniques in accordance with the nucleotide: sequence information provided by the invention. The nucleic acids of the invention can be DNA or RNA. Preferred nucleic acids of the invention are contained in the Sequence Listing.

The nucleic acids of the invention can also be chemically synthesized using standard techniques. Various methods of chemically 'synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Nucleic acids isolated or synthesized in accordance with features of the present invention are useful, by way of example, without limitation, as probes, primers, capture ligands, antisense genes and for developing expression systems for the synthesis of proteins and peptides corresponding to such sequences. As probes, primers, capture ligands and antisense agents, the nucleic acid normally consists of all or part (approximately twenty or more nucleotides for specificity as well as the ability to form stable hybridization products) of the nucleic acids of the invention contained in the Sequence Listing. These uses are described in further detail below.

Probes

A nucleic acid isolated or synthesized in accordance with the sequence of the invention contained in the Sequence Listing can be used as a probe to specifically detect *S. pneumoniae*. With the sequence information set forth in the present application, sequences of twenty or more nucleotides are identified which provide the desired inclusivity and exclusivity with respect to *S. pneumoniae*, and extraneous nucleic acids likely to be encountered during hybridization conditions. More preferably, the sequence will comprise at least twenty to thirty nucleotides to convey stability to the hybridization product formed between the probe and the intended target molecules.

Sequences larger than 1000 nucleotides in length are difficult to synthesize but can be generated by recombinant DNA techniques. Individuals skilled in the art will readily recognize that the nucleic acids, for use as probes, can be provided with a label to facilitate detection of a hybridization product.

Nucleic acid isolated and synthesized in accordance with the sequence of the invention contained in the Sequence Listing can also be useful as probes to detect homologous regions (especially homologous genes) of other Streptococcus species using appropriate stringency hybridization conditions as described herein.

Capture Ligand

For use as a capture ligand, the nucleic acid selected in the manner described above with respect to probes, can be readily associated with a support. The manner in which nucleic acid is associated with supports is well known. Nucleic acid having twenty or more nucleotides in a sequence of the invention contained in the Sequence Listing have utility to separate *S. pneumoniae* nucleic acid from the nucleic acid of each other and other organisms. Nucleic acid having twenty or more nucleotides in a sequence of the invention contained in the Sequence Listing can also have utility to separate other Streptococcus species from each other and from other organisms. Preferably, the sequence will comprise at least twenty nucleotides to convey stability to the hybridization product formed between the probe and the intended target molecules. Sequences larger than 1000 nucleotides in length are difficult to synthesize but can be generated by recombinant DNA techniques.

Primers

Nucleic acid isolated or synthesized in accordance with the sequences described herein have utility as primers for the amplification of *S. pneumoniae* nucleic acid. These nucleic acids may also have utility as primers for the amplification of nucleic acids in other Streptococcus species. With respect to polymerase chain reaction (PCR) techniques, nucleic acid sequences of $\geq$10–15 nucleotides of the invention contained in the Sequence Listing have utility in conjunction with suitable enzymes and reagents to create copies of *S. pneumoniae* nucleic acid. More preferably, the sequence will comprise twenty or more nucleotides to convey stability to the hybridization product formed between the primer and the intended target molecules. Binding conditions of primers greater than 100 nucleotides are more difficult to control to obtain specificity. High fidelity PCR can be used to ensure a faithful DNA copy prior to expression. In addition, amplified products can be checked by conventional sequencing methods.

The copies can be used in diagnostic assays to detect specific sequences, including genes from *S. pneumoniae* and/or other Streptococcus species. The copies can also be incorporated into cloning and expression vectors to generate polypeptides corresponding to the nucleic acid synthesized by PCR, as is described in greater detail herein.

Antisense

Nucleic acid or nucleic acid-hybridizing derivatives isolated or synthesized in accordance with the sequences described herein have utility as antisense agents to prevent the expression of *S. pneumoniae* genes. These sequences also have utility as antisense agents to prevent expression of genes of other Streptococcus species.

In one embodiment, nucleic acid or derivatives corresponding to *S. pneumoniae* nucleic acids is loaded into a suitable carrier such as a liposome or bacteriophage for introduction into bacterial cells. For example, a nucleic acid having twenty or more nucleotides is capable of binding to bacteria nucleic acid or bacteria messenger RNA. Preferably, the antisense nucleic acid is comprised of 20 or more nucleotides to provide necessary stability of a hybridization product of non-naturally occurring nucleic acid and bacterial nucleic acid and/or bacterial messenger RNA. Nucleic acid having a sequence greater than 1000 nucleotides in length is difficult to synthesize but can be generated by recombinant DNA techniques. Methods for loading antisense nucleic acid in liposomes is known in the art as exemplified by U.S. Pat. No. 4,241,046 issued Dec. 23, 1980 to Papahadjopoulos et al.

The present invention encompasses isolated polypeptides and nucleic acids derived from *S. pneumoniae* that are useful as reagents for diagnosis of bacterial infection, components of effective antibacterial vaccines, and/or as targets for antibacterial drugs, including anti-*S. pneumoniae* drugs.

Expression of S pneumoniae Nucleic Acids

Table 2 provides a list of open reading frames (ORFs) in both strands. An ORF is a region of nucleic acid which encodes a polypeptide. This region normally represents a complete coding sequence or a total sequence and was determined from an initial analysis of stop to stop codons followed by the prediction of start codons. The first column lists the ORF designation. The second and third columns list the SEQ ID numbers for the nucleic acid and amino acid sequences corresponding to each ORF, respectively. The fourth and fifth columns list the length of the nucleic acid ORF and the length of the amino acid ORF, respectively. Most of the nucleotide sequences corresponding to each ORF begin at the first nucleotide of the start codon and end at the nucleotide immediately preceding the next downstream stop codon in the same reading frame. It will be recognized by one skilled in the art that the natural translation initiation sites will correspond to ATG, GTG, or TTG codons located within the ORFs. The natural initiation sites depend not only on the sequence of a start codon but also on the context of the DNA sequence adjacent to the start codon. Usually, a recognizable ribosome binding site is found within 20 nucleotides upstream from the initiation codon. In some cases where genes are translationally coupled and coordinately expressed together in "operons", ribosome binding sites are not present, but the initiation codon of a downstream gene may occur very close to, or overlap, the stop codon of the an upstream gene in the same operon. The correct start codons can be generally identified rapidly and efficiently because only a few codons need be tested. It is recognized that the translational machinery in bacteria initiates most polypeptide chains with the amino acid methionine. In some cases, polypeptides are post-translationally modified, resulting in an N-terminal amino acid other than methionine in vivo. The sixth and seventh columns provide metrics for assessing the likelihood of the homology match (determined by the BLASTP2 algorithm), as is known in the art, to the genes indicated in the description field. Specifically, the sixth column represents the "Score" for the match (a higher score is a better match), and the seventh column represents the "P-value" for the match (the probability that such a match could have occurred by chance; the lower the value, the more likely the match is valid). If a BLASTP2 score of less than 46 was obtained, no value is reported in the table the "P-value". The description field provides, where available, the accession number (AC) or the Swissprot accession number (SP), the locus name (LN), Superfamily Classification (CL), the Organism (OR), Source of variant (SR), E.C. number (EC), the gene name (GN), the product name (PN), the Function Description (FN), the Map Position (MP), Left End (LE), Right End (RE), Coding Direction (DI), the Database from which the sequence originates (DB), and the description (DE) or notes (NT) for each ORF. This information allows one of ordinary skill in the art to determine a potential use and function for each identified coding sequence and, as a result, allows the use of the polypeptides of the present invention for commercial and industrial purposes.

Using the information provided in SEQ ID NO: 1–SEQ ID NO: 2661 and in Table 2 together with routine cloning and sequencing methods, one of ordinary skill in the art will be able to clone and sequence all the nucleic acid fragments of interest including open reading frames (ORFs) encoding a large variety proteins of S. pneumoniae.

Nucleic acid isolated or synthesized in accordance with the sequences described herein have utility to generate polypeptides. The nucleic acid of the invention exemplified in SEQ ID NO: 1–SEQ ID NO: 2661 and in Table 2 or fragments of said nucleic acid encoding active portions of S. pneumoniae polypeptides can be cloned into suitable vectors or used to isolate nucleic acid. The isolated nucleic acid is combined with suitable DNA linkers and cloned into a suitable vector.

The function of a specific gene or operon can be ascertained by expression in a bacterial strain under conditions where the activity of the gene product(s) specified by the gene or operon in question can be specifically measured. Alternatively, a gene product may be produced in large quantities in an expressing strain for use as an antigen, an industrial reagent, for structural studies, etc. This expression can be accomplished in a mutant strain which lacks the activity of the gene to be tested, or in a strain that does not produce the same gene product(s). This includes, but is not limited to, Eucaryotic species such as the yeast Saccharomyces cerevisiae, Methanobacterium strains or other Archaea, and Eubacteria such as E. coli, B. subtilis, S. aureus, S. pneumonia or Pseudomonas putida. In some cases the expression host will utilize the natural S. pneumoniae promoter whereas in others, it will be necessary to drive the gene with a promoter sequence derived from the expressing organism (e.g., an E. coli beta-galactosidase promoter for expression in E. coli).

To express a gene product using the natural S. pneumoniae promoter, a procedure such as the following can be used. A restriction fragment containing the gene of interest, together with its associated natural promoter element and regulatory sequences (identified using the DNA sequence data) is cloned into an appropriate recombinant plasmid containing an origin of replication that functions in the host organism and an appropriate selectable marker. This can be accomplished by a number of procedures known to those skilled in the art. It is most preferably done by cutting the plasmid and the fragment to be cloned with the same restriction enzyme to produce compatible ends that can be ligated to join the two pieces together. The recombinant plasmid is introduced into the host organism by, for example, electroporation and cells containing the recombinant plasmid are identified by selection for the marker on the plasmid. Expression of the desired gene product is detected using an assay specific for that gene product.

In the case of a gene that requires a different promoter, the body of the gene (coding sequence) is specifically excised and cloned into an appropriate expression plasmid. This subcloning can be done by several methods, but is most easily accomplished by PCR amplification of a specific fragment and ligation into an expression plasmid after treating the PCR product with a restriction enzyme or exonuclease to create suitable ends for cloning.

A suitable host cell for expression of a gene can be any procaryotic or eucaryotic cell. For example, an S. pneumoniae polypeptide can be expressed in bacterial cells such as E. coli or B. subtilis, insect cells (baculovirus), yeast, or mammalian cells such as Chinese hamster ovary cell (CHO). Other suitable host cells are known to those skilled in the art.

Expression in eucaryotic cells such as mammalian, yeast, or insect cells can lead to partial or complete glycosylation and/or formation of relevant inter- or intra-chain disulfide bonds of a recombinant peptide product. Examples of vectors for expression in yeast S. cerivisae include pYepSec1 (Baldari. et al., (1987) Embo J. 6:229–234), pMFa (Kurjan and Herskowitz, (1982) Cell 30:933–943), pJRY88 (Schultz et al., (1987) Gene 54:113–123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:215.6–2165) and the pVL series (Lucklow, V. A., and Summers, M. D., (1989) *Virology* 170:31–39). Generally, COS cells (Gluzman, Y., (1981) Cell 23:175–182) are used in conjunction with such vectors as pCDM 8 (Aruffo, A. and Seed, B., (1987) *Proc. Natl. Acad. Sci. USA* 84:8573–8577) for transient amplification/expression in mammalian cells, while CHO (dhfr⁻ Chinese Hamster Ovary) cells are used with vectors such as pMT2PC (Kaufman et al. (1987), *EMBO J.* 6:187–195) for stable amplification/expression in mammalian cells. Vector DNA can be introduced into mammalian cells via conventional techniques such as calcium phosphate or calcium chloride co-precipitation, DEAE-dextran-mediated transfection, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks.

Expression in procaryotes is most often carried out in *E. coli* with either fusion or non-fusion inducible expression vectors. Fusion vectors usually add a number of $NH_2$ terminal amino acids to the expressed target gene. These $NH_2$ terminal amino acids often are referred to as a reporter group or an affinity purification group. Such reporter groups usually serve two purposes: 1) to increase the solubility of the target recombinant protein; and 2) to aid in the purification of the target recombinant protein by acting as a ligand in affinity purification. Often, in fusion expression vectors, a proteolytic cleavage site is introduced at the junction of the reporter group and the target recombinant protein to enable separation of the target recombinant protein from the reporter group subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein. A preferred reporter group is poly(His), which may be fused to the amino or carboxy terminus of the protein and which renders the recombinant fusion protein easily purifiable by metal chelate chromatography.

Inducible non-fusion expression vectors include pTrc (Amann et al., (1988) Gene 69:301–315) and pET11d (Studier et al., *Gene Expression Technology: Methods in Enzymology* 185, Academic Press, San Diego, Calif. (1990) 60–89). While target gene expression relies on host RNA polymerase transcription from the hybrid trp-lac fusion promoter in pTrc, expression of target genes inserted into pET11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident λ prophage harboring a T7 gn1 under the transcriptional control of the lacUV 5 promoter.

For example, a host cell transfected with a nucleic acid vector directing expression of a nucleotide sequence encoding an *S. pneumoniae* polypeptide can be cultured under appropriate conditions to allow expression of the polypeptide to occur. The polypeptide may be secreted and isolated from a mixture of cells and medium containing the peptide. Alternatively, the polypeptide may be retained cytoplasmically and the cells harvested, lysed and the protein isolated. A cell culture includes host cells, media and other byproducts. Suitable media for cell culture are well known in the art. Polypeptides of the invention can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such polypeptides. Additionally, in many situations, polypeptides can be produced by chemical cleavage of a native protein (e.g., tryptic digestion) and the cleavage products can then be purified by standard techniques.

In the case of membrane bound proteins, these can be isolated from a host cell by contacting a membrane-associated protein fraction with a detergent forming a solubilized complex, where the membrane-associated protein is no longer entirely embedded in the membrane fraction and is solubilized at least to an extent which allows it to be chromatographically isolated from the membrane fraction. Several different criteria are used for choosing a detergent suitable for solubilizing these complexes. For example, one property considered is the ability of the detergent to solubilize the *S. pneumoniae* protein within the membrane fraction at minimal denaturation of the membrane-associated protein allowing for the activity or functionality of the membrane-associated protein to return upon reconstitution of the protein. Another property considered when selecting the detergent is the critical micelle concentration (CMC) of the detergent in that the detergent of choice preferably has a high CMC value allowing for ease of removal after reconstitution. A third property considered when selecting a detergent is the hydrophobicity of the detergent. Typically, membrane-associated proteins are very hydrophobic and therefore detergents which are also hydrophobic, e.g., the triton series, would be useful for solubilizing the hydrophobic proteins. Another property important to a detergent can be the capability of the detergent to remove the *S. pneumoniae* protein with minimal protein-protein interaction facilitating further purification. A fifth property of the detergent which should be considered is the charge of the detergent. For example, if it is desired to use ion exchange resins in the purification process then preferably detergent should be an uncharged detergent. Chromatographic techniques which can be used in the final purification step are known in the art and include hydrophobic interaction, lectin affinity, ion exchange, dye affinity and immunoaffinity.

One strategy to maximize recombinant *S. pneumoniae* peptide expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy would be to alter the nucleic acid encoding an *S. pneumoniae* peptide to be inserted into an expression vector so that the individual codons for each amino acid would be those preferentially utilized in highly expressed *E. coli* proteins (Wada et al., (1992) *Nuc. Acids Res.* 20:2111–2118). Such alteration of nucleic acids of the invention can be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See, e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

The present invention provides a library of *S. pneumoniae*-derived nucleic acid sequences. The libraries provide probes, primers, and markers which can be used as markers in epidemiological studies. The present invention also provides a library of *S. pneumoniae*-derived nucleic acid sequences which comprise or encode targets for therapeutic drugs.

Nucleic acids comprising any of the sequences disclosed herein or sub-sequences thereof can be prepared by standard methods using the nucleic acid sequence information provided in SEQ ID NO: 1–SEQ ID NO: 2661. For example, DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. This can be done by sequentially linking a series of oligonucleotide cassettes comprising pairs of synthetic oligonucleotides, as described below.

Of course, due to the degeneracy of the genetic code, many different nucleotide sequences can encode polypeptides having the amino acid sequences defined by SEQ ID NO: 2662–SEQ ID NO: 5322 or sub-sequences thereof. The codons can be selected for optimal expression in prokaryotic or eukaryotic systems. Such degenerate variants are also encompassed by this invention.

Insertion of nucleic acids (typically DNAs) encoding the polypeptides of the invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239:48. The cleaved vector and the DNA fragments may also be modified if required by homopolymeric tailing.

In certain embodiments, the invention encompasses isolated nucleic acid fragments comprising all or part of the individual nucleic acid sequences disclosed herein. The fragments are at least about 8 nucleotides in length, preferably at least about 12 nucleotides in length, and most preferably at least about 15–20 nucleotides in length.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural *S. pneumoniae* regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed *S. pneumoniae*-derived sequences or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression.

The encoded *S. pneumoniae* polypeptides may be expressed by using many known vectors, such as pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. The particular choice of vector/host is not critical to the practice of the invention.

Recombinant cloning vectors will often include one or more replication systems for cloning or expression, one or more markers for selection in the host, e.g. antibiotic resistance, and one or more expression cassettes. The inserted *S. pneumoniae* coding sequences may be synthesized by standard methods, isolated from natural sources, or prepared as hybrids, etc. Ligation of the *S. pneumoniae* coding sequences to transcriptional regulatory elements and/ or to other amino acid coding sequences may be achieved by known methods. Suitable host cells may be transformed/ transfected/infected as appropriate by any suitable method including electroporation, $CaCl_2$ mediated DNA uptake, fungal infection, microinjection, microprojectile, or other established methods.

Appropriate host cells include bacteria, archebacteria, fungi, especially yeast, and plant and animal cells, especially mammalian cells. Of particular interest are *S. pneumoniae, E. coli, B. Subtilis, Saccharomyces cerevisiae, Saccharomyces carlsbergensis, Schizosaccharomyces pombi*, SF9 cells, C129 cells, 293 cells, Neurospora, and CHO cells, COS cells, HeLa cells, and immortalized mammalian myeloid and lymphoid cell lines. Preferred replication systems include M13, Co1E1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced *S. pneumoniae*-derived peptides and polypeptides.

Advantageously, vectors may also include a transcription regulatory element (i.e., a promoter) operably linked to the *S. pneumoniae* portion. The promoter may optionally contain operator portions and/or ribosome binding sites. Non-limiting examples of bacterial promoters compatible with E. coli include: b-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences, polyA addition sequences and enhancer sequences to increase expression. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are well described in the art.

Nucleic acids encoding wild-type or variant S. pneumoniae-derived polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

The nucleic acids of the present invention find use as templates for the recombinant production of S. pneumoniae-derived peptides or polypeptides.

Identification and Use of S. pneumoniae Nucleic Acid Sequences

The disclosed S. pneumoniae polypeptide and nucleic acid sequences, or other sequences that are contained within ORFs, including complete protein-coding sequences, of which any of the disclosed S. pneumoniae-specific sequences forms a part, are useful as target components for diagnosis and/or treatment of S. pneumoniae-caused infection.

It will be understood that the sequence of an entire protein-coding sequence of which each disclosed nucleic acid sequence forms a part can be isolated and identified based on each disclosed sequence. This can be achieved, for example, by using an isolated nucleic acid encoding the disclosed sequence, or fragments thereof, to prime a sequencing reaction with genomic S. pneumoniae DNA as template; this is followed by sequencing the amplified product. The isolated nucleic acid encoding the disclosed sequence, or fragments thereof, can also be hybridized to S. pneumoniae genomic libraries to identify clones containing additional complete segments of the protein-coding sequence of which the shorter sequence forms a part. Then, the entire protein-coding sequence, or fragments thereof, or nucleic acids encoding all or part of the sequence, or sequence-conservative or function-conservative variants thereof, may be employed in practicing the present invention.

Preferred sequences are those that are useful in diagnostic and/or therapeutic applications. Diagnostic applications include without limitation nucleic-acid-based and antibody-based methods for detecting bacterial infection. Therapeutic applications include without limitation vaccines, passive immunotherapy, and drug treatments directed against gene products that are both unique to bacteria and essential for growth and/or replication of bacteria.

Identification of Nucleic Acids Encoding Vaccine Components and Targets for Agents Effective Against S. pneumoniae The disclosed S. pneumoniae genome sequence includes segments that direct the synthesis of ribonucleic acids and polypeptides, as well as origins of replication, promoters, other types of regulatory sequences, and intergenic nucleic acids. The invention encompasses nucleic acids encoding immunogenic components of vaccines and targets for agents effective against S. pneumoniae. Identification of said immunogenic components involved in the determination of the function of the disclosed sequences, which can be achieved using a variety of approaches. Non-limiting examples of these approaches are described briefly below.

Homology to Known Sequences:

Computer-assisted comparison of the disclosed S. pneumoniae sequences with previously reported sequences present in publicly available databases is useful for identifying functional S. pneumoniae nucleic acid and polypeptide sequences. It will be understood that protein-coding sequences, for example, may be compared as a whole, and that a high degree of sequence homology between two proteins (such as, for example, >80–90%) at the amino acid level indicates that the two proteins also possess some degree of functional homology, such as, for example, among enzymes involved in metabolism, DNA synthesis, or cell wall synthesis, and proteins involved in transport, cell division, etc. In addition, many structural features of particular protein classes have been identified and correlate with specific consensus sequences, such as, for example, binding domains for nucleotides, DNA, metal ions, and other small molecules; sites for covalent modifications such as phosphorylation, acylation, and the like; sites of protein-:protein interactions, etc. These consensus sequences may be quite short and thus may represent only a fraction of the entire protein-coding sequence. Identification of such a feature in an S. pneumoniae sequence is therefore useful in determining the function of the encoded protein and identifying useful targets of antibacterial drugs.

Of particular relevance to the present invention are structural features that are common to secretory, transmembrane, and surface proteins, including secretion signal peptides and hydrophobic transmembrane domains. S. pneumoniae proteins identified as containing putative signal sequences and/or transmembrane domains are useful as immunogenic components of vaccines.

Targets for therapeutic drugs according to the invention include, but are not limited to, polypeptides of the invention, whether unique to S. pneumoniae or not, that are essential for growth and/or viability of S. pneumoniae under at least one growth condition. Polypeptides essential for growth and/or viability can be determined by examining the effect of deleting and/or disrupting the genes, i.e., by so-called gene "knockout". Alternatively, genetic footprinting can be used (Smith et al., 1995, Proc. Natl. Acad. Sci. USA 92:5479–6433; Published International Application WO 94/26933; U.S. Pat. No. 5,612,180). Still other methods for assessing essentiality includes the ability to isolate conditional lethal mutations in the specific gene (e.g., temperature sensitive mutations). Other useful targets for therapeutic drugs, which include polypeptides that are not essential for growth or viability per se but lead to loss of viability of the cell, can be used to target therapeutic agents to cells.

Strain-specific Sequences:

Because of the evolutionary relationship between different *S. pneumoniae* strains, it is believed that the presently disclosed *S. pneumoniae* sequences are useful for identifying, and/or discriminating between, previously known and new *S. pneumoniae* strains. It is believed that other *S. pneumoniae* strains will exhibit at least 70% sequence homology with the presently disclosed sequence. Systematic and routine analyses of DNA sequences derived from samples containing *S. pneumoniae* strains, and comparison with the present sequence allows for the identification of sequences that can be used to discriminate between strains, as well as those that are common to all *S. pneumoniae* strains. In one embodiment, the invention provides nucleic acids, including probes, and peptide and polypeptide sequences that discriminate between different strains of *S. pneumoniae*. Strain-specific components can also be identified functionally by their ability to elicit or react with antibodies that selectively recognize one or more *S. pneumoniae* strains.

In another embodiment, the invention provides nucleic acids, including probes, and peptide and polypeptide sequences that are common to all *S. pneumoniae* strains but are not found in other bacterial species.

S. pneumoniae Polypeptides

This invention encompasses isolated *S. pneumoniae* polypeptides encoded by the disclosed *S. pneumoniae* genomic sequences, including the polypeptides of the invention contained in the Sequence Listing. Polypeptides of the invention are preferably at least 5 amino acid residues in length. Using the DNA sequence information provided herein, the amino acid sequences of the polypeptides encompassed by the invention can be deduced using methods well-known in the art. It will be understood that the sequence of an entire nucleic acid encoding an *S. pneumoniae* polypeptide can be isolated and identified based on an ORF that encodes only a fragment of the cognate protein-coding region. This can be achieved, for example, by using the isolated nucleic acid encoding the ORF, or fragments thereof, to prime a polymerase chain reaction with genomic *S. pneumoniae* DNA as template; this is followed by sequencing the amplified product.

The polypeptides of the present invention, including function-conservative variants of the disclosed ORFs, may be isolated from wild-type or mutant *S. pneumoniae* cells, or from heterologous organisms or cells (including, but not limited to, bacteria, fungi, insect, plant, and mammalian cells) including *S. pneumoniae* into which a *S. pneumoniae*-derived protein-coding sequence has been introduced and expressed. Furthermore, the polypeptides may be part of recombinant fusion proteins.

*S. pneumoniae* polypeptides of the invention can be chemically synthesized using commercially automated procedures such as those referenced herein, including, without limitation, exclusive solid phase synthesis, partial solid phase methods, fragment condensation or classical solution synthesis. The polypeptides are preferably prepared by solid phase peptide synthesis as described by Merrifield, 1963, *J. Am. Chem. Soc.* 85:2149. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups, e.g., formyl, trifluoroacetyl, acetyl, aromatic urethane type protecting groups, e.g., benzyloxycarbonyl (Cbz), substituted benzyloxycarbonyl and 9-fluorenylmethyloxycarbonyl (Fmoc), aliphatic urethane protecting groups, e.g., t-butyloxycarbonyl (Boc), isopropyloxycarbonyl, cyclohexyloxycarbonyl, and alkyl type protecting groups, e.g., benzyl, triphenylmethyl. The preferred protecting group is Boc. The side-chain protecting groups for Tyr include tetrahydropyranyl, tert-butyl, trityl, benzyl, Cbz, 4-Br-Cbz and 2,6-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group for Asp is cyclohexyl. The side-chain protecting groups for Thr and Ser include acetyl, benzoyl, trityl, tetrahydropyranyl, benzyl, 2,6-dichlorobenzyl and Cbz. The preferred protecting group for Thr and Ser is benzyl. The side-chain protecting groups for Arg include nitro, Tos, Cbz, adamantyloxycarbonyl and Boc. The preferred protecting group for Arg is Tos. The side-chain amino group of Lys may be protected with Cbz, 2-Cl-Cbz, Tos or Boc. The 2-Cl-Cbz group is the preferred protecting group for Lys.

The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished polypeptide.

Solid phase synthesis is usually carried out from the carboxy-terminus by coupling the alpha-amino protected (side-chain protected) amino acid to a suitable solid support. An ester linkage is formed when the attachment is made to a chloromethyl or hydroxymethyl resin, and the resulting polypeptide will have a free carboxyl group at the C-terminus. Alternatively, when a benzhydrylamine or p-methylbenzhydrylamine resin is used, an amide bond is formed and the resulting polypeptide will have a carboxamide group at the C-terminus. These resins are commercially available, and their preparation was described by Stewart et al., 1984, *Solid Phase Peptide Synthesis* (2nd Edition), Pierce Chemical Co., Rockford, Ill.

The C-terminal amino acid, protected at the side chain if necessary and at the alpha-amino group, is coupled to the benzhydrylamine resin using various activating agents including dicyclohexylcarbodiimide (DCC), N,N'-diisopropyl-carbodiimide and carbonyldiimidazole. Following the attachment to the resin support, the alpha-amino protecting group is removed using trifluoroacetic acid (TFA) or HCl in dioxane at a temperature between 0 and 25° C. Dimethylsulfide is added to the TFA after the introduction of methionine (Met) to suppress possible S-alkylation. After removal of the alpha-amino protecting group, the remaining protected amino acids are coupled stepwise in the required order to obtain the desired sequence.

Various activating agents can be used for the coupling reactions including DCC, N,N'-diisopropyl-carbodiimide, benzotriazol-1-yl-oxy-tris-(dimethylamino)-phosphonium hexa-fluorophosphate (BOP) and DCC-hydroxybenzotriazole (HOBt). Each protected amino acid is used in excess (>2.0 equivalents), and the couplings are usually carried out in N-methylpyrrolidone (NMP) or in DMF, $CH_2Cl_2$ or mixtures thereof. The extent of completion of the coupling reaction is monitored at each stage, e.g., by the ninhydrin reaction as described by Kaiser et al., 1970, *Anal. Biochem.* 34:595. In cases where incomplete coupling is found, the coupling reaction is repeated. The coupling reactions can be performed automatically with commercially available instruments.

After the entire assembly of the desired polypeptide, the polypeptide-resin is cleaved with a reagent such as liquid HF for 1–2 hours at 0° C., which cleaves the polypeptide from the resin and removes all side-chain protecting groups. A scavenger such as anisole is usually used with the liquid HF to prevent cations formed during the cleavage from alkylating the amino acid residues present in the polypeptide. The polypeptide-resin may be deprotected with TFA/dithioethane prior to cleavage if desired.

Side-chain to side-chain cyclization on the solid support requires the use of an orthogonal protection scheme which enables selective cleavage of the side-chain functions of acidic amino acids (e.g., Asp) and the basic amino acids (e.g., Lys). The 9-fluorenylmethyl (Fm) protecting group for the side-chain of Asp and the 9-fluorenylmethyloxycarbonyl (Fmoc) protecting group for the side-chain of Lys can be used for this purpose. In these cases, the side-chain protecting groups of the Boc-protected polypeptide-resin are selectively removed with piperidine in DMF. Cyclization is achieved on the solid support using various activating agents including DCC, DCC/HOBt or BOP. The HF reaction is carried out on the cyclized polypeptide-resin as described above.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the *S. pneumoniae* protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a *S. pneumoniae* protein or against peptides derived therefrom can be used as purification reagents. Other purification methods are possible.

The present invention also encompasses derivatives and homologues of *S. pneumoniae*-encoded polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids. The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds. agents.

To identify *S. pneumoniae*-derived polypeptides for use in the present invention, essentially the complete genomic sequence of a virulent, methicillin-resistant isolate of *Streptococcus pneumoniae* isolate was analyzed. While, in very rare instances, a nucleic acid sequencing error may be revealed, resolving a rare sequencing error is well within the art, and such an occurrence will not prevent one skilled in the art from practicing the invention.

Also encompassed are any *S. pneumoniae* polypeptide sequences that are contained within the open reading frames (ORFs), including complete protein-coding sequences, of which any of SEQ ID NO: 2662–SEQ ID NO: 5322 forms a part. Table 2, which is appended herewith and which forms part of the present specification, provides a putative identification of the particular function of a polypeptide which is encoded by each ORF. As a result, one skilled in the art can use the polypeptides of the present invention for commercial and industrial purposes consistent with the type of putative identification of the polypeptide.

The present invention provides a library of *S. Pneumoniae*-derived polypeptide sequences, and a corresponding library of nucleic acid sequences encoding the polypeptides, wherein the polypeptides themselves, or polypeptides contained within ORFs of which they form a part, comprise sequences that are contemplated for use as components of vaccines. Non-limiting examples of such sequences are listed by SEQ ID NO in Table 2, which is appended herewith and which forms part of the present specification.

The present invention also provides a library of *S. pneumoniae*-derived polypeptide sequences, and a corresponding library of nucleic acid sequences encoding the polypeptides, wherein the polypeptides themselves, or polypeptides contained within ORFs of which they form a part, comprise sequences lacking homology to any known prokaryotic or eukaryotic sequences. Such libraries provide probes, primers, and markers which can be used to diagnose *S. pneumoniae* infection, including use as markers in epidemiological studies. Non-limiting examples of such sequences are listed by SEQ ID NO in Table 2, which is appended The present invention also provides a library of *S. pneumoniae*-derived polypeptide sequences, and a corresponding library of nucleic acid sequences encoding the polypeptides, wherein the polypeptides themselves, or polypeptides contained within ORFs of which they form a part, comprise targets for therapeutic drugs.

Specific Example: Determination of Candidate Protein Antigens for Antibody and Vaccine Development The selection of candidate protein antigens for vaccine development can be derived from the nucleic acids encoding *S. pneumoniae* polypeptides. First, the ORF's can be analyzed for homology to other known exported or membrane proteins and analyzed using the discriminant analysis described by Klein, et al. (Klein, P., Kanehsia, M., and DeLisi, C. (1985) *Biochimica et Biophysica Acta* 815, 468–476) for predicting exported and membrane proteins.

Homology searches can be performed using the BLAST algorithm contained in the Wisconsin Sequence Analysis Package (Genetics Computer Group, University Research Park, 575 Science Drive, Madison, Wis. 53711) to compare each predicted ORF amino acid sequence with all sequences found in the current GenBank, SWISS-PROT and PIR databases. BLAST searches for local alignments between the ORF and the databank sequences and reports a probability score which indicates the probability of finding this sequence by chance in the database. ORF's with significant homology (e.g. probabilities lower than $1 \times 10^{-6}$ that the homology is only due to random chance) to membrane or exported proteins represent protein antigens for vaccine development. Possible functions can be provided to *S. pneumoniae* genes based on sequence homology to genes cloned in other organisms.

Discriminant analysis (Klein, et al. supra) can be used to examine the ORF amino acid sequences. This algorithm uses the intrinsic information contained in the ORF amino acid sequence and compares it to information derived from the properties of known membrane and exported proteins. This comparison predicts which proteins will be exported, membrane associated or cytoplasmic. ORF amino acid sequences identified as exported or membrane associated by this algorithm are likely protein antigens for vaccine development.

Production of Fragments and Analogs of S. pneumoniae Nucleic Acids and Polypeptides Based on the discovery of the *S. pneumoniae* gene products of the invention provided in the Sequence Listing, one skilled in the art can alter the disclosed structure (of *S. pneumoniae* genes), e.g., by producing fragments or analogs, and test the newly produced structures for activity. Examples of techniques known to those skilled in the relevant art which allow the production and testing of fragments and analogs are discussed below. These, or analogous methods can be used to make and screen libraries of polypeptides, e.g., libraries of random peptides or libraries of fragments or analogs of cellular proteins for the ability to bind *S. pneumoniae* polypeptides. Such screens are useful for the identification of inhibitors of *S. pneumoniae.*

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNA's which encode an array of fragments. DNA's which encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention may be arbitrarily divided into fragments of desired length with no overlap of the fragments, or divided into overlapping fragments of a desired length.

Alteration of Nucleic Acids and Polypeptides: Random Methods

Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein).

PCR Mutagenesis

In PCR mutagenesis, reduced Taq polymerase fidelity is used to introduce random mutations into a cloned fragment of DNA (Leung et al., 1989, *Technique* 1:11–15). The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Alteration of Nucleic Acids and Polypeptides: Methods for Directed Mutagenesis

Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1–3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081–1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad Sci. USA*, 75: 5765[1978]).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants (Ladner et al., WO 88/06630). In this method, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Other Modifications of *S. pneumoniae* Nucleic Acids and Polypeptides

It is possible to modify the structure of an *S. pneumoniae* polypeptide for such purposes as increasing solubility, enhancing stability (e.g., shelf life ex vivo and resistance to proteolytic degradation in vivo). A modified *S. pneumoniae* protein or peptide can be produced in which the amino acid sequence has been altered, such as by amino acid substitution, deletion, or addition as described herein.

An *S. pneumoniae* peptide can also be modified by substitution of cysteine residues preferably with alanine, serine, threonine, leucine or glutamic acid residues to minimize dimerization via disulfide linkages. In addition, amino acid side chains of fragments of the protein of the invention can be chemically modified. Another modification is cyclization of the peptide.

In order to enhance stability and/or reactivity, an *S. pneumoniae* polypeptide can be modified to incorporate one or more polymorphisms in the amino acid sequence of the protein resulting from any natural allelic variation. Additionally, D-amino acids, non-natural amino acids, or non-amino acid analogs can be substituted or added to produce a modified protein within the scope of this invention. Furthermore, an *S. pneumoniae* polypeptide can be modified using polyethylene glycol. (PEG) according to the method of A. Sehon and co-workers (Wie et al., supra) to produce a protein conjugated with PEG. In addition, PEG can be added during chemical synthesis of the protein. Other modifications of *S. pneumoniae* proteins include reduction/alkylation (Tarr, *Methods of Protein Microcharacterization*, J. E. Silver ed., Humana Press, Clifton N.J. 155–194 (1986)); acylation (Tarr, supra); chemical coupling to an appropriate carrier (Mishell and Shiigi, eds, *Selected Methods in Cellular Immunology*, W H Freeman, San Francisco, Calif. (1980), U.S. Pat. No. 4,939,239; or mild formalin treatment (Marsh, (1971) *Int. Arch. of Allergy and Appl. Immunol.*, 41: 199–215).

To facilitate purification and potentially increase solubility of an *S. pneumoniae* protein or peptide, it is possible to add an amino acid fusion moiety to the peptide backbone. For example, hexa-histidine can be added to the protein for purification by immobilized metal ion affinity chromatography (Hochuli, E. et al., (1988) *Bio/Technology*, 6: 1321–1325). In addition, to facilitate isolation of peptides free of irrelevant sequences, specific endoprotease cleavage sites can be introduced between the sequences of the fusion moiety and the peptide.

To potentially aid proper antigen processing of epitopes within an *S. pneumoniae* polypeptide, canonical protease sensitive sites can be engineered between regions, each comprising at least one epitope via recombinant or synthetic methods. For example, charged amino acid pairs, such as KK or RR, can be introduced between regions within a protein or fragment during recombinant construction thereof. The resulting peptide can be rendered sensitive to cleavage by cathepsin and/or other trypsin-like enzymes which would generate portions of the protein containing one or more epitopes. In addition, such charged amino acid residues can result in an increase in the solubility of the peptide.

Primary Methods for Screening Polypeptides and Analogs

Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., in this case, binding to *S. pneumoniae* polypeptide or an interacting protein, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid assays such as the system described above (as with the other screening methods described herein), can be used to identify polypeptides, e.g., fragments or analogs of a naturally-occurring *S. pneumoniae* polypeptide, e.g., of cellular proteins, or of randomly generated polypeptides which bind to an *S. pneumoniae* protein. (The *S. pneumoniae* domain is used as the bait protein and the library of variants are expressed as prey fusion proteins.) In an analogous fashion, a two hybrid assay (as with the other screening methods described herein), can be used to find polypeptides which bind a *S. pneumoniae* polypeptide.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, a detectably labeled ligand can be used to score for potentially functional peptide homologs. Fluorescently labeled ligands, e.g., receptors, can be used to detect homologs which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007–16010; Griffiths et al. (1993) *EMBO J* 12:725–734; Clackson et al. (1991) *Nature* 352:624–628; and Barbas et al. (1992) *PNAS* 89:4457–4461).

A common approach uses the maltose receptor of *E. coli* (the outer membrane protein, LamB) as a peptide fusion partner (Charbit et al. (1986) *EMBO* 5, 3029–3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387–392), PhoE (Agterberg, et al. (1990) *Gene* 88, 37–45), and PAL (Fuchs et al. (1991) *Bio/Tech* 9, 1369–1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984–993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of many peptide copies on the host cells (Kuwajima et al. (1988) *Bio/Tech.* 6, 1080–1083). Surface proteins of other bacterial species have also served as peptide fusion partners. Examples include the Staphylococcus protein A and the outer membrane IgA protease of Neisseria (Hansson et al. (1992) *J. Bacteriol.* 174, 4239–4245 and Klauser et al. (1 990) *EMBO J.* 9, 1991–1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865–1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89–1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Nat. Acad. Sci. U.S.A.* 87, 6378–6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233–1251). These particular biases are not a factor in the LacI display system.

The number of small peptides available in recombinant random libraries is enormous. Libraries of $10^7$–$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3–6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233–1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem.* 204,357–364). To identify the sequences of the active peptides one sequences the DNA produced by the phagemid host.

Secondary Screening of Polypeptides and Analogs

The high through-put assays described above can be followed by secondary screens in order to identify further biological activities which will, e.g., allow one skilled in the art to differentiate agonists from antagonists. The type of a secondary screen used will depend on the desired activity that needs to be tested. For example, an assay can be developed in which the ability to inhibit an interaction between a protein of interest and its respective ligand can be used to identify antagonists from a group of peptide fragments isolated though one of the primary screens described above.

Therefore, methods for generating fragments and analogs and testing them for activity are known in the art. Once the core sequence of interest is identified, it is routine for one skilled in the art to obtain analogs and fragments.

Peptide Mimetics of *S. pneumoniae* Polypeptides

The invention also provides for reduction of the protein binding domains of the subject *S. pneumoniae* polypeptides to generate mimetics, e.g. peptide or non-peptide agents. The peptide mimetics are able to disrupt binding of a polypeptide to its counter ligand, e.g., in the case of an *S. pneumoniae* polypeptide binding to a naturally occurring ligand. The critical residues of a subject *S. pneumoniae* polypeptide which are involved in molecular recognition of a polypeptide can be determined and used to generate *S. pneumoniae*-derived peptidomimetics which competitively or noncompetitively inhibit binding of the *S. pneumoniae* polypeptide with an interacting polypeptide (see, for example, European patent applications EP-412,762A and EP-B31,080A).

For example, scanning mutagenesis can be used to map the amino acid residues of a particular *S. pneumoniae* polypeptide involved in binding an interacting polypeptide, peptidomimetic compounds (e.g. diazepine or isoquinoline derivatives) can be generated which mimic those residues in binding to an interacting polypeptide, and which therefore can inhibit binding of an *S. pneumoniae* polypeptide to an interacting polypeptide and thereby interfere with the function of *S. pneumoniae* polypeptide. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), b-turn dipeptide cores (Nagai et al. (1985) *Tetrahedron Lett* 26:647; and Sato et al. (1986) *J Chem Soc Perkin Trans* 1:1231), and b-aminoalcohols (Gordon et al. (1985) *Biochem Biophys Res Commun* 126:419; and et al. (1986) *Biochem Biophys Res Commun* 134:71).

Vaccine Formulations for *S. pneumoniae* Nucleic Acids and Polypeptides

This invention also features vaccine compositions for protection against infection by *S. pneumoniae* or for treatment of *S. pneumoniae* infection, a gram-negative spiral microaerophilic bacterium. In one embodiment, the vaccine compositions contain one or more immunogenic components such as a surface protein from *S. pneumoniae*, or portion thereof, and a pharmaceutically acceptable carrier. Nucleic acids within the scope of the invention are exemplified by the nucleic acids of the invention contained in the Sequence Listing which encode *S. pneumoniae* surface proteins. Any nucleic acid encoding an immunogenic *S. pneumoniae* protein, or portion thereof, which is capable of expression in a cell, can be used in the present invention. These vaccines have therapeutic and prophylactic utilities.

One aspect of the invention provides a vaccine composition for protection against infection by *S. pneumoniae* which contains at least one immunogenic fragment of an *S. pneumoniae* protein and a pharmaceutically acceptable carrier. Preferred fragments include peptides of at least about 10 amino acid residues in length, preferably about 10–20 amino acid residues in length, and more preferably about 12–16 amino acid residues in length.

Immunogenic components of the invention can be obtained, for example, by screening polypeptides recombinantly produced from the corresponding fragment of the nucleic acid encoding the full-length *S. pneumoniae* protein. In addition, fragments can be chemically synthesized using techniques known in the art such as conventional Merrifield solid phase f-Moc or t-Boc chemistry.

In one embodiment, immunogenic components are identified by the ability of the peptide to stimulate T cells. Peptides which stimulate T cells, as determined by, for example, T cell proliferation or cytokine secretion are defined herein as comprising at least one T cell epitope. T cell epitopes are believed to be involved in initiation and perpetuation of the immune response to the protein allergen which is responsible for the clinical symptoms of allergy. These T cell epitopes are thought to trigger early events at the level of the T helper cell by binding to an appropriate HLA molecule on the surface of an antigen presenting cell, thereby stimulating the T cell subpopulation with the relevant T cell receptor for the epitope. These events lead to T cell proliferation, lymphokine secretion, local inflammatory reactions, recruitment of additional immune cells to the site of antigen/F cell interaction, and activation of the B cell cascade, leading to the production of antibodies. A T cell epitope is the basic element, or smallest unit of recognition by a T cell receptor, where the epitope comprises amino acids essential to receptor recognition (e.g., approximately 6 or 7 amino acid residues). Amino acid sequences which mimic those of the T cell epitopes are within the scope of this invention.

Screening immunogenic components can be accomplished using one or more of several different assays. For example, in vitro, peptide T cell stimulatory activity is assayed by contacting a peptide known or suspected of being immunogenic with an antigen presenting cell which presents appropriate MHC molecules in a T cell culture. Presentation of an immunogenic *S. pneumoniae* peptide in association with appropriate MHC molecules to T cells in conjunction with the necessary co-stimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA*, 86: 1333 (1989) the pertinent portions of which are incorporated herein by reference. A kit for an assay for the production of interferon is also available from Genzyme Corporation (Cambridge, Mass.).

Alternatively, a common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Vaccine compositions of the invention containing immunogenic components (e.g., *S. pneumoniae* polypeptide or fragment thereof or nucleic acid encoding an *S. pneumoniae* polypeptide or fragment thereof) preferably include a pharmaceutically acceptable carrier. The term "pharmaceutically acceptable carrier" refers to a carrier that does not cause an allergic reaction or other untoward effect in patients to whom it is administered. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. For vaccines of the invention containing *S. pneumoniae* polypeptides, the polypeptide is co-administered with a suitable adjuvant.

It will be apparent to those of skill in the art that the therapeutically effective amount of DNA or protein of this invention will depend, inter alia, upon the administration schedule, the unit dose of antibody administered, whether the protein or DNA is administered in combination with other therapeutic agents, the immune status and health of the patient, and the therapeutic activity of the particular protein or DNA.

Vaccine compositions are conventionally administered parenterally, e.g., by injection, either subcutaneously or intramuscularly. Methods for intramuscular immunization are described by Wolff et al. (1990) *Science* 247: 1465–1468 and by Sedegah et al. (1994) *Immunology* 91: 9866–9870. Other modes of administration include oral and pulmonary formulations, suppositories, and transdermal applications. Oral immunization is preferred over parenteral methods for inducing protection against infection by *S. pneumoniae*. Cain et. al. (1 993) *Vaccine* 11:637–642. Oral formulations include such normally employed excipients as, for example, pharmaceutical grades of mannitol, lactose, starch, magnesium stearate, sodium saccharine, cellulose, magnesium carbonate, and the like.

The vaccine compositions of the invention can include an adjuvant, including, but not limited to aluminum hydroxide; N-acetyl-muramyl—L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphos-phoryloxy)-ethylamine (CGP 19835A, referred to a MTP-PE); RIBI, which contains three components from bacteria; monophosphoryl lipid A; trehalose dimycoloate; cell wall skeleton (MPL+TDM+CWS) in a 2% squalene/Tween 80 emulsion; and cholera toxin. Others which may be used are non-toxic derivatives of cholera toxin, including its B subunit, and/or conjugates or genetically engineered fusions of the *S. pneumoniae* polypeptide with cholera toxin or its B subunit, procholeragenoid, fungal polysaccharides, including schizophyllan, muramyl dipeptide, muramyl dipeptide derivatives, phorbol esters, labile toxin of *E. coli*, non-*S. pneumoniae* bacterial lysates, block polymers or saponins.

Other suitable delivery methods include biodegradable microcapsules or immuno-stimulating complexes (ISCOMs), cochleates, or liposomes, genetically engineered attenuated live vectors such as viruses or bacteria, and recombinant (chimeric) virus-like particles, e.g., bluetongue. The amount of adjuvant employed will depend on the type of adjuvant used. For example, when the mucosal adjuvant is cholera toxin, it is suitably used in an amount of 5 mg to 50 mg, for example 10 mg to 35 mg. When used in the form of microcapsules, the amount used will depend on the amount employed in the matrix of the microcapsule to achieve the desired dosage. The determination of this amount is within the skill of a person of ordinary skill in the art.

Carrier systems in humans may include enteric release capsules protecting the antigen from the acidic environment of the stomach, and including *S. pneumoniae* polypeptide in an insoluble form as fusion proteins. Suitable carriers for the vaccines of the invention are enteric coated capsules and polylactide-glycolide microspheres. Suitable diluents are 0.2 N NaHCO3 and/or saline.

Vaccines of the invention can be administered as a primary prophylactic agent in adults or in children, as a secondary prevention, after successful eradication of S. pneumoniae in an infected host, or as a therapeutic agent in the aim to induce an immune response in a susceptible host to prevent infection by S. pneumoniae. The vaccines of the invention are administered in amounts readily determined by persons of ordinary skill in the art. Thus, for adults a suitable dosage will be in the range of 10 mg to 10 g, preferably 10 mg to 100 mg. A suitable dosage for adults will also be in the range of 5 mg to 500 mg. Similar dosage ranges will be applicable for children. Those skilled in the art will recognize that the optimal dose may be more or less depending upon the patient's body weight, disease, the route of administration, and other factors. Those skilled in the art will also recognize that appropriate dosage levels can be obtained based on results with known oral vaccines such as, for example, a vaccine based on an E. coli lysate (6 mg dose daily up to total of 540 mg) and with an enterotoxigenic E. coli purified antigen (4 doses of 1 mg) (Schulman et al., J. Urol. 150:917–921 (1993); Boedecker et al., American Gastroenterological Assoc. 999:A-222 (1993)). The number of doses will depend upon the disease, the formulation, and efficacy data from clinical trials. Without intending any limitation as to the course of treatment, the treatment can be administered over 3 to 8 doses for a primary immunization schedule over 1 month (Boedeker, American Gastroenterological Assoc. 888:A-222 (1993)).

In a preferred embodiment, a vaccine composition of the invention can be based on a killed whole E. coli preparation with an immunogenic fragment of an S. pneumoniae protein of the invention expressed on its surface or it can be based on an E. coli lysate, wherein the killed E. coli acts as a carrier or an adjuvant.

It will be apparent to those skilled in the art that some of the vaccine compositions of the invention are useful only for preventing S. pneumoniae infection, some are useful only for treating S. pneumoniae infection, and some are useful for both preventing and treating S. pneumoniae infection. In a preferred embodiment, the vaccine composition of the invention provides protection against S. pneumoniae infection by stimulating humoral and/or cell-mediated immunity against S. pneumoniae. It should be understood that amelioration of any of the symptoms of S. pneumoniae infection is a desirable clinical goal, including a lessening of the dosage of medication used to treat S. pneumoniae-caused disease, or an increase in the production of antibodies in the serum or mucous of patients.

Antibodies Reactive With S. pneumoniae Polypeptides

The invention also includes antibodies specifically reactive with the subject S. pneumoniae polypeptide. Anti-protein/anti-peptide antisera or monoclonal antibodies can be made by standard protocols (See, for example, Antibodies. A Laboratory Manual ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject S. pneumoniae polypeptide can be administered in the presence of adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of the S. pneumoniae polypeptides of the invention, e.g. antigenic determinants of a polypeptide of the invention contained in the Sequence Listing, or a closely related human or non-human mammalian homolog (e.g., 90% homologous, more preferably at least 95% homologous). In yet a further preferred embodiment of the invention, the anti-S. pneumoniae antibodies do not substantially cross react (i.e., react specifically) with a protein which is for example, less than 80% percent homologous to a sequence of the invention contained in the Sequence Listing. By "not substantially cross react", it is meant that the antibody has a binding affinity for a non-homologous protein which is less than 10 percent, more preferably less than 5 percent, and even more preferably less than 1 percent, of the binding affinity for a protein of the invention contained in the Sequence Listing. In a most preferred embodiment, there is no cross-reactivity between bacterial and mammalian antigens.

The term antibody as used herein is intended to include fragments thereof which are also specifically reactive with S. pneumoniae polypeptides. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the invention is further intended to include bispecific and chimeric molecules having an anti-S. pneumoniae portion.

Both monoclonal and polyclonal antibodies (Ab) directed against S. pneumoniae polypeptides or S. pneumoniae polypeptide variants, and antibody fragments such as Fab' and F(ab')2, can be used to block the action of S. pneumoniae polypeptide and allow the study of the role of a particular S. pneumoniae polypeptide of the invention in aberrant or unwanted intracellular signaling, as well as the normal cellular function of the S. pneumoniae and by microinjection of anti-S. pneumoniae polypeptide antibodies of the present invention.

Antibodies which specifically bind S. pneumoniae epitopes can also be used in immunohistochemical staining of tissue samples in order to evaluate the abundance and pattern of expression of S. pneumoniae antigens. Anti S. pneumoniae polypeptide antibodies can be used diagnostically in immuno-precipitation and immuno-blotting to detect and evaluate S. pneumoniae levels in tissue or bodily fluid as part of a clinical testing procedure. Likewise, the ability to monitor S. pneumoniae polypeptide levels in an individual can allow determination of the efficacy of a given treatment regimen for an individual afflicted with such a disorder. The level of an S. pneumoniae polypeptide can be measured in cells found in bodily fluid, such as in urine samples or can be measured in tissue, such as produced by gastric biopsy. Diagnostic assays using anti-S. pneumoniae antibodies can include, for example, immunoassays designed to aid in early diagnosis of S. pneumoniae infections. The present invention can also be used as a method of detecting antibodies contained in samples from individuals infected by this bacterium using specific S. pneumoniae antigens.

Another application of anti-S. pneumoniae polypeptide antibodies of the invention is in the immunological screening of cDNA libraries constructed in expression vectors such as lgt11, lgt18–23, lZAP, and lORF8. Messenger libraries of this type, having coding sequences inserted in the correct reading frame and orientation, can produce fusion proteins. For instance, lgt11 will produce fusion proteins whose amino termini consist of β-galactosidase amino acid sequences and whose carboxy termini consist of a foreign polypeptide. Antigenic epitopes of a subject *S. pneumoniae* polypeptide can then be detected with antibodies, as, for example, reacting nitrocellulose filters lifted from infected plates with anti-*S. pneumoniae* polypeptide antibodies. Phage, scored by this assay, can then be isolated from the infected plate. Thus, the presence of *S. pneumoniae* gene homologs can be detected and cloned from other species, and alternate isoforms (including splicing variants) can be detected and cloned.

Kits Containing Nucleic Acids, Polypeptides or Antibodies of the Invention

The nucleic acid, polypeptides and antibodies of the invention can be combined with other reagents and articles to form kits. Kits for diagnostic purposes typically comprise the nucleic acid, polypeptides or antibodies in vials or other suitable vessels. Kits typically comprise other reagents for performing hybridization reactions, polymerase chain reactions (PCR), or for reconstitution of lyophilized components, such as aqueous media, salts, buffers, and the like. Kits may also comprise reagents for sample processing such as detergents, chaotropic salts and the like. Kits may also comprise immobilization means such as particles, supports, wells, dipsticks and the like. Kits may also comprise labeling means such as dyes, developing reagents, radioisotopes, fluorescent agents, luminescent or chemiluminescent agents, enzymes, intercalating agents and the like. With the nucleic acid and amino acid sequence information provided herein, individuals skilled in art can readily assemble kits to serve their particular purpose. Kits further can include instructions for use.

Bio Chips and Microarrays

The nucleic acid sequence of the present invention may be used to detect *S. pneumoniae* or other species of Streptococcus acid sequence using bio chip technology. Bio chips containing arrays of nucleic acid sequence can also be used to measure expression of genes of *S. pneumoniae* or other species of Streptococcus. For example, to diagnose a patient with a *S. pneumoniae* or other Streptococcus infection, a sample from a human or animal can be used as a probe on a bio chip containing an array of nucleic acid sequence from the present invention. In addition, a sample from a disease state can be compared to a sample from a non-disease state which would help identify a gene that is up-regulated or expressed in the disease state. This would provide valuable insight as to the mechanism by which the disease manifests. Changes in gene expression can also be used to identify critical pathways involved in drug transport or metabolism, and may enable the identification of novel targets involved in virulence or host cell interactions involved in maintenance of an infection. Procedures using such techniques have been described by Brown et al., 1995, *Science* 270: 467–470.

Bio chips can also be used to monitor the genetic changes of potential therapeutic compounds including, deletions, insertions or mismatches. Once the therapeutic is added to the patient, changes to the genetic sequence can be evaluated for its efficacy. In addition, the nucleic acid sequence of the present invention can be used to determine essential genes in cell cycling. As described in Iyer et al., 1999 (*Science*, 283:83–87) genes essential in the cell cycle can be identified using bio chips. Furthermore, the present invention provides nucleic acid sequence which can be used with bio chip technology to understand regulatory networks in bacteria, measure the response to environmental signals or drugs as in drug screening, and study virulence induction. (Mons et al., 1998, *Nature Biotechnology*, 16: 45–48. Patents teaching this technology include U.S. Pat. Nos. 5,445,934, 5,744,305, and 5,800,992.

Drug Screening Assays Using *S. pneumoniae* Polypeptides

By making available purified and recombinant *S. pneumoniae* polypeptides, the present invention provides assays which can be used to screen for drugs which are either agonists or antagonists of the normal cellular function, in this case, of the subject *S. pneumoniae* polypeptides, or of their role in intracellular signaling. Such inhibitors or potentiators may be useful as new therapeutic agents to combat *S. pneumoniae* infections in humans. A variety of assay formats will suffice and, in light of the present inventions, will be comprehended by the skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or change in enzymatic properties of the molecular target. Accordingly, in an exemplary screening assay of the present invention, the compound of interest is contacted with an isolated and purified *S. pneumoniae* polypeptide.

Screening assays can be constructed in vitro with a purified *S. pneumoniae* polypeptide or fragment thereof, such as an *S. pneumoniae* polypeptide having enzymatic activity, such that the activity of the polypeptide produces a detectable reaction product. The efficacy of the compound can be assessed by generating dose response curves from data obtained using various concentrations of the test compound. Moreover, a control assay can also be performed to provide a baseline for comparison. Suitable products include those with distinctive absorption, fluorescence, or chemiluminescence properties, for example, because detection may be easily automated. A variety of synthetic or naturally occurring compounds can be tested in the assay to identify those which inhibit or potentiate the activity of the *S. pneumoniae* polypeptide. Some of these active compounds may directly, or with chemical alterations to promote membrane permeability or solubility, also inhibit or potentiate the same activity (e.g., enzymatic activity) in whole, live *S. pneumoniae* cells.

Overexpression Assays

Overexpression assays are based on the premise that overproduction of a protein would lead to a higher level of resistance to compounds that selectively interfere with the function of that protein. Overexpression assays may be used to identify compounds that interfere with the function of virtually any type of protein, including without limitation enzymes, receptors, DNA- or RNA-binding proteins, or any proteins that are directly or indirectly involved in regulating cell growth.

Typically, two bacterial strains are constructed. One contains a single copy of the gene of interest, and a second contains several copies of the same gene. Identification of useful inhibitory compounds of this type of assay is based on a comparison of the activity of a test compound in inhibiting growth and/or viability of the two strains. The method involves constructing a nucleic acid vector that directs high level expression of a particular target nucleic acid. The vectors are then transformed into host cells in single or multiple copies to produce strains that express low to moderate and high levels of protein encoding by the target sequence (strain A and B, respectively). Nucleic acid comprising sequences encoding the target gene can, of course, be directly integrated into the host cell.

Large numbers of compounds (or crude substances which may contain active compounds) are screened for their effect on the growth of the two strains. Agents which interfere with an unrelated target equally inhibit the growth of both strains. Agents which interfere with the function of the target at high concentration should inhibit the growth of both strains. It should be possible, however, to titrate out the inhibitory effect of the compound in the overexpressing strain. That is, if the compound is affecting the particular target that is being tested, it should be possible to inhibit the growth of strain A at a concentration of the compound that allows strain B to grow.

Alternatively, a bacterial strain is constructed that contains the gene of interest under the control of an inducible promoter. Identification of useful inhibitory agents using this type of assay is based on a comparison of the activity of a test compound in inhibiting growth and/or viability of this strain under both inducing and non-inducing conditions. The method involves constructing a nucleic acid vector that directs high-level expression of a particular target nucleic acid. The vector is then transformed into host cells that are grown under both non-inducing and inducing conditions (conditions A and B, respectively).

Large numbers of compounds (or crude substances which may contain active compounds) are screened for their effect on growth under these two conditions. Agents that interfere with the function of the target should inhibit growth under both conditions. It should be possible, however, to titrate out the inhibitory effect of the compound in the overexpressing strain. That is, if the compound is affecting the particular target that is being tested, it should be possible to inhibit growth under condition A at a concentration that allows the strain to grow under condition B.

Ligand-binding Assays

Many of the targets according to the invention have functions that have not yet been identified. Ligand-binding assays are useful to identify inhibitor compounds that interfere with the function of a particular target, even when that function is unknown. These assays are designed to detect binding of test compounds to particular targets. The detection may involve direct measurement of binding. Alternatively, indirect indications of binding may involve stabilization of protein structure or disruption of a biological function. Non-limiting examples of useful ligand-binding assays are detailed below.

A useful method for the detection and isolation of binding proteins is the Biomolecular Interaction Assay (BIAcore) system developed by Pharmacia Biosensor and described in the manufacturer's protocol (LKB Phannacia, Sweden). The BIAcore system uses an affinity purified anti-GST antibody to immobilize GST-fusion proteins onto a sensor chip. The sensor utilizes surface plasmon resonance which is an optical phenomenon that detects changes in refractive indices. In accordance with the practice of the invention, a protein of interest is coated onto a chip and test compounds are passed over the chip. Binding is detected by a change in the refractive index (surface plasmon resonance).

A different type of ligand-binding assay involves scintillation proximity assays (SPA, described in U.S. Pat. No. 4,568,649).

Another type of ligand binding assay, also undergoing development, is based on the fact that proteins containing mitochondrial targeting signals are imported into isolated mitochondria in vitro (Hurt et al., 1985, Embo J. 4:2061–2068; Eilers and Schatz, Nature, 1986, 322:228–231). In a mitochondrial import assay, expression vectors are constructed in which nucleic acids encoding particular target proteins are inserted downstream of sequences encoding mitochondrial import signals. The chimeric proteins are synthesized and tested for their ability to be imported into isolated mitochondria in the absence and presence of test compounds. A test compound that binds to the target protein should inhibit its uptake into isolated mitochondria in vitro.

Another ligand-binding assay is the yeast two-hybrid system (Fields and Song, 1989, Nature 340:245–246). The yeast two-hybrid system takes advantage of the properties of the GAL4 protein of the yeast Saccharomyces cerevisiae. The GAL4 protein is a transcriptional activator required for the expression of genes encoding. enzymes of galactose utilization. This protein consists of two separable and functionally essential domains: an N-terminal domain which binds to specific DNA sequences ($UAS_G$); and a C-terminal domain containing acidic regions, which is necessary to activate transcription. The native GAL4 protein, containing both domains, is a potent activator of transcription when yeast are grown on galactose media. The N-terminal domain binds to DNA in a sequence-specific manner but is unable to activate transcription. The C-terminal domain contains the activating regions but cannot activate transcription because it fails to be localized to $UAS_G$. In the two-hybrid system, a system of two hybrid proteins containing parts of GAL4: (1) a GAL4 DNA-binding domain fused to a protein 'X' and (2) a GAL4 activation region fused to a protein 'Y'. If X and Y can form a protein-protein complex and reconstitute proximity of the GAL4 domains, transcription of a gene regulated by $UAS_G$ occurs. Creation of two hybrid proteins, each containing one of the interacting proteins X and Y, allows the activation region of $UAS_G$ to be brought to its normal site of action.

The binding assay described in Fodor et al., 1991, Science 251:767–773, which involves testing the binding affinity of test compounds for a plurality of defined polymers synthesized on a solid substrate, may also be useful.

Compounds which bind to the polypeptides of the invention are potentially useful as antibacterial agents for use in therapeutic compositions.

Pharmaceutical formulations suitable for antibacterial therapy comprise the antibacterial agent in conjunction with one or more biologically acceptable carriers. Suitable biologically acceptable carriers include, but are not limited to, phosphate-buffered saline, saline, deionized water, or the like. Preferred biologically acceptable carriers are physiologically or pharmaceutically acceptable carriers.

The antibacterial compositions include an antibacterial effective amount of active agent. Antibacterial effective amounts are those quantities of the antibacterial agents of the present invention that afford prophylactic protection against bacterial infections or which result in amelioration or cure of an existing bacterial infection. This antibacterial effective amount will depend on the agent, the location and nature of the infection, and the particular host. The amount can be determined by experimentation known in the art, such as by establishing a matrix of dosages and frequencies and comparing a group of experimental units or subjects to each point in the matrix.

The antibacterial active agents or compositions can be formed into dosage unit forms, such as for example, creams, ointments, lotions, powders, liquids, tablets, capsules, suppositories, sprays, aerosols or the like. If the antibacterial composition is formulated into a dosage unit form, the dosage unit form may contain an antibacterial effective amount of active agent. Alternatively, the dosage unit form may include less than such an amount if multiple dosage unit forms or multiple dosages are to be used to administer a total dosage of the active agent. Dosage unit forms can include, in addition, one or more excipient(s), diluent(s), disintegrant(s), lubricant(s), plasticizer(s), colorant(s), dosage vehicle(s), absorption enhancer(s), stabilizer(s), bactericide(s), or the like.

For general information concerning formulations, see, e.g., Gilman et al. (eds.), 1990, *Goodman and Gilman's: The Pharmacological Basis of Therapeutics*, 8th ed., Pergamon Press; and *Remington's Pharmaceutical Sciences*, 17th ed., 1990, Mack Publishing Co., Easton, Pa.; Avis et al. (eds.), 1993, *Pharmaceutical Dosage Forms: Parenteral Medications*, Dekker, New York; Lieberman et al (eds.), 1990, *Pharmaceutical Dosage Forms: Disperse Systems*, Dekker, New York.

The antibacterial agents and compositions of the present invention are useful for preventing or treating *S. pneumoniae* infections. Infection prevention methods incorporate a prophylactically effective amount of an antibacterial agent or composition. A prophylactically effective amount is an amount effective to prevent *S. pneumoniae* infection and will depend upon the specific bacterial strain, the agent, and the host. These amounts can be determined experimentally by methods known in the art and as described above.

*S. pneumoniae* infection treatment methods incorporate a therapeutically effective amount of an antibacterial agent or composition. A therapeutically effective amount is an amount sufficient to ameliorate or eliminate the infection. The prophylactically and/or therapeutically effective amounts can be administered in one administration or over repeated administrations. Therapeutic administration can be followed by prophylactic administration, once the initial bacterial infection has been resolved.

The antibacterial agents and compositions can be administered topically or systemically. Topical application is typically achieved by administration of creams, ointments, lotions, or sprays as described above. Systemic administration includes both oral and parental routes. Parental routes include, without limitation, subcutaneous, intramuscular, intraperitoneal, intravenous, transdermal, inhalation and intranasal administration.

EXEMPLIFICATION

I. Cloning and Sequencing of *S. pneumoniae* DNA

*S. pneumoniae* chromosomal DNA was isolated according to a basic DNA protocol outlined in Schleif R. F. and Wensink P. C., Practical Methods in Molecular Biology, p.98, Springer-Verlag, NY., 1981, with minor modifications. Briefly, cells were pelleted, resuspended in TE (10 mM Tris, 1 mM EDTA, pH 7.6) and GES lysis buffer (5.1 M guanidium thiocyanate, 0.1 M EDTA, pH 8.0, 0.5% N-laurylsarcosine) was added. Suspension was chilled and ammonium acetate (NH4Ac) was added to final concentration of 2.0 M. DNA was extracted, first with chloroform, then with phenol-chloroform, and reextracted with chloroform. DNA was precipitated with isopropanol, washed twice with 70% EtOH, dried and resuspended in TE.

Following isolation whole genomic *S. pneumoniae* DNA was nebulized (Bodenteich et al., Automated DNA Sequencing and Analysis (J. C. Venter, ed.), Academic Press, 1994) to a median size of 2000 bp. After nebulization, the DNA was concentrated and separated on a standard 1% agarose gel. Several fractions, corresponding to approximate sizes 1000–1500 bp, 1500–2000 bp, 2000–2500 bp, 2500–3000 bp, were excised from the gel and purified by the GeneClean procedure (Bio101, Inc.).

The purified DNA fragments were then blunt-ended using T4 DNA polymerase. The healed DNA was then ligated to unique BstXI-linker adapters (5' GTCTTCACCACGGGG and 5' GTGGTGAAGAC in 100–1000 fold molar excess). These linkers are complimentary to the BstXI-cut pMPX vectors, while the overhang is not self-complimentary. Therefore, the linkers will not concatemerize nor will the cut-vector religate itself easily. The linker-adopted inserts were separated from the unincorporated linkers on a 1% agarose gel and purified using GeneClean. The linker-adopted inserts were then ligated to each of 20 pMPX vectors to construct a series of "shotgun" subclone libraries. Blunt ended vector was used for cloning into the PUC19 vector. The vectors contain an out-of-frame lacZ gene at the cloning site which becomes in-frame in the event that an adapter-dimer is cloned, allowing these to be avoided by their blue-color.

All subsequent steps were based either on the multiplex DNA sequencing protocols outlined in Church G. M. and Kieffer-Higgins S., Science 240:185–188, 1988 or by ABI377 automated DNA sequencing methods. Only major modifications to the protocols are highlighted. Briefly, each of the 20 vectors was then transformed into DH5a competent cells (Gibco/BRL, DH5a transformation protocol). The libraries were assessed by plating onto antibiotic plates containing ampicillin, methicillin and IPTG/Xgal. The plates were incubated overnight at 37° C. Successful transformants were then used for plating of clones and pooling into the multiplex pools. The clones were picked and pooled into 40 ml growth medium cultures. The cultures were grown overnight at 37° C. DNA was purified using the Qiagen Midi-prep kits and Tip-100 columns (Qiagen, Inc.). In this manner, 100 mg of DNA was obtained per pool.

These purified DNA samples were then sequenced either using the multiplex DNA sequencing based on chemical degradation methods (Church G. M. and Kieffer-Higgins S., Science 240:185–188, 1988) or by Sequithrem (Epicenter Technologies) dideoxy sequencing protocols or by ABI dye-terminator chemistry. For the multiplex portion the sequencing reactions were electrophoresed and transferred onto nylon membranes by direct transfer electrophoresis from 40 cm gels (Richterich P. and Church G. M., Methods in Enzymology 218:187–222, 1993). The DNA was covalently bound to the membranes by exposure to ultraviolet light, and hybridized with labeled oligonucleotides complimentary to tag sequences on the vectors (Church, supra). The membranes were washed to rinse off nonspecifically bound probe, and exposed to X-ray film to visualize individual sequence ladders. After autoradiography, the hybridized probe was removed by incubation at 65° C., and the hybridization cycle repeated with another tag sequence until the membrane had been probed 41 times. Thus, each gel produced a large number of films, each containing new sequencing information. Whenever a new blot was processed, it was initially probed for an internal standard sequence added to each of the pools. Digital images of the films were generated using a laser-scanning densitometer (Molecular Dynamics, Sunnyvale, Calif.). The digitized images were processed on computer workstations (VaxStation 4000's) using the program REPLICA™ (Church et al., Automated DNA Sequencing and Analysis (J. C. Venter, ed.), Academic Press, 1994). Image processing included lane straightening, contrast adjustment to smooth out intensity differences, and resolution enhancement by iterative gaussian deconvolution. The sequences were then converted to an SCF format so that processing and assembly could proceed on UNIX machines. The ABI dye terminator sequence reads were run on ABI377 machines and the data was directly transferred to UNIX machinnes following lane tracking of the gels. All multiplex and ABI reads were assembled using PHRAP (P. Green, Abstracts of DOE Human Genome Program Contractor-Grantee Workshop V, Jan. 1996, p. 157) with default parameters and not using quality scores. The initial assembly was done at 7fold coverage and yielded 511 contigs. Short read length fragments of 200 bp or less found on the ends of contigs facing in the appropriate direction were used to extendoff the end of the contigs. These reads were then resequenced with primers using ABI technology to give sequences with a read length of 500 or more bases. This allowed end extensions to be performed without ordering new primers. In addition, missing mates (sequences from clones that only gave one strand reads) were identified and sequenced with ABI technology to allow the identification of additional overlapping contigs.

End-sequencing of randomly picked genomic lambda was also performed. Sequencing on a both sides was done for all lambda sequences. The lambdalibrary backbone helped to verify the integrity of the assembly and allowed closure of some of the physical gaps.

To identify S. pneumoniae polypeptides the complete genomic sequence of S. pneumoniae were analyzed essentially as follows: First, all possible stop-to-stop open reading frames (ORFs) greater than 180 nucleotides in all six reading frames were translated into amino acid sequences. Second, the identified ORFs were analyzed for homology to known (archeabacter, prokaryotic and eukaryotic) protein sequences. Third, the predicted coding regions of the sequences and start codons were evaluated with the programs GENEMARK™ (Borodovsky and McIninch, 1993, Comp. Chem. 17:123) and Glimmer (Fraser et al, Nature, 1997).

Identification, Cloning and Expression of S. pneumoniae Nucleic Acids

Expression and purification of the S. pneumoniae polypeptides of the invention can be performed essentially as outlined below.

To facilitate the cloning, expression and purification of membrane and secreted proteins from S. pneumoniae, a gene expression system, such as the pET System (Novagen), for cloning and expression of recombinant proteins in E. coli, is selected. Also, a DNA sequence encoding a peptide tag, the His-Tag, is fused to the 3' end of DNA sequences of interest in order to facilitate purification of the recombinant protein products. The 3' end is selected for fusion in order to avoid alteration of any 5' terminal signal sequence.

PCR Amplification and Cloning of Nucleic Acids Containing ORF's Encoding Enzymes Nucleic acids chosen (for example, from the nucleic acids set forth in SEQ ID NO: 1–SEQ ID NO: 2661 ) for cloning from the 14453 strain of S. pneumoniae are prepared for amplification cloning by polymerase chain reaction (PCR). Synthetic oligonucleotide primers specific for the 5' and 3' ends of open reading frames (ORFs) are designed and purchased from GibcoBRL Life Technologies (Gaithersburg, Md., USA). All forward primers (specific for the 5' end of the sequence) are designed to include an NcoI cloning site at the extreme 5' terminus. These primers are designed to permit initiation of protein translation at a methionine residue followed by a valine residue and the coding sequence for the remainder of the native S. pneumoniae DNA sequence. All reverse primers (specific for the 3' end of any S. pneumoniae ORF.) include a EcoRI site at the extreme 5' terminus to permit cloning of each S. pneumoniae sequence into the reading frame of the pET-28b. The pET-28b vector provides sequence encoding an additional 20 carboxy-terminal amino acids including six histidine residues (at the extreme C-terminus), which comprise the His-Tag.

Genomic DNA prepared from strain 14453 of S. pneumoniae is used as the source of template DNA for PCR amplification reactions (Current Protocols in Molecular Biology, John Wiley and Sons, Inc., F. Ausubel et al., eds., 1994). To amplify a DNA sequence containing an S. pneumoniae ORF, genomic DNA (50 nanograms) is introduced into a reaction vial containing 2 mM $MgCl_2$, 1 micromolar synthetic oligonucleotide primers (forward and reverse primers) complementary to and flanking a defined S. pneumoniae ORF, 0.2 mM of each deoxynucleotide triphosphate; dATP, dGTP, dCTP, dTTP and 2.5 units of heat stable DNA polymerase (Amplitaq, Roche Molecular Systems, Inc., Branchburg, N.J., USA) in a final volume of 100 microliters.

Upon completion of thermal cycling reactions, each sample of amplified DNA is washed and purified using the Qiaquick Spin PCR purification kit (Qiagen, Gaithersburg, Md., USA). All amplified DNA samples are subjected to digestion with the restriction endonucleases, e.g., NcoI and EcoRI (New England BioLabs, Beverly, Mass., USA) (Current Protocols in Molecular Biology, John Wiley and Sons, Inc., F. Ausubel et al., eds., 1994). DNA samples are then subjected to electrophoresis on 1.0 % NuSieve (FMC BioProducts, Rockland, Me. USA) agarose gels. DNA is visualized by exposure to ethidium bromide and long wave uv irradiation. DNA contained in slices isolated from the agarose gel is purified using the Bio 101 GeneClean Kit protocol (Bio 101 Vista, Calif., USA).

Cloning of S. pneumoniae Nucleic Acids Into an Expression Vector

The pET-28b vector is prepared for cloning by digestion with endonucleases, e.g., NcoI and EcoRI (Current Protocols in Molecular Biology, John Wiley and Sons, Inc., F. Ausubel et al., eds., 1994). The pET-28a vector, which encodes a His-Tag that can be fused to the 5' end of an inserted gene, is prepared by digestion with appropriate restriction endonucleases.

Following digestion, DNA inserts are cloned (Current Protocols in Molecular Biology, John Wiley and Sons, Inc., F. Ausubel et al., eds., 1994) into the previously digested pET-28b expression vector. Products of the ligation reaction are then used to transform the BL21 strain of *E. coli* (Current Protocols in Molecular Biology, John Wiley and Sons, Inc., F. Ausubel et al., eds., 1994) as described below.

Transformation of Competent Bacteria With Recombinant Plasmids

Competent bacteria, *E. coli* strain BL21 or *E. coli* strain BL21(DE3), are transformed with recombinant pET expression plasmids carrying the cloned *S. pneumoniae* sequences according to standard methods (Current Protocols in Molecular, John Wiley and Sons, Inc., F. Ausubel et al., eds., 1994). Briefly, 1 microliter of ligation reaction is mixed with 50 microliters of electrocompetent cells and subjected to a high voltage pulse, after which, samples are incubated in 0.45 milliliters SOC medium (0.5% yeast extract, 2.0 % tryptone, 10 mM NaCl, 2.5 mM KCl, 10 mM MgCl2, 10 mM MgSO4 and 20, mM glucose) at 37° C. with shaking for 1 hour. Samples are then spread on LB agar plates containing 25 microgram/ml kanamycin sulfate for growth overnight. Transformed colonies of BL21 are then picked and analyzed to evaluate cloned inserts as described below.

Identification of Recombinant Expression Vectors With *S. pneumoniae* Nucleic Acids Individual BL21 clones transformed with recombinant pET-28b *S. pneumoniae* ORFs are analyzed by PCR amplification of the cloned inserts using the same forward and reverse primers, specific for each *S. pneumoniae* sequence, that were used in the original PCR amplification cloning reactions. Successful amplification verifies the integration of the *S. pneumoniae* sequences in the expression vector (Current Protocols in Molecular Biology, John Wiley and Sons, Inc., F. Ausubel et al., eds., 1994).

Isolation and Preparation of Nucleic Acids From Transformants

Individual clones of recombinant pET-28b vectors carrying properly cloned *S. pneumoniae* ORFs are picked and incubated in 5 mls of LB broth plus 25 microgram/ml kanamycin sulfate overnight. The following day plasmid DNA is isolated and purified using the Qiagen plasmid purification protocol (Qiagen Inc., Chatsworth, Calif., USA).

Expression of Recombinant *S. pneumoniae* Sequences in *E. coli*

The pET vector can be propagated in any *E. coli* K-12 strain e.g. HMS174, HB101, JM 109, DH5, etc. for the purpose of cloning or plasmid preparation. Hosts for expression include *E. coli* strains containing a chromosomal copy of the gene for T7 RNA polymerase. These hosts are lysogens of bacteriophage DE3, a lambda derivative that carries the lacI gene, the lacUV5 promoter and the gene for T7 RNA polymerase. T7 RNA polymerase is induced by addition of isopropyl-B-D-thiogalactoside (IPTG), and the T7 RNA polymerase transcribes any target plasmid, such as pET-28b, carrying its gene of interest. Strains used include: BL21(DE3) (Studier, F. W., Rosenberg, A. H., Dunn, J. J., and Dubendorff, J. W. (1990) Meth. Enzymol. 185, 60–89).

To express recombinant *S. pneumoniae* sequences, 50 nanograms of plasmid DNA isolated as described above is used to transform competent BL21(DE3) bacteria as described above (provided by Novagen as part of the pET expression system kit). The lacZ gene (beta-galactosidase) is expressed in the pET-System as described for the *S. pneumoniae* recombinant constructions. Transformed cells are cultured in SOC medium for 1 hour, and the culture is then plated on LB plates containing 25 micrograms/ml kanamycin sulfate. The following day, bacterial colonies are pooled and grown in LB medium containing kanamycin sulfate (25 micrograms/ml) to an optical density at 600 nM of 0.5 to 1.0 O.D. units, at which point, 1 millimolar IPTG was added to the culture for 3 hours to induce gene expression of the *S. pneumoniae* recombinant DNA constructions.

After induction of gene expression with IPTG, bacteria are pelleted by centrifugation in a Sorvall RC-3B centrifuge at 3500×g for 15 minutes at 4° C. Pellets are resuspended in 50 milliliters of cold 10 mM Tris-HCl, pH 8.0, 0.1 M NaCl and 0.1 mM EDTA (STE buffer). Cells are then centrifuged at 2000×g for 20 min at 4° C. Wet pellets are weighed and frozen at −80° C. until ready for protein purification.

A variety of methodologies known in the art can be utilized to purify the isolated proteins. (Current Protocols in Protein Science, John Wiley and Sons, Inc., J. E. Coligan et al., eds., 1995). For example, the frozen cells may be thawed, resupended in buffer and ruptured by several passages through a small volume microfluidizer (Model M-110S, Microfluidics International Corporation, Newton, Mass.). The resultant homogenate may be centrifuged to yield a clear supernatant (crude extract) and following filtration the crude extract may be fractionated over columns. Fractions may be monitored by absorbance at $OD_{280}$ nm. and peak fractions may analyzed by SDS-PAGE The concentrations of purified protein preparations may be quantified spectrophotometrically using absorbance coefficients calculated from amino acid content (Perkins, S. J. 1986 Eur. J. Biochem. 157, 169–180). Protein concentrations are also measured by the method of Bradford, M. M. (1976) Anal. Biochem. 72,.248–254, and Lowry, O. H., Rosebrough, N., Farr, A. L. & Randall, R. J. (1951) J. Biol. Chem. 193, pages 265–275, using bovine serum albumin as a standard.

SDS-polyacrylamide gels of various concentrations may be purchased from BioRad (Hercules, Calif., USA), and stained with Coomassie blue. Molecular weight markers may include rabbit skeletal muscle myosin (200 kDa), *E. coli* (-galactosidase (116 kDa), rabbit muscle phosphorylase B (97.4 kDa), bovine serum albumin (66.2 kDa), ovalbumin (45 kDa), bovine carbonic anhydrase (31 kDa), soybean trypsin inhibitor (21.5 kDa), egg white lysozyme (14.4 kDa) and bovine aprotinin (6.5 kDa).

EQUIVALENTS

Those skilled in the art will recognize, or be able to ascertain using no more than routine experimentation, many equivalents to the specific embodiments and methods described herein. The specific embodiments described herein are offered by way of example only , and the invention is to limited only by the terms of the appended claims, along with the full scope of equivalents to which such claims are entitled.

TABLE 2

| ORF Name | NT ID | AA ID | NT/LN | AA/LN | Score | P-Value |
|---|---|---|---|---|---|---|
| SPX0001 | 1 | 2662 | 333 | 111 | 552 | 2.20E-74 |

Description

[GI:2804700] [LN:AF030361] [AC:AF030361] [PN:transposase] [OR:Streptococcus pneumoniae]

| ORF Name | NT ID | AA ID | NT/LN | AA/LN | Score | P-Value |
|---|---|---|---|---|---|---|
| SPX0002 | 2 | 2663 | 519 | 173 | 885 | 3.60E-120 |

Description

[GI:663278] [LN:STRCOMAA] [AC:M36180:L15190] [PN:transposase] [OR:Streptococcus pneumoniae] [SR:Streptococcus pneumoniae (strain RX1) DNA]

| ORF Name | NT ID | AA ID | NT/LN | AA/LN | Score | P-Value |
|---|---|---|---|---|---|---|
| SPX0003 | 3 | 2664 | 327 | 109 | 281 | 1.40E-34 |

Description

[GI:2804700] [LN:AF030361] [AC:AF030361] [PN:transposase] [OR:Streptococcus pneumoniae]

| ORF Name | NT ID | AA ID | NT/LN | AA/LN | Score | P-Value |
|---|---|---|---|---|---|---|
| SPX0004 | 4 | 2665 | 570 | 190 | 948 | 7.40E-131 |

Description

[GI:663279] [LN:STRCOMAA] [AC:M36180:L15190] [PN:transposase] [OR:Streptococcus pneumoniae] [SR:Streptococcus pneumoniae (strain RX1) DNA]

| ORF Name | NT ID | AA ID | NT/LN | AA/LN | Score | P-Value |
|---|---|---|---|---|---|---|
| SPX0005 | 5 | 2666 | 366 | 122 | | |

Description

NO-HIT

| ORF Name | NT ID | AA ID | NT/LN | AA/LN | Score | P-Value |
|---|---|---|---|---|---|---|
| SPX0006 | 6 | 2667 | 1203 | 401 | 815 | 7.40E-125 |

Description

[LN:RS1_LEULA] [AC:P50889:P71450] [GN:RPS1] [OR:Leuconostoc lactis] [DE:40S RIBOSOMAL PROTEIN S1] [SP:P50889:P71450]

| ORF Name | NT ID | AA ID | NT/LN | AA/LN | Score | P-Value |
|---|---|---|---|---|---|---|
| SPX0007 | 7 | 2668 | 237 | 79 | 89 | 2.90E-05 |

Description

[LN:E64801] [AC:E64801] [PN:hypothetical protein b0663] [OR:Escherichia coli]

| ORF Name | NT ID | AA ID | NT/LN | AA/LN | Score | P-Value |
|---|---|---|---|---|---|---|
| SPX0008 | 8 | 2669 | 231 | 77 | | |

Description

NO-HIT

| ORF Name | NT ID | AA ID | NT/LN | AA/LN | Score | P-Value |
|---|---|---|---|---|---|---|
| SPX0009 | 9 | 2670 | 645 | 215 | 832 | 6.30E-114 |

Description

[LN:PCP_STRPY] [AC:Q01328] [GN:PCP] [OR:Streptococcus pyogenes] [EC:3.4.19.3] [DE:PEPTIDASE) (PYROGLUTAMYL-PEPTIDASE I) (PGP-I) (PYRASE)] [SP:Q01328]

| ORF Name | NT ID | AA ID | NT/LN | AA/LN | Score | P-Value |
|---|---|---|---|---|---|---|
| SPX0010 | 10 | 2671 | 924 | 308 | 234 | 3.90E-61 |

Description

[LN:A81402] [AC:A81402] [PN:probable integral membrane protein Cj0553 [imported]] [GN:Cj0553] [OR:Campylobacter jejuni]

| ORF Name | NT ID | AA ID | NT/LN | AA/LN | Score | P-Value |
|---|---|---|---|---|---|---|
| SPX0011 | 11 | 2672 | 711 | 237 | 208 | 1.30E-37 |

Description

[GI:6002226] [LN:SC51A] [AC:AL121596] [PN:possible integral membrane protein] [GN:SCF51A.18c] [OR:Streptomyces coelicolor A3(2)]

| ORF Name | NT ID | AA ID | NT/LN | AA/LN | Score | P-Value |
|---|---|---|---|---|---|---|
| SPX0012 | 12 | 2673 | 705 | 235 | 213 | 1.30E-53 |

Description

[GI:2804687] [LN:AF030359] [AC:AF030359] [PN:oligopeptide binding protein] [GN:aliA] [OR:Streptococcus pneumoniae]

| ORF Name | NT ID | AA ID | NT/LN | AA/LN | Score | P-Value |
|---|---|---|---|---|---|---|
| SPX0013 | 13 | 2674 | 1023 | 341 | 1359 | 9.60E-184 |
| Description | | | | | | |

[GI:6979306] [LN:AF164204] [AC:AF164204] [PN:branched-chain amino acid aminotransferase] [GN:bcaT] [FN:catalyzes the first reaction in the catabolism] [OR:Lactococcus lactis subsp. cremoris]

| ORF Name | NT ID | AA ID | NT/LN | AA/LN | Score | P-Value |
|---|---|---|---|---|---|---|
| SPX0014 | 14 | 2675 | 2472 | 824 | 4143 | 0 |
| Description | | | | | | |

[GI:6851038] [LN:SPPARCETP] [AC:Z67739] [PN:DNA topoisomerase IV] [GN:parC] [OR:Streptococcus pneumoniae]

| ORF Name | NT ID | AA ID | NT/LN | AA/LN | Score | P-Value |
|---|---|---|---|---|---|---|
| SPX0015 | 15 | 2676 | 1944 | 648 | 3318 | 0 |
| Description | | | | | | |

[GI:6851037] [LN:SPPARCETP] [AC:Z67739] [PN:DNA topoisomerase IV] [GN:parE] [OR:Streptococcus pneumoniae]

| ORF Name | NT ID | AA ID | NT/LN | AA/LN | Score | P-Value |
|---|---|---|---|---|---|---|
| SPX0016 | 16 | 2677 | 642 | 214 | 1073 | 2.50E-150 |
| Description | | | | | | |

[LN:YPAE_STRPN] [AC:Q54916] [OR:Streptococcus pneumoniae] [DE:HYPOTHETICAL 23.0 KD PROTEIN IN PARE 5'REGION (ORF2)] [SP:Q54916]

| ORF Name | NT ID | AA ID | NT/LN | AA/LN | Score | P-Value |
|---|---|---|---|---|---|---|
| SPX0017 | 17 | 2678 | 1230 | 410 | 1044 | 8.20E-270 |
| Description | | | | | | |

[GI:2804700] [LN:AF030361] [AC:AF030361] [PN:transposase] [OR:Streptococcus pneumoniae]

| ORF Name | NT ID | AA ID | NT/LN | AA/LN | Score | P-Value |
|---|---|---|---|---|---|---|
| SPX0018 | 18 | 2679 | 834 | 278 | 591 | 9.50E-139 |
| Description | | | | | | |

[LN:A33595] [AC:A33595:A30868] [PN:probable transposase] [CL:transposase IS3] [OR:Streptococcus agalactiae]

| ORF Name | NT ID | AA ID | NT/LN | AA/LN | Score | P-Value |
|---|---|---|---|---|---|---|
| SPX0019 | 19 | 2680 | 573 | 191 | 422 | 2.30E-53 |

Description

[LN:B30868] [AC:B30868] [PN:hypothetical protein 1] [OR:Streptococcus agalactiae]

| ORF Name | NT ID | AA ID | NT/LN | AA/LN | Score | P-Value |
|---|---|---|---|---|---|---|
| SPX0020 | 20 | 2681 | 102 | 34 | 124 | 5.30E-12 |

Description

[LN:B30868] [AC:B30868] [PN:hypothetical protein 1] [OR:Streptococcus agalactiae]

| ORF Name | NT ID | AA ID | NT/LN | AA/LN | Score | P-Value |
|---|---|---|---|---|---|---|
| SPX0021 | 21 | 2682 | 957 | 319 | 1002 | 3.80E-138 |

Description

[LN:F70009] [AC:F70009] [PN:conserved hypothetical protein yufQ] [GN:yufQ] [CL:probable ribose ABC transporter rbsC-2] [OR:Bacillus subtilis]

| ORF Name | NT ID | AA ID | NT/LN | AA/LN | Score | P-Value |
|---|---|---|---|---|---|---|
| SPX0022 | 22 | 2683 | 1086 | 362 | 385 | 3.70E-85 |

Description

[LN:E70009] [AC:E70009] [PN:conserved hypothetical protein yufP] [GN:yufP] [OR:Bacillus subtilis]

| ORF Name | NT ID | AA ID | NT/LN | AA/LN | Score | P-Value |
|---|---|---|---|---|---|---|
| SPX0023 | 23 | 2684 | 1536 | 512 | 1623 | 2.30E-217 |

Description

[LN:D70009] [AC:D70009] [PN:probable ABC transporter yufO] [GN:yufO] [CL:Bacillus subtilis probable ABC transporter yufO:ATP-binding cassette homology] [OR:Bacillus subtilis]

| ORF Name | NT ID | AA ID | NT/LN | AA/LN | Score | P-Value |
|---|---|---|---|---|---|---|
| SPX0024 | 24 | 2685 | 420 | 140 | 83 | 1.80E-06 |

Description

[LN:G72493] [AC:G72493] [PN:hypothetical protein APE2590] [GN:APE2590] [OR:Aeropyrum pernix]

| ORF Name | NT ID | AA ID | NT/LN | AA/LN | Score | P-Value |
|---|---|---|---|---|---|---|
| SPX0025 | 25 | 2686 | 1092 | 364 | 354 | 8.80E-82 |
| Description | | | | | | |

[LN:YUFN_BACSU] [AC:O05252] [GN:YUFN] [OR:Bacillus subtilis]
[DE:HYPOTHETICAL LIPOPROTEIN YUFN PRECURSOR] [SP:O05252]

| ORF Name | NT ID | AA ID | NT/LN | AA/LN | Score | P-Value |
|---|---|---|---|---|---|---|
| SPX0026 | 26 | 2687 | 390 | 130 | 324 | 5.40E-40 |
| Description | | | | | | |

[GI:6478520] [LN:AF187304] [AC:AF187304] [PN:cytidine deaminase] [GN:cdd]
[OR:Bacillus caldolyticus]

| ORF Name | NT ID | AA ID | NT/LN | AA/LN | Score | P-Value |
|---|---|---|---|---|---|---|
| SPX0027 | 27 | 2688 | 300 | 100 | 276 | 2.40E-33 |
| Description | | | | | | |

[LN:D75424] [AC:D75424] [PN:deoxyribose-phosphate aldolase] [GN:DR1205]
[CL:deoxyribose-phosphate aldolase] [OR:Deinococcus radiodurans]

| ORF Name | NT ID | AA ID | NT/LN | AA/LN | Score | P-Value |
|---|---|---|---|---|---|---|
| SPX0028 | 28 | 2689 | 183 | 61 | | |
| Description | | | | | | |

NO-HIT

| ORF Name | NT ID | AA ID | NT/LN | AA/LN | Score | P-Value |
|---|---|---|---|---|---|---|
| SPX0029 | 29 | 2690 | 357 | 119 | 344 | 3.30E-42 |
| Description | | | | | | |

[LN:DEOC_BACSU] [AC:P39121] [GN:DRA] [OR:Bacillus subtilis] [EC:4.1.2.4]
[DE:(DEOXYRIBOALDOLASE)] [SP:P39121]

| ORF Name | NT ID | AA ID | NT/LN | AA/LN | Score | P-Value |
|---|---|---|---|---|---|---|
| SPX0030 | 30 | 2691 | 1278 | 426 | 921 | 9.70E-147 |
| Description | | | | | | |

"[LN:PDP_BACST] [AC:P77836] [GN:PYN] [OR:Bacillus stearothermophilus]
[EC:2.4.2.2] [DE:PYRIMIDINE-NUCLEOSIDE PHOSPHORYLASE, (PYNP)] [SP:P77836]"

| ORF Name | NT ID | AA ID | NT/LN | AA/LN | Score | P-Value |
|---|---|---|---|---|---|---|
| SPX0031 | 31 | 2692 | 591 | 197 | 250 | 2.00E-56 |

Description

[LN:S59955] [AC:S59955] [PN:hypothetical protein 202] [CL:hypothetical protein MJ0882] [OR:Staphylococcus aureus]

| ORF Name | NT ID | AA ID | NT/LN | AA/LN | Score | P-Value |
|---|---|---|---|---|---|---|
| SPX0032 | 32 | 2693 | 219 | 73 | | |

Description

NO-HIT

| ORF Name | NT ID | AA ID | NT/LN | AA/LN | Score | P-Value |
|---|---|---|---|---|---|---|
| SPX0033 | 33 | 2694 | 300 | 100 | | |

Description

NO-HIT

| ORF Name | NT ID | AA ID | NT/LN | AA/LN | Score | P-Value |
|---|---|---|---|---|---|---|
| SPX0034 | 34 | 2695 | 951 | 317 | 345 | 3.80E-79 |

Description

[GI:6960352] [LN:STYSTMF1] [AC:AF170176] [PN:96% identity over 316 amino acids with E. coli] [GN:coaA] [OR:Salmonella typhimurium LT2]

| ORF Name | NT ID | AA ID | NT/LN | AA/LN | Score | P-Value |
|---|---|---|---|---|---|---|
| SPX0035 | 35 | 2696 | 237 | 79 | 98 | 8.40E-17 |

Description

[LN:R3EC20] [AC:A30425:A02748:S40547:G64722:S07374] [PN:ribosomal protein S20/L26 [validated]:ribosomal protein L26:ribosomal protein S20] [GN:rpsT] [CL:Escherichia coli ribosomal protein S20] [OR:Escherichia coli]

| ORF Name | NT ID | AA ID | NT/LN | AA/LN | Score | P-Value |
|---|---|---|---|---|---|---|
| SPX0036 | 36 | 2697 | 525 | 175 | 270 | 6.30E-50 |

Description

[GI:6434823] [LN:SPU78969] [AC:U78969] [PN:FlaR] [GN:flaR] [OR:Streptococcus pyogenes]

| ORF_Name | NT_ID | AA_ID | NT/LN | AA/LN | Score | P-Value |
|---|---|---|---|---|---|---|
| SPX0037 | 37 | 2698 | 711 | 237 | 1042 | 4.10E-140 |
| Description | | | | | | |

[LN:DEOD_STRTR] [AC:Q56037] [GN:DEOD] [OR:Streptococcus thermophilus]
[EC:2.4.2.1] [DE:(PNP) (FRAGMENT)] [SP:Q56037]

| ORF_Name | NT_ID | AA_ID | NT/LN | AA/LN | Score | P-Value |
|---|---|---|---|---|---|---|
| SPX0038 | 38 | 2699 | 513 | 171 | 271 | 1.10E-30 |
| Description | | | | | | |

[GI:6729344] [LN:AB029317] [AC:AB029317] [PN:intermedilysin] [GN:ily]
[OR:Streptococcus intermedius] [SR:Streptococcus intermedius (strain:UNS46)
DNA]

| ORF_Name | NT_ID | AA_ID | NT/LN | AA/LN | Score | P-Value |
|---|---|---|---|---|---|---|
| SPX0039 | 39 | 2700 | 576 | 192 | 117 | 2.80E-07 |
| Description | | | | | | |

"[LN:PXN1_XENLA] [AC:P49263] [GN:PXN1] [OR:Xenopus laevis] [SR:,African
clawed frog] [DE:PENTRAXIN FUSION PROTEIN PRECURSOR] [SP:P49263]"

| ORF_Name | NT_ID | AA_ID | NT/LN | AA/LN | Score | P-Value |
|---|---|---|---|---|---|---|
| SPX0040 | 40 | 2701 | 408 | 136 | 92 | 0.00026 |
| Description | | | | | | |

"[LN:CP23_CHICK] [AC:P23614] [OR:Gallus gallus] [SR:,Chicken] [DE:23 KD
CORTICAL CYTOSKELETON-ASSOCIATED PROTEIN (CAP-23)] [SP:P23614]"

| ORF_Name | NT_ID | AA_ID | NT/LN | AA/LN | Score | P-Value |
|---|---|---|---|---|---|---|
| SPX0041 | 41 | 2702 | 810 | 270 | 395 | 1.40E-105 |
| Description | | | | | | |

[LN:DEOD_BACSU] [AC:P46354] [GN:DEOD:PNP] [OR:Bacillus subtilis]
[EC:2.4.2.1] [DE:(PNP)] [SP:P46354]

| ORF_Name | NT_ID | AA_ID | NT/LN | AA/LN | Score | P-Value |
|---|---|---|---|---|---|---|
| SPX0042 | 42 | 2703 | 543 | 181 | | |
| Description | | | | | | |

NO-HIT

| ORF Name | NT ID | AA ID | NT/LN | AA/LN | Score | P-Value |
|---|---|---|---|---|---|---|
| SPX0043 | 43 | 2704 | 1212 | 404 | 736 | 2.30E-199 |

Description

"[LN:DEOB_LACLC] [AC:O32808] [GN:DEOB] [OR:Lactococcus lactis]
[SR:,subspcremoris:Streptococcus cremoris] [EC:5.4.2.7]
[DE:PHOSPHOPENTOMUTASE, (PHOSPHODEOXYRIBOMUTASE)] [SP:O32808]"

| ORF Name | NT ID | AA ID | NT/LN | AA/LN | Score | P-Value |
|---|---|---|---|---|---|---|
| SPX0044 | 44 | 2705 | 741 | 247 | 206 | 1.40E-52 |

Description

[LN:G69180] [AC:G69180] [PN:ribose 5-phosphate isomerase] [GN:MTH608]
[CL:Haemophilus influenzae ribose-5-phosphate isomerase]
[OR:Methanobacterium thermoautotrophicum]

| ORF Name | NT ID | AA ID | NT/LN | AA/LN | Score | P-Value |
|---|---|---|---|---|---|---|
| SPX0045 | 45 | 2706 | 186 | 62 | | |

Description

NO-HIT

| ORF Name | NT ID | AA ID | NT/LN | AA/LN | Score | P-Value |
|---|---|---|---|---|---|---|
| SPX0046 | 46 | 2707 | 873 | 291 | 386 | 5.80E-99 |

Description

[LN:YFOL_STRTR] [AC:P96051] [OR:Streptococcus thermophilus] [DE:(ORF1091)]
[SP:P96051]

| ORF Name | NT ID | AA ID | NT/LN | AA/LN | Score | P-Value |
|---|---|---|---|---|---|---|
| SPX0047 | 47 | 2708 | 921 | 307 | 1049 | 3.00E-140 |

Description

[LN:FOLD_STRTR] [AC:P96050] [GN:FOLD] [OR:Streptococcus thermophilus]
[EC:1.5.1.5:3.5.4.9] [DE:(EC 3.5.4.9)]] [SP:P96050]

| ORF Name | NT ID | AA ID | NT/LN | AA/LN | Score | P-Value |
|---|---|---|---|---|---|---|
| SPX0048 | 48 | 2709 | 216 | 72 | 99 | 5.40E-08 |

Description

[LN:G72510] [AC:G72510] [PN:hypothetical protein APE2061] [GN:APE2061]
[OR:Aeropyrum pernix]

| ORF Name | NT ID | AA ID | NT/LN | AA/LN | Score | P-Value |
|---|---|---|---|---|---|---|
| SPX0049 | 49 | 2710 | 735 | 245 | 796 | 7.00E-105 |

Description

[LN:H69334] [AC:H69334] [PN:glutamine transport protein glnQ] [GN:glnQ] [CL:inner membrane protein malK:ATP-binding cassette homology] [OR:Archaeoglobus fulgidus]

| ORF Name | NT ID | AA ID | NT/LN | AA/LN | Score | P-Value |
|---|---|---|---|---|---|---|
| SPX0050 | 50 | 2711 | 384 | 128 | 88 | 5.60E-05 |

Description

[LN:D72757] [AC:D72757] [PN:hypothetical protein APE0049] [GN:APE0049] [OR:Aeropyrum pernix]

| ORF Name | NT ID | AA ID | NT/LN | AA/LN | Score | P-Value |
|---|---|---|---|---|---|---|
| SPX0051 | 51 | 2712 | 684 | 228 | 314 | 1.10E-52 |

Description

"[LN:H69278] [AC:H69278] [PN:glutamine ABC transporter, permease protein (glnP) homolog] [CL:histidine permease protein M] [OR:Archaeoglobus fulgidus]"

| ORF Name | NT ID | AA ID | NT/LN | AA/LN | Score | P-Value |
|---|---|---|---|---|---|---|
| SPX0052 | 52 | 2713 | 231 | 77 | 89 | 8.60E-09 |

Description

[LN:G69865] [AC:G69865] [PN:hypothetical protein ykuJ] [GN:ykuJ] [OR:Bacillus subtilis]

| ORF Name | NT ID | AA ID | NT/LN | AA/LN | Score | P-Value |
|---|---|---|---|---|---|---|
| SPX0053 | 53 | 2714 | 2259 | 753 | 2641 | 0 |

Description

[GI:4103470] [LN:AF023421] [AC:AF023421] [PN:ClpE] [GN:clpE] [OR:Lactococcus lactis]

| ORF Name | NT ID | AA ID | NT/LN | AA/LN | Score | P-Value |
|---|---|---|---|---|---|---|
| SPX0054 | 54 | 2715 | 249 | 83 | 116 | 9.50E-10 |

Description

[GI:4098132] [LN:MBU73653] [AC:U73653] [PN:63 kDa protein] [OR:Mycobacterium bovis]

| ORF Name | NT ID | AA ID | NT/LN | AA/LN | Score | P-Value |
|---|---|---|---|---|---|---|
| SPX0055 | 55 | 2716 | 183 | 61 | | |
| Description | | | | | | |

NO-HIT

| ORF Name | NT ID | AA ID | NT/LN | AA/LN | Score | P-Value |
|---|---|---|---|---|---|---|
| SPX0056 | 56 | 2717 | 210 | 70 | | |
| Description | | | | | | |

NO-HIT

| ORF Name | NT ID | AA ID | NT/LN | AA/LN | Score | P-Value |
|---|---|---|---|---|---|---|
| SPX0057 | 57 | 2718 | 342 | 114 | 477 | 2.00E-73 |
| Description | | | | | | |

[GI:5019553] [LN:SPN239004] [AC:AJ239004] [PN:putative transposase] [OR:Streptococcus pneumoniae]

| ORF Name | NT ID | AA ID | NT/LN | AA/LN | Score | P-Value |
|---|---|---|---|---|---|---|
| SPX0058 | 58 | 2719 | 348 | 116 | 569 | 6.90E-75 |
| Description | | | | | | |

[GI:4200438] [LN:AF026471] [AC:AF026471] [PN:putative transposase] [OR:Streptococcus pneumoniae]

| ORF Name | NT ID | AA ID | NT/LN | AA/LN | Score | P-Value |
|---|---|---|---|---|---|---|
| SPX0059 | 59 | 2720 | 423 | 141 | 101 | 5.60E-07 |
| Description | | | | | | |

[LN:A70315] [AC:A70315] [PN:AP4A hydrolase] [GN:apfA] [CL:Methanococcus jannaschii mutator protein mutT:mutT domain homology] [OR:Aquifex aeolicus]

| ORF Name | NT ID | AA ID | NT/LN | AA/LN | Score | P-Value |
|---|---|---|---|---|---|---|
| SPX0060 | 60 | 2721 | 300 | 100 | | |
| Description | | | | | | |

NO-HIT

| ORF Name | NT ID | AA ID | NT/LN | AA/LN | Score | P-Value |
|---|---|---|---|---|---|---|
| SPX0061 | 61 | 2722 | 594 | 198 | 597 | 3.80E-95 |

Description

[LN:A33595] [AC:A33595:A30868] [PN:probable transposase] [CL:transposase IS3] [OR:Streptococcus agalactiae]

| ORF Name | NT ID | AA ID | NT/LN | AA/LN | Score | P-Value |
|---|---|---|---|---|---|---|
| SPX0062 | 62 | 2723 | 264 | 88 | 308 | 1.70E-38 |

Description

[LN:A33595] [AC:A33595:A30868] [PN:probable transposase] [CL:transposase IS3] [OR:Streptococcus agalactiae]

| ORF Name | NT ID | AA ID | NT/LN | AA/LN | Score | P-Value |
|---|---|---|---|---|---|---|
| SPX0063 | 63 | 2724 | 102 | 34 | 126 | 2.60E-12 |

Description

[LN:B30868] [AC:B30868] [PN:hypothetical protein 1] [OR:Streptococcus agalactiae]

| ORF Name | NT ID | AA ID | NT/LN | AA/LN | Score | P-Value |
|---|---|---|---|---|---|---|
| SPX0064 | 64 | 2725 | 351 | 117 | 210 | 5.10E-24 |

Description

"[LN:JC1151] [AC:JC1151] [PN:hypothetical protein, 20.3K] [OR:Agrobacterium tumefaciens]"

| ORF Name | NT ID | AA ID | NT/LN | AA/LN | Score | P-Value |
|---|---|---|---|---|---|---|
| SPX0065 | 65 | 2726 | 306 | 102 | 154 | 5.60E-19 |

Description

[GI:722339] [LN:AXU22323] [AC:U22323] [PN:unknown] [OR:Acetobacter xylinus] [SR:Acetobacter xylinum]

| ORF Name | NT ID | AA ID | NT/LN | AA/LN | Score | P-Value |
|---|---|---|---|---|---|---|
| SPX0066 | 66 | 2727 | 267 | 89 | | |

Description

NO-HIT

| ORF Name | NT ID | AA ID | NT/LN | AA/LN | Score | P-Value |
|---|---|---|---|---|---|---|
| SPX0067 | 67 | 2728 | 1728 | 576 | 285 | 5.20E-53 |
| Description | | | | | | |

[LN:G70002] [AC:G70002] [PN:hypothetical protein ytwP] [GN:ytwP] [OR:Bacillus subtilis]

| ORF Name | NT ID | AA ID | NT/LN | AA/LN | Score | P-Value |
|---|---|---|---|---|---|---|
| SPX0068 | 68 | 2729 | 1947 | 649 | 3322 | 0 |
| Description | | | | | | |

[GI:1490397] [LN:SPGYRBORF] [AC:Z67740] [PN:DNA gyrase] [GN:gyrB] [OR:Streptococcus pneumoniae]

| ORF Name | NT ID | AA ID | NT/LN | AA/LN | Score | P-Value |
|---|---|---|---|---|---|---|
| SPX0069 | 69 | 2730 | 573 | 191 | 709 | 2.40E-93 |
| Description | | | | | | |

[GI:1052803] [LN:SPGYRBG] [AC:X83917] [GN:orf1gyrb] [OR:Streptococcus pneumoniae]

| ORF Name | NT ID | AA ID | NT/LN | AA/LN | Score | P-Value |
|---|---|---|---|---|---|---|
| SPX0070 | 70 | 2731 | 555 | 185 | 118 | 9.00E-28 |
| Description | | | | | | |

"[LN:D70177] [AC:D70177] [PN:4-methyl-5(b-hydroxyethyl)-thiazole monophosphate biosynthesis protein (thiJ) homolog] [CL:signal transduction protein DJ-1] [OR:Borrelia burgdorferi] [SR:, Lyme disease spirochete]"

| ORF Name | NT ID | AA ID | NT/LN | AA/LN | Score | P-Value |
|---|---|---|---|---|---|---|
| SPX0071 | 71 | 2732 | 1251 | 417 | 398 | 1.00E-50 |
| Description | | | | | | |

[LN:S22738] [AC:S22738:S22728] [PN:hypothetical protein] [OR:Streptococcus salivarius]

| ORF Name | NT ID | AA ID | NT/LN | AA/LN | Score | P-Value |
|---|---|---|---|---|---|---|
| SPX0072 | 72 | 2733 | 2451 | 817 | 203 | 3.80E-66 |
| Description | | | | | | |

[LN:DING_BACSU] [AC:P54394] [GN:DING] [OR:Bacillus subtilis] [DE:PROBABLE ATP-DEPENDENT HELICASE DING HOMOLOG] [SP:P54394]

| ORF Name | NT ID | AA ID | NT/LN | AA/LN | Score | P-Value |
|---|---|---|---|---|---|---|
| SPX0073 | 73 | 2734 | 930 | 310 | 189 | 6.20E-42 |

Description

[LN:G69979] [AC:G69979] [PN:proteinase homolog yrrN] [GN:yrrN] [OR:Bacillus subtilis]

| ORF Name | NT ID | AA ID | NT/LN | AA/LN | Score | P-Value |
|---|---|---|---|---|---|---|
| SPX0074 | 74 | 2735 | 288 | 96 | | |

Description

NO-HIT

| ORF Name | NT ID | AA ID | NT/LN | AA/LN | Score | P-Value |
|---|---|---|---|---|---|---|
| SPX0075 | 75 | 2736 | 1335 | 445 | 2202 | 4.50E-301 |

Description

"[LN:CIAH_STRPN] [AC:Q54955] [GN:CIAH] [OR:Streptococcus pneumoniae] [EC:2.7.3.-] [DE:SENSOR PROTEIN CIAH,] [SP:Q54955]"

| ORF Name | NT ID | AA ID | NT/LN | AA/LN | Score | P-Value |
|---|---|---|---|---|---|---|
| SPX0076 | 76 | 2737 | 675 | 225 | 1130 | 1.70E-152 |

Description

[LN:CIAR_STRPN] [AC:Q54954] [GN:CIAR] [OR:Streptococcus pneumoniae] [DE:TRANSCRIPTIONAL REGULATORY PROTEIN CIAR] [SP:Q54954]

| ORF Name | NT ID | AA ID | NT/LN | AA/LN | Score | P-Value |
|---|---|---|---|---|---|---|
| SPX0077 | 77 | 2738 | 2547 | 849 | 1653 | 0 |

Description

[GI:5524752] [LN:STH007700] [AC:AJ007700] [PN:aminopeptidase N] [GN:pepN] [OR:Streptococcus thermophilus]

| ORF Name | NT ID | AA ID | NT/LN | AA/LN | Score | P-Value |
|---|---|---|---|---|---|---|
| SPX0078 | 78 | 2739 | 441 | 147 | 176 | 1.80E-20 |

Description

[LN:T35570] [AC:T35570] [PN:hypothetical protein SC6G4.19c SC6G4.19c] [GN:SC6G4.19c] [OR:Streptomyces coelicolor]

| ORF Name | NT ID | AA ID | NT/LN | AA/LN | Score | P-Value |
|---|---|---|---|---|---|---|
| SPX0079 | 79 | 2740 | 876 | 292 | 80 | 8.00E-10 |

Description

[LN:PPSA_PYRFU] [AC:P42850:Q59672] [GN:PPSA] [OR:Pyrococcus furiosus]
[EC:2.7.9.2] [DE:DIKINASE) (PEP SYNTHASE)] [SP:P42850:Q59672]

| ORF Name | NT ID | AA ID | NT/LN | AA/LN | Score | P-Value |
|---|---|---|---|---|---|---|
| SPX0080 | 80 | 2741 | 729 | 243 | | |

Description

NO-HIT

| ORF Name | NT ID | AA ID | NT/LN | AA/LN | Score | P-Value |
|---|---|---|---|---|---|---|
| SPX0081 | 81 | 2742 | 480 | 160 | 113 | 1.60E-07 |

Description

[LN:C72513] [AC:C72513] [PN:hypothetical protein APE2080] [GN:APE2080]
[OR:Aeropyrum pernix]

| ORF Name | NT ID | AA ID | NT/LN | AA/LN | Score | P-Value |
|---|---|---|---|---|---|---|
| SPX0082 | 82 | 2743 | 228 | 76 | | |

Description

NO-HIT

| ORF Name | NT ID | AA ID | NT/LN | AA/LN | Score | P-Value |
|---|---|---|---|---|---|---|
| SPX0083 | 83 | 2744 | 699 | 233 | 231 | 3.20E-28 |

Description

[LN:GNO_GLUOX] [AC:P50199] [GN:GNO] [OR:Gluconobacter oxydans] [EC:1.1.1.69]
[DE:REDUCTASE)] [SP:P50199]

| ORF Name | NT ID | AA ID | NT/LN | AA/LN | Score | P-Value |
|---|---|---|---|---|---|---|
| SPX0084 | 84 | 2745 | 267 | 89 | | |

Description

NO-HIT

| ORF Name | NT ID | AA ID | NT LN | AA LN | Score | P-Value |
|---|---|---|---|---|---|---|
| SPX0085 | 85 | 2746 | 927 | 309 | 210 | 2.40E-41 |
| Description | | | | | | |

[LN:YDHF_ECOLI] [AC:P76187] [GN:YDHF] [OR:Escherichia coli] [DE:HYPOTHETICAL OXIDOREDUCTASE IN SODC-NEMA INTERGENIC REGION] [SP:P76187]

| ORF Name | NT ID | AA ID | NT LN | AA LN | Score | P-Value |
|---|---|---|---|---|---|---|
| SPX0086 | 86 | 2747 | 816 | 272 | 114 | 3.70E-09 |
| Description | | | | | | |

[GI:3043880] [LN:LLU95841] [AC:U95841] [PN:transmembrane protein Tmp6] [OR:Lactococcus lactis]

| ORF Name | NT ID | AA ID | NT LN | AA LN | Score | P-Value |
|---|---|---|---|---|---|---|
| SPX0087 | 87 | 2748 | 216 | 72 | 146 | 1.50E-15 |
| Description | | | | | | |

[GI:3582220] [LN:AE001272] [AC:AE001272] [PN:conserved hypothetical protein] [GN:ORF00047] [OR:Lactococcus lactis]

| ORF Name | NT ID | AA ID | NT LN | AA LN | Score | P-Value |
|---|---|---|---|---|---|---|
| SPX0088 | 88 | 2749 | 237 | 79 | | |
| Description | | | | | | |

NO-HIT

| ORF Name | NT ID | AA ID | NT LN | AA LN | Score | P-Value |
|---|---|---|---|---|---|---|
| SPX0089 | 89 | 2750 | 246 | 82 | 269 | 2.80E-32 |
| Description | | | | | | |

[LN:T30285] [AC:T30285] [PN:hypothetical protein] [OR:Streptococcus pneumoniae]

| ORF Name | NT ID | AA ID | NT LN | AA LN | Score | P-Value |
|---|---|---|---|---|---|---|
| SPX0090 | 90 | 2751 | 2040 | 680 | 734 | 6.10E-239 |
| Description | | | | | | |

[LN:SYM_BACST] [AC:P23920] [GN:METS] [OR:Bacillus stearothermophilus] [EC:6.1.1.10] [DE:(METRS)] [SP:P23920]

| ORF Name | NT ID | AA ID | NT/LN | AA/LN | Score | P-Value |
|---|---|---|---|---|---|---|
| SPX0091 | 91 | 2752 | 1260 | 420 | 287 | 2.30E-62 |

Description

[LN:E69858] [AC:E69858] [PN:conserved hypothetical protein yknZ] [GN:yknZ] [OR:Bacillus subtilis]

| ORF Name | NT ID | AA ID | NT/LN | AA/LN | Score | P-Value |
|---|---|---|---|---|---|---|
| SPX0092 | 92 | 2753 | 702 | 234 | 663 | 9.00E-86 |

Description

[GI:2822199] [LN:SCU96166] [AC:U96166:AF227987] [PN:ATP-binding cassette protein] [GN:tptC] [OR:Streptococcus cristatus]

| ORF Name | NT ID | AA ID | NT/LN | AA/LN | Score | P-Value |
|---|---|---|---|---|---|---|
| SPX0093 | 93 | 2754 | 1200 | 400 | 144 | 5.60E-36 |

Description

[LN:C69858] [AC:C69858] [PN:conserved hypothetical protein yknX] [GN:yknX] [OR:Bacillus subtilis]

| ORF Name | NT ID | AA ID | NT/LN | AA/LN | Score | P-Value |
|---|---|---|---|---|---|---|
| SPX0094 | 94 | 2755 | 1347 | 449 | 730 | 1.70E-192 |

Description

"[LN:S41386] [AC:S41386] [PN:glutathione reductase (NADPH),] [CL:dihydrolipoamide dehydrogenase:dihydrolipoamide dehydrogenase homology] [OR:Streptococcus thermophilus] [EC:1.6.4.2]"

| ORF Name | NT ID | AA ID | NT/LN | AA/LN | Score | P-Value |
|---|---|---|---|---|---|---|
| SPX0095 | 95 | 2756 | 537 | 179 | 218 | 6.90E-30 |

Description

[LN:H72334] [AC:H72334] [PN:bioY protein] [GN:TM0799] [OR:Thermotoga maritima]

| ORF Name | NT ID | AA ID | NT/LN | AA/LN | Score | P-Value |
|---|---|---|---|---|---|---|
| SPX0096 | 96 | 2757 | 336 | 112 | | |

Description

NO-HIT

| ORF Name | NT ID | AA ID | NT/LN | AA/LN | Score | P-Value |
|---|---|---|---|---|---|---|
| SPX0097 | 97 | 2758 | 240 | 80 | 171 | 1.50E-18 |

Description

[LN:Y352_TREPA] [AC:O83371] [GN:TP0352] [OR:Treponema pallidum]
[DE:HYPOTHETICAL PROTEIN TP0352] [SP:O83371]

| ORF Name | NT ID | AA ID | NT/LN | AA/LN | Score | P-Value |
|---|---|---|---|---|---|---|
| SPX0098 | 98 | 2759 | 321 | 107 | | |

Description

NO-HIT

| ORF Name | NT ID | AA ID | NT/LN | AA/LN | Score | P-Value |
|---|---|---|---|---|---|---|
| SPX0099 | 99 | 2760 | 339 | 113 | 109 | 1.40E-12 |

Description

[GI:4098081] [LN:LLU73336] [AC:U73336] [PN:anaerobic ribonucleotide reductase] [GN:nrdD] [OR:Lactococcus lactis subsp. cremoris]

| ORF Name | NT ID | AA ID | NT/LN | AA/LN | Score | P-Value |
|---|---|---|---|---|---|---|
| SPX0100 | 100 | 2761 | 720 | 240 | 372 | 1.30E-85 |

Description

[LN:TRMD_BACSU] [AC:O31741] [GN:TRMD] [OR:Bacillus subtilis] [EC:2.1.1.31]
[DE:METHYLTRANSFERASE) (TRNA [GM37] METHYLTRANSFERASE)] [SP:O31741]

| ORF Name | NT ID | AA ID | NT/LN | AA/LN | Score | P-Value |
|---|---|---|---|---|---|---|
| SPX0101 | 101 | 2762 | 519 | 173 | 292 | 5.20E-61 |

Description

[LN:RIMM_BACSU] [AC:O31740] [GN:RIMM] [OR:Bacillus subtilis] [DE:PROBABLE
16S RRNA PROCESSING PROTEIN RIMM] [SP:O31740]

| ORF Name | NT ID | AA ID | NT/LN | AA/LN | Score | P-Value |
|---|---|---|---|---|---|---|
| SPX0102 | 102 | 2763 | 801 | 267 | | |

Description

NO-HIT

| ORF Name | NT ID | AA ID | NT LN | AA LN | Score | P-Value |
|---|---|---|---|---|---|---|
| SPX0103 | 103 | 2764 | 240 | 80 | 141 | 9.70E-15 |

Description

[LN:C69880] [AC:C69880] [PN:conserved hypothetical protein ylqC] [GN:ylqC]
[CL:Bacillus conserved hypothetical protein ylqC] [OR:Bacillus subtilis]

| ORF Name | NT ID | AA ID | NT LN | AA LN | Score | P-Value |
|---|---|---|---|---|---|---|
| SPX0104 | 104 | 2765 | 273 | 91 | 315 | 5.10E-39 |

Description

[LN:C47154] [AC:C47154:S11366:G69700] [PN:ribosomal protein S16 (BS17)
rpsP:ribosomal protein BS17] [GN:rpsP] [CL:Escherichia coli ribosomal
protein S16] [OR:Bacillus subtilis]

| ORF Name | NT ID | AA ID | NT LN | AA LN | Score | P-Value |
|---|---|---|---|---|---|---|
| SPX0105 | 105 | 2766 | 210 | 70 | | |

Description

NO-HIT

| ORF Name | NT ID | AA ID | NT LN | AA LN | Score | P-Value |
|---|---|---|---|---|---|---|
| SPX0106 | 106 | 2767 | 405 | 135 | | |

Description

NO-HIT

| ORF Name | NT ID | AA ID | NT LN | AA LN | Score | P-Value |
|---|---|---|---|---|---|---|
| SPX0107 | 107 | 2768 | 213 | 71 | | |

Description

NO-HIT

| ORF Name | NT ID | AA ID | NT LN | AA LN | Score | P-Value |
|---|---|---|---|---|---|---|
| SPX0108 | 108 | 2769 | 804 | 268 | 243 | 3.60E-38 |

Description

[LN:T41399] [AC:T41399] [PN:probable cyclophilin-related peptidyl prolyl
cis-trans isomerase] [GN:SPCC553.04] [OR:Schizosaccharomyces pombe]

| ORF Name | NT ID | AA ID | NT/LN | AA/LN | Score | P-Value |
|---|---|---|---|---|---|---|
| SPX0109 | 109 | 2770 | 360 | 120 | 83 | 5.10E-05 |

Description

[GI:1773206] [LN:ECU82664] [AC:U82664] [OR:Escherichia coli]

| ORF Name | NT ID | AA ID | NT/LN | AA/LN | Score | P-Value |
|---|---|---|---|---|---|---|
| SPX0110 | 110 | 2771 | 1542 | 514 | 1502 | 3.70E-258 |

Description

[LN:D69813] [AC:D69813] [PN:ABC transporter (ATP-binding protein) homolog yfmM] [GN:yfmM] [CL:unassigned ATP-binding cassette proteins:ATP-binding cassette homology] [OR:Bacillus subtilis]

| ORF Name | NT ID | AA ID | NT/LN | AA/LN | Score | P-Value |
|---|---|---|---|---|---|---|
| SPX0111 | 111 | 2772 | 483 | 161 | 88 | 2.20E-11 |

Description

[GI:7110140] [LN:AF155139] [AC:AF155139:AF019976] [PN:VanZF] [GN:vanZF] [OR:Paenibacillus popilliae]

| ORF Name | NT ID | AA ID | NT/LN | AA/LN | Score | P-Value |
|---|---|---|---|---|---|---|
| SPX0112 | 112 | 2773 | 1086 | 362 | 452 | 1.30E-135 |

Description

[LN:YLON_BACSU] [AC:O34617] [GN:YLON] [OR:Bacillus subtilis] [DE:HYPOTHETICAL 41.6 KD PROTEIN IN FMT-SPOVM INTERGENIC REGION] [SP:O34617]

| ORF Name | NT ID | AA ID | NT/LN | AA/LN | Score | P-Value |
|---|---|---|---|---|---|---|
| SPX0113 | 113 | 2774 | 531 | 177 | 152 | 3.20E-25 |

Description

[LN:F70023] [AC:F70023] [PN:hypothetical protein yutD] [GN:yutD] [CL:Bacillus subtilis hypothetical protein yutD] [OR:Bacillus subtilis]

| ORF Name | NT ID | AA ID | NT/LN | AA/LN | Score | P-Value |
|---|---|---|---|---|---|---|
| SPX0114 | 114 | 2775 | 606 | 202 | 1034 | 4.90E-138 |

Description

[GI:5758312] [LN:AF162664] [AC:AF162664] [PN:manganese co-factored superoxide dismutase] [GN:sodA] [FN:removes superoxide] [OR:Streptococcus pneumoniae]

| ORF Name | NT ID | AA ID | NT LN | AA LN | Score | P-Value |
|---|---|---|---|---|---|---|
| SPX0115 | 115 | 2776 | 1038 | 346 | 952 | 2.60E-127 |

Description

[GI:2765186] [LN:SASODA] [AC:Y12224] [PN:hypothetical protein]
[OR:Streptococcus agalactiae]

| ORF Name | NT ID | AA ID | NT LN | AA LN | Score | P-Value |
|---|---|---|---|---|---|---|
| SPX0116 | 116 | 2777 | 936 | 312 | 1616 | 3.20E-220 |

Description

[GI:5578893] [LN:SPN131985] [AC:AJ131985] [PN:dihydroorotate dehydrogenase]
[GN:pyrDA] [OR:Streptococcus pneumoniae]

| ORF Name | NT ID | AA ID | NT LN | AA LN | Score | P-Value |
|---|---|---|---|---|---|---|
| SPX0117 | 117 | 2778 | 1191 | 397 | 1399 | 3.90E-187 |

Description

[LN:METK_STAAU] [AC:P50307] [GN:METK] [OR:Staphylococcus aureus]
[EC:2.5.1.6] [DE:ADENOSYLTRANSFERASE) (ADOMET SYNTHETASE)] [SP:P50307]

| ORF Name | NT ID | AA ID | NT LN | AA LN | Score | P-Value |
|---|---|---|---|---|---|---|
| SPX0118 | 118 | 2779 | 1344 | 448 | 972 | 1.00E-140 |

Description

[LN:YQFR_BACSU] [AC:P54475] [GN:YQFR] [OR:Bacillus subtilis] [DE:PROBABLE
RNA HELICASE IN CCCA-SODA INTERGENIC REGION] [SP:P54475]

| ORF Name | NT ID | AA ID | NT LN | AA LN | Score | P-Value |
|---|---|---|---|---|---|---|
| SPX0119 | 119 | 2780 | 816 | 272 | | |

Description

NO-HIT

| ORF Name | NT ID | AA ID | NT LN | AA LN | Score | P-Value |
|---|---|---|---|---|---|---|
| SPX0120 | 120 | 2781 | 264 | 88 | | |

Description

NO-HIT

| ORF Name | NT ID | AA ID | NT LN | AA LN | Score | P-Value |
|---|---|---|---|---|---|---|
| SPX0121 | 121 | 2782 | 2181 | 727 | 735 | 4.60E-182 |

Description

[GI:4098489] [LN:SMU78600] [AC:U78600] [PN:putative ptsG protein]
[OR:Streptococcus mutans]

| ORF Name | NT ID | AA ID | NT LN | AA LN | Score | P-Value |
|---|---|---|---|---|---|---|
| SPX0122 | 122 | 2783 | 936 | 312 | 330 | 2.80E-63 |

Description

[LN:G69627] [AC:G69627] [PN:cell-division protein ftsX] [GN:ftsX]
[OR:Bacillus subtilis]

| ORF Name | NT ID | AA ID | NT LN | AA LN | Score | P-Value |
|---|---|---|---|---|---|---|
| SPX0123 | 123 | 2784 | 207 | 69 | | |

Description

NO-HIT

| ORF Name | NT ID | AA ID | NT LN | AA LN | Score | P-Value |
|---|---|---|---|---|---|---|
| SPX0124 | 124 | 2785 | 693 | 231 | 798 | 9.90E-106 |

Description

[LN:D69627] [AC:D69627] [PN:cell-division ATP-binding protein ftsE]
[GN:ftsE] [CL:unassigned ATP-binding cassette proteins:ATP-binding cassette
homology] [OR:Bacillus subtilis]

| ORF Name | NT ID | AA ID | NT LN | AA LN | Score | P-Value |
|---|---|---|---|---|---|---|
| SPX0125 | 125 | 2786 | 225 | 75 | 94 | 1.10E-07 |

Description

[LN:A71007] [AC:A71007] [PN:hypothetical protein PH1351] [GN:PH1351]
[OR:Pyrococcus horikoshii]

| ORF Name | NT ID | AA ID | NT LN | AA LN | Score | P-Value |
|---|---|---|---|---|---|---|
| SPX0126 | 126 | 2787 | 921 | 307 | 936 | 6.80E-124 |

Description

[LN:RF2_BACSU] [AC:P28367:O34444] [GN:PRFB] [OR:Bacillus subtilis]
[DE:PEPTIDE CHAIN RELEASE FACTOR 2 (RF-2)] [SP:P28367:O34444]

| ORF Name | NT ID | AA ID | NT LN | AA LN | Score | P-Value |
|---|---|---|---|---|---|---|
| SPX0127 | 127 | 2788 | 657 | 219 | 279 | 3.40E-41 |

Description

[LN:H72290] [AC:H72290] [PN:conserved hypothetical protein] [GN:TM1140] [OR:Thermotoga maritima]

| ORF Name | NT ID | AA ID | NT LN | AA LN | Score | P-Value |
|---|---|---|---|---|---|---|
| SPX0128 | 128 | 2789 | 711 | 237 | 711 | 7.60E-93 |

Description

[LN:T35757] [AC:T35757] [PN:probable branched chain amino acid transport ATP-binding protein] [GN:SC7H2.26] [CL:unassigned ATP-binding cassette proteins:ATP-binding cassette homology] [OR:Streptomyces coelicolor]

| ORF Name | NT ID | AA ID | NT LN | AA LN | Score | P-Value |
|---|---|---|---|---|---|---|
| SPX0129 | 129 | 2790 | 201 | 67 | 109 | 6.60E-10 |

Description

[LN:G72485] [AC:G72485] [PN:hypothetical protein APE2527] [GN:APE2527] [OR:Aeropyrum pernix]

| ORF Name | NT ID | AA ID | NT LN | AA LN | Score | P-Value |
|---|---|---|---|---|---|---|
| SPX0130 | 130 | 2791 | 765 | 255 | 387 | 4.20E-90 |

Description

"[LN:F72290] [AC:F72290] [PN:branched chain amino acid ABC transporter, ATP-binding protein] [GN:TM1138] [CL:unassigned ATP-binding cassette proteins:ATP-binding cassette homology] [OR:Thermotoga maritima]"

| ORF Name | NT ID | AA ID | NT LN | AA LN | Score | P-Value |
|---|---|---|---|---|---|---|
| SPX0131 | 131 | 2792 | 957 | 319 | 334 | 1.10E-63 |

Description

[LN:E81303] [AC:E81303] [PN:probable branched-chain amino-acid ABC transport system permease protein Cj1016c [imported]] [GN:livM:Cj1016c] [OR:Campylobacter jejuni]

| ORF Name | NT ID | AA ID | NT/LN | AA/LN | Score | P-Value |
|---|---|---|---|---|---|---|
| SPX0132 | 132 | 2793 | 879 | 293 | 325 | 1.30E-90 |
| Description | | | | | | |

"[LN:D72290] [AC:D72290] [PN:branched chain amino acid ABC transporter, permease protein] [GN:TM1136] [CL:leucine transport protein livH] [OR:Thermotoga maritima]"

| ORF Name | NT ID | AA ID | NT/LN | AA/LN | Score | P-Value |
|---|---|---|---|---|---|---|
| SPX0133 | 133 | 2794 | 1161 | 387 | 193 | 5.70E-39 |
| Description | | | | | | |

[LN:H81303] [AC:H81303] [PN:branched-chain amino-acid ABC transport system periplasmic binding protein Cj1019c [imported]] [GN:livJ:Cj1019c] [OR:Campylobacter jejuni]

| ORF Name | NT ID | AA ID | NT/LN | AA/LN | Score | P-Value |
|---|---|---|---|---|---|---|
| SPX0134 | 134 | 2795 | 450 | 150 | | |
| Description | | | | | | |

NO-HIT

| ORF Name | NT ID | AA ID | NT/LN | AA/LN | Score | P-Value |
|---|---|---|---|---|---|---|
| SPX0135 | 135 | 2796 | 249 | 83 | 116 | 2.40E-11 |
| Description | | | | | | |

[LN:D69874] [AC:D69874] [PN:conserved hypothetical protein ylbG] [GN:ylbG] [OR:Bacillus subtilis]

| ORF Name | NT ID | AA ID | NT/LN | AA/LN | Score | P-Value |
|---|---|---|---|---|---|---|
| SPX0136 | 136 | 2797 | 591 | 197 | 933 | 8.10E-124 |
| Description | | | | | | |

[LN:CLPP_STRSL] [AC:P36398] [GN:CLPP] [OR:Streptococcus salivarius] [EC:3.4.21.92] [DE:(ENDOPEPTIDASE CLP)] [SP:P36398]

| ORF Name | NT ID | AA ID | NT/LN | AA/LN | Score | P-Value |
|---|---|---|---|---|---|---|
| SPX0137 | 137 | 2798 | 651 | 217 | 961 | 5.20E-129 |
| Description | | | | | | |

[LN:UPP_STRSL] [AC:P36399] [GN:UPP] [OR:Streptococcus salivarius] [EC:2.4.2.9] [DE:PYROPHOSPHORYLASE) (UPRTASE)] [SP:P36399]

| ORF Name | NT ID | AA ID | NT LN | AA LN | Score | P-Value |
|---|---|---|---|---|---|---|
| SPX0138 | 138 | 2799 | 162 | 54 | | |

Description

NO-HIT

| ORF Name | NT ID | AA ID | NT LN | AA LN | Score | P-Value |
|---|---|---|---|---|---|---|
| SPX0139 | 139 | 2800 | 468 | 156 | 265 | 4.40E-49 |

Description

[LN:CME2_BACSU] [AC:P32393] [GN:COMEB:COME2] [OR:Bacillus subtilis] [DE:COME OPERON PROTEIN 2] [SP:P32393]

| ORF Name | NT ID | AA ID | NT LN | AA LN | Score | P-Value |
|---|---|---|---|---|---|---|
| SPX0140 | 140 | 2801 | 558 | 186 | 114 | 1.10E-07 |

Description

[LN:G70325] [AC:G70325] [PN:transcription regulator TetR/AcrR family] [GN:acrR3] [OR:Aquifex aeolicus]

| ORF Name | NT ID | AA ID | NT LN | AA LN | Score | P-Value |
|---|---|---|---|---|---|---|
| SPX0141 | 141 | 2802 | 846 | 282 | 813 | 2.60E-107 |

Description

[GI:4580621] [LN:AF118389] [AC:AF118389] [PN:unknown] [OR:Streptococcus suis]

| ORF Name | NT ID | AA ID | NT LN | AA LN | Score | P-Value |
|---|---|---|---|---|---|---|
| SPX0142 | 142 | 2803 | 1176 | 392 | 330 | 1.60E-83 |

Description

[GI:2293312] [LN:AF008220] [AC:AF008220] [PN:YtfP] [GN:ytfP] [OR:Bacillus subtilis]

| ORF Name | NT ID | AA ID | NT LN | AA LN | Score | P-Value |
|---|---|---|---|---|---|---|
| SPX0143 | 143 | 2804 | 456 | 152 | 106 | 6.50E-12 |

Description

[LN:G70031] [AC:G70031] [PN:mutator MutT protein homolog yvcI] [GN:yvcI] [CL:mutT domain homology] [OR:Bacillus subtilis]

| ORF Name | NT ID | AA ID | NT LN | AA LN | Score | P-Value |
|---|---|---|---|---|---|---|
| SPX0144 | 144 | 2805 | 519 | 173 | 876 | 2.10E-115 |

Description

[GI:6179679] [LN:SPN239034] [AC:AJ239034] [PN:regulator of pmrA] [GN:mta]
[FN:regulator of pmrA expression] [OR:Streptococcus pneumoniae]

| ORF Name | NT ID | AA ID | NT LN | AA LN | Score | P-Value |
|---|---|---|---|---|---|---|
| SPX0145 | 145 | 2806 | 1470 | 490 | 805 | 5.40E-151 |

Description

[LN:F69825] [AC:F69825] [PN:sodium-dependent transporter homolog yhdH]
[GN:yhdH] [CL:gamma-aminobutyric acid transporter] [OR:Bacillus subtilis]

| ORF Name | NT ID | AA ID | NT LN | AA LN | Score | P-Value |
|---|---|---|---|---|---|---|
| SPX0146 | 146 | 2807 | 945 | 315 | 1165 | 3.00E-155 |

Description

[LN:MANA_STRMU] [AC:Q59935] [GN:PMI] [OR:Streptococcus mutans] [EC:5.3.1.8]
[DE:(PMI) (PHOSPHOHEXOMUTASE)] [SP:Q59935]

| ORF Name | NT ID | AA ID | NT LN | AA LN | Score | P-Value |
|---|---|---|---|---|---|---|
| SPX0147 | 147 | 2808 | 402 | 134 | | |

Description

NO-HIT

| ORF Name | NT ID | AA ID | NT LN | AA LN | Score | P-Value |
|---|---|---|---|---|---|---|
| SPX0148 | 148 | 2809 | 330 | 110 | 270 | 1.80E-43 |

Description

[LN:JE0396] [AC:JE0396] [PN:phospho-beta-galactosidase II] [CL:Agrobacterium
beta-glucosidase] [OR:Lactobacillus gasseri]

| ORF Name | NT ID | AA ID | NT LN | AA LN | Score | P-Value |
|---|---|---|---|---|---|---|
| SPX0149 | 149 | 2810 | 267 | 89 | | |

Description

NO-HIT

| ORF Name | NT ID | AA ID | NT/LN | AA/LN | Score | P-Value |
|---|---|---|---|---|---|---|
| SPX0150 | 150 | 2811 | 654 | 218 | 154 | 1.00E-20 |

Description

[GI:722339] [LN:AXU22323] [AC:U22323] [PN:unknown] [OR:Acetobacter xylinus] [SR:Acetobacter xylinum]

| ORF Name | NT ID | AA ID | NT/LN | AA/LN | Score | P-Value |
|---|---|---|---|---|---|---|
| SPX0151 | 151 | 2812 | 348 | 116 | | |

Description

NO-HIT

| ORF Name | NT ID | AA ID | NT/LN | AA/LN | Score | P-Value |
|---|---|---|---|---|---|---|
| SPX0152 | 152 | 2813 | 1776 | 592 | 3033 | 0 |

Description

"[LN:POXB_STRPN] [AC:Q54970] [GN:SPXB] [OR:Streptococcus pneumoniae] [EC:1.2.3.3] [DE:PYRUVATE OXIDASE, (PYRUVIC OXIDASE) (POX)] [SP:Q54970]"

| ORF Name | NT ID | AA ID | NT/LN | AA/LN | Score | P-Value |
|---|---|---|---|---|---|---|
| SPX0153 | 153 | 2814 | 201 | 67 | 149 | 2.30E-14 |

Description

[GI:1513069] [LN:LMU15554] [AC:U15554] [PN:P-type adenosine triphosphatase] [GN:ctpA] [FN:involved in cation transport] [OR:Listeria monocytogenes]

| ORF Name | NT ID | AA ID | NT/LN | AA/LN | Score | P-Value |
|---|---|---|---|---|---|---|
| SPX0154 | 154 | 2815 | 2199 | 733 | 648 | 8.80E-202 |

Description

[GI:1513069] [LN:LMU15554] [AC:U15554] [PN:P-type adenosine triphosphatase] [GN:ctpA] [FN:involved in cation transport] [OR:Listeria monocytogenes]

| ORF Name | NT ID | AA ID | NT/LN | AA/LN | Score | P-Value |
|---|---|---|---|---|---|---|
| SPX0155 | 155 | 2816 | 255 | 85 | 107 | 2.40E-09 |

Description

[LN:H72624] [AC:H72624] [PN:hypothetical protein APE1456] [GN:APE1456] [OR:Aeropyrum pernix]

| ORF Name | NT ID | AA ID | NT/LN | AA/LN | Score | P-Value |
|---|---|---|---|---|---|---|
| SPX0156 | 156 | 2817 | 183 | 61 | | |

Description

NO-HIT

| ORF Name | NT ID | AA ID | NT/LN | AA/LN | Score | P-Value |
|---|---|---|---|---|---|---|
| SPX0157 | 157 | 2818 | 372 | 124 | 70 | 6.10E-06 |

Description

"[LN:H69267] [AC:H69267] [PN:cytochrome-c oxidase, chain II AF0144]
[CL:cytochrome-c oxidase chain II:cytochrome-c oxidase chain II homology]
[OR:Archaeoglobus fulgidus] [EC:1.9.3.1]"

| ORF Name | NT ID | AA ID | NT/LN | AA/LN | Score | P-Value |
|---|---|---|---|---|---|---|
| SPX0158 | 158 | 2819 | 426 | 142 | 240 | 1.00E-28 |

Description

[LN:COPY_ENTHR] [AC:Q47839] [GN:COPY] [OR:Enterococcus hirae] [DE:COPAB
ATPASES METAL-FIST TYPE REPRESSOR] [SP:Q47839]

| ORF Name | NT ID | AA ID | NT/LN | AA/LN | Score | P-Value |
|---|---|---|---|---|---|---|
| SPX0159 | 159 | 2820 | 807 | 269 | 308 | 4.00E-99 |

Description

[GI:6707002] [LN:AF109218] [AC:AF109218:U96108] [PN:ThiD] [GN:thiD]
[OR:Staphylococcus carnosus]

| ORF Name | NT ID | AA ID | NT/LN | AA/LN | Score | P-Value |
|---|---|---|---|---|---|---|
| SPX0160 | 160 | 2821 | 633 | 211 | 245 | 8.10E-55 |

Description

[LN:D75087] [AC:D75087] [PN:thiamin phosphate pyrophosphorylase (thie)
PAB1645] [GN:PAB1645] [CL:probable thiamin-phosphate
pyrophosphorylase:thiamin-phosphate pyrophosphorylase homology]
[OR:Pyrococcus abyssi]

| ORF Name | NT ID | AA ID | NT/LN | AA/LN | Score | P-Value |
|---|---|---|---|---|---|---|
| SPX0161 | 161 | 2822 | 807 | 269 | 228 | 2.70E-27 |

Description

[LN:THIM_ECOLI] [AC:P76423] [GN:THIM] [OR:Escherichia coli] [EC:2.7.1.50]
[DE:HYDROXYETHYLTHIAZOLE KINASE) (THZ KINASE) (TH KINASE)] [SP:P76423]

| ORF Name | NT ID | AA ID | NT/LN | AA/LN | Score | P-Value |
|---|---|---|---|---|---|---|
| SPX0162 | 162 | 2823 | 525 | 175 | | |

Description

NO-HIT

| ORF Name | NT ID | AA ID | NT/LN | AA/LN | Score | P-Value |
|---|---|---|---|---|---|---|
| SPX0163 | 163 | 2824 | 693 | 231 | 384 | 2.00E-48 |

Description

[LN:TENA_BACSU] [AC:P25052] [GN:TENA] [OR:Bacillus subtilis]
[DE:TRANSCRIPTIONAL ACTIVATOR TENA] [SP:P25052]

| ORF Name | NT ID | AA ID | NT/LN | AA/LN | Score | P-Value |
|---|---|---|---|---|---|---|
| SPX0164 | 164 | 2825 | 651 | 217 | 112 | 1.10E-13 |

Description

[GI:1296823] [LN:LHPEPIGN] [AC:Z56283] [GN:orf2] [OR:Lactobacillus helveticus]

| ORF Name | NT ID | AA ID | NT/LN | AA/LN | Score | P-Value |
|---|---|---|---|---|---|---|
| SPX0165 | 165 | 2826 | 1386 | 462 | 279 | 4.50E-59 |

Description

[GI:1296822] [LN:LHPEPIGN] [AC:Z56283] [GN:orf1] [OR:Lactobacillus helveticus]

| ORF Name | NT ID | AA ID | NT/LN | AA/LN | Score | P-Value |
|---|---|---|---|---|---|---|
| SPX0166 | 166 | 2827 | 561 | 187 | 203 | 2.20E-27 |

Description

[LN:A69859] [AC:A69859] [PN:hypothetical protein ykoE] [GN:ykoE]
[OR:Bacillus subtilis]

| ORF Name | NT ID | AA ID | NT/LN | AA/LN | Score | P-Value |
|---|---|---|---|---|---|---|
| SPX0167 | 167 | 2828 | 225 | 75 | | |

Description

NO-HIT

| ORF Name | NT ID | AA ID | NT/LN | AA/LN | Score | P-Value |
|---|---|---|---|---|---|---|
| SPX0168 | 168 | 2829 | 207 | 69 | | |

Description

NO-HIT

| ORF Name | NT ID | AA ID | NT/LN | AA/LN | Score | P-Value |
|---|---|---|---|---|---|---|
| SPX0169 | 169 | 2830 | 630 | 210 | 520 | 4.10E-72 |

Description

[GI:6707004] [LN:AF109218] [AC:AF109218:U96108] [PN:ThiE] [GN:thiE] [OR:Staphylococcus carnosus]

| ORF Name | NT ID | AA ID | NT/LN | AA/LN | Score | P-Value |
|---|---|---|---|---|---|---|
| SPX0170 | 170 | 2831 | 804 | 268 | 523 | 4.60E-67 |

Description

[GI:6707003] [LN:AF109218] [AC:AF109218:U96108] [PN:ThiM] [GN:thiM] [OR:Staphylococcus carnosus]

| ORF Name | NT ID | AA ID | NT/LN | AA/LN | Score | P-Value |
|---|---|---|---|---|---|---|
| SPX0171 | 171 | 2832 | 411 | 137 | 114 | 2.00E-08 |

Description

[LN:H71057] [AC:H71057] [PN:hypothetical protein PH1158] [GN:PH1158] [OR:Pyrococcus horikoshii]

| ORF Name | NT ID | AA ID | NT/LN | AA/LN | Score | P-Value |
|---|---|---|---|---|---|---|
| SPX0172 | 172 | 2833 | 246 | 82 | | |

Description

NO-HIT

| ORF Name | NT ID | AA ID | NT/LN | AA/LN | Score | P-Value |
|---|---|---|---|---|---|---|
| SPX0173 | 173 | 2834 | 225 | 75 | 203 | 1.90E-23 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX0174 | 174 | 2835 | 669 | 223 | 127 | 6.60E-15 |

Description

"[LN:PT18_YEAST] [AC:P25362] [GN:PET18:HIT2:YCR020C:YCR20C]
[OR:Saccharomyces cerevisiae] [SR:,Baker's yeast] [DE:PET18 PROTEIN]
[SP:P25362]"

| ORF Name | NT ID | AA ID | NT/LN | AA/LN | Score | P-Value |
|---|---|---|---|---|---|---|
| SPX0175 | 175 | 2836 | 1137 | 379 | 1379 | 5.20E-216 |

Description

[GI:2239174] [LN:SILCT] [AC:Y07622] [PN:lactate oxidase] [GN:lctO]
[FN:lactate utilisation] [OR:Streptococcus iniae]

| ORF Name | NT ID | AA ID | NT/LN | AA/LN | Score | P-Value |
|---|---|---|---|---|---|---|
| SPX0176 | 176 | 2837 | 1491 | 497 | 1157 | 1.60E-228 |

Description

"[LN:SYK_BACSU] [AC:P37477] [GN:LYSS] [OR:Bacillus subtilis] [EC:6.1.1.6]
[DE:LYSYL-TRNA SYNTHETASE, (LYSINE--TRNA LIGASE) (LYSRS)] [SP:P37477]"

| ORF Name | NT ID | AA ID | NT/LN | AA/LN | Score | P-Value |
|---|---|---|---|---|---|---|
| SPX0177 | 177 | 2838 | 681 | 227 | 351 | 2.10E-70 |

Description

"[LN:D71849] [AC:D71849] [PN:amino acid ABC transporter, permease protein]
[GN:jhp1096] [CL:histidine permease protein M] [OR:Helicobacter pylori]
[SR:strain J99, , strain J99] [SR:strain J99, ]"

| ORF Name | NT ID | AA ID | NT/LN | AA/LN | Score | P-Value |
|---|---|---|---|---|---|---|
| SPX0178 | 178 | 2839 | 381 | 127 | 279 | 2.10E-35 |

Description

"[LN:B64666] [AC:B64666] [PN:glutamine ABC transporter, permease protein]
[CL:histidine permease protein M] [OR:Helicobacter pylori]"

| ORF Name | NT ID | AA ID | NT/LN | AA/LN | Score | P-Value |
|---|---|---|---|---|---|---|
| SPX0179 | 179 | 2840 | 288 | 96 | 249 | 4.10E-30 |

Description

"[LN:B64666] [AC:B64666] [PN:glutamine ABC transporter, permease protein]
[CL:histidine permease protein M] [OR:Helicobacter pylori]"

| ORF Name | NT ID | AA ID | NT/LN | AA/LN | Score | P-Value |
|---|---|---|---|---|---|---|
| SPX0180 | 180 | 2841 | 213 | 71 | 92 | 5.90E-05 |

Description

[GI:4163988] [LN:AF082511] [AC:AF082511] [PN:putative ATP-binding protein MglA] [GN:mglA] [OR:Treponema denticola]

| ORF Name | NT ID | AA ID | NT/LN | AA/LN | Score | P-Value |
|---|---|---|---|---|---|---|
| SPX0181 | 181 | 2842 | 507 | 169 | 531 | 5.00E-70 |

Description

[LN:H81391] [AC:H81391] [PN:amino-acid ABC transporter ATP-binding protein Cj0469 [imported]] [GN:Cj0469] [OR:Campylobacter jejuni]

| ORF Name | NT ID | AA ID | NT/LN | AA/LN | Score | P-Value |
|---|---|---|---|---|---|---|
| SPX0182 | 182 | 2843 | 201 | 67 | 72 | 3.30E-07 |

Description

[LN:G72510] [AC:G72510] [PN:hypothetical protein APE2061] [GN:APE2061] [OR:Aeropyrum pernix]

| ORF Name | NT ID | AA ID | NT/LN | AA/LN | Score | P-Value |
|---|---|---|---|---|---|---|
| SPX0183 | 183 | 2844 | 243 | 81 | 132 | 5.50E-12 |

Description

[GI:4204972] [LN:LLU60994] [AC:U60994] [FN:transport systems for basic amino acids and] [OR:Leuconostoc lactis]

| ORF Name | NT ID | AA ID | NT/LN | AA/LN | Score | P-Value |
|---|---|---|---|---|---|---|
| SPX0184 | 184 | 2845 | 555 | 185 | 531 | 1.40E-67 |

Description

[LN:C81373] [AC:C81373] [PN:probable amino-acid transporter periplasmic solute-binding protein Cj0982c [imported]] [GN:Cj0982c] [OR:Campylobacter jejuni]

| ORF Name | NT ID | AA ID | NT/LN | AA/LN | Score | P-Value |
|---|---|---|---|---|---|---|
| SPX0185 | 185 | 2846 | 648 | 216 | 353 | 6.60E-51 |

Description

[LN:YYBJ_BACSU] [AC:P37494] [GN:YYBJ] [OR:Bacillus subtilis] [DE:INTERGENIC REGION] [SP:P37494]

| ORF Name | NT ID | AA ID | NT LN | AA LN | Score | P-Value |
|---|---|---|---|---|---|---|
| SPX0186 | 186 | 2847 | 705 | 235 | | |
| Description | | | | | | |

NO-HIT

| ORF Name | NT ID | AA ID | NT LN | AA LN | Score | P-Value |
|---|---|---|---|---|---|---|
| SPX0187 | 187 | 2848 | 204 | 68 | | |
| Description | | | | | | |

NO-HIT

| ORF Name | NT ID | AA ID | NT LN | AA LN | Score | P-Value |
|---|---|---|---|---|---|---|
| SPX0188 | 188 | 2849 | 807 | 269 | | |
| Description | | | | | | |

NO-HIT

| ORF Name | NT ID | AA ID | NT LN | AA LN | Score | P-Value |
|---|---|---|---|---|---|---|
| SPX0189 | 189 | 2850 | 765 | 255 | | |
| Description | | | | | | |

NO-HIT

| ORF Name | NT ID | AA ID | NT LN | AA LN | Score | P-Value |
|---|---|---|---|---|---|---|
| SPX0190 | 190 | 2851 | 351 | 117 | | |
| Description | | | | | | |

NO-HIT

| ORF Name | NT ID | AA ID | NT LN | AA LN | Score | P-Value |
|---|---|---|---|---|---|---|
| SPX0191 | 191 | 2852 | 633 | 211 | 1057 | 1.30E-140 |
| Description | | | | | | |

[GI:4009484] [LN:AF068902] [AC:AF068902] [PN:orotate phosphoribosyltransferase PyrE] [GN:pyrE] [OR:Streptococcus pneumoniae]

| ORF Name | NT ID | AA ID | NT/LN | AA/LN | Score | P-Value |
|---|---|---|---|---|---|---|
| SPX0192 | 192 | 2853 | 702 | 234 | 1173 | 1.80E-157 |

Description

[GI:4009483] [LN:AF068902] [AC:AF068902] [PN:orotidine-5'-decarboxylase PyrF] [GN:pyrF] [OR:Streptococcus pneumoniae]

| ORF Name | NT ID | AA ID | NT/LN | AA/LN | Score | P-Value |
|---|---|---|---|---|---|---|
| SPX0193 | 193 | 2854 | 201 | 67 | | |

Description

NO-HIT

| ORF Name | NT ID | AA ID | NT/LN | AA/LN | Score | P-Value |
|---|---|---|---|---|---|---|
| SPX0194 | 194 | 2855 | 1200 | 400 | 1946 | 3.00E-251 |

Description

[GI:4009482] [LN:AF068902] [AC:AF068902] [PN:cell division protein DivIB] [GN:divIB] [OR:Streptococcus pneumoniae]

| ORF Name | NT ID | AA ID | NT/LN | AA/LN | Score | P-Value |
|---|---|---|---|---|---|---|
| SPX0195 | 195 | 2856 | 444 | 148 | 110 | 2.20E-07 |

Description

"[GI:6473880] [LN:AB027890] [AC:AB027890] [PN:Hypothetical protein] [GN:SPBC3D5.14C] [OR:Schizosaccharomyces pombe] [SR:Schizosaccharomyces pombe (strain:968 h90) DNA, clone:TA46]"

| ORF Name | NT ID | AA ID | NT/LN | AA/LN | Score | P-Value |
|---|---|---|---|---|---|---|
| SPX0196 | 196 | 2857 | 1059 | 353 | 1780 | 1.40E-242 |

Description

[GI:4009481] [LN:AF068902] [AC:AF068902] [PN:undecaprenyl-PP-MurNAc-pentapeptide-UDPGlcNAc] [GN:murG] [OR:Streptococcus pneumoniae]

| ORF Name | NT ID | AA ID | NT/LN | AA/LN | Score | P-Value |
|---|---|---|---|---|---|---|
| SPX0197 | 197 | 2858 | 1353 | 451 | 2206 | 1.20E-297 |

Description

[GI:4009480] [LN:AF068902] [AC:AF068902] [PN:D-glutamic acid adding enzyme MurD] [GN:murD] [OR:Streptococcus pneumoniae]

| ORF Name | NT ID | AA ID | NT/LN | AA/LN | Score | P-Value |
|---|---|---|---|---|---|---|
| SPX0198 | 198 | 2859 | 642 | 214 | 1062 | 1.20E-142 |
| Description | | | | | | |

[GI:4009479] [LN:AF068902] [AC:AF068902] [PN:unknown] [OR:Streptococcus pneumoniae]

| ORF Name | NT ID | AA ID | NT/LN | AA/LN | Score | P-Value |
|---|---|---|---|---|---|---|
| SPX0199 | 199 | 2860 | 2022 | 674 | 2263 | 0 |
| Description | | | | | | |

[GI:4009478] [LN:AF068902] [AC:AF068902] [PN:unknown] [OR:Streptococcus pneumoniae]

| ORF Name | NT ID | AA ID | NT/LN | AA/LN | Score | P-Value |
|---|---|---|---|---|---|---|
| SPX0200 | 200 | 2861 | 405 | 135 | 86 | 1.80E-05 |
| Description | | | | | | |

[GI:7576923] [LN:AF242367] [AC:AF242367] [PN:lactococcin 972] [GN:lclA] [OR:Lactococcus lactis subsp. lactis]

| ORF Name | NT ID | AA ID | NT/LN | AA/LN | Score | P-Value |
|---|---|---|---|---|---|---|
| SPX0201 | 201 | 2862 | 219 | 73 | | |
| Description | | | | | | |

NO-HIT

| ORF Name | NT ID | AA ID | NT/LN | AA/LN | Score | P-Value |
|---|---|---|---|---|---|---|
| SPX0202 | 202 | 2863 | 255 | 85 | 89 | 2.50E-05 |
| Description | | | | | | |

[LN:T20916] [AC:T20916] [PN:hypothetical protein F14F8.3] [GN:F14F8.3] [OR:Caenorhabditis elegans]

| ORF Name | NT ID | AA ID | NT/LN | AA/LN | Score | P-Value |
|---|---|---|---|---|---|---|
| SPX0203 | 203 | 2864 | 1863 | 621 | 1706 | 0 |
| Description | | | | | | |

[LN:TYPA_BACSU] [AC:O07631] [GN:TYPA] [OR:Bacillus subtilis] [DE:GTP-BINDING PROTEIN TYPA/BIPA HOMOLOG] [SP:O07631]

| ORF Name | NT ID | AA ID | NT/LN | AA/LN | Score | P-Value |
|---|---|---|---|---|---|---|
| SPX0204 | 204 | 2865 | 726 | 242 | 154 | 3.00E-34 |

Description

[GI:7328274] [LN:SAY14816] [AC:Y14816] [PN:hypothetical protein] [GN:ORF231] [OR:Staphylococcus aureus]

| ORF Name | NT ID | AA ID | NT/LN | AA/LN | Score | P-Value |
|---|---|---|---|---|---|---|
| SPX0205 | 205 | 2866 | 198 | 66 | | |

Description

NO-HIT

| ORF Name | NT ID | AA ID | NT/LN | AA/LN | Score | P-Value |
|---|---|---|---|---|---|---|
| SPX0206 | 206 | 2867 | 381 | 127 | 174 | 3.80E-28 |

Description

[LN:YQHL_BACSU] [AC:P54510] [GN:YQHL] [OR:Bacillus subtilis]
[DE:HYPOTHETICAL 14.6 KD PROTEIN IN GCVT-SPOIIIAA INTERGENIC REGION]
[SP:P54510]

| ORF Name | NT ID | AA ID | NT/LN | AA/LN | Score | P-Value |
|---|---|---|---|---|---|---|
| SPX0207 | 207 | 2868 | 222 | 74 | 158 | 1.80E-17 |

Description

[LN:T44786] [AC:T44786] [PN:hypothetical protein 1 [imported]] [OR:Bacillus megaterium]

| ORF Name | NT ID | AA ID | NT/LN | AA/LN | Score | P-Value |
|---|---|---|---|---|---|---|
| SPX0208 | 208 | 2869 | 909 | 303 | 1241 | 5.30E-168 |

Description

[LN:T44638] [AC:T44638] [PN:capsular polysaccharide biosynthesis protein cpsY [imported]] [GN:cpsY] [CL:probable transcription regulator lsyR] [OR:Streptococcus agalactiae]

| ORF Name | NT ID | AA ID | NT/LN | AA/LN | Score | P-Value |
|---|---|---|---|---|---|---|
| SPX0209 | 209 | 2870 | 756 | 252 | 476 | 5.30E-66 |

Description

[LN:YQJQ_BACSU] [AC:P54554] [GN:YQJQ] [OR:Bacillus subtilis] [EC:1.-.-.-]
[DE:(EC 1.-.-.-)] [SP:P54554]

| ORF Name | NT ID | AA ID | NT/LN | AA/LN | Score | P-Value |
|---|---|---|---|---|---|---|
| SPX0210 | 210 | 2871 | 930 | 310 | 368 | 9.50E-98 |

Description

[LN:YQJK_BACSU] [AC:P54548] [GN:YQJK] [OR:Bacillus subtilis]
[DE:HYPOTHETICAL 34.0 KD PROTEIN IN GLNQ-ANSR INTERGENIC REGION] [SP:P54548]

| ORF Name | NT ID | AA ID | NT/LN | AA/LN | Score | P-Value |
|---|---|---|---|---|---|---|
| SPX0211 | 211 | 2872 | 624 | 208 | | |

Description

NO-HIT

| ORF Name | NT ID | AA ID | NT/LN | AA/LN | Score | P-Value |
|---|---|---|---|---|---|---|
| SPX0212 | 212 | 2873 | 1239 | 413 | 792 | 1.40E-103 |

Description

[LN:B69888] [AC:B69888] [PN:GTP-binding protein proteinase modulator homolog ynbA] [GN:ynbA] [CL:GTP-binding protein hflX:translation elongation factor Tu homology] [OR:Bacillus subtilis]

| ORF Name | NT ID | AA ID | NT/LN | AA/LN | Score | P-Value |
|---|---|---|---|---|---|---|
| SPX0213 | 213 | 2874 | 936 | 312 | 317 | 7.10E-70 |

Description

[LN:G69657] [AC:G69657] [PN:tRNA isopentenylpyrophosphate transferase miaA] [GN:miaA] [CL:delta(2)-isopentenylpyrophosphate transferase] [OR:Bacillus subtilis]

| ORF Name | NT ID | AA ID | NT/LN | AA/LN | Score | P-Value |
|---|---|---|---|---|---|---|
| SPX0214 | 214 | 2875 | 189 | 63 | | |

Description

NO-HIT

| ORF Name | NT ID | AA ID | NT/LN | AA/LN | Score | P-Value |
|---|---|---|---|---|---|---|
| SPX0215 | 215 | 2876 | 198 | 66 | 129 | 6.10E-12 |

Description

"[LN:TYSY_LACLA] [AC:P19368] [GN:THYA] [OR:Lactococcus lactis]
[SR:,subsplactis:Streptococcus lactis] [EC:2.1.1.45] [DE:THYMIDYLATE SYNTHASE, (TS)] [SP:P19368]"

| ORF Name | NT ID | AA ID | NT/LN | AA/LN | Score | P-Value |
|---|---|---|---|---|---|---|
| SPX0216 | 216 | 2877 | 663 | 221 | 318 | 1.20E-39 |

Description

[GI:7328278] [LN:SAY14816] [AC:Y14816] [PN:hypothetical protein] [GN:ORF242]
[OR:Staphylococcus aureus]

| ORF Name | NT ID | AA ID | NT/LN | AA/LN | Score | P-Value |
|---|---|---|---|---|---|---|
| SPX0217 | 217 | 2878 | 636 | 212 | 691 | 4.80E-91 |

Description

[LN:B69997] [AC:B69997] [PN:conserved hypothetical protein ytmQ] [GN:ytmQ]
[CL:hypothetical protein HI0340] [OR:Bacillus subtilis]

| ORF Name | NT ID | AA ID | NT/LN | AA/LN | Score | P-Value |
|---|---|---|---|---|---|---|
| SPX0218 | 218 | 2879 | 267 | 89 | | |

Description

NO-HIT

| ORF Name | NT ID | AA ID | NT/LN | AA/LN | Score | P-Value |
|---|---|---|---|---|---|---|
| SPX0219 | 219 | 2880 | 309 | 103 | 215 | 6.90E-25 |

Description

[LN:YLXS_BACSU] [AC:P32726] [GN:YLXS] [OR:Bacillus subtilis]
[DE:HYPOTHETICAL 17.6 KD PROTEIN IN NUSA 5'REGION (P15A) (ORF1)] [SP:P32726]

| ORF Name | NT ID | AA ID | NT/LN | AA/LN | Score | P-Value |
|---|---|---|---|---|---|---|
| SPX0220 | 220 | 2881 | 1137 | 379 | 715 | 6.00E-122 |

Description

[GI:2634032] [LN:BSUB0009] [AC:Z99112:AL009126] [GN:nusA] [FN:transcription
termination] [OR:Bacillus subtilis]

| ORF Name | NT ID | AA ID | NT/LN | AA/LN | Score | P-Value |
|---|---|---|---|---|---|---|
| SPX0221 | 221 | 2882 | 294 | 98 | 220 | 1.70E-25 |

Description

[LN:YLXR_BACSU] [AC:P32728] [GN:YLXR] [OR:Bacillus subtilis]
[DE:HYPOTHETICAL 10.4 KD PROTEIN IN NUSA-INFB INTERGENIC REGION (ORF3)]
[SP:P32728]

114

| ORF Name | NT ID | AA ID | NT/LN | AA/LN | Score | P-Value |
|---|---|---|---|---|---|---|
| SPX0222 | 222 | 2883 | 300 | 100 | 259 | 3.80E-31 |

Description

"[LN:YLXQ_ENTFC] [AC:P55768] [OR:Enterococcus faecium] [SR:,Streptococcus faecium] [DE:PROBABLE RIBOSOMAL PROTEIN IN INFB 5'REGION] [SP:P55768]"

| ORF Name | NT ID | AA ID | NT/LN | AA/LN | Score | P-Value |
|---|---|---|---|---|---|---|
| SPX0223 | 223 | 2884 | 495 | 165 | | |

Description

NO-HIT

| ORF Name | NT ID | AA ID | NT/LN | AA/LN | Score | P-Value |
|---|---|---|---|---|---|---|
| SPX0224 | 224 | 2885 | 2793 | 931 | 2768 | 0 |

Description

[GI:3947714] [LN:SAAJ3164] [AC:AJ003164] [PN:initiation factor IF2] [GN:infB] [FN:translation initiation factor] [OR:Streptococcus agalactiae]

| ORF Name | NT ID | AA ID | NT/LN | AA/LN | Score | P-Value |
|---|---|---|---|---|---|---|
| SPX0225 | 225 | 2886 | 246 | 82 | | |

Description

NO-HIT

| ORF Name | NT ID | AA ID | NT/LN | AA/LN | Score | P-Value |
|---|---|---|---|---|---|---|
| SPX0226 | 226 | 2887 | 351 | 117 | 478 | 2.00E-61 |

Description

[GI:3947715] [LN:SAAJ3164] [AC:AJ003164] [PN:ribosome binding factor A] [GN:rbfA] [FN:ribosome maturation] [OR:Streptococcus agalactiae]

| ORF Name | NT ID | AA ID | NT/LN | AA/LN | Score | P-Value |
|---|---|---|---|---|---|---|
| SPX0227 | 227 | 2888 | 780 | 260 | 217 | 3.30E-40 |

Description

[LN:T35040] [AC:T35040] [PN:hypothetical protein SC4G2.05 SC4G2.05] [GN:SC4G2.05] [OR:Streptomyces coelicolor]

| ORF Name | NT ID | AA ID | NT LN | AA LN | Score | P-Value |
|---|---|---|---|---|---|---|
| SPX0228 | 228 | 2889 | 252 | 84 | | |

Description

NO-HIT

| ORF Name | NT ID | AA ID | NT LN | AA LN | Score | P-Value |
|---|---|---|---|---|---|---|
| SPX0229 | 229 | 2890 | 222 | 74 | | |

Description

NO-HIT

| ORF Name | NT ID | AA ID | NT LN | AA LN | Score | P-Value |
|---|---|---|---|---|---|---|
| SPX0230 | 230 | 2891 | 195 | 65 | 202 | 2.70E-24 |

Description

[LN:T30285] [AC:T30285] [PN:hypothetical protein] [OR:Streptococcus pneumoniae]

| ORF Name | NT ID | AA ID | NT LN | AA LN | Score | P-Value |
|---|---|---|---|---|---|---|
| SPX0231 | 231 | 2892 | 234 | 78 | 102 | 4.60E-08 |

Description

[LN:A69271] [AC:A69271] [PN:hypothetical protein AF0169] [CL:Archaeoglobus fulgidus hypothetical protein AF0169] [OR:Archaeoglobus fulgidus]

| ORF Name | NT ID | AA ID | NT LN | AA LN | Score | P-Value |
|---|---|---|---|---|---|---|
| SPX0232 | 232 | 2893 | 1335 | 445 | 123 | 1.30E-41 |

Description

[LN:B69271] [AC:B69271] [PN:hypothetical protein AF0170] [OR:Archaeoglobus fulgidus]

| ORF Name | NT ID | AA ID | NT LN | AA LN | Score | P-Value |
|---|---|---|---|---|---|---|
| SPX0233 | 233 | 2894 | 255 | 85 | | |

Description

NO-HIT

| ORF Name | NT ID | AA ID | NT LN | AA LN | Score | P-Value |
|---|---|---|---|---|---|---|
| SPX0234 | 234 | 2895 | 396 | 132 | | |

Description

NO-HIT

| ORF Name | NT ID | AA ID | NT LN | AA LN | Score | P-Value |
|---|---|---|---|---|---|---|
| SPX0235 | 235 | 2896 | 207 | 69 | | |

Description

NO-HIT

| ORF Name | NT ID | AA ID | NT LN | AA LN | Score | P-Value |
|---|---|---|---|---|---|---|
| SPX0236 | 236 | 2897 | 450 | 150 | | |

Description

NO-HIT

| ORF Name | NT ID | AA ID | NT LN | AA LN | Score | P-Value |
|---|---|---|---|---|---|---|
| SPX0237 | 237 | 2898 | 558 | 186 | 148 | 2.10E-18 |

Description

[LN:YP20_BACLI] [AC:P05332] [GN:P20] [OR:Bacillus licheniformis] [DE:HYPOTHETICAL P20 PROTEIN] [SP:P05332]

| ORF Name | NT ID | AA ID | NT LN | AA LN | Score | P-Value |
|---|---|---|---|---|---|---|
| SPX0238 | 238 | 2899 | 963 | 321 | | |

Description

NO-HIT

| ORF Name | NT ID | AA ID | NT LN | AA LN | Score | P-Value |
|---|---|---|---|---|---|---|
| SPX0239 | 239 | 2900 | 2652 | 884 | 1594 | 0 |

Description

"[LN:SYV_BACSU] [AC:Q05873] [GN:VALS] [OR:Bacillus subtilis] [EC:6.1.1.9] [DE:VALYL-TRNA SYNTHETASE, (VALINE--TRNA LIGASE) (VALRS)] [SP:Q05873]"

| ORF Name | NT ID | AA ID | NT LN | AA LN | Score | P-Value |
|---|---|---|---|---|---|---|
| SPX0240 | 240 | 2901 | 756 | 252 | 642 | 7.80E-85 |

Description

"[LN:B71947] [AC:B71947] [PN:hypothetical protein jhp0330] [GN:jhp0330] [OR:Helicobacter pylori] [SR:strain J99, , strain J99] [SR:strain J99, ]"

| ORF Name | NT ID | AA ID | NT LN | AA LN | Score | P-Value |
|---|---|---|---|---|---|---|
| SPX0241 | 241 | 2902 | 804 | 268 | 91 | 1.80E-05 |

Description

"[LN:Y4LH_RHISN] [AC:P55548] [GN:Y4LH] [OR:Rhizobium sp] [SR:,strain NGR234] [DE:HYPOTHETICAL 22.4 KD PROTEIN Y4LH] [SP:P55548]"

| ORF Name | NT ID | AA ID | NT LN | AA LN | Score | P-Value |
|---|---|---|---|---|---|---|
| SPX0242 | 242 | 2903 | 285 | 95 | 387 | 3.10E-49 |

Description

[GI:1490399] [LN:SPPARCETP] [AC:Z67739] [PN:DNA transposase] [OR:Streptococcus pneumoniae]

| ORF Name | NT ID | AA ID | NT LN | AA LN | Score | P-Value |
|---|---|---|---|---|---|---|
| SPX0243 | 243 | 2904 | 306 | 102 | 323 | 2.70E-40 |

Description

[GI:1490399] [LN:SPPARCETP] [AC:Z67739] [PN:DNA transposase] [OR:Streptococcus pneumoniae]

| ORF Name | NT ID | AA ID | NT LN | AA LN | Score | P-Value |
|---|---|---|---|---|---|---|
| SPX0244 | 244 | 2905 | 273 | 91 | 315 | 2.50E-39 |

Description

[LN:A33595] [AC:A33595:A30868] [PN:probable transposase] [CL:transposase IS3] [OR:Streptococcus agalactiae]

| ORF Name | NT ID | AA ID | NT LN | AA LN | Score | P-Value |
|---|---|---|---|---|---|---|
| SPX0245 | 245 | 2906 | 276 | 92 | 135 | 3.80E-13 |

Description

[LN:B30868] [AC:B30868] [PN:hypothetical protein 1] [OR:Streptococcus agalactiae]

| ORF Name | NT ID | AA ID | NT LN | AA LN | Score | P-Value |
|---|---|---|---|---|---|---|
| SPX0246 | 246 | 2907 | 1266 | 422 | | |

Description

NO-HIT

| ORF Name | NT ID | AA ID | NT LN | AA LN | Score | P-Value |
|---|---|---|---|---|---|---|
| SPX0247 | 247 | 2908 | 1197 | 399 | 109 | 9.90E-10 |

Description

[GI:6689196] [LN:SCE20] [AC:AL136058] [PN:putative helicase] [GN:SCE20.37] [OR:Streptomyces coelicolor A3(2)]

| ORF Name | NT ID | AA ID | NT LN | AA LN | Score | P-Value |
|---|---|---|---|---|---|---|
| SPX0248 | 248 | 2909 | 294 | 98 | | |

Description

NO-HIT

| ORF Name | NT ID | AA ID | NT LN | AA LN | Score | P-Value |
|---|---|---|---|---|---|---|
| SPX0249 | 249 | 2910 | 840 | 280 | 489 | 2.30E-81 |

Description

[LN:LICT_BACSU] [AC:P39805] [GN:LICT:N15A] [OR:Bacillus subtilis] [DE:TRANSCRIPTION ANTITERMINATOR LICT] [SP:P39805]

| ORF Name | NT ID | AA ID | NT LN | AA LN | Score | P-Value |
|---|---|---|---|---|---|---|
| SPX0250 | 250 | 2911 | 1839 | 613 | 534 | 8.10E-147 |

Description

"[LN:PTBA_BACSU] [AC:P40739:Q45661] [GN:BGLP:N17C] [OR:Bacillus subtilis] [EC:2.7.1.69] [DE:ENZYME II, ABC COMPONENT), (EII-BGL)] [SP:P40739:Q45661]"

| ORF Name | NT ID | AA ID | NT LN | AA LN | Score | P-Value |
|---|---|---|---|---|---|---|
| SPX0251 | 251 | 2912 | 1416 | 472 | 1046 | 3.70E-228 |

Description

"[LN:ABGA_CLOLO] [AC:Q46130] [GN:ABGA] [OR:Clostridium longisporum] [EC:3.2.1.86] [DE:6-PHOSPHO-BETA-GLUCOSIDASE,] [SP:Q46130]"

| ORF_Name | NT_ID | AA_ID | $\frac{NT}{LN}$ | $\frac{AA}{LN}$ | Score | P-Value |
|---|---|---|---|---|---|---|
| SPX0252 | 252 | 2913 | 1047 | 349 | 656 | 3.10E-156 |

Description

[LN:SYFA_BACSU] [AC:P17921:P94539] [GN:PHES] [OR:Bacillus subtilis]
[EC:6.1.1.20] [DE:-TRNA LIGASE ALPHA CHAIN) (PHERS)] [SP:P17921:P94539]

| ORF_Name | NT_ID | AA_ID | $\frac{NT}{LN}$ | $\frac{AA}{LN}$ | Score | P-Value |
|---|---|---|---|---|---|---|
| SPX0253 | 253 | 2914 | 993 | 331 | | |

Description

NO-HIT

| ORF_Name | NT_ID | AA_ID | $\frac{NT}{LN}$ | $\frac{AA}{LN}$ | Score | P-Value |
|---|---|---|---|---|---|---|
| SPX0254 | 254 | 2915 | 510 | 170 | 333 | 1.80E-41 |

Description

"[LN:YPIP_LACDL] [AC:P46543] [OR:Lactobacillus delbrueckii]
[SR:,subsplactis] [DE:HYPOTHETICAL 19.8 KD PROTEIN IN PEPI 3'REGION]
[SP:P46543]"

| ORF_Name | NT_ID | AA_ID | $\frac{NT}{LN}$ | $\frac{AA}{LN}$ | Score | P-Value |
|---|---|---|---|---|---|---|
| SPX0255 | 255 | 2916 | 2403 | 801 | 312 | 2.20E-132 |

Description

"[LN:SYFB_SYNY3] [AC:P74296] [GN:PHET:SLL1553] [OR:Synechocystis sp]
[SR:,strain PCC 6803] [EC:6.1.1.20] [DE:TRNA LIGASE BETA CHAIN) (PHERS)]
[SP:P74296]"

| ORF_Name | NT_ID | AA_ID | $\frac{NT}{LN}$ | $\frac{AA}{LN}$ | Score | P-Value |
|---|---|---|---|---|---|---|
| SPX0256 | 256 | 2917 | 888 | 296 | | |

Description

NO-HIT

| ORF_Name | NT_ID | AA_ID | $\frac{NT}{LN}$ | $\frac{AA}{LN}$ | Score | P-Value |
|---|---|---|---|---|---|---|
| SPX0257 | 257 | 2918 | 447 | 149 | 437 | 4.90E-55 |

Description

[GI:517210] [LN:SPU11799] [AC:U11799] [OR:Streptococcus pyogenes]

| ORF Name | NT ID | AA ID | NT/LN | AA/LN | Score | P-Value |
|---|---|---|---|---|---|---|
| SPX0258 | 258 | 2919 | 267 | 89 | 245 | 2.00E-28 |

Description

[LN:Y659_HAEIN] [AC:P44030] [GN:HI0659] [OR:Haemophilus influenzae] [DE:HYPOTHETICAL PROTEIN HI0659] [SP:P44030]

| ORF Name | NT ID | AA ID | NT/LN | AA/LN | Score | P-Value |
|---|---|---|---|---|---|---|
| SPX0259 | 259 | 2920 | 297 | 99 | | |

Description

NO-HIT

| ORF Name | NT ID | AA ID | NT/LN | AA/LN | Score | P-Value |
|---|---|---|---|---|---|---|
| SPX0260 | 260 | 2921 | 2250 | 750 | 1309 | 6.60E-297 |

Description

"[LN:C81326] [AC:C81326] [PN:5-methyltetrahydropteroyltriglutamate--homocystei methyltransferase, Cj1201 [imported]] [GN:metE:Cj1201] [OR:Campylobacter jejuni] [EC:2.1.1.14]"

| ORF Name | NT ID | AA ID | NT/LN | AA/LN | Score | P-Value |
|---|---|---|---|---|---|---|
| SPX0261 | 261 | 2922 | 867 | 289 | 261 | 3.90E-77 |

Description

"[LN:D81326] [AC:D81326] [PN:5,10-methylenetetrahydrofolate reductase, Cj1202 [imported]] [GN:metF:Cj1202] [OR:Campylobacter jejuni] [EC:1.7.99.5]"

| ORF Name | NT ID | AA ID | NT/LN | AA/LN | Score | P-Value |
|---|---|---|---|---|---|---|
| SPX0262 | 262 | 2923 | 270 | 90 | | |

Description

NO-HIT

| ORF Name | NT ID | AA ID | NT/LN | AA/LN | Score | P-Value |
|---|---|---|---|---|---|---|
| SPX0263 | 263 | 2924 | 2214 | 738 | 1323 | 3.80E-298 |

Description

[LN:PNPA_BACSU] [AC:P50849] [GN:PNPA:COMR] [OR:Bacillus subtilis] [EC:2.7.7.8] [DE:PHOSPHORYLASE) (PNPASE) (VEGETATIVE PROTEIN 15) (VEG15)] [SP:P50849]

| ORF Name | NT ID | AA ID | NT LN | AA LN | Score | P-Value |
|---|---|---|---|---|---|---|
| SPX0264 | 264 | 2925 | 618 | 206 | 493 | 1.20E-63 |

Description

[GI:6899995] [LN:CST130879] [AC:AJ130879] [PN:serine acetyltransferase] [GN:cysE] [OR:Clostridium sticklandii]

| ORF Name | NT ID | AA ID | NT LN | AA LN | Score | P-Value |
|---|---|---|---|---|---|---|
| SPX0265 | 265 | 2926 | 885 | 295 | 113 | 3.80E-07 |

Description

[LN:E69786] [AC:E69786] [PN:ribosomal-protein-alanine N-acetyltransfer homolog ydiD] [GN:ydiD] [CL:Escherichia coli ribosomal-protein-alanine N-acetyltransferase rimI] [OR:Bacillus subtilis]

| ORF Name | NT ID | AA ID | NT LN | AA LN | Score | P-Value |
|---|---|---|---|---|---|---|
| SPX0266 | 266 | 2927 | 456 | 152 | | |

Description

NO-HIT

| ORF Name | NT ID | AA ID | NT LN | AA LN | Score | P-Value |
|---|---|---|---|---|---|---|
| SPX0267 | 267 | 2928 | 1344 | 448 | 570 | 9.00E-167 |

Description

[GI:6899996] [LN:CST130879] [AC:AJ130879] [PN:cysteinyl tRNA synthetase] [GN:cysRS] [OR:Clostridium sticklandii]

| ORF Name | NT ID | AA ID | NT LN | AA LN | Score | P-Value |
|---|---|---|---|---|---|---|
| SPX0268 | 268 | 2929 | 387 | 129 | 316 | 6.30E-39 |

Description

[LN:C69742] [AC:C69742] [PN:conserved hypothetical protein yazC] [GN:yazC] [OR:Bacillus subtilis]

| ORF Name | NT ID | AA ID | NT LN | AA LN | Score | P-Value |
|---|---|---|---|---|---|---|
| SPX0269 | 269 | 2930 | 885 | 295 | 224 | 3.10E-30 |

Description

[LN:LRPR_STREQ] [AC:Q54087] [GN:LRP] [OR:Streptococcus equisimilis] [DE:LEUCINE RICH PROTEIN] [SP:Q54087]

| ORF Name | NT ID | AA ID | NT/LN | AA/LN | Score | P-Value |
|---|---|---|---|---|---|---|
| SPX0270 | 270 | 2931 | 264 | 88 | | |
| Description | | | | | | |

NO-HIT

| ORF Name | NT ID | AA ID | NT/LN | AA/LN | Score | P-Value |
|---|---|---|---|---|---|---|
| SPX0271 | 271 | 2932 | 600 | 200 | | |
| Description | | | | | | |

NO-HIT

| ORF Name | NT ID | AA ID | NT/LN | AA/LN | Score | P-Value |
|---|---|---|---|---|---|---|
| SPX0272 | 272 | 2933 | 156 | 52 | 87 | 3.30E-06 |
| Description | | | | | | |

[LN:D75542] [AC:D75542] [PN:hypothetical protein] [GN:DR0254]
[OR:Deinococcus radiodurans]

| ORF Name | NT ID | AA ID | NT/LN | AA/LN | Score | P-Value |
|---|---|---|---|---|---|---|
| SPX0273 | 273 | 2934 | 246 | 82 | 247 | 1.10E-29 |
| Description | | | | | | |

[LN:F81737] [AC:F81737] [PN:hypothetical protein TC0129 [imported]]
[GN:TC0129] [OR:Chlamydia muridarum:Chlamydia trachomatis MoPn]

| ORF Name | NT ID | AA ID | NT/LN | AA/LN | Score | P-Value |
|---|---|---|---|---|---|---|
| SPX0274 | 274 | 2935 | 234 | 78 | 143 | 4.90E-15 |
| Description | | | | | | |

[LN:F71245] [AC:F71245] [PN:hypothetical protein PHS004] [GN:PHS004]
[OR:Pyrococcus horikoshii]

| ORF Name | NT ID | AA ID | NT/LN | AA/LN | Score | P-Value |
|---|---|---|---|---|---|---|
| SPX0275 | 275 | 2936 | 216 | 72 | | |
| Description | | | | | | |

NO-HIT

| ORF Name | NT ID | AA ID | NT/LN | AA/LN | Score | P-Value |
|---|---|---|---|---|---|---|
| SPX0276 | 276 | 2937 | 189 | 63 | 68 | 2.40E-07 |

Description

[LN:C64571] [AC:C64571] [PN:hypothetical protein HP0411] [CL:Helicobacter pylori hypothetical protein HP0411] [OR:Helicobacter pylori]

| ORF Name | NT ID | AA ID | NT/LN | AA/LN | Score | P-Value |
|---|---|---|---|---|---|---|
| SPX0277 | 277 | 2938 | 936 | 312 | 194 | 2.60E-36 |

Description

"[GI:773349] [LN:BSU20445] [AC:U20445] [PN:BirA protein] [GN:birA] [FN:biotin protein ligase, biotin operon repressor] [OR:Bacillus subtilis]"

| ORF Name | NT ID | AA ID | NT/LN | AA/LN | Score | P-Value |
|---|---|---|---|---|---|---|
| SPX0278 | 278 | 2939 | 861 | 287 | 255 | 1.70E-56 |

Description

[LN:MSMR_STRMU] [AC:Q00753] [GN:MSMR] [OR:Streptococcus mutans] [DE:MSM OPERON REGULATORY PROTEIN] [SP:Q00753]

| ORF Name | NT ID | AA ID | NT/LN | AA/LN | Score | P-Value |
|---|---|---|---|---|---|---|
| SPX0279 | 279 | 2940 | 2163 | 721 | 2528 | 0 |

Description

"[LN:AGAL_STRMU] [AC:P27756] [GN:AGA] [OR:Streptococcus mutans] [EC:3.2.1.22] [DE:ALPHA-GALACTOSIDASE, (MELIBIASE)] [SP:P27756]"

| ORF Name | NT ID | AA ID | NT/LN | AA/LN | Score | P-Value |
|---|---|---|---|---|---|---|
| SPX0280 | 280 | 2941 | 1260 | 420 | 1106 | 2.40E-180 |

Description

[LN:MSME_STRMU] [AC:Q00749] [GN:MSME] [OR:Streptococcus mutans] [DE:MULTIPLE SUGAR-BINDING PROTEIN PRECURSOR] [SP:Q00749]

| ORF Name | NT ID | AA ID | NT/LN | AA/LN | Score | P-Value |
|---|---|---|---|---|---|---|
| SPX0281 | 281 | 2942 | 246 | 82 | | |

Description

NO-HIT

| ORF Name | NT ID | AA ID | NT LN | AA LN | Score | P-Value |
|---|---|---|---|---|---|---|
| SPX0282 | 282 | 2943 | 867 | 289 | 1188 | 1.40E-166 |

Description

[LN:MSMF_STRMU] [AC:Q00750] [GN:MSMF] [OR:Streptococcus mutans] [DE:MULTIPLE SUGAR-BINDING TRANSPORT SYSTEM PERMEASE PROTEIN MSMF] [SP:Q00750]

| ORF Name | NT ID | AA ID | NT LN | AA LN | Score | P-Value |
|---|---|---|---|---|---|---|
| SPX0283 | 283 | 2944 | 834 | 278 | 1174 | 3.40E-164 |

Description

[LN:MSMG_STRMU] [AC:Q00751] [GN:MSMG] [OR:Streptococcus mutans] [DE:MULTIPLE SUGAR-BINDING TRANSPORT SYSTEM PERMEASE PROTEIN MSMG] [SP:Q00751]

| ORF Name | NT ID | AA ID | NT LN | AA LN | Score | P-Value |
|---|---|---|---|---|---|---|
| SPX0284 | 284 | 2945 | 1446 | 482 | 2154 | 6.70E-294 |

Description

"[LN:A27626] [AC:A27626] [PN:sucrose phosphorylase,] [CL:gtfA protein] [OR:Streptococcus mutans] [EC:2.4.1.7]"

| ORF Name | NT ID | AA ID | NT LN | AA LN | Score | P-Value |
|---|---|---|---|---|---|---|
| SPX0285 | 285 | 2946 | 1194 | 398 | | |

Description

NO-HIT

| ORF Name | NT ID | AA ID | NT LN | AA LN | Score | P-Value |
|---|---|---|---|---|---|---|
| SPX0286 | 286 | 2947 | 402 | 134 | | |

Description

NO-HIT

| ORF Name | NT ID | AA ID | NT LN | AA LN | Score | P-Value |
|---|---|---|---|---|---|---|
| SPX0287 | 287 | 2948 | 1986 | 662 | 3341 | 0 |

Description

[LN:AMIA_STRPN] [AC:P18791:P18792] [GN:AMIA] [OR:Streptococcus pneumoniae] [DE:OLIGOPEPTIDE-BINDING PROTEIN AMIA PRECURSOR] [SP:P18791:P18792]

| ORF Name | NT ID | AA ID | NT LN | AA LN | Score | P-Value |
|---|---|---|---|---|---|---|
| SPX0288 | 288 | 2949 | 1497 | 499 | 2538 | 0 |

Description

[LN:AMIC_STRPN] [AC:P18793] [GN:AMIC] [OR:Streptococcus pneumoniae]
[DE:OLIGOPEPTIDE TRANSPORT PERMEASE PROTEIN AMIC] [SP:P18793]

| ORF Name | NT ID | AA ID | NT LN | AA LN | Score | P-Value |
|---|---|---|---|---|---|---|
| SPX0289 | 289 | 2950 | 927 | 309 | 1564 | 1.10E-217 |

Description

[LN:AMID_STRPN] [AC:P18794] [GN:AMID] [OR:Streptococcus pneumoniae]
[DE:OLIGOPEPTIDE TRANSPORT PERMEASE PROTEIN AMID] [SP:P18794]

| ORF Name | NT ID | AA ID | NT LN | AA LN | Score | P-Value |
|---|---|---|---|---|---|---|
| SPX0290 | 290 | 2951 | 1068 | 356 | 1806 | 2.10E-245 |

Description

[LN:AMIE_STRPN] [AC:P18765] [GN:AMIE] [OR:Streptococcus pneumoniae]
[DE:OLIGOPEPTIDE TRANSPORT ATP-BINDING PROTEIN AMIE] [SP:P18765]

| ORF Name | NT ID | AA ID | NT LN | AA LN | Score | P-Value |
|---|---|---|---|---|---|---|
| SPX0291 | 291 | 2952 | 339 | 113 | | |

Description

NO-HIT

| ORF Name | NT ID | AA ID | NT LN | AA LN | Score | P-Value |
|---|---|---|---|---|---|---|
| SPX0292 | 292 | 2953 | 927 | 309 | 1534 | 5.40E-208 |

Description

[LN:AMIF_STRPN] [AC:P18766] [GN:AMIF] [OR:Streptococcus pneumoniae]
[DE:OLIGOPEPTIDE TRANSPORT ATP-BINDING PROTEIN AMIF] [SP:P18766]

| ORF Name | NT ID | AA ID | NT LN | AA LN | Score | P-Value |
|---|---|---|---|---|---|---|
| SPX0293 | 293 | 2954 | 1257 | 419 | 2039 | 1.30E-284 |

Description

[GI:2804700] [LN:AF030361] [AC:AF030361] [PN:transposase] [OR:Streptococcus pneumoniae]

| ORF Name | NT ID | AA ID | NT LN | AA LN | Score | P-Value |
|---|---|---|---|---|---|---|
| SPX0294 | 294 | 2955 | 288 | 96 | 274 | 1.10E-34 |

Description

[GI:663279] [LN:STRCOMAA] [AC:M36180:L15190] [PN:transposase]
[OR:Streptococcus pneumoniae] [SR:Streptococcus pneumoniae (strain RX1) DNA]

| ORF Name | NT ID | AA ID | NT LN | AA LN | Score | P-Value |
|---|---|---|---|---|---|---|
| SPX0295 | 295 | 2956 | 519 | 173 | 840 | 6.50E-114 |

Description

[GI:663278] [LN:STRCOMAA] [AC:M36180:L15190] [PN:transposase]
[OR:Streptococcus pneumoniae] [SR:Streptococcus pneumoniae (strain RX1) DNA]

| ORF Name | NT ID | AA ID | NT LN | AA LN | Score | P-Value |
|---|---|---|---|---|---|---|
| SPX0296 | 296 | 2957 | 711 | 237 | 471 | 2.40E-60 |

Description

[LN:TRER_BACSU] [AC:P39796] [GN:TRER] [OR:Bacillus subtilis] [DE:TREHALOSE
OPERON TRANSCRIPTIONAL REPRESSOR] [SP:P39796]

| ORF Name | NT ID | AA ID | NT LN | AA LN | Score | P-Value |
|---|---|---|---|---|---|---|
| SPX0297 | 297 | 2958 | 1968 | 656 | 383 | 7.20E-135 |

Description

[LN:PTTB_ECOLI] [AC:P36672] [GN:TREB] [OR:Escherichia coli] [EC:2.7.1.69]
[DE:(EC 2.7.1.69) (EII-TRE)] [SP:P36672]

| ORF Name | NT ID | AA ID | NT LN | AA LN | Score | P-Value |
|---|---|---|---|---|---|---|
| SPX0298 | 298 | 2959 | 1626 | 542 | 1617 | 2.00E-272 |

Description

[GI:2208998] [LN:SSU35633] [AC:U35633] [PN:dextran glucosidase DexS]
[GN:dexS] [OR:Streptococcus suis]

| ORF Name | NT ID | AA ID | NT LN | AA LN | Score | P-Value |
|---|---|---|---|---|---|---|
| SPX0299 | 299 | 2960 | 180 | 60 | 125 | 2.30E-12 |

Description

[LN:T30285] [AC:T30285] [PN:hypothetical protein] [OR:Streptococcus
pneumoniae]

| ORF Name | NT ID | AA ID | NT/LN | AA/LN | Score | P-Value |
|---|---|---|---|---|---|---|
| SPX0300 | 300 | 2961 | 252 | 84 | 104 | 4.40E-09 |

Description

[GI:6899236] [LN:AE002123] [AC:AE002123:AF222894] [PN:conserved hypothetical] [GN:UU265] [OR:Ureaplasma urealyticum]

| ORF Name | NT ID | AA ID | NT/LN | AA/LN | Score | P-Value |
|---|---|---|---|---|---|---|
| SPX0301 | 301 | 2962 | 795 | 265 | 476 | 2.60E-84 |

Description

[GI:2462097] [LN:BCBCTLGLR] [AC:Y10927] [PN:glutamate racemase] [GN:bcglr] [OR:Bacillus cereus]

| ORF Name | NT ID | AA ID | NT/LN | AA/LN | Score | P-Value |
|---|---|---|---|---|---|---|
| SPX0302 | 302 | 2963 | 891 | 297 | 273 | 9.10E-35 |

Description

[LN:C69986] [AC:C69986] [PN:conserved hypothetical protein ysnA] [GN:ysnA] [CL:Methanococcus jannaschii conserved hypothetical protein MJ0226] [OR:Bacillus subtilis]

| ORF Name | NT ID | AA ID | NT/LN | AA/LN | Score | P-Value |
|---|---|---|---|---|---|---|
| SPX0303 | 303 | 2964 | 222 | 74 | 158 | 1.60E-15 |

Description

[LN:YGGV_ECOLI] [AC:P52061] [GN:YGGV] [OR:Escherichia coli] [DE:HYPOTHETICAL 21.0 KD PROTEIN IN GSHB-ANSB INTERGENIC REGION (O197)] [SP:P52061]

| ORF Name | NT ID | AA ID | NT/LN | AA/LN | Score | P-Value |
|---|---|---|---|---|---|---|
| SPX0304 | 304 | 2965 | 522 | 174 | 229 | 8.10E-27 |

Description

[LN:YSNB_BACSU] [AC:P94559] [GN:YSNB] [OR:Bacillus subtilis] [DE:HYPOTHETICAL 19.2 KD PROTEIN IN RPH-ILVB INTERGENIC REGION] [SP:P94559]

| ORF Name | NT ID | AA ID | NT/LN | AA/LN | Score | P-Value |
|---|---|---|---|---|---|---|
| SPX0305 | 305 | 2966 | 462 | 154 | 75 | 8.30E-08 |

Description

[LN:A69866] [AC:A69866] [PN:hypothetical protein ykuL] [GN:ykuL] [CL:Bacillus subtilis hypothetical protein ykuL] [OR:Bacillus subtilis]

| ORF Name | NT ID | AA ID | NT/LN | AA/LN | Score | P-Value |
|---|---|---|---|---|---|---|
| SPX0306 | 306 | 2967 | 741 | 247 | 61 | 0.0006 |

Description

[LN:A75153] [AC:A75153] [PN:integrase/recombinase xerd PAB0255]
[GN:xerD-like:PAB0255] [CL:probable site-specific integrase/recombinase
XerC] [OR:Pyrococcus abyssi]

| ORF Name | NT ID | AA ID | NT/LN | AA/LN | Score | P-Value |
|---|---|---|---|---|---|---|
| SPX0307 | 307 | 2968 | 729 | 243 | 233 | 1.60E-40 |

Description

[LN:YPUG_BACSU] [AC:P35154] [GN:YPUG] [OR:Bacillus subtilis]
[DE:HYPOTHETICAL 29.6 KD PROTEIN IN RIBT-DACB INTERGENIC REGION (ORFX7)]
[SP:P35154]

| ORF Name | NT ID | AA ID | NT/LN | AA/LN | Score | P-Value |
|---|---|---|---|---|---|---|
| SPX0308 | 308 | 2969 | 570 | 190 | 216 | 2.00E-28 |

Description

[LN:Y214_MYCPN] [AC:P75477] [OR:Mycoplasma pneumoniae] [DE:HYPOTHETICAL
PROTEIN MG214 HOMOLOG] [SP:P75477]

| ORF Name | NT ID | AA ID | NT/LN | AA/LN | Score | P-Value |
|---|---|---|---|---|---|---|
| SPX0309 | 309 | 2970 | 723 | 241 | 660 | 5.60E-86 |

Description

[LN:RLUB_BACSU] [AC:P35159] [GN:RLUB] [OR:Bacillus subtilis] [EC:4.2.1.70]
[DE:(PSEUDOURIDYLATE SYNTHASE) (URACIL HYDROLYASE)] [SP:P35159]

| ORF Name | NT ID | AA ID | NT/LN | AA/LN | Score | P-Value |
|---|---|---|---|---|---|---|
| SPX0310 | 310 | 2971 | 243 | 81 | 166 | 1.10E-32 |

Description

[LN:G72251] [AC:G72251] [PN:conserved hypothetical protein] [GN:TM1462]
[CL:conserved hypothetical protein HI1000] [OR:Thermotoga maritima]

| ORF Name | NT ID | AA ID | NT/LN | AA/LN | Score | P-Value |
|---|---|---|---|---|---|---|
| SPX0311 | 311 | 2972 | 525 | 175 | | |

Description

NO-HIT

| ORF Name | NT ID | AA ID | NT/LN | AA/LN | Score | P-Value |
|---|---|---|---|---|---|---|
| SPX0312 | 312 | 2973 | 966 | 322 | 218 | 2.70E-57 |
| Description | | | | | | |

[LN:E69763] [AC:E69763] [PN:probable ferrichrome ABC transporter yclQ]
[GN:yclQ] [CL:iron(III) dicitrate transport protein] [OR:Bacillus subtilis]

| ORF Name | NT ID | AA ID | NT/LN | AA/LN | Score | P-Value |
|---|---|---|---|---|---|---|
| SPX0313 | 313 | 2974 | 753 | 251 | 702 | 2.90E-92 |
| Description | | | | | | |

[LN:D69763] [AC:D69763] [PN:ferrichrome ABC transporter (ATP-binding p)
homolog yclP] [GN:yclP] [CL:unassigned ATP-binding cassette
proteins:ATP-binding cassette homology] [OR:Bacillus subtilis]

| ORF Name | NT ID | AA ID | NT/LN | AA/LN | Score | P-Value |
|---|---|---|---|---|---|---|
| SPX0314 | 314 | 2975 | 201 | 67 | 89 | 6.60E-07 |
| Description | | | | | | |

[LN:G72510] [AC:G72510] [PN:hypothetical protein APE2061] [GN:APE2061]
[OR:Aeropyrum pernix]

| ORF Name | NT ID | AA ID | NT/LN | AA/LN | Score | P-Value |
|---|---|---|---|---|---|---|
| SPX0315 | 315 | 2976 | 957 | 319 | 474 | 8.60E-64 |
| Description | | | | | | |

[LN:C69763] [AC:C69763] [PN:ferrichrome ABC transporter (permease) homolog
yclO] [GN:yclO] [CL:ferrichrome ABC transporter] [OR:Bacillus subtilis]

| ORF Name | NT ID | AA ID | NT/LN | AA/LN | Score | P-Value |
|---|---|---|---|---|---|---|
| SPX0316 | 316 | 2977 | 960 | 320 | 625 | 2.80E-84 |
| Description | | | | | | |

[LN:B69763] [AC:B69763] [PN:ferrichrome ABC transporter (permease) homolog
yclN] [GN:yclN] [CL:vitamin B12 transport protein btuC] [OR:Bacillus
subtilis]

| ORF Name | NT ID | AA ID | NT/LN | AA/LN | Score | P-Value |
|---|---|---|---|---|---|---|
| SPX0317 | 317 | 2978 | 408 | 136 | 288 | 3.50E-36 |
| Description | | | | | | |

[GI:6707010] [LN:AF109295] [AC:AF109295:AF022796] [PN:GalE] [GN:galE]
[OR:Staphylococcus carnosus]

| ORF Name | NT ID | AA ID | NT LN | AA LN | Score | P-Value |
|---|---|---|---|---|---|---|
| SPX0318 | 318 | 2979 | 243 | 81 | 164 | 6.20E-18 |

Description

[GI:3703059] [LN:AF082009] [AC:AF082009] [PN:UDP-galactose-4-epimerase]
[GN:galE] [OR:Lactococcus lactis]

| ORF Name | NT ID | AA ID | NT LN | AA LN | Score | P-Value |
|---|---|---|---|---|---|---|
| SPX0319 | 319 | 2980 | 1062 | 354 | 388 | 8.30E-143 |

Description

"[LN:PEPA_LACLC] [AC:Q48677] [GN:PEPA] [OR:Lactococcus lactis]
[SR:,subspcremoris:Streptococcus cremoris] [EC:3.4.11.7]
[DE:GLUTAMYL-AMINOPEPTIDASE,] [SP:Q48677]"

| ORF Name | NT ID | AA ID | NT LN | AA LN | Score | P-Value |
|---|---|---|---|---|---|---|
| SPX0320 | 320 | 2981 | 297 | 99 | | |

Description

NO-HIT

| ORF Name | NT ID | AA ID | NT LN | AA LN | Score | P-Value |
|---|---|---|---|---|---|---|
| SPX0321 | 321 | 2982 | 189 | 63 | | |

Description

NO-HIT

| ORF Name | NT ID | AA ID | NT LN | AA LN | Score | P-Value |
|---|---|---|---|---|---|---|
| SPX0322 | 322 | 2983 | 444 | 148 | 87 | 0.00059 |

Description

[GI:2791904] [LN:SSK3MECA1] [AC:Y13052] [GN:ORF145] [OR:Staphylococcus sciuri]

| ORF Name | NT ID | AA ID | NT LN | AA LN | Score | P-Value |
|---|---|---|---|---|---|---|
| SPX0323 | 323 | 2984 | 765 | 255 | | |

Description

NO-HIT

| ORF Name | NT ID | AA ID | NT LN | AA LN | Score | P-Value |
|---|---|---|---|---|---|---|
| SPX0324 | 324 | 2985 | 729 | 243 | 1211 | 8.40E-163 |

Description

[GI:5579394] [LN:AF162655] [AC:AF162655] [PN:choline transporter] [GN:proV] [FN:ATPase] [OR:Streptococcus pneumoniae]

| ORF Name | NT ID | AA ID | NT LN | AA LN | Score | P-Value |
|---|---|---|---|---|---|---|
| SPX0325 | 325 | 2986 | 87 | 29 | | |

Description

NO-HIT

| ORF Name | NT ID | AA ID | NT LN | AA LN | Score | P-Value |
|---|---|---|---|---|---|---|
| SPX0326 | 326 | 2987 | 933 | 311 | 1434 | 2.40E-200 |

Description

[LN:T44634] [AC:T44634] [PN:choline transporter [imported]] [GN:proWX] [OR:Streptococcus pneumoniae]

| ORF Name | NT ID | AA ID | NT LN | AA LN | Score | P-Value |
|---|---|---|---|---|---|---|
| SPX0327 | 327 | 2988 | 630 | 210 | 1042 | 3.30E-137 |

Description

[LN:T44634] [AC:T44634] [PN:choline transporter [imported]] [GN:proWX] [OR:Streptococcus pneumoniae]

| ORF Name | NT ID | AA ID | NT LN | AA LN | Score | P-Value |
|---|---|---|---|---|---|---|
| SPX0328 | 328 | 2989 | 810 | 270 | 125 | 1.90E-15 |

Description

[LN:YA7B_HAEIN] [AC:Q57425:P96338] [GN:HI1077.1] [OR:Haemophilus influenzae] [DE:HYPOTHETICAL PROTEIN HI1077.1] [SP:Q57425:P96338]

| ORF Name | NT ID | AA ID | NT LN | AA LN | Score | P-Value |
|---|---|---|---|---|---|---|
| SPX0329 | 329 | 2990 | 537 | 179 | 150 | 8.10E-17 |

Description

[GI:5881867] [LN:SC5G9] [AC:AL117385] [PN:putative tetR-family transcriptional regulator] [GN:SC5G9.19c] [OR:Streptomyces coelicolor A3(2)]

| ORF Name | NT ID | AA ID | NT/LN | AA/LN | Score | P-Value |
|---|---|---|---|---|---|---|
| SPX0330 | 330 | 2991 | 900 | 300 | 202 | 5.60E-39 |

Description

[GI:1944409] [LN:D87026] [AC:D87026:D28136] [PN:membrane protein] [OR:Bacillus stearothermophilus] [SR:Bacillus stearothermophilus (strain:TRBE14) DNA]

| ORF Name | NT ID | AA ID | NT/LN | AA/LN | Score | P-Value |
|---|---|---|---|---|---|---|
| SPX0331 | 331 | 2992 | 354 | 118 | 282 | 3.60E-34 |

Description

[LN:B69970] [AC:B69970] [PN:transcription regulator MerR family homolog yraB] [GN:yraB] [CL:transcription repressor glnR] [OR:Bacillus subtilis]

| ORF Name | NT ID | AA ID | NT/LN | AA/LN | Score | P-Value |
|---|---|---|---|---|---|---|
| SPX0332 | 332 | 2993 | 1038 | 346 | 403 | 3.80E-82 |

Description

[LN:T44975] [AC:T44975] [PN:dehydrogenase [imported]] [CL:alcohol dehydrogenase:long-chain alcohol dehydrogenase homology] [OR:Haloferax volcanii]

| ORF Name | NT ID | AA ID | NT/LN | AA/LN | Score | P-Value |
|---|---|---|---|---|---|---|
| SPX0333 | 333 | 2994 | 1008 | 336 | 729 | 4.00E-144 |

Description

[GI:4097439] [LN:STU61402] [AC:U61402] [PN:GalR] [GN:galR] [OR:Streptococcus thermophilus]

| ORF Name | NT ID | AA ID | NT/LN | AA/LN | Score | P-Value |
|---|---|---|---|---|---|---|
| SPX0334 | 334 | 2995 | 1179 | 393 | 1674 | 3.10E-227 |

Description

[GI:4097440] [LN:STU61402] [AC:U61402] [PN:galactokinase] [GN:galK] [FN:galactose metabolism] [OR:Streptococcus thermophilus]

| ORF Name | NT ID | AA ID | NT/LN | AA/LN | Score | P-Value |
|---|---|---|---|---|---|---|
| SPX0335 | 335 | 2996 | 1482 | 494 | 1612 | 1.90E-230 |

Description

[GI:4097441] [LN:STU61402] [AC:U61402] [PN:gal-1-P uridylyltransferase] [GN:galT] [FN:galactose metabolism] [OR:Streptococcus thermophilus]

| ORF Name | NT ID | AA ID | NT LN | AA LN | Score | P-Value |
|---|---|---|---|---|---|---|
| SPX0336 | 336 | 2997 | 405 | 135 | 467 | 1.10E-60 |

Description

[GI:1196924] [LN:STRDPN2A] [AC:M14339] [PN:unknown] [OR:Streptococcus pneumoniae]

| ORF Name | NT ID | AA ID | NT LN | AA LN | Score | P-Value |
|---|---|---|---|---|---|---|
| SPX0337 | 337 | 2998 | 888 | 296 | 1461 | 6.00E-199 |

Description

[LN:MT21_STRPN] [AC:P04043] [GN:DPNM] [OR:Streptococcus pneumoniae] [EC:2.1.1.72] [DE:METHYLTRANSFERASE DPNII 1) (M.DPNII 1)] [SP:P04043]

| ORF Name | NT ID | AA ID | NT LN | AA LN | Score | P-Value |
|---|---|---|---|---|---|---|
| SPX0338 | 338 | 2999 | 771 | 257 | 1366 | 2.60E-183 |

Description

[LN:MT22_STRPN] [AC:P09358] [GN:DPNA] [OR:Streptococcus pneumoniae] [EC:2.1.1.72] [DE:METHYLTRANSFERASE DPNII 2) (M.DPNII 2)] [SP:P09358]

| ORF Name | NT ID | AA ID | NT LN | AA LN | Score | P-Value |
|---|---|---|---|---|---|---|
| SPX0339 | 339 | 3000 | 867 | 289 | 1492 | 5.50E-202 |

Description

[LN:T2D2_STRPN] [AC:P09357] [GN:DPNB] [OR:Streptococcus pneumoniae] [EC:3.1.21.4] [DE:(R.DPNII)] [SP:P09357]

| ORF Name | NT ID | AA ID | NT LN | AA LN | Score | P-Value |
|---|---|---|---|---|---|---|
| SPX0340 | 340 | 3001 | 357 | 119 | 462 | 1.20E-61 |

Description

[GI:6978345] [LN:STRDPN2A] [AC:M14339] [PN:unknown] [OR:Streptococcus pneumoniae]

| ORF Name | NT ID | AA ID | NT LN | AA LN | Score | P-Value |
|---|---|---|---|---|---|---|
| SPX0341 | 341 | 3002 | 849 | 283 | 436 | 8.70E-87 |

Description

[LN:YUNK_BACSU] [AC:O32140] [GN:YUNK] [OR:Bacillus subtilis] [DE:HYPOTHETICAL 44.9 KD PROTEIN IN HOM-MRGA INTERGENIC REGION] [SP:O32140]

| ORF Name | NT ID | AA ID | NT/LN | AA/LN | Score | P-Value |
|---|---|---|---|---|---|---|
| SPX0342 | 342 | 3003 | 582 | 194 | 786 | 3.40E-105 |

Description

[GI:7160242] [LN:SPN272465] [AC:AJ272465] [PN:xanthine phosphoribosyltransferase] [GN:xpt] [OR:Streptococcus pneumoniae]

| ORF Name | NT ID | AA ID | NT/LN | AA/LN | Score | P-Value |
|---|---|---|---|---|---|---|
| SPX0343 | 343 | 3004 | 174 | 58 | 79 | 7.70E-11 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX0344 | 344 | 3005 | 240 | 80 | 113 | 5.90E-10 |

Description

[LN:C75408] [AC:C75408] [PN:hypothetical protein] [GN:DR1341] [OR:Deinococcus radiodurans]

| ORF Name | NT ID | AA ID | NT/LN | AA/LN | Score | P-Value |
|---|---|---|---|---|---|---|
| SPX0345 | 345 | 3006 | 828 | 276 | 1432 | 8.60E-192 |

Description

"[LN:EXOA_STRPN] [AC:P21998] [GN:EXOA] [OR:Streptococcus pneumoniae] [EC:3.1.11.2] [DE:EXODEOXYRIBONUCLEASE,] [SP:P21998]"

| ORF Name | NT ID | AA ID | NT/LN | AA/LN | Score | P-Value |
|---|---|---|---|---|---|---|
| SPX0346 | 346 | 3007 | 228 | 76 | | |

Description

NO-HIT

| ORF Name | NT ID | AA ID | NT/LN | AA/LN | Score | P-Value |
|---|---|---|---|---|---|---|
| SPX0347 | 347 | 3008 | 270 | 90 | | |

Description

NO-HIT

| ORF_Name | NT_ID | AA_ID | NT/LN | AA/LN | Score | P-Value |
|---|---|---|---|---|---|---|
| SPX0348 | 348 | 3009 | 531 | 177 | 132 | 9.60E-19 |

Description

[LN:F69972] [AC:F69972] [PN:probable membrane protein yrbG] [GN:yrbG] [CL:probable membrane protein ycaP] [OR:Bacillus subtilis]

| ORF_Name | NT_ID | AA_ID | NT/LN | AA/LN | Score | P-Value |
|---|---|---|---|---|---|---|
| SPX0349 | 349 | 3010 | 237 | 79 | 129 | 5.90E-21 |

Description

[GI:1914870] [LN:SPZ82001] [AC:Z82001] [PN:unknown] [OR:Streptococcus pneumoniae]

| ORF_Name | NT_ID | AA_ID | NT/LN | AA/LN | Score | P-Value |
|---|---|---|---|---|---|---|
| SPX0350 | 350 | 3011 | 1746 | 582 | 685 | 1.90E-170 |

Description

[LN:A69829] [AC:A69829] [PN:ABC transporter (ATP-binding protein) homolog yheI] [GN:yheI] [CL:unassigned ATP-binding cassette proteins:ATP-binding cassette homology] [OR:Bacillus subtilis]

| ORF_Name | NT_ID | AA_ID | NT/LN | AA/LN | Score | P-Value |
|---|---|---|---|---|---|---|
| SPX0351 | 351 | 3012 | 882 | 294 | 364 | 6.80E-49 |

Description

[LN:H69828] [AC:H69828] [PN:ABC transporter (ATP-binding protein) homolog yheH] [GN:yheH] [CL:unassigned ATP-binding cassette proteins:ATP-binding cassette homology] [OR:Bacillus subtilis]

| ORF_Name | NT_ID | AA_ID | NT/LN | AA/LN | Score | P-Value |
|---|---|---|---|---|---|---|
| SPX0352 | 352 | 3013 | 207 | 69 | 82 | 0.00022 |

Description

[LN:H69828] [AC:H69828] [PN:ABC transporter (ATP-binding protein) homolog yheH] [GN:yheH] [CL:unassigned ATP-binding cassette proteins:ATP-binding cassette homology] [OR:Bacillus subtilis]

| ORF Name | NT ID | AA ID | NT LN | AA LN | Score | P-Value |
|---|---|---|---|---|---|---|
| SPX0353 | 353 | 3014 | 792 | 264 | 383 | 3.90E-79 |

Description

[LN:H69828] [AC:H69828] [PN:ABC transporter (ATP-binding protein) homolog yheH] [GN:yheH] [CL:unassigned ATP-binding cassette proteins:ATP-binding cassette homology] [OR:Bacillus subtilis]

| ORF Name | NT ID | AA ID | NT LN | AA LN | Score | P-Value |
|---|---|---|---|---|---|---|
| SPX0354 | 354 | 3015 | 696 | 232 | 632 | 1.10E-83 |

Description

[GI:6601354] [LN:AF164515] [AC:AF164515] [PN:putative glycosyltransferase Cps7F] [GN:cps7F] [OR:Streptococcus suis]

| ORF Name | NT ID | AA ID | NT LN | AA LN | Score | P-Value |
|---|---|---|---|---|---|---|
| SPX0355 | 355 | 3016 | 1227 | 409 | 973 | 4.70E-214 |

Description

[GI:6601355] [LN:AF164515] [AC:AF164515] [PN:Cps7G] [GN:cps7G] [OR:Streptococcus suis]

| ORF Name | NT ID | AA ID | NT LN | AA LN | Score | P-Value |
|---|---|---|---|---|---|---|
| SPX0356 | 356 | 3017 | 189 | 63 | | |

Description

NO-HIT

| ORF Name | NT ID | AA ID | NT LN | AA LN | Score | P-Value |
|---|---|---|---|---|---|---|
| SPX0357 | 357 | 3018 | 267 | 89 | | |

Description

NO-HIT

| ORF Name | NT ID | AA ID | NT LN | AA LN | Score | P-Value |
|---|---|---|---|---|---|---|
| SPX0358 | 358 | 3019 | 2127 | 709 | 107 | 4.60E-08 |

Description

[GI:2952545] [LN:AF051898] [AC:AF051898] [PN:coronin binding protein] [GN:DB10] [OR:Dictyostelium discoideum]

| ORF Name | NT ID | AA ID | NT/LN | AA/LN | Score | P-Value |
|---|---|---|---|---|---|---|
| SPX0359 | 359 | 3020 | 246 | 82 | | |

Description

NO-HIT

| ORF Name | NT ID | AA ID | NT/LN | AA/LN | Score | P-Value |
|---|---|---|---|---|---|---|
| SPX0360 | 360 | 3021 | 207 | 69 | | |

Description

NO-HIT

| ORF Name | NT ID | AA ID | NT/LN | AA/LN | Score | P-Value |
|---|---|---|---|---|---|---|
| SPX0361 | 361 | 3022 | 285 | 95 | | |

Description

NO-HIT

| ORF Name | NT ID | AA ID | NT/LN | AA/LN | Score | P-Value |
|---|---|---|---|---|---|---|
| SPX0362 | 362 | 3023 | 288 | 96 | 289 | 6.60E-34 |

Description

[GI:43589] [LN:HILIC3] [AC:X57315] [PN:UDP-galactose-4-epimerase] [GN:galE] [OR:Haemophilus influenzae]

| ORF Name | NT ID | AA ID | NT/LN | AA/LN | Score | P-Value |
|---|---|---|---|---|---|---|
| SPX0363 | 363 | 3024 | 198 | 66 | | |

Description

NO-HIT

| ORF Name | NT ID | AA ID | NT/LN | AA/LN | Score | P-Value |
|---|---|---|---|---|---|---|
| SPX0364 | 364 | 3025 | 660 | 220 | | |

Description

NO-HIT

| ORF_Name | NT_ID | AA_ID | NT/LN | AA/LN | Score | P-Value |
|---|---|---|---|---|---|---|
| SPX0365 | 365 | 3026 | 1068 | 356 | 286 | 2.20E-30 |

Description

"[LN:Y4FP_RHISN] [AC:P55454] [GN:Y4FP] [OR:Rhizobium sp] [SR:,strain NGR234] [DE:PROBABLE ABC TRANSPORTER PERIPLASMIC BINDING PROTEIN Y4FP PRECURSOR] [SP:P55454]"

| ORF_Name | NT_ID | AA_ID | NT/LN | AA/LN | Score | P-Value |
|---|---|---|---|---|---|---|
| SPX0366 | 366 | 3027 | 1011 | 337 | 395 | 3.30E-90 |

Description

"[LN:A70180] [AC:A70180] [PN:spermidine/putrescine ABC transporter, ATP-binding protein (potA) homolog] [CL:unassigned ATP-binding cassette proteins:ATP-binding cassette homology] [OR:Borrelia burgdorferi] [SR:, Lyme disease spirochete]"

| ORF_Name | NT_ID | AA_ID | NT/LN | AA/LN | Score | P-Value |
|---|---|---|---|---|---|---|
| SPX0367 | 367 | 3028 | 1692 | 564 | 433 | 1.50E-93 |

Description

"[LN:Y4FN_RHISN] [AC:P55452] [GN:Y4FN] [OR:Rhizobium sp] [SR:,strain NGR234] [DE:PROBABLE ABC TRANSPORTER PERMEASE PROTEIN Y4FN] [SP:P55452]"

| ORF_Name | NT_ID | AA_ID | NT/LN | AA/LN | Score | P-Value |
|---|---|---|---|---|---|---|
| SPX0368 | 368 | 3029 | 711 | 237 | 192 | 4.80E-28 |

Description

[LN:Y647_HAEIN] [AC:Q57424:O05028] [GN:HI0647] [OR:Haemophilus influenzae] [DE:HYPOTHETICAL PROTEIN HI0647] [SP:Q57424:O05028]

| ORF_Name | NT_ID | AA_ID | NT/LN | AA/LN | Score | P-Value |
|---|---|---|---|---|---|---|
| SPX0369 | 369 | 3030 | 309 | 103 | | |

Description

NO-HIT

| ORF Name | NT ID | AA ID | NT/LN | AA/LN | Score | P-Value |
|---|---|---|---|---|---|---|
| SPX0370 | 370 | 3031 | 1002 | 334 | 144 | 3.70E-25 |

Description

[LN:CCPA_BACME] [AC:P46828] [GN:CCPA] [OR:Bacillus megaterium]
[DE:GLUCOSE-RESISTANCE AMYLASE REGULATOR (CATABOLITE CONTROL PROTEIN)]
[SP:P46828]

| ORF Name | NT ID | AA ID | NT/LN | AA/LN | Score | P-Value |
|---|---|---|---|---|---|---|
| SPX0371 | 371 | 3032 | 198 | 66 | | |

Description

NO-HIT

| ORF Name | NT ID | AA ID | NT/LN | AA/LN | Score | P-Value |
|---|---|---|---|---|---|---|
| SPX0372 | 372 | 3033 | 207 | 69 | | |

Description

NO-HIT

| ORF Name | NT ID | AA ID | NT/LN | AA/LN | Score | P-Value |
|---|---|---|---|---|---|---|
| SPX0373 | 373 | 3034 | 1464 | 488 | 1100 | 2.50E-173 |

Description

"[LN:TRPE_LACLA] [AC:Q02001] [GN:TRPE] [OR:Lactococcus lactis]
[SR:,subsplactis:Streptococcus lactis] [EC:4.1.3.27] [DE:ANTHRANILATE
SYNTHASE COMPONENT I,] [SP:Q02001]"

| ORF Name | NT ID | AA ID | NT/LN | AA/LN | Score | P-Value |
|---|---|---|---|---|---|---|
| SPX0374 | 374 | 3035 | 201 | 67 | 108 | 6.30E-10 |

Description

[LN:C72489] [AC:C72489] [PN:hypothetical protein APE2554] [GN:APE2554]
[OR:Aeropyrum pernix]

| ORF Name | NT ID | AA ID | NT/LN | AA/LN | Score | P-Value |
|---|---|---|---|---|---|---|
| SPX0375 | 375 | 3036 | 567 | 189 | 440 | 8.80E-75 |

Description

"[LN:TRPG_LACLA] [AC:Q02003] [GN:TRPG] [OR:Lactococcus lactis]
[SR:,subsplactis:Streptococcus lactis] [EC:4.1.3.27] [DE:TRANSFERASE)]
[SP:Q02003]"

| ORF Name | NT ID | AA ID | NT/LN | AA/LN | Score | P-Value |
|---|---|---|---|---|---|---|
| SPX0376 | 376 | 3037 | 1005 | 335 | 1008 | 9.70E-134 |

Description

"[LN:TRPD_LACLA] [AC:Q02000] [GN:TRPD] [OR:Lactococcus lactis]
[SR:,subsplactis:Streptococcus lactis] [EC:2.4.2.18] [DE:ANTHRANILATE
PHOSPHORIBOSYLTRANSFERASE,] [SP:Q02000]"

| ORF Name | NT ID | AA ID | NT/LN | AA/LN | Score | P-Value |
|---|---|---|---|---|---|---|
| SPX0377 | 377 | 3038 | 768 | 256 | 446 | 6.20E-107 |

Description

"[LN:TRPC_LACLA] [AC:Q01999] [GN:TRPC] [OR:Lactococcus lactis]
[SR:,subsplactis:Streptococcus lactis] [EC:4.1.1.48] [DE:INDOLE-3-GLYCEROL
PHOSPHATE SYNTHASE, (IGPS)] [SP:Q01999]"

| ORF Name | NT ID | AA ID | NT/LN | AA/LN | Score | P-Value |
|---|---|---|---|---|---|---|
| SPX0378 | 378 | 3039 | 630 | 210 | 225 | 3.50E-49 |

Description

"[LN:TRPF_LACLA] [AC:Q02002] [GN:TRPF] [OR:Lactococcus lactis]
[SR:,subsplactis:Streptococcus lactis] [EC:5.3.1.24]
[DE:N-(5'-PHOSPHORIBOSYL)ANTHRANILATE ISOMERASE, (PRAI)] [SP:Q02002]"

| ORF Name | NT ID | AA ID | NT/LN | AA/LN | Score | P-Value |
|---|---|---|---|---|---|---|
| SPX0379 | 379 | 3040 | 1224 | 408 | 930 | 9.00E-225 |

Description

"[LN:TRPB_LACLA] [AC:Q01998] [GN:TRPB] [OR:Lactococcus lactis]
[SR:,subsplactis:Streptococcus lactis] [EC:4.2.1.20] [DE:TRYPTOPHAN SYNTHASE
BETA CHAIN,] [SP:Q01998]"

| ORF Name | NT ID | AA ID | NT/LN | AA/LN | Score | P-Value |
|---|---|---|---|---|---|---|
| SPX0380 | 380 | 3041 | 834 | 278 | 1137 | 5.00E-153 |

Description

[GI:5231181] [LN:AF157817] [AC:AF157817] [PN:tryptophan synthase alpha
chain] [GN:trpA] [OR:Streptococcus pneumoniae]

| ORF Name | NT ID | AA ID | NT/LN | AA/LN | Score | P-Value |
|---|---|---|---|---|---|---|
| SPX0381 | 381 | 3042 | 204 | 68 | | |

Description

NO-HIT

| ORF Name | NT ID | AA ID | NT/LN | AA/LN | Score | P-Value |
|---|---|---|---|---|---|---|
| SPX0382 | 382 | 3043 | 732 | 244 | | |

Description

NO-HIT

| ORF Name | NT ID | AA ID | NT/LN | AA/LN | Score | P-Value |
|---|---|---|---|---|---|---|
| SPX0383 | 383 | 3044 | 1152 | 384 | 92 | 2.70E-13 |

Description

[LN:H70940] [AC:H70940] [PN:probable helix-turn-helix motif at aa 18-39] [GN:Rv2017] [OR:Mycobacterium tuberculosis]

| ORF Name | NT ID | AA ID | NT/LN | AA/LN | Score | P-Value |
|---|---|---|---|---|---|---|
| SPX0384 | 384 | 3045 | 660 | 220 | 109 | 1.00E-14 |

Description

[LN:B72220] [AC:B72220] [PN:type IV prepilin peptidase] [GN:TM1696] [CL:type IV prepilin peptidase] [OR:Thermotoga maritima]

| ORF Name | NT ID | AA ID | NT/LN | AA/LN | Score | P-Value |
|---|---|---|---|---|---|---|
| SPX0385 | 385 | 3046 | 447 | 149 | 92 | 0.00011 |

Description

[LN:E72312] [AC:E72312] [PN:conserved hypothetical protein] [GN:TM0968] [CL:Escherichia coli ribosomal-protein-alanine N-acetyltransferase rimJ] [OR:Thermotoga maritima]

| ORF Name | NT ID | AA ID | NT/LN | AA/LN | Score | P-Value |
|---|---|---|---|---|---|---|
| SPX0386 | 386 | 3047 | 312 | 104 | 138 | 1.30E-12 |

Description

"[GI:6332767] [LN:AB033763] [AC:AB033763:AB014419:AB014429:AB014439] [PN:hypothetical protein] [OR:Staphylococcus aureus] [SR:Staphylococcus aureus (strain:NCTC10442) DNA, clone_lib:Lambda das]"

| ORF Name | NT ID | AA ID | NT/LN | AA/LN | Score | P-Value |
|---|---|---|---|---|---|---|
| SPX0387 | 387 | 3048 | 204 | 68 | 98 | 8.10E-08 |

Description

[GI:2772940] [LN:AF034574] [AC:AF034574] [PN:putative cruciform DNA binding protein] [GN:Gv1] [OR:Glomus versiforme]

| ORF Name | NT ID | AA ID | NT/LN | AA/LN | Score | P-Value |
|---|---|---|---|---|---|---|
| SPX0388 | 388 | 3049 | 609 | 203 | 515 | 8.70E-64 |

Description

[GI:727436] [LN:LLU23376] [AC:U23376] [OR:Lactococcus lactis]

| ORF Name | NT ID | AA ID | NT/LN | AA/LN | Score | P-Value |
|---|---|---|---|---|---|---|
| SPX0389 | 389 | 3050 | 573 | 191 | | |

Description

NO-HIT

| ORF Name | NT ID | AA ID | NT/LN | AA/LN | Score | P-Value |
|---|---|---|---|---|---|---|
| SPX0390 | 390 | 3051 | 1539 | 513 | 193 | 6.90E-35 |

Description

"[GI:6782400] [LN:STC133440] [AC:AJ133440] [PN:multigene regulator protein Mgc, putative] [GN:mgc] [FN:gene regulatory function, putative] [OR:Streptococcus dysgalactiae]"

| ORF Name | NT ID | AA ID | NT/LN | AA/LN | Score | P-Value |
|---|---|---|---|---|---|---|
| SPX0391 | 391 | 3052 | 1002 | 334 | 185 | 3.80E-46 |

Description

[LN:SCRR_STRMU] [AC:Q54430] [GN:SCRR] [OR:Streptococcus mutans] [DE:SUCROSE OPERON REPRESSOR (SCR OPERON REGULATORY PROTEIN)] [SP:Q54430]

| ORF Name | NT ID | AA ID | NT/LN | AA/LN | Score | P-Value |
|---|---|---|---|---|---|---|
| SPX0392 | 392 | 3053 | 945 | 315 | 376 | 2.50E-89 |

Description

[LN:A69653] [AC:A69653] [PN:transmembrane lipoprotein lplB] [GN:lplB] [CL:inner membrane protein ugpA] [OR:Bacillus subtilis]

| ORF_Name | NT ID | AA ID | NT/LN | AA/LN | Score | P-Value |
|---|---|---|---|---|---|---|
| SPX0393 | 393 | 3054 | 918 | 306 | 450 | 1.20E-73 |

Description

[LN:LPLC_BACSU] [AC:P39129] [GN:LPLC] [OR:Bacillus subtilis] [DE:LPLC PROTEIN] [SP:P39129]

| ORF_Name | NT ID | AA ID | NT/LN | AA/LN | Score | P-Value |
|---|---|---|---|---|---|---|
| SPX0394 | 394 | 3055 | 1617 | 539 | 167 | 2.90E-15 |

Description

[GI:4056657] [LN:AF098273] [AC:AF098273] [PN:peripheral protein] [GN:glucuronic acid catabolism operon] [OR:Bacillus stearothermophilus]

| ORF_Name | NT ID | AA ID | NT/LN | AA/LN | Score | P-Value |
|---|---|---|---|---|---|---|
| SPX0395 | 395 | 3056 | 423 | 141 | | |

Description

NO-HIT

| ORF_Name | NT ID | AA ID | NT/LN | AA/LN | Score | P-Value |
|---|---|---|---|---|---|---|
| SPX0396 | 396 | 3057 | 1320 | 440 | 305 | 2.30E-76 |

Description

"[LN:RAFD_ECOLI] [AC:P16553] [GN:RAFD] [OR:Escherichia coli] [EC:3.2.1.26] [DE:RAFFINOSE INVERTASE, (INVERTASE)] [SP:P16553]"

| ORF_Name | NT ID | AA ID | NT/LN | AA/LN | Score | P-Value |
|---|---|---|---|---|---|---|
| SPX0397 | 397 | 3058 | 1272 | 424 | 722 | 7.10E-167 |

Description

[LN:D69981] [AC:D69981] [PN:conserved hypothetical protein yrvN] [GN:yrvN] [CL:Haemophilus influenzae conserved hypothetical protein HI1590] [OR:Bacillus subtilis]

| ORF_Name | NT ID | AA ID | NT/LN | AA/LN | Score | P-Value |
|---|---|---|---|---|---|---|
| SPX0398 | 398 | 3059 | 222 | 74 | | |

Description

NO-HIT

| ORF Name | NT ID | AA ID | NT/LN | AA/LN | Score | P-Value |
|---|---|---|---|---|---|---|
| SPX0399 | 399 | 3060 | 180 | 60 | | |
| Description | | | | | | |

NO-HIT

| ORF Name | NT ID | AA ID | NT/LN | AA/LN | Score | P-Value |
|---|---|---|---|---|---|---|
| SPX0400 | 400 | 3061 | 252 | 84 | | |
| Description | | | | | | |

NO-HIT

| ORF Name | NT ID | AA ID | NT/LN | AA/LN | Score | P-Value |
|---|---|---|---|---|---|---|
| SPX0401 | 401 | 3062 | 453 | 151 | 92 | 4.90E-09 |
| Description | | | | | | |

[LN:T13557] [AC:T13557] [PN:hypothetical protein 17] [CL:Archaeoglobus fulgidus conserved hypothetical protein AF1072] [OR:Bacillus phage phi-105]

| ORF Name | NT ID | AA ID | NT/LN | AA/LN | Score | P-Value |
|---|---|---|---|---|---|---|
| SPX0402 | 402 | 3063 | 471 | 157 | | |
| Description | | | | | | |

NO-HIT

| ORF Name | NT ID | AA ID | NT/LN | AA/LN | Score | P-Value |
|---|---|---|---|---|---|---|
| SPX0403 | 403 | 3064 | 1089 | 363 | | |
| Description | | | | | | |

NO-HIT

| ORF Name | NT ID | AA ID | NT/LN | AA/LN | Score | P-Value |
|---|---|---|---|---|---|---|
| SPX0404 | 404 | 3065 | 1035 | 345 | 130 | 8.00E-15 |
| Description | | | | | | |

[GI:758793] [LN:ECU23723] [AC:U23723] [FN:unknown] [OR:Escherichia coli]

| ORF Name | NT ID | AA ID | NT/LN | AA/LN | Score | P-Value |
|---|---|---|---|---|---|---|
| SPX0405 | 405 | 3066 | 2244 | 748 | 68 | 0.00048 |
| Description | | | | | | |

[GI:758794] [LN:ECU23723] [AC:U23723] [FN:unknown] [OR:Escherichia coli]

| ORF Name | NT ID | AA ID | NT/LN | AA/LN | Score | P-Value |
|---|---|---|---|---|---|---|
| SPX0406 | 406 | 3067 | 1020 | 340 | | |

Description

NO-HIT

| ORF Name | NT ID | AA ID | NT/LN | AA/LN | Score | P-Value |
|---|---|---|---|---|---|---|
| SPX0407 | 407 | 3068 | 951 | 317 | 395 | 1.40E-81 |

Description

"[LN:T43740] [AC:T43740] [PN:probable ribosomal protein L11 methyltransferase, [imported]:hypothetical protein 35] [CL:ribosomal protein L11 methyltransferase:bioC homology] [OR:Listeria monocytogenes] [EC:2.1.1.-]"

| ORF Name | NT ID | AA ID | NT/LN | AA/LN | Score | P-Value |
|---|---|---|---|---|---|---|
| SPX0408 | 408 | 3069 | 744 | 248 | 461 | 1.90E-64 |

Description

[LN:T43741] [AC:T43741] [PN:conserved hypothetical protein orf29 [imported]] [OR:Listeria monocytogenes]

| ORF Name | NT ID | AA ID | NT/LN | AA/LN | Score | P-Value |
|---|---|---|---|---|---|---|
| SPX0409 | 409 | 3070 | 1797 | 599 | 300 | 2.10E-57 |

Description

"[LN:PEPF_BACSU] [AC:O31605] [GN:YJBG] [OR:Bacillus subtilis] [EC:3.4.24.-] [DE:OLIGOENDOPEPTIDASE F HOMOLOG,] [SP:O31605]"

| ORF Name | NT ID | AA ID | NT/LN | AA/LN | Score | P-Value |
|---|---|---|---|---|---|---|
| SPX0410 | 410 | 3071 | 678 | 226 | 312 | 1.80E-58 |

Description

[LN:D69780] [AC:D69780] [PN:hypothetical protein ydfF] [GN:ydfF] [OR:Bacillus subtilis]

| ORF Name | NT ID | AA ID | NT/LN | AA/LN | Score | P-Value |
|---|---|---|---|---|---|---|
| SPX0411 | 411 | 3072 | 651 | 217 | 394 | 1.40E-54 |

Description

[LN:G69803] [AC:G69803] [PN:ABC transporter (ATP-binding protein) homolog yfiL] [GN:yfiL] [CL:unassigned ATP-binding cassette proteins:ATP-binding cassette homology] [OR:Bacillus subtilis]

| ORF Name | NT ID | AA ID | NT LN | AA LN | Score | P-Value |
|---|---|---|---|---|---|---|
| SPX0412 | 412 | 3073 | 765 | 255 | 346 | 4.20E-44 |

Description

"[LN:NODJ_RHILV] [AC:P06755] [GN:NODJ] [OR:Rhizobium leguminosarum] [SR:,biovar viciae] [DE:NODULATION PROTEIN J] [SP:P06755]"

| ORF Name | NT ID | AA ID | NT LN | AA LN | Score | P-Value |
|---|---|---|---|---|---|---|
| SPX0413 | 413 | 3074 | 792 | 264 | | |

Description

NO-HIT

| ORF Name | NT ID | AA ID | NT LN | AA LN | Score | P-Value |
|---|---|---|---|---|---|---|
| SPX0414 | 414 | 3075 | 630 | 210 | 257 | 3.90E-39 |

Description

"[LN:A69428] [AC:A69428] [PN:glycerol uptake facilitator, MIP channel (glpF) homolog] [CL:nodulin-26] [OR:Archaeoglobus fulgidus]"

| ORF Name | NT ID | AA ID | NT LN | AA LN | Score | P-Value |
|---|---|---|---|---|---|---|
| SPX0415 | 415 | 3076 | 180 | 60 | | |

Description

NO-HIT

| ORF Name | NT ID | AA ID | NT LN | AA LN | Score | P-Value |
|---|---|---|---|---|---|---|
| SPX0416 | 416 | 3077 | 573 | 191 | 467 | 1.10E-60 |

Description

[LN:D69868] [AC:D69868] [PN:conserved hypothetical protein ykvM] [GN:ykvM] [CL:hypothetical protein ykvM] [OR:Bacillus subtilis]

| ORF Name | NT ID | AA ID | NT LN | AA LN | Score | P-Value |
|---|---|---|---|---|---|---|
| SPX0417 | 417 | 3078 | 315 | 105 | 193 | 1.80E-43 |

Description

[GI:5640117] [LN:LMO133006] [AC:AJ133006] [PN:thioredoxin] [GN:trxA] [FN:thiol:disulfide interchange] [OR:Listeria monocytogenes]

| ORF Name | NT ID | AA ID | NT LN | AA LN | Score | P-Value |
|---|---|---|---|---|---|---|
| SPX0418 | 418 | 3079 | 303 | 101 | | |
| Description | | | | | | |

NO-HIT

| ORF Name | NT ID | AA ID | NT LN | AA LN | Score | P-Value |
|---|---|---|---|---|---|---|
| SPX0419 | 419 | 3080 | 201 | 67 | | |
| Description | | | | | | |

NO-HIT

| ORF Name | NT ID | AA ID | NT LN | AA LN | Score | P-Value |
|---|---|---|---|---|---|---|
| SPX0420 | 420 | 3081 | 225 | 75 | | |
| Description | | | | | | |

NO-HIT

| ORF Name | NT ID | AA ID | NT LN | AA LN | Score | P-Value |
|---|---|---|---|---|---|---|
| SPX0421 | 421 | 3082 | 954 | 318 | 433 | 2.70E-56 |
| Description | | | | | | |

[LN:YQJA_BACSU] [AC:P54538] [GN:YQJA] [OR:Bacillus subtilis]
[DE:HYPOTHETICAL 37.1 KD PROTEIN IN BMRU-ANSR INTERGENIC REGION] [SP:P54538]

| ORF Name | NT ID | AA ID | NT LN | AA LN | Score | P-Value |
|---|---|---|---|---|---|---|
| SPX0422 | 422 | 3083 | 861 | 287 | 745 | 1.50E-100 |
| Description | | | | | | |

[LN:YGJU_HAEIN] [AC:P45246] [GN:HI1545] [OR:Haemophilus influenzae]
[DE:HYPOTHETICAL SYMPORTER HI1545] [SP:P45246]

| ORF Name | NT ID | AA ID | NT LN | AA LN | Score | P-Value |
|---|---|---|---|---|---|---|
| SPX0423 | 423 | 3084 | 225 | 75 | 153 | 4.00E-15 |
| Description | | | | | | |

[LN:YGJU_ECOLI] [AC:P42602] [GN:YGJU] [OR:Escherichia coli] [DE:HYPOTHETICAL
43.5 KD PROTEIN IN EBGC-UXAA INTERGENIC REGION (O414)] [SP:P42602]

| ORF Name | NT ID | AA ID | NT LN | AA LN | Score | P-Value |
|---|---|---|---|---|---|---|
| SPX0424 | 424 | 3085 | 420 | 140 | 163 | 2.90E-17 |

Description

"[GI:2828366] [LN:AB010789] [AC:AB010789] [OR:Lactococcus lactis]
[SR:Lactococcus lactis (sub_species:lactis, strain:01-7) DNA]"

| ORF Name | NT ID | AA ID | NT LN | AA LN | Score | P-Value |
|---|---|---|---|---|---|---|
| SPX0425 | 425 | 3086 | 198 | 66 | 102 | 1.80E-07 |

Description

[LN:A69867] [AC:A69867] [PN:conserved hypothetical protein ykuT] [GN:ykuT]
[CL:Escherichia coli hypothetical 30.9K protein (sbm-fba intergenic region)]
[OR:Bacillus subtilis]

| ORF Name | NT ID | AA ID | NT LN | AA LN | Score | P-Value |
|---|---|---|---|---|---|---|
| SPX0426 | 426 | 3087 | 177 | 59 | | |

Description

NO-HIT

| ORF Name | NT ID | AA ID | NT LN | AA LN | Score | P-Value |
|---|---|---|---|---|---|---|
| SPX0427 | 427 | 3088 | 909 | 303 | 270 | 1.70E-35 |

Description

[GI:5123526] [LN:AF036485] [AC:AF036485:AF036486:AF036487:U93364]
[PN:hypothetical protein] [OR:Plasmid pNZ4000]

| ORF Name | NT ID | AA ID | NT LN | AA LN | Score | P-Value |
|---|---|---|---|---|---|---|
| SPX0428 | 428 | 3089 | 528 | 176 | 326 | 9.70E-41 |

Description

[LN:YQEG_BACSU] [AC:P54452] [GN:YQEG] [OR:Bacillus subtilis]
[DE:HYPOTHETICAL 20.1 KD PROTEIN IN NUCB-AROD INTERGENIC REGION] [SP:P54452]

| ORF Name | NT ID | AA ID | NT LN | AA LN | Score | P-Value |
|---|---|---|---|---|---|---|
| SPX0429 | 429 | 3090 | 1107 | 369 | 1037 | 1.30E-164 |

Description

[LN:YQEH_BACSU] [AC:P54453] [GN:YQEH] [OR:Bacillus subtilis]
[DE:HYPOTHETICAL 41.0 KD PROTEIN IN NUCB-AROD INTERGENIC REGION] [SP:P54453]

| ORF Name | NT ID | AA ID | NT/LN | AA/LN | Score | P-Value |
|---|---|---|---|---|---|---|
| SPX0430 | 430 | 3091 | 312 | 104 | 211 | 5.20E-24 |

Description

[LN:YQEI_BACSU] [AC:P54454] [GN:YQEI] [OR:Bacillus subtilis]
[DE:HYPOTHETICAL 10.8 KD PROTEIN IN AROD-COMER INTERGENIC REGION]
[SP:P54454]

| ORF Name | NT ID | AA ID | NT/LN | AA/LN | Score | P-Value |
|---|---|---|---|---|---|---|
| SPX0431 | 431 | 3092 | 615 | 205 | 491 | 1.30E-63 |

Description

[LN:YQEJ_BACSU] [AC:P54455] [GN:YQEJ] [OR:Bacillus subtilis]
[DE:HYPOTHETICAL 22.2 KD PROTEIN IN AROD-COMER INTERGENIC REGION]
[SP:P54455]

| ORF Name | NT ID | AA ID | NT/LN | AA/LN | Score | P-Value |
|---|---|---|---|---|---|---|
| SPX0432 | 432 | 3093 | 594 | 198 | 375 | 2.90E-47 |

Description

[LN:YQEK_BACSU] [AC:P54456] [GN:YQEK] [OR:Bacillus subtilis]
[DE:HYPOTHETICAL 21.3 KD PROTEIN IN AROD-COMER INTERGENIC REGION]
[SP:P54456]

| ORF Name | NT ID | AA ID | NT/LN | AA/LN | Score | P-Value |
|---|---|---|---|---|---|---|
| SPX0433 | 433 | 3094 | 501 | 167 | 110 | 4.90E-10 |

Description

[GI:7160132] [LN:SC5C11] [AC:AL158060] [PN:putative isochorismatase.]
[GN:SC5C11.12] [OR:Streptomyces coelicolor A3(2)]

| ORF Name | NT ID | AA ID | NT/LN | AA/LN | Score | P-Value |
|---|---|---|---|---|---|---|
| SPX0434 | 434 | 3095 | 354 | 118 | 267 | 7.00E-32 |

Description

[LN:YQEL_BACSU] [AC:P54457] [GN:YQEL] [OR:Bacillus subtilis]
[DE:HYPOTHETICAL 13.3 KD PROTEIN IN AROD-COMER INTERGENIC REGION]
[SP:P54457]

| ORF Name | NT ID | AA ID | NT/LN | AA/LN | Score | P-Value |
|---|---|---|---|---|---|---|
| SPX0435 | 435 | 3096 | 741 | 247 | 287 | 4.60E-55 |愉

Description

[LN:YQEM_BACSU] [AC:P54458] [GN:YQEM] [OR:Bacillus subtilis]
[DE:HYPOTHETICAL 28.3 KD PROTEIN IN AROD-COMER INTERGENIC REGION]
[SP:P54458]

| ORF Name | NT ID | AA ID | NT/LN | AA/LN | Score | P-Value |
|---|---|---|---|---|---|---|
| SPX0436 | 436 | 3097 | 564 | 188 | | |

Description

NO-HIT

| ORF Name | NT ID | AA ID | NT/LN | AA/LN | Score | P-Value |
|---|---|---|---|---|---|---|
| SPX0437 | 437 | 3098 | 1098 | 366 | 222 | 9.30E-38 |

Description

[LN:B69875] [AC:B69875] [PN:conserved hypothetical protein ylbM] [GN:ylbM]
[OR:Bacillus subtilis]

| ORF Name | NT ID | AA ID | NT/LN | AA/LN | Score | P-Value |
|---|---|---|---|---|---|---|
| SPX0438 | 438 | 3099 | 189 | 63 | | |

Description

NO-HIT

| ORF Name | NT ID | AA ID | NT/LN | AA/LN | Score | P-Value |
|---|---|---|---|---|---|---|
| SPX0439 | 439 | 3100 | 2748 | 916 | 86 | 1.00E-10 |

Description

[GI:1890605] [LN:RMEXPGNS] [AC:Z79692] [PN:ORF25] [OR:Sinorhizobium meliloti]

| ORF Name | NT ID | AA ID | NT/LN | AA/LN | Score | P-Value |
|---|---|---|---|---|---|---|
| SPX0440 | 440 | 3101 | 1611 | 537 | 1547 | 2.30E-211 |

Description

[GI:6984124] [LN:AF228345] [AC:AF228345] [PN:unknown] [OR:Listeria monocytogenes]

| ORF Name | NT ID | AA ID | NT/LN | AA/LN | Score | P-Value |
|---|---|---|---|---|---|---|
| SPX0441 | 441 | 3102 | 627 | 209 | 614 | 1.40E-80 |

Description

[LN:B69878] [AC:B69878] [PN:guanylate kinase homolog yloD] [GN:yloD]
[CL:guanylate kinase:guanylate kinase homology] [OR:Bacillus subtilis]

| ORF Name | NT ID | AA ID | NT/LN | AA/LN | Score | P-Value |
|---|---|---|---|---|---|---|
| SPX0442 | 442 | 3103 | 315 | 105 | 91 | 1.00E-09 |

Description

[LN:C69878] [AC:C69878] [PN:hypothetical protein yloH] [GN:yloH]
[OR:Bacillus subtilis]

| ORF Name | NT ID | AA ID | NT/LN | AA/LN | Score | P-Value |
|---|---|---|---|---|---|---|
| SPX0443 | 443 | 3104 | 2397 | 799 | 953 | 2.70E-237 |

Description

[LN:PRIA_BACSU] [AC:P94461:O34941] [GN:PRIA] [OR:Bacillus subtilis]
[DE:PRIMOSOMAL PROTEIN N' (REPLICATION FACTOR Y)] [SP:P94461:O34941]

| ORF Name | NT ID | AA ID | NT/LN | AA/LN | Score | P-Value |
|---|---|---|---|---|---|---|
| SPX0444 | 444 | 3105 | 936 | 312 | 434 | 1.70E-64 |

Description

[GI:1772500] [LN:BSPRIADFS] [AC:Y10304] [PN:Met-tRNAi formyl transferase]
[GN:fmt] [OR:Bacillus subtilis]

| ORF Name | NT ID | AA ID | NT/LN | AA/LN | Score | P-Value |
|---|---|---|---|---|---|---|
| SPX0445 | 445 | 3106 | 528 | 176 | 248 | 1.40E-39 |

Description

[GI:1772501] [LN:BSPRIADFS] [AC:Y10304] [GN:sun] [OR:Bacillus subtilis]

| ORF Name | NT ID | AA ID | NT/LN | AA/LN | Score | P-Value |
|---|---|---|---|---|---|---|
| SPX0446 | 446 | 3107 | 417 | 139 | 130 | 1.30E-09 |

Description

[GI:4210751] [LN:LLA132604] [AC:AJ132604] [PN:sunL protein] [GN:sunL]
[OR:Lactococcus lactis]

| ORF Name | NT ID | AA ID | NT/LN | AA/LN | Score | P-Value |
|---|---|---|---|---|---|---|
| SPX0447 | 447 | 3108 | 699 | 233 | 606 | 2.70E-80 |

Description

[GI:4210751] [LN:LLA132604] [AC:AJ132604] [PN:sunL protein] [GN:sunL] [OR:Lactococcus lactis]

| ORF Name | NT ID | AA ID | NT/LN | AA/LN | Score | P-Value |
|---|---|---|---|---|---|---|
| SPX0448 | 448 | 3109 | 741 | 247 | 371 | 1.50E-85 |

Description

[GI:4210752] [LN:LLA132604] [AC:AJ132604] [PN:pppL protein] [GN:pppL] [FN:putative phosphoprotein phosphatase] [OR:Lactococcus lactis]

| ORF Name | NT ID | AA ID | NT/LN | AA/LN | Score | P-Value |
|---|---|---|---|---|---|---|
| SPX0449 | 449 | 3110 | 1980 | 660 | 985 | 1.70E-128 |

Description

[GI:4210753] [LN:LLA132604] [AC:AJ132604] [PN:hypothetical protein] [OR:Lactococcus lactis]

| ORF Name | NT ID | AA ID | NT/LN | AA/LN | Score | P-Value |
|---|---|---|---|---|---|---|
| SPX0450 | 450 | 3111 | 204 | 68 | | |

Description

NO-HIT

| ORF Name | NT ID | AA ID | NT/LN | AA/LN | Score | P-Value |
|---|---|---|---|---|---|---|
| SPX0451 | 451 | 3112 | 222 | 74 | | |

Description

NO-HIT

| ORF Name | NT ID | AA ID | NT/LN | AA/LN | Score | P-Value |
|---|---|---|---|---|---|---|
| SPX0452 | 452 | 3113 | 510 | 170 | 125 | 1.80E-09 |

Description

[LN:YJJP_ECOLI] [AC:P39402] [GN:YJJP] [OR:Escherichia coli] [DE:HYPOTHETICAL 30.5 KD PROTEIN IN DNAT-BGLJ INTERGENIC REGION (F277)] [SP:P39402]

| ORF Name | NT ID | AA ID | NT LN | AA LN | Score | P-Value |
|---|---|---|---|---|---|---|
| SPX0453 | 453 | 3114 | 336 | 112 | 94 | 4.60E-07 |

Description

[LN:G81321] [AC:G81321] [PN:probable integral membrane protein Cj1165c [imported]] [GN:Cj1165c] [OR:Campylobacter jejuni]

| ORF Name | NT ID | AA ID | NT LN | AA LN | Score | P-Value |
|---|---|---|---|---|---|---|
| SPX0454 | 454 | 3115 | 201 | 67 | 217 | 3.80E-24 |

Description

[LN:S52544] [AC:S52544] [PN:ISL2 protein] [OR:Lactobacillus helveticus]

| ORF Name | NT ID | AA ID | NT LN | AA LN | Score | P-Value |
|---|---|---|---|---|---|---|
| SPX0455 | 455 | 3116 | 390 | 130 | 362 | 7.00E-46 |

Description

[LN:S52544] [AC:S52544] [PN:ISL2 protein] [OR:Lactobacillus helveticus]

| ORF Name | NT ID | AA ID | NT LN | AA LN | Score | P-Value |
|---|---|---|---|---|---|---|
| SPX0456 | 456 | 3117 | 288 | 96 | | |

Description

NO-HIT

| ORF Name | NT ID | AA ID | NT LN | AA LN | Score | P-Value |
|---|---|---|---|---|---|---|
| SPX0457 | 457 | 3118 | 1173 | 391 | 775 | 1.30E-101 |

Description

[GI:4096796] [LN:SCU40157] [AC:U40157] [OR:Staphylococcus carnosus]

| ORF Name | NT ID | AA ID | NT LN | AA LN | Score | P-Value |
|---|---|---|---|---|---|---|
| SPX0458 | 458 | 3119 | 1275 | 425 | 354 | 8.70E-92 |

Description

[LN:MVAA_PSEMV] [AC:P13702] [GN:MVAA] [OR:Pseudomonas mevalonii] [EC:1.1.1.88] [DE:REDUCTASE)] [SP:P13702]

| ORF Name | NT ID | AA ID | NT LN | AA LN | Score | P-Value |
|---|---|---|---|---|---|---|
| SPX0459 | 459 | 3120 | 966 | 322 | 1108 | 1.00E-150 |
| Description | | | | | | |

[LN:SCRR_STRMU] [AC:Q54430] [GN:SCRR] [OR:Streptococcus mutans] [DE:SUCROSE OPERON REPRESSOR (SCR OPERON REGULATORY PROTEIN)] [SP:Q54430]

| ORF Name | NT ID | AA ID | NT LN | AA LN | Score | P-Value |
|---|---|---|---|---|---|---|
| SPX0460 | 460 | 3121 | 1455 | 485 | 1691 | 3.60E-229 |
| Description | | | | | | |

"[LN:S68598] [AC:S68598] [PN:sucrose-6-phosphate hydrolase ScrB] [GN:scrB] [CL:sucrose-6-phosphate hydrolase] [OR:Streptococcus sobrinus] [SR:strain 6715, , strain 6715] [SR:strain 6715, ]"

| ORF Name | NT ID | AA ID | NT LN | AA LN | Score | P-Value |
|---|---|---|---|---|---|---|
| SPX0461 | 461 | 3122 | 231 | 77 | | |
| Description | | | | | | |

NO-HIT

| ORF Name | NT ID | AA ID | NT LN | AA LN | Score | P-Value |
|---|---|---|---|---|---|---|
| SPX0462 | 462 | 3123 | 198 | 66 | | |
| Description | | | | | | |

NO-HIT

| ORF Name | NT ID | AA ID | NT LN | AA LN | Score | P-Value |
|---|---|---|---|---|---|---|
| SPX0463 | 463 | 3124 | 1884 | 628 | 717 | 6.70E-255 |
| Description | | | | | | |

"[LN:S68599] [AC:S68599] [PN:phosphotransferase system enzyme II,, sucrose-specific:sucrose-specific enzyme II:sucrose-specific enzyme II] [GN:scrA] [OR:Streptococcus sobrinus]"

| ORF Name | NT ID | AA ID | NT LN | AA LN | Score | P-Value |
|---|---|---|---|---|---|---|
| SPX0464 | 464 | 3125 | 888 | 296 | 701 | 3.80E-158 |
| Description | | | | | | |

"[LN:SCRK_STRMU] [AC:Q07211] [GN:SCRK] [OR:Streptococcus mutans] [EC:2.7.1.4] [DE:FRUCTOKINASE,] [SP:Q07211]"

| ORF Name | NT ID | AA ID | NT LN | AA LN | Score | P-Value |
|---|---|---|---|---|---|---|
| SPX0465 | 465 | 3126 | 213 | 71 | | |
| Description | | | | | | |

NO-HIT

| ORF Name | NT ID | AA ID | NT LN | AA LN | Score | P-Value |
|---|---|---|---|---|---|---|
| SPX0466 | 466 | 3127 | 600 | 200 | 103 | 2.90E-07 |
| Description | | | | | | |

[LN:YDJZ_ECOLI] [AC:P76221] [GN:YDJZ] [OR:Escherichia coli] [DE:HYPOTHETICAL 26.2 KD PROTEIN IN XTHA-GDHA INTERGENIC REGION] [SP:P76221]

| ORF Name | NT ID | AA ID | NT LN | AA LN | Score | P-Value |
|---|---|---|---|---|---|---|
| SPX0467 | 467 | 3128 | 225 | 75 | 200 | 1.30E-21 |
| Description | | | | | | |

[GI:517210] [LN:SPU11799] [AC:U11799] [OR:Streptococcus pyogenes]

| ORF Name | NT ID | AA ID | NT LN | AA LN | Score | P-Value |
|---|---|---|---|---|---|---|
| SPX0468 | 468 | 3129 | 252 | 84 | | |
| Description | | | | | | |

NO-HIT

| ORF Name | NT ID | AA ID | NT LN | AA LN | Score | P-Value |
|---|---|---|---|---|---|---|
| SPX0469 | 469 | 3130 | 228 | 76 | 187 | 3.50E-21 |
| Description | | | | | | |

[LN:T30285] [AC:T30285] [PN:hypothetical protein] [OR:Streptococcus pneumoniae]

| ORF Name | NT ID | AA ID | NT LN | AA LN | Score | P-Value |
|---|---|---|---|---|---|---|
| SPX0470 | 470 | 3131 | 894 | 298 | 460 | 1.20E-78 |
| Description | | | | | | |

[GI:3688825] [LN:AF084104] [AC:AF084104] [PN:NatA] [GN:natA] [OR:Bacillus firmus]

| ORF Name | NT ID | AA ID | NT LN | AA LN | Score | P-Value |
|---|---|---|---|---|---|---|
| SPX0471 | 471 | 3132 | 1200 | 400 | 200 | 4.70E-36 |

Description

[GI:1150487] [LN:LSLASAMPT] [AC:Z54312] [PN:unknown] [GN:orf414]
[OR:Lactobacillus sakei]

| ORF Name | NT ID | AA ID | NT LN | AA LN | Score | P-Value |
|---|---|---|---|---|---|---|
| SPX0472 | 472 | 3133 | 168 | 56 | | |

Description

NO-HIT

| ORF Name | NT ID | AA ID | NT LN | AA LN | Score | P-Value |
|---|---|---|---|---|---|---|
| SPX0473 | 473 | 3134 | 849 | 283 | | |

Description

NO-HIT

| ORF Name | NT ID | AA ID | NT LN | AA LN | Score | P-Value |
|---|---|---|---|---|---|---|
| SPX0474 | 474 | 3135 | 723 | 241 | 460 | 1.50E-58 |

Description

"[LN:G71842] [AC:G71842] [PN:probable ABC transporter, ATP-binding protein]
[GN:jhp1141] [CL:unassigned ATP-binding cassette proteins:ATP-binding
cassette homology] [OR:Helicobacter pylori] [SR:strain J99, , strain J99]
[SR:strain J99, ]"

| ORF Name | NT ID | AA ID | NT LN | AA LN | Score | P-Value |
|---|---|---|---|---|---|---|
| SPX0475 | 475 | 3136 | 210 | 70 | 95 | 4.40E-07 |

Description

[LN:E72756] [AC:E72756] [PN:hypothetical protein APE0042] [GN:APE0042]
[OR:Aeropyrum pernix]

| ORF Name | NT ID | AA ID | NT LN | AA LN | Score | P-Value |
|---|---|---|---|---|---|---|
| SPX0476 | 476 | 3137 | 366 | 122 | 256 | 3.70E-30 |

Description

[GI:5822822] [LN:AB024564] [AC:AB024564] [PN:YHCF] [GN:yhcF] [OR:Bacillus
halodurans] [SR:Bacillus halodurans (strain:C-125) DNA]

| ORF Name | NT ID | AA ID | NT/LN | AA/LN | Score | P-Value |
|---|---|---|---|---|---|---|
| SPX0477 | 477 | 3138 | 474 | 158 | 405 | 8.00E-51 |

Description

[LN:E72221] [AC:E72221] [PN:conserved hypothetical protein] [GN:TM1707] [CL:conserved hypothetical protein HI0943] [OR:Thermotoga maritima]

| ORF Name | NT ID | AA ID | NT/LN | AA/LN | Score | P-Value |
|---|---|---|---|---|---|---|
| SPX0478 | 478 | 3139 | 1170 | 390 | | |

Description

NO-HIT

| ORF Name | NT ID | AA ID | NT/LN | AA/LN | Score | P-Value |
|---|---|---|---|---|---|---|
| SPX0479 | 479 | 3140 | 897 | 299 | 300 | 2.40E-58 |

Description

[LN:DNAI_BACSU] [AC:P06567] [GN:DNAI] [OR:Bacillus subtilis] [DE:PRIMOSOMAL PROTEIN DNAI] [SP:P06567]

| ORF Name | NT ID | AA ID | NT/LN | AA/LN | Score | P-Value |
|---|---|---|---|---|---|---|
| SPX0480 | 480 | 3141 | 714 | 238 | 239 | 3.90E-35 |

Description

"[LN:CHRR_PSESP] [AC:P96977] [GN:CHRR] [OR:Pseudomonas sp] [SR:,strain G-1] [DE:CR(VI) REDUCTASE] [SP:P96977]"

| ORF Name | NT ID | AA ID | NT/LN | AA/LN | Score | P-Value |
|---|---|---|---|---|---|---|
| SPX0481 | 481 | 3142 | 1311 | 437 | 1986 | 1.10E-270 |

Description

"[GI:6681650] [LN:AB016077] [AC:AB016077] [PN:phosphoglycerate dehydrogenase] [GN:pgdA] [OR:Streptococcus mutans] [SR:Streptococcus mutans (strain:MT8148) DNA, clone:pYT570]"

| ORF Name | NT ID | AA ID | NT/LN | AA/LN | Score | P-Value |
|---|---|---|---|---|---|---|
| SPX0482 | 482 | 3143 | 345 | 115 | | |

Description

NO-HIT

| ORF Name | NT ID | AA ID | NT LN | AA LN | Score | P-Value |
|---|---|---|---|---|---|---|
| SPX0483 | 483 | 3144 | 354 | 118 | | |

Description

NO-HIT

| ORF Name | NT ID | AA ID | NT LN | AA LN | Score | P-Value |
|---|---|---|---|---|---|---|
| SPX0484 | 484 | 3145 | 192 | 64 | | |

Description

NO-HIT

| ORF Name | NT ID | AA ID | NT LN | AA LN | Score | P-Value |
|---|---|---|---|---|---|---|
| SPX0485 | 485 | 3146 | 852 | 284 | 103 | 3.00E-11 |

Description

[GI:4102023] [LN:AF007761] [AC:AF007761] [PN:MutR] [GN:mutR] [FN:positive transcriptional regulator of mutA] [OR:Streptococcus mutans]

| ORF Name | NT ID | AA ID | NT LN | AA LN | Score | P-Value |
|---|---|---|---|---|---|---|
| SPX0486 | 486 | 3147 | 393 | 131 | | |

Description

NO-HIT

| ORF Name | NT ID | AA ID | NT LN | AA LN | Score | P-Value |
|---|---|---|---|---|---|---|
| SPX0487 | 487 | 3148 | 792 | 264 | | |

Description

NO-HIT

| ORF Name | NT ID | AA ID | NT LN | AA LN | Score | P-Value |
|---|---|---|---|---|---|---|
| SPX0488 | 488 | 3149 | 678 | 226 | | |

Description

NO-HIT

| ORF Name | NT ID | AA ID | NT/LN | AA/LN | Score | P-Value |
|---|---|---|---|---|---|---|
| SPX0489 | 489 | 3150 | 633 | 211 | 282 | 3.20E-42 |

Description

[LN:YYBJ_BACSU] [AC:P37494] [GN:YYBJ] [OR:Bacillus subtilis] [DE:INTERGENIC REGION] [SP:P37494]

| ORF Name | NT ID | AA ID | NT/LN | AA/LN | Score | P-Value |
|---|---|---|---|---|---|---|
| SPX0490 | 490 | 3151 | 288 | 96 | | |

Description

NO-HIT

| ORF Name | NT ID | AA ID | NT/LN | AA/LN | Score | P-Value |
|---|---|---|---|---|---|---|
| SPX0491 | 491 | 3152 | 2514 | 838 | 989 | 0 |

Description

[LN:SECA_LISMO] [AC:P47847] [GN:SECA] [OR:Listeria monocytogenes] [DE:PREPROTEIN TRANSLOCASE SECA SUBUNIT] [SP:P47847]

| ORF Name | NT ID | AA ID | NT/LN | AA/LN | Score | P-Value |
|---|---|---|---|---|---|---|
| SPX0492 | 492 | 3153 | 1032 | 344 | 156 | 7.30E-47 |

Description

[GI:7380801] [LN:NMA7Z2491] [AC:AL162758:AL157959] [PN:phospho-2-dehydr-3-deoxyheptonate aldolase] [GN:aroG] [OR:Neisseria meningitidis]

| ORF Name | NT ID | AA ID | NT/LN | AA/LN | Score | P-Value |
|---|---|---|---|---|---|---|
| SPX0493 | 493 | 3154 | 645 | 215 | 178 | 3.50E-34 |

Description

[LN:AROF_ECOLI] [AC:P00888] [GN:AROF] [OR:Escherichia coli] [EC:4.1.2.15] [DE:SYNTHETASE) (3-DEOXY-D-ARABINO-HEPTULOSONATE 7-PHOSPHATE SYNTHASE)] [SP:P00888]

| ORF Name | NT ID | AA ID | NT/LN | AA/LN | Score | P-Value |
|---|---|---|---|---|---|---|
| SPX0494 | 494 | 3155 | 333 | 111 | | |

Description

NO-HIT

| ORF Name | NT ID | AA ID | NT/LN | AA/LN | Score | P-Value |
|---|---|---|---|---|---|---|
| SPX0495 | 495 | 3156 | 267 | 89 | 132 | 2.60E-14 |

Description

[GI:7380801] [LN:NMA7Z2491] [AC:AL162758:AL157959] [PN:phospho-2-dehydr-3-deoxyheptonate aldolase] [GN:aroG] [OR:Neisseria meningitidis]

| ORF Name | NT ID | AA ID | NT/LN | AA/LN | Score | P-Value |
|---|---|---|---|---|---|---|
| SPX0496 | 496 | 3157 | 363 | 121 | 177 | 1.70E-30 |

Description

"[LN:H69772] [AC:H69772] [PN:holo-[acyl-carrier-protein] synthase,] [GN:ydcB] [CL:holo-ACP synthase] [OR:Bacillus subtilis] [EC:2.7.8.7]"

| ORF Name | NT ID | AA ID | NT/LN | AA/LN | Score | P-Value |
|---|---|---|---|---|---|---|
| SPX0497 | 497 | 3158 | 1104 | 368 | 1852 | 1.10E-252 |

Description

[GI:5759209] [LN:AF171873] [AC:AF171873] [PN:alanine racemase] [GN:alr] [OR:Streptococcus pneumoniae]

| ORF Name | NT ID | AA ID | NT/LN | AA/LN | Score | P-Value |
|---|---|---|---|---|---|---|
| SPX0498 | 498 | 3159 | 2016 | 672 | 3357 | 0 |

Description

"[LN:RECG_STRPN] [AC:Q54900] [GN:RECG:MMSA] [OR:Streptococcus pneumoniae] [EC:3.6.1.-] [DE:ATP-DEPENDENT DNA HELICASE RECG,] [SP:Q54900]"

| ORF Name | NT ID | AA ID | NT/LN | AA/LN | Score | P-Value |
|---|---|---|---|---|---|---|
| SPX0499 | 499 | 3160 | 267 | 89 | 263 | 2.70E-32 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX0500 | 500 | 3161 | 204 | 68 | | |

Description

NO-HIT

| ORF Name | NT ID | AA ID | NT/LN | AA/LN | Score | P-Value |
|---|---|---|---|---|---|---|
| SPX0501 | 501 | 3162 | 981 | 327 | 447 | 1.40E-92 |

Description

[GI:2353697] [LN:AF001926] [AC:AF001926] [PN:xylan esterase 1] [GN:axe1] [OR:Thermoanaerobacterium sp. 'JW/SL YS485']

| ORF Name | NT ID | AA ID | NT/LN | AA/LN | Score | P-Value |
|---|---|---|---|---|---|---|
| SPX0502 | 502 | 3163 | 618 | 206 | 355 | 1.20E-44 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX0503 | 503 | 3164 | 504 | 168 | 172 | 1.10E-15 |

Description

[GI:4101572] [LN:AF004842] [AC:AF004842] [PN:major royal jelly protein MRJP5] [GN:MRJP5] [OR:Apis mellifera] [SR:honeybee]

| ORF Name | NT ID | AA ID | NT/LN | AA/LN | Score | P-Value |
|---|---|---|---|---|---|---|
| SPX0504 | 504 | 3165 | 228 | 76 | 371 | 3.40E-50 |

Description

[LN:T30286] [AC:T30286:S26297] [PN:hypothetical protein 76] [OR:Streptococcus pneumoniae]

| ORF Name | NT ID | AA ID | NT/LN | AA/LN | Score | P-Value |
|---|---|---|---|---|---|---|
| SPX0505 | 505 | 3166 | 2814 | 938 | 4378 | 0 |

Description

"[LN:NANA_STRPN] [AC:Q59959:Q54722] [GN:NANA] [OR:Streptococcus pneumoniae] [EC:3.2.1.18] [DE:SIALIDASE A PRECURSOR, (NEURAMINIDASE A)] [SP:Q59959:Q54722]"

| ORF Name | NT ID | AA ID | NT/LN | AA/LN | Score | P-Value |
|---|---|---|---|---|---|---|
| SPX0506 | 506 | 3167 | 216 | 72 | | |

Description

NO-HIT

| ORF Name | NT ID | AA ID | NT LN | AA LN | Score | P-Value |
|---|---|---|---|---|---|---|
| SPX0507 | 507 | 3168 | 453 | 151 | 773 | 6.10E-103 |

Description

[GI:1163111] [LN:SPU43526] [AC:U43526] [OR:Streptococcus pneumoniae]

| ORF Name | NT ID | AA ID | NT LN | AA LN | Score | P-Value |
|---|---|---|---|---|---|---|
| SPX0508 | 508 | 3169 | 1338 | 446 | 2307 | 0 |

Description

[GI:1163112] [LN:SPU43526] [AC:U43526] [OR:Streptococcus pneumoniae]

| ORF Name | NT ID | AA ID | NT LN | AA LN | Score | P-Value |
|---|---|---|---|---|---|---|
| SPX0509 | 509 | 3170 | 885 | 295 | 1542 | 2.00E-218 |

Description

[GI:1163113] [LN:SPU43526] [AC:U43526] [OR:Streptococcus pneumoniae]

| ORF Name | NT ID | AA ID | NT LN | AA LN | Score | P-Value |
|---|---|---|---|---|---|---|
| SPX0510 | 510 | 3171 | 834 | 278 | 1375 | 3.80E-192 |

Description

[GI:1163114] [LN:SPU43526] [AC:U43526] [OR:Streptococcus pneumoniae]

| ORF Name | NT ID | AA ID | NT LN | AA LN | Score | P-Value |
|---|---|---|---|---|---|---|
| SPX0511 | 511 | 3172 | 762 | 254 | 1250 | 1.40E-167 |

Description

"[LN:NANB_STRPN] [AC:Q54727] [GN:NANB] [OR:Streptococcus pneumoniae] [EC:3.2.1.18] [DE:SIALIDASE B PRECURSOR, (NEURAMINIDASE B)] [SP:Q54727]"

| ORF Name | NT ID | AA ID | NT LN | AA LN | Score | P-Value |
|---|---|---|---|---|---|---|
| SPX0512 | 512 | 3173 | 378 | 126 | 333 | 1.60E-40 |

Description

[GI:517210] [LN:SPU11799] [AC:U11799] [OR:Streptococcus pyogenes]

| ORF Name | NT ID | AA ID | NT LN | AA LN | Score | P-Value |
|---|---|---|---|---|---|---|
| SPX0513 | 513 | 3174 | 633 | 211 | 762 | 7.90E-101 |

Description

[GI:517210] [LN:SPU11799] [AC:U11799] [OR:Streptococcus pyogenes]

| ORF Name | NT ID | AA ID | NT/LN | AA/LN | Score | P-Value |
|---|---|---|---|---|---|---|
| SPX0514 | 514 | 3175 | 1401 | 467 | 2363 | 0 |

Description

"[LN:NANB_STRPN] [AC:Q54727] [GN:NANB] [OR:Streptococcus pneumoniae] [EC:3.2.1.18] [DE:SIALIDASE B PRECURSOR, (NEURAMINIDASE B)] [SP:Q54727]"

| ORF Name | NT ID | AA ID | NT/LN | AA/LN | Score | P-Value |
|---|---|---|---|---|---|---|
| SPX0515 | 515 | 3176 | 1104 | 368 | 1838 | 1.30E-249 |

Description

[LN:YJHC_STRPN] [AC:Q54728] [OR:Streptococcus pneumoniae] [DE:HYPOTHETICAL PROTEIN IN NANB 3'REGION (ORF-5) (FRAGMENT)] [SP:Q54728]

| ORF Name | NT ID | AA ID | NT/LN | AA/LN | Score | P-Value |
|---|---|---|---|---|---|---|
| SPX0516 | 516 | 3177 | 390 | 130 | | |

Description

NO-HIT

| ORF Name | NT ID | AA ID | NT/LN | AA/LN | Score | P-Value |
|---|---|---|---|---|---|---|
| SPX0517 | 517 | 3178 | 699 | 233 | 331 | 1.90E-64 |

Description

"[LN:C70180] [AC:C70180] [PN:conserved hypothetical protein BB0644] [OR:Borrelia burgdorferi] [SR:, Lyme disease spirochete]"

| ORF Name | NT ID | AA ID | NT/LN | AA/LN | Score | P-Value |
|---|---|---|---|---|---|---|
| SPX0518 | 518 | 3179 | 1518 | 506 | 839 | 2.60E-178 |

Description

"[LN:D70180] [AC:D70180] [PN:phosphotransferase system enzyme II,, glucose-specific, factor II] [OR:Borrelia burgdorferi] [SR:, Lyme disease spirochete] [EC:2.7.1.69]"

| ORF Name | NT ID | AA ID | NT/LN | AA/LN | Score | P-Value |
|---|---|---|---|---|---|---|
| SPX0519 | 519 | 3180 | 1329 | 443 | 110 | 1.90E-08 |

Description

[GI:6137033] [LN:SCF11] [AC:AL132662] [PN:putative sugar transporter sugar binding] [GN:SCF11.11] [OR:Streptomyces coelicolor A3(2)]

| ORF Name | NT ID | AA ID | NT/LN | AA/LN | Score | P-Value |
|---|---|---|---|---|---|---|
| SPX0520 | 520 | 3181 | 888 | 296 | 211 | 1.60E-50 |

Description

"[LN:E72357] [AC:E72357] [PN:sugar ABC transporter, permease protein] [GN:TM0596] [CL:inner membrane protein malF] [OR:Thermotoga maritima]"

| ORF Name | NT ID | AA ID | NT/LN | AA/LN | Score | P-Value |
|---|---|---|---|---|---|---|
| SPX0521 | 521 | 3182 | 840 | 280 | 434 | 1.10E-65 |

Description

"[LN:F72379] [AC:F72379] [PN:sugar ABC transporter, permease protein] [GN:TM0430] [CL:maltose transport protein malG] [OR:Thermotoga maritima]"

| ORF Name | NT ID | AA ID | NT/LN | AA/LN | Score | P-Value |
|---|---|---|---|---|---|---|
| SPX0522 | 522 | 3183 | 453 | 151 | 109 | 2.60E-13 |

Description

[LN:YJGK_ECOLI] [AC:P39335] [GN:YJGK] [OR:Escherichia coli] [DE:HYPOTHETICAL 17.3 KD PROTEIN IN PYRL-ARGI INTERGENIC REGION (O153B)] [SP:P39335]

| ORF Name | NT ID | AA ID | NT/LN | AA/LN | Score | P-Value |
|---|---|---|---|---|---|---|
| SPX0523 | 523 | 3184 | 354 | 118 | | |

Description

NO-HIT

| ORF Name | NT ID | AA ID | NT/LN | AA/LN | Score | P-Value |
|---|---|---|---|---|---|---|
| SPX0524 | 524 | 3185 | 198 | 66 | | |

Description

NO-HIT

| ORF Name | NT ID | AA ID | NT/LN | AA/LN | Score | P-Value |
|---|---|---|---|---|---|---|
| SPX0525 | 525 | 3186 | 645 | 215 | | |

Description

NO-HIT

| ORF Name | NT ID | AA ID | NT/LN | AA/LN | Score | P-Value |
|---|---|---|---|---|---|---|
| SPX0526 | 526 | 3187 | 660 | 220 | 830 | 1.30E-109 |
| Description | | | | | | |

[GI:2385360] [LN:CTSIALIDA] [AC:Y08695] [PN:putative acylneuraminate lyase] [OR:Clostridium tertium]

| ORF Name | NT ID | AA ID | NT/LN | AA/LN | Score | P-Value |
|---|---|---|---|---|---|---|
| SPX0527 | 527 | 3188 | 300 | 100 | 68 | 0.00016 |
| Description | | | | | | |

[GI:42131] [LN:ECNPL] [AC:X03345] [OR:Escherichia coli]

| ORF Name | NT ID | AA ID | NT/LN | AA/LN | Score | P-Value |
|---|---|---|---|---|---|---|
| SPX0528 | 528 | 3189 | 885 | 295 | 423 | 2.50E-53 |
| Description | | | | | | |

[LN:YNGA_CLOPE] [AC:P26832] [OR:Clostridium perfringens] [DE:HYPOTHETICAL PROTEIN IN NAGH 5'REGION (ORFA) (FRAGMENT)] [SP:P26832]

| ORF Name | NT ID | AA ID | NT/LN | AA/LN | Score | P-Value |
|---|---|---|---|---|---|---|
| SPX0529 | 529 | 3190 | 849 | 283 | 170 | 2.10E-25 |
| Description | | | | | | |

[LN:Y143_HAEIN] [AC:P44540] [GN:HI0143] [OR:Haemophilus influenzae] [DE:HYPOTHETICAL PROTEIN HI0143] [SP:P44540]

| ORF Name | NT ID | AA ID | NT/LN | AA/LN | Score | P-Value |
|---|---|---|---|---|---|---|
| SPX0530 | 530 | 3191 | 2043 | 681 | 3365 | 0 |
| Description | | | | | | |

[GI:4009463] [LN:AF068901] [AC:AF068901] [PN:penicillin-binding protein 2b] [GN:pbp2b] [OR:Streptococcus pneumoniae]

| ORF Name | NT ID | AA ID | NT/LN | AA/LN | Score | P-Value |
|---|---|---|---|---|---|---|
| SPX0531 | 531 | 3192 | 357 | 119 | 524 | 5.00E-69 |
| Description | | | | | | |

[GI:49383] [LN:SPPBP2BH] [AC:Z21808] [PN:internal region of the penicillin-binding] [FN:penicillin-resistantance] [OR:Streptococcus pneumoniae]

| ORF Name | NT ID | AA ID | NT LN | AA LN | Score | P-Value |
|---|---|---|---|---|---|---|
| SPX0532 | 532 | 3193 | 513 | 171 | 625 | 4.80E-83 |

Description

[GI:4009464] [LN:AF068901] [AC:AF068901] [PN:RecM] [GN:recM] [OR:Streptococcus pneumoniae]

| ORF Name | NT ID | AA ID | NT LN | AA LN | Score | P-Value |
|---|---|---|---|---|---|---|
| SPX0533 | 533 | 3194 | 1044 | 348 | 1766 | 1.30E-239 |

Description

[GI:4009465] [LN:AF068901] [AC:AF068901] [PN:D-Ala-D-Ala ligase] [GN:ddl] [OR:Streptococcus pneumoniae]

| ORF Name | NT ID | AA ID | NT LN | AA LN | Score | P-Value |
|---|---|---|---|---|---|---|
| SPX0534 | 534 | 3195 | 1374 | 458 | 2278 | 0 |

Description

[GI:4009466] [LN:AF068901] [AC:AF068901] [PN:D-Ala-D-Ala adding enzyme] [GN:murF] [OR:Streptococcus pneumoniae]

| ORF Name | NT ID | AA ID | NT LN | AA LN | Score | P-Value |
|---|---|---|---|---|---|---|
| SPX0535 | 535 | 3196 | 1347 | 449 | 403 | 3.50E-76 |

Description

[GI:5822769] [LN:AB024553] [AC:AB024553] [OR:Bacillus halodurans] [SR:Bacillus halodurans (strain:C-125) DNA]

| ORF Name | NT ID | AA ID | NT LN | AA LN | Score | P-Value |
|---|---|---|---|---|---|---|
| SPX0536 | 536 | 3197 | 576 | 192 | 954 | 1.80E-127 |

Description

[GI:4009467] [LN:AF068901] [AC:AF068901] [PN:MutT] [GN:mutT] [OR:Streptococcus pneumoniae]

| ORF Name | NT ID | AA ID | NT LN | AA LN | Score | P-Value |
|---|---|---|---|---|---|---|
| SPX0537 | 537 | 3198 | 597 | 199 | 1003 | 1.80E-140 |

Description

[GI:4009468] [LN:AF068901] [AC:AF068901] [PN:unknown] [OR:Streptococcus pneumoniae]

| ORF Name | NT ID | AA ID | NT/LN | AA/LN | Score | P-Value |
|---|---|---|---|---|---|---|
| SPX0538 | 538 | 3199 | 261 | 87 | | |

Description

NO-HIT

| ORF Name | NT ID | AA ID | NT/LN | AA/LN | Score | P-Value |
|---|---|---|---|---|---|---|
| SPX0539 | 539 | 3200 | 1374 | 458 | 2266 | 0 |

Description

[GI:4009469] [LN:AF068901] [AC:AF068901] [PN:cell division protein FtsA] [GN:ftsA] [OR:Streptococcus pneumoniae]

| ORF Name | NT ID | AA ID | NT/LN | AA/LN | Score | P-Value |
|---|---|---|---|---|---|---|
| SPX0540 | 540 | 3201 | 1257 | 419 | 2094 | 4.10E-280 |

Description

[GI:4009470] [LN:AF068901] [AC:AF068901] [PN:cell division protein FtsZ] [GN:ftsZ] [OR:Streptococcus pneumoniae]

| ORF Name | NT ID | AA ID | NT/LN | AA/LN | Score | P-Value |
|---|---|---|---|---|---|---|
| SPX0541 | 541 | 3202 | 237 | 79 | 178 | 2.40E-19 |

Description

[LN:A71218] [AC:A71218] [PN:hypothetical protein PH0004] [GN:PH0004] [OR:Pyrococcus horikoshii]

| ORF Name | NT ID | AA ID | NT/LN | AA/LN | Score | P-Value |
|---|---|---|---|---|---|---|
| SPX0542 | 542 | 3203 | 672 | 224 | 1101 | 6.20E-148 |

Description

[GI:4009471] [LN:AF068901] [AC:AF068901] [PN:YlmE] [GN:ylmE] [OR:Streptococcus pneumoniae]

| ORF Name | NT ID | AA ID | NT/LN | AA/LN | Score | P-Value |
|---|---|---|---|---|---|---|
| SPX0543 | 543 | 3204 | 540 | 180 | 920 | 1.10E-122 |

Description

[GI:4009472] [LN:AF068901] [AC:AF068901] [PN:YlmF] [GN:ylmF] [OR:Streptococcus pneumoniae]

| ORF Name | NT ID | AA ID | NT/LN | AA/LN | Score | P-Value |
|---|---|---|---|---|---|---|
| SPX0544 | 544 | 3205 | 264 | 88 | 431 | 1.50E-58 |

Description

[GI:4009473] [LN:AF068901] [AC:AF068901] [PN:YlmG] [GN:ylmG] [OR:Streptococcus pneumoniae]

| ORF Name | NT ID | AA ID | NT/LN | AA/LN | Score | P-Value |
|---|---|---|---|---|---|---|
| SPX0545 | 545 | 3206 | 786 | 262 | 1318 | 2.10E-179 |

Description

[GI:4009474] [LN:AF068901] [AC:AF068901] [PN:YlmH] [GN:ylmH] [OR:Streptococcus pneumoniae]

| ORF Name | NT ID | AA ID | NT/LN | AA/LN | Score | P-Value |
|---|---|---|---|---|---|---|
| SPX0546 | 546 | 3207 | 789 | 263 | 1297 | 1.90E-171 |

Description

[GI:4009475] [LN:AF068901] [AC:AF068901] [PN:cell division protein DivIVA] [GN:divIVA] [OR:Streptococcus pneumoniae]

| ORF Name | NT ID | AA ID | NT/LN | AA/LN | Score | P-Value |
|---|---|---|---|---|---|---|
| SPX0547 | 547 | 3208 | 2793 | 931 | 4840 | 0 |

Description

[GI:4009476] [LN:AF068901] [AC:AF068901] [PN:isoleucine-tRNA synthetase] [GN:ileS] [OR:Streptococcus pneumoniae]

| ORF Name | NT ID | AA ID | NT/LN | AA/LN | Score | P-Value |
|---|---|---|---|---|---|---|
| SPX0548 | 548 | 3209 | 186 | 62 | 82 | 0.00016 |

Description

"[LN:A56034] [AC:A56034] [PN:insulin activator factor] [CL:human insulin activator factor] [OR:Homo sapiens] [SR:, man]"

| ORF Name | NT ID | AA ID | NT/LN | AA/LN | Score | P-Value |
|---|---|---|---|---|---|---|
| SPX0549 | 549 | 3210 | 261 | 87 | 192 | 2.20E-20 |

Description

"[LN:A56034] [AC:A56034] [PN:insulin activator factor] [CL:human insulin activator factor] [OR:Homo sapiens] [SR:, man]"

| ORF Name | NT ID | AA ID | NT/LN | AA/LN | Score | P-Value |
|---|---|---|---|---|---|---|
| SPX0550 | 550 | 3211 | 189 | 63 | | |

Description

NO-HIT

| ORF Name | NT ID | AA ID | NT/LN | AA/LN | Score | P-Value |
|---|---|---|---|---|---|---|
| SPX0551 | 551 | 3212 | 216 | 72 | | |

Description

NO-HIT

| ORF Name | NT ID | AA ID | NT/LN | AA/LN | Score | P-Value |
|---|---|---|---|---|---|---|
| SPX0552 | 552 | 3213 | 693 | 231 | 1201 | 1.00E-160 |

Description

[GI:5578891] [LN:SPN131985] [AC:AJ131985] [PN:phosphoglyceromutase] [GN:gpmA] [OR:Streptococcus pneumoniae]

| ORF Name | NT ID | AA ID | NT/LN | AA/LN | Score | P-Value |
|---|---|---|---|---|---|---|
| SPX0553 | 553 | 3214 | 2412 | 804 | 232 | 2.70E-95 |

Description

[GI:5912520] [LN:SCF12] [AC:AL117669] [PN:putative large secreted protein] [GN:SCF12.20c] [OR:Streptomyces coelicolor A3(2)]

| ORF Name | NT ID | AA ID | NT/LN | AA/LN | Score | P-Value |
|---|---|---|---|---|---|---|
| SPX0554 | 554 | 3215 | 711 | 237 | 642 | 7.20E-84 |

Description

"[LN:B69477] [AC:B69477] [PN:ABC transporter, ATP-binding protein homolog] [CL:unassigned ATP-binding cassette proteins:ATP-binding cassette homology] [OR:Archaeoglobus fulgidus]"

| ORF Name | NT ID | AA ID | NT/LN | AA/LN | Score | P-Value |
|---|---|---|---|---|---|---|
| SPX0555 | 555 | 3216 | 2775 | 925 | 106 | 1.10E-16 |

Description

[LN:C69477] [AC:C69477] [PN:hypothetical protein AF1820] [OR:Archaeoglobus fulgidus]

| ORF Name | NT ID | AA ID | NT LN | AA LN | Score | P-Value |
|---|---|---|---|---|---|---|
| SPX0556 | 556 | 3217 | 519 | 173 | 878 | 1.10E-117 |

Description

[GI:4193357] [LN:AF055088] [AC:AF055088:AF055087] [PN:putative hydrophobic transmembrane protein] [GN:psaD] [OR:Streptococcus pneumoniae]

| ORF Name | NT ID | AA ID | NT LN | AA LN | Score | P-Value |
|---|---|---|---|---|---|---|
| SPX0557 | 557 | 3218 | 930 | 310 | 1579 | 2.30E-209 |

Description

[GI:3258602] [LN:SPU40786] [AC:U40786] [PN:surface antigen A variant precursor] [GN:psaA] [FN:putative fimbrial adhesin] [OR:Streptococcus pneumoniae]

| ORF Name | NT ID | AA ID | NT LN | AA LN | Score | P-Value |
|---|---|---|---|---|---|---|
| SPX0558 | 558 | 3219 | 849 | 283 | 1171 | 8.00E-165 |

Description

[LN:P29K_STRGC] [AC:P42361] [OR:Streptococcus gordonii challis] [DE:29 KD MEMBRANE PROTEIN IN PSAA 5'REGION (ORF1)] [SP:P42361]

| ORF Name | NT ID | AA ID | NT LN | AA LN | Score | P-Value |
|---|---|---|---|---|---|---|
| SPX0559 | 559 | 3220 | 756 | 252 | 1208 | 2.80E-164 |

Description

[GI:4193356] [LN:AF055088] [AC:AF055088:AF055087] [PN:ATP-binding cassette] [GN:psaB] [OR:Streptococcus pneumoniae]

| ORF Name | NT ID | AA ID | NT LN | AA LN | Score | P-Value |
|---|---|---|---|---|---|---|
| SPX0560 | 560 | 3221 | 1953 | 651 | 1477 | 0 |

Description

[GI:5139244] [LN:AF116532] [AC:AF116532] [PN:endopeptidase O] [GN:pepO] [OR:Streptococcus parasanguinis]

| ORF Name | NT ID | AA ID | NT LN | AA LN | Score | P-Value |
|---|---|---|---|---|---|---|
| SPX0561 | 561 | 3222 | 630 | 210 | 181 | 2.90E-36 |

Description

[LN:YQGX_BACSU] [AC:P54501] [GN:YQGX] [OR:Bacillus subtilis] [DE:HYPOTHETICAL 23.2 KD PROTEIN IN SODA-COMGA INTERGENIC REGION] [SP:P54501]

| ORF Name | NT ID | AA ID | NT LN | AA LN | Score | P-Value |
|---|---|---|---|---|---|---|
| SPX0562 | 562 | 3223 | 201 | 67 | 131 | 2.00E-13 |

Description

[GI:1914870] [LN:SPZ82001] [AC:Z82001] [PN:unknown] [OR:Streptococcus pneumoniae]

| ORF Name | NT ID | AA ID | NT LN | AA LN | Score | P-Value |
|---|---|---|---|---|---|---|
| SPX0563 | 563 | 3224 | 243 | 81 | | |

Description

NO-HIT

| ORF Name | NT ID | AA ID | NT LN | AA LN | Score | P-Value |
|---|---|---|---|---|---|---|
| SPX0564 | 564 | 3225 | 2223 | 741 | 1601 | 0 |

Description

[LN:RELA_STREQ] [AC:Q54089] [GN:RELA:REL] [OR:Streptococcus equisimilis] [EC:2.7.6.5] [DE:PROTEIN)] [SP:Q54089]

| ORF Name | NT ID | AA ID | NT LN | AA LN | Score | P-Value |
|---|---|---|---|---|---|---|
| SPX0565 | 565 | 3226 | 243 | 81 | 70 | 0.0001 |

Description

[LN:Q3ECS7] [AC:A30374:Q90796] [PN:hypothetical 77K protein (spoT 3' region)] [CL:Escherichia coli hypothetical 77K protein (spoT 3' region)] [OR:Escherichia coli]

| ORF Name | NT ID | AA ID | NT LN | AA LN | Score | P-Value |
|---|---|---|---|---|---|---|
| SPX0566 | 566 | 3227 | 444 | 148 | 585 | 2.40E-76 |

Description

[LN:S39974] [AC:S39974] [PN:hypothetical protein] [CL:conserved hypothetical protein HI0670] [OR:Streptococcus equisimilis]

| ORF Name | NT ID | AA ID | NT LN | AA LN | Score | P-Value |
|---|---|---|---|---|---|---|
| SPX0567 | 567 | 3228 | 228 | 76 | | |

Description

NO-HIT

| ORF Name | NT ID | AA ID | NT LN | AA LN | Score | P-Value |
|---|---|---|---|---|---|---|
| SPX0568 | 568 | 3229 | 423 | 141 | | |
| Description | | | | | | |

NO-HIT

| ORF Name | NT ID | AA ID | NT LN | AA LN | Score | P-Value |
|---|---|---|---|---|---|---|
| SPX0569 | 569 | 3230 | 708 | 236 | | |
| Description | | | | | | |

NO-HIT

| ORF Name | NT ID | AA ID | NT LN | AA LN | Score | P-Value |
|---|---|---|---|---|---|---|
| SPX0570 | 570 | 3231 | 420 | 140 | 433 | 7.90E-56 |
| Description | | | | | | |

[GI:6694218] [LN:AF182402] [AC:AF182402] [PN:metalloregulator RmtA] [GN:rmtA] [OR:Streptococcus gordonii]

| ORF Name | NT ID | AA ID | NT LN | AA LN | Score | P-Value |
|---|---|---|---|---|---|---|
| SPX0571 | 571 | 3232 | 240 | 80 | 307 | 4.00E-38 |
| Description | | | | | | |

[GI:6694218] [LN:AF182402] [AC:AF182402] [PN:metalloregulator RmtA] [GN:rmtA] [OR:Streptococcus gordonii]

| ORF Name | NT ID | AA ID | NT LN | AA LN | Score | P-Value |
|---|---|---|---|---|---|---|
| SPX0572 | 572 | 3233 | 843 | 281 | 125 | 2.00E-13 |
| Description | | | | | | |

[LN:G75297] [AC:G75297] [PN:conserved hypothetical protein] [GN:DR2233] [CL:probable phosphoesterase MJ0912:phosphoesterase core homology] [OR:Deinococcus radiodurans]

| ORF Name | NT ID | AA ID | NT LN | AA LN | Score | P-Value |
|---|---|---|---|---|---|---|
| SPX0573 | 573 | 3234 | 195 | 65 | | |
| Description | | | | | | |

NO-HIT

| ORF Name | NT ID | AA ID | NT LN | AA LN | Score | P-Value |
|---|---|---|---|---|---|---|
| SPX0574 | 574 | 3235 | 315 | 105 | 142 | 7.90E-15 |

Description

[LN:D70063] [AC:D70063] [PN:hypothetical protein ywnA] [GN:ywnA]
[OR:Bacillus subtilis]

| ORF Name | NT ID | AA ID | NT LN | AA LN | Score | P-Value |
|---|---|---|---|---|---|---|
| SPX0575 | 575 | 3236 | 219 | 73 | 129 | 2.40E-12 |

Description

[LN:D70063] [AC:D70063] [PN:hypothetical protein ywnA] [GN:ywnA]
[OR:Bacillus subtilis]

| ORF Name | NT ID | AA ID | NT LN | AA LN | Score | P-Value |
|---|---|---|---|---|---|---|
| SPX0576 | 576 | 3237 | 303 | 101 | | |

Description

NO-HIT

| ORF Name | NT ID | AA ID | NT LN | AA LN | Score | P-Value |
|---|---|---|---|---|---|---|
| SPX0577 | 577 | 3238 | 1074 | 358 | | |

Description

NO-HIT

| ORF Name | NT ID | AA ID | NT LN | AA LN | Score | P-Value |
|---|---|---|---|---|---|---|
| SPX0578 | 578 | 3239 | 678 | 226 | 1146 | 1.70E-157 |

Description

[GI:5830520] [LN:SPAJ6391] [AC:AJ006391] [PN:response regulator] [GN:rr01]
[OR:Streptococcus pneumoniae]

| ORF Name | NT ID | AA ID | NT LN | AA LN | Score | P-Value |
|---|---|---|---|---|---|---|
| SPX0579 | 579 | 3240 | 975 | 325 | 1628 | 3.20E-226 |

Description

[GI:5830521] [LN:SPAJ6391] [AC:AJ006391] [PN:histidine kinase] [GN:hk01]
[OR:Streptococcus pneumoniae]

| ORF_Name | NT ID | AA ID | NT LN | AA LN | Score | P-Value |
|---|---|---|---|---|---|---|
| SPX0580 | 580 | 3241 | 1983 | 661 | 1149 | 2.20E-274 |

Description

[LN:SYT1_BACSU] [AC:P18255:P06570] [GN:THRS:THRSV] [OR:Bacillus subtilis]
[EC:6.1.1.3] [DE:(THRRS)] [SP:P18255:P06570]

| ORF_Name | NT ID | AA ID | NT LN | AA LN | Score | P-Value |
|---|---|---|---|---|---|---|
| SPX0581 | 581 | 3242 | 390 | 130 | | |

Description

NO-HIT

| ORF_Name | NT ID | AA ID | NT LN | AA LN | Score | P-Value |
|---|---|---|---|---|---|---|
| SPX0582 | 582 | 3243 | 291 | 97 | | |

Description

NO-HIT

| ORF_Name | NT ID | AA ID | NT LN | AA LN | Score | P-Value |
|---|---|---|---|---|---|---|
| SPX0583 | 583 | 3244 | 210 | 70 | | |

Description

NO-HIT

| ORF_Name | NT ID | AA ID | NT LN | AA LN | Score | P-Value |
|---|---|---|---|---|---|---|
| SPX0584 | 584 | 3245 | 630 | 210 | 371 | 1.30E-60 |

Description

[LN:E70063] [AC:E70063] [PN:hypothetical protein ywnB] [GN:ywnB]
[OR:Bacillus subtilis]

| ORF_Name | NT ID | AA ID | NT LN | AA LN | Score | P-Value |
|---|---|---|---|---|---|---|
| SPX0585 | 585 | 3246 | 270 | 90 | 311 | 1.10E-38 |

Description

[LN:F69700] [AC:F69700:S11365:S70690] [PN:ribosomal protein S15
(rpsO):ribosomal protein BS18] [GN:rpsO] [CL:Escherichia coli ribosomal
protein S15:eubacterial ribosomal protein S15 homology] [OR:Bacillus
subtilis]

| ORF Name | NT ID | AA ID | NT/LN | AA/LN | Score | P-Value |
|---|---|---|---|---|---|---|
| SPX0586 | 586 | 3247 | 225 | 75 | | |
| Description | | | | | | |

NO-HIT

| ORF Name | NT ID | AA ID | NT/LN | AA/LN | Score | P-Value |
|---|---|---|---|---|---|---|
| SPX0587 | 587 | 3248 | 477 | 159 | 243 | 1.30E-38 |
| Description | | | | | | |

[GI:1916729] [LN:AF134905] [AC:AF134905:U76550] [PN:CadD] [GN:cadD] [OR:Staphylococcus aureus]

| ORF Name | NT ID | AA ID | NT/LN | AA/LN | Score | P-Value |
|---|---|---|---|---|---|---|
| SPX0588 | 588 | 3249 | 750 | 250 | 165 | 1.10E-23 |
| Description | | | | | | |

[LN:E69826] [AC:E69826] [PN:1-acylglycerol-3-phosphate O-acyltransfera homolog yhdO] [GN:yhdO] [OR:Bacillus subtilis]

| ORF Name | NT ID | AA ID | NT/LN | AA/LN | Score | P-Value |
|---|---|---|---|---|---|---|
| SPX0589 | 589 | 3250 | 2337 | 779 | 414 | 1.80E-126 |
| Description | | | | | | |

"[LN:CTPE_MYCTU] [AC:O08365] [GN:CTPE:RV0908:MTCY21C12.02] [OR:Mycobacterium tuberculosis] [EC:3.6.1.-] [DE:PROBABLE CATION-TRANSPORTING ATPASE E,] [SP:O08365]"

| ORF Name | NT ID | AA ID | NT/LN | AA/LN | Score | P-Value |
|---|---|---|---|---|---|---|
| SPX0590 | 590 | 3251 | 231 | 77 | | |
| Description | | | | | | |

NO-HIT

| ORF Name | NT ID | AA ID | NT/LN | AA/LN | Score | P-Value |
|---|---|---|---|---|---|---|
| SPX0591 | 591 | 3252 | 1464 | 488 | 122 | 9.60E-23 |
| Description | | | | | | |

[GI:1480429] [LN:BSU18943] [AC:U18943:X99465] [GN:MtlR] [OR:Bacillus stearothermophilus]

| ORF Name | NT ID | AA ID | NT LN | AA LN | Score | P-Value |
|---|---|---|---|---|---|---|
| SPX0592 | 592 | 3253 | 429 | 143 | 60 | 0.00018 |

Description

[GI:2317740] [LN:AF013987] [AC:AF013987] [PN:nitrogen regulatory IIA protein] [GN:ptsN] [OR:Vibrio cholerae]

| ORF Name | NT ID | AA ID | NT LN | AA LN | Score | P-Value |
|---|---|---|---|---|---|---|
| SPX0593 | 593 | 3254 | 453 | 151 | 223 | 5.60E-24 |

Description

"[LN:HRSA_ECOLI] [AC:P54745] [GN:HRSA] [OR:Escherichia coli] [EC:2.7.1.69] [DE:HRSA PROTEIN,] [SP:P54745]"

| ORF Name | NT ID | AA ID | NT LN | AA LN | Score | P-Value |
|---|---|---|---|---|---|---|
| SPX0594 | 594 | 3255 | 312 | 104 | 236 | 1.30E-27 |

Description

"[LN:PTWB_ECOLI] [AC:P32673] [GN:FRWB] [OR:Escherichia coli] [EC:2.7.1.69] [DE:II, B COMPONENT),] [SP:P32673]"

| ORF Name | NT ID | AA ID | NT LN | AA LN | Score | P-Value |
|---|---|---|---|---|---|---|
| SPX0595 | 595 | 3256 | 1107 | 369 | 398 | 8.00E-60 |

Description

"[LN:PTFB_XANCP] [AC:P23355] [GN:FRUA] [OR:Xanthomonas campestris] [SR:,pvcampestris] [EC:2.7.1.69] [DE:(EC 2.7.1.69) (EII-FRU)] [SP:P23355]"

| ORF Name | NT ID | AA ID | NT LN | AA LN | Score | P-Value |
|---|---|---|---|---|---|---|
| SPX0596 | 596 | 3257 | 696 | 232 | 560 | 6.50E-74 |

Description

"[LN:ALSE_ECOLI] [AC:P32719] [GN:ALSE] [OR:Escherichia coli] [EC:5.1.3.-] [DE:D-ALLULOSE-6-PHOSPHATE 3-EPIMERASE,] [SP:P32719]"

| ORF Name | NT ID | AA ID | NT LN | AA LN | Score | P-Value |
|---|---|---|---|---|---|---|
| SPX0597 | 597 | 3258 | 1971 | 657 | 1371 | 2.00E-292 |

Description

"[LN:TKT_STRPN] [AC:P22976] [GN:RECP] [OR:Streptococcus pneumoniae] [EC:2.2.1.1] [DE:PROBABLE TRANSKETOLASE, (TK)] [SP:P22976]"

| ORF Name | NT ID | AA ID | NT LN | AA LN | Score | P-Value |
|---|---|---|---|---|---|---|
| SPX0598 | 598 | 3259 | 573 | 191 | 422 | 2.30E-53 |

Description

[LN:B30868] [AC:B30868] [PN:hypothetical protein 1] [OR:Streptococcus agalactiae]

| ORF Name | NT ID | AA ID | NT LN | AA LN | Score | P-Value |
|---|---|---|---|---|---|---|
| SPX0599 | 599 | 3260 | 573 | 191 | 422 | 2.30E-53 |

Description

[LN:B30868] [AC:B30868] [PN:hypothetical protein 1] [OR:Streptococcus agalactiae]

| ORF Name | NT ID | AA ID | NT LN | AA LN | Score | P-Value |
|---|---|---|---|---|---|---|
| SPX0600 | 600 | 3261 | 834 | 278 | 587 | 1.60E-140 |

Description

[LN:A33595] [AC:A33595:A30868] [PN:probable transposase] [CL:transposase IS3] [OR:Streptococcus agalactiae]

| ORF Name | NT ID | AA ID | NT LN | AA LN | Score | P-Value |
|---|---|---|---|---|---|---|
| SPX0601 | 601 | 3262 | 531 | 177 | | |

Description

NO-HIT

| ORF Name | NT ID | AA ID | NT LN | AA LN | Score | P-Value |
|---|---|---|---|---|---|---|
| SPX0602 | 602 | 3263 | 417 | 139 | 138 | 1.40E-10 |

Description

[LN:T35180] [AC:T35180] [PN:hypothetical protein SC5A7.31] [GN:SC5A7.31]
[CL:Streptomyces coelicolor hypothetical protein SC5A7.31] [OR:Streptomyces coelicolor]

| ORF Name | NT ID | AA ID | NT LN | AA LN | Score | P-Value |
|---|---|---|---|---|---|---|
| SPX0603 | 603 | 3264 | 678 | 226 | 612 | 1.10E-79 |

Description

[GI:1813343] [LN:D78182] [AC:D78182] [GN:ORF3] [OR:Streptococcus mutans]
[SR:Streptococcus mutans (strain:Xc) DNA]

| ORF Name | NT ID | AA ID | NT/LN | AA/LN | Score | P-Value |
|---|---|---|---|---|---|---|
| SPX0604 | 604 | 3265 | 798 | 266 | 344 | 5.40E-120 |

Description

[GI:1813344] [LN:D78182] [AC:D78182] [GN:ORF4] [OR:Streptococcus mutans]
[SR:Streptococcus mutans (strain:Xc) DNA]

| ORF Name | NT ID | AA ID | NT/LN | AA/LN | Score | P-Value |
|---|---|---|---|---|---|---|
| SPX0605 | 605 | 3266 | 1104 | 368 | 335 | 4.50E-71 |

Description

[LN:YURR_BACSU] [AC:O32159] [GN:YURR] [OR:Bacillus subtilis]
[DE:HYPOTHETICAL 39.4 KD OXIDOREDUCTASE IN HOM-MRGA INTERGENIC REGION]
[SP:O32159]

| ORF Name | NT ID | AA ID | NT/LN | AA/LN | Score | P-Value |
|---|---|---|---|---|---|---|
| SPX0606 | 606 | 3267 | 192 | 64 | | |

Description

NO-HIT

| ORF Name | NT ID | AA ID | NT/LN | AA/LN | Score | P-Value |
|---|---|---|---|---|---|---|
| SPX0607 | 607 | 3268 | 1020 | 340 | 1167 | 7.10E-156 |

Description

[LN:GALE_BACSU] [AC:P55180] [GN:GALE] [OR:Bacillus subtilis] [EC:5.1.3.2]
[DE:GALACTOSE 4-EPIMERASE)] [SP:P55180]

| ORF Name | NT ID | AA ID | NT/LN | AA/LN | Score | P-Value |
|---|---|---|---|---|---|---|
| SPX0608 | 608 | 3269 | 954 | 318 | 441 | 7.80E-87 |

Description

[LN:CSBB_BACSU] [AC:Q45539] [GN:CSBB] [OR:Bacillus subtilis] [DE:CSBB
PROTEIN] [SP:Q45539]

| ORF Name | NT ID | AA ID | NT/LN | AA/LN | Score | P-Value |
|---|---|---|---|---|---|---|
| SPX0609 | 609 | 3270 | 666 | 222 | | |

Description

NO-HIT

| ORF Name | NT ID | AA ID | NT LN | AA LN | Score | P-Value |
|---|---|---|---|---|---|---|
| SPX0610 | 610 | 3271 | 207 | 69 | 55 | 0.00029 |

Description

"[LN:FER_MOOTH] [AC:P00203] [OR:Moorella thermoacetica] [SR:,Clostridium thermoaceticum] [DE:FERREDOXIN] [SP:P00203]"

| ORF Name | NT ID | AA ID | NT LN | AA LN | Score | P-Value |
|---|---|---|---|---|---|---|
| SPX0611 | 611 | 3272 | 477 | 159 | | |

Description

NO-HIT

| ORF Name | NT ID | AA ID | NT LN | AA LN | Score | P-Value |
|---|---|---|---|---|---|---|
| SPX0612 | 612 | 3273 | 672 | 224 | 413 | 6.00E-74 |

Description

[LN:KCY_BACSU] [AC:P38493] [GN:CMK:JOFC] [OR:Bacillus subtilis] [EC:2.7.4.14] [DE:(CMP KINASE)] [SP:P38493]

| ORF Name | NT ID | AA ID | NT LN | AA LN | Score | P-Value |
|---|---|---|---|---|---|---|
| SPX0613 | 613 | 3274 | 339 | 113 | 432 | 5.60E-55 |

Description

[LN:PHNA_ECOLI] [AC:P16680] [GN:PHNA] [OR:Escherichia coli] [DE:PHNA PROTEIN] [SP:P16680]

| ORF Name | NT ID | AA ID | NT LN | AA LN | Score | P-Value |
|---|---|---|---|---|---|---|
| SPX0614 | 614 | 3275 | 630 | 210 | | |

Description

NO-HIT

| ORF Name | NT ID | AA ID | NT LN | AA LN | Score | P-Value |
|---|---|---|---|---|---|---|
| SPX0615 | 615 | 3276 | 228 | 76 | 192 | 3.60E-23 |

Description

[GI:1914870] [LN:SPZ82001] [AC:Z82001] [PN:unknown] [OR:Streptococcus pneumoniae]

| ORF Name | NT ID | AA ID | NT/LN | AA/LN | Score | P-Value |
|---|---|---|---|---|---|---|
| SPX0616 | 616 | 3277 | 1152 | 384 | 68 | 6.80E-05 |

Description

[LN:C81266] [AC:C81266] [PN:probable efflux protein Cj1687 [imported]]
[GN:Cj1687] [OR:Campylobacter jejuni]

| ORF Name | NT ID | AA ID | NT/LN | AA/LN | Score | P-Value |
|---|---|---|---|---|---|---|
| SPX0617 | 617 | 3278 | 750 | 250 | 309 | 4.30E-69 |

Description

[LN:TRUA_BACSU] [AC:P70973] [GN:TRUA] [OR:Bacillus subtilis] [EC:4.2.1.70]
[DE:I) (PSEUDOURIDINE SYNTHASE I) (URACIL HYDROLYASE)] [SP:P70973]

| ORF Name | NT ID | AA ID | NT/LN | AA/LN | Score | P-Value |
|---|---|---|---|---|---|---|
| SPX0618 | 618 | 3279 | 774 | 258 | 155 | 3.70E-39 |

Description

[LN:THID_BACSU] [AC:P39610] [GN:THID:IPA-52R] [OR:Bacillus subtilis]
[EC:2.7.4.7] [DE:(HMP-P KINASE)] [SP:P39610]

| ORF Name | NT ID | AA ID | NT/LN | AA/LN | Score | P-Value |
|---|---|---|---|---|---|---|
| SPX0619 | 619 | 3280 | 462 | 154 | 69 | 5.80E-12 |

Description

[LN:G75153] [AC:G75153] [PN:hypothetical protein PAB2090] [GN:PAB2090]
[OR:Pyrococcus abyssi]

| ORF Name | NT ID | AA ID | NT/LN | AA/LN | Score | P-Value |
|---|---|---|---|---|---|---|
| SPX0620 | 620 | 3281 | 573 | 191 | 422 | 2.30E-53 |

Description

[LN:B30868] [AC:B30868] [PN:hypothetical protein 1] [OR:Streptococcus agalactiae]

| ORF Name | NT ID | AA ID | NT/LN | AA/LN | Score | P-Value |
|---|---|---|---|---|---|---|
| SPX0621 | 621 | 3282 | 273 | 91 | 288 | 2.30E-35 |

Description

[LN:A33595] [AC:A33595:A30868] [PN:probable transposase] [CL:transposase IS3] [OR:Streptococcus agalactiae]

| ORF Name | NT ID | AA ID | NT/LN | AA/LN | Score | P-Value |
|---|---|---|---|---|---|---|
| SPX0622 | 622 | 3283 | 594 | 198 | 583 | 9.30E-95 |

Description

[LN:A33595] [AC:A33595:A30868] [PN:probable transposase] [CL:transposase IS3] [OR:Streptococcus agalactiae]

| ORF Name | NT ID | AA ID | NT/LN | AA/LN | Score | P-Value |
|---|---|---|---|---|---|---|
| SPX0623 | 623 | 3284 | 477 | 159 | | |

Description

NO-HIT

| ORF Name | NT ID | AA ID | NT/LN | AA/LN | Score | P-Value |
|---|---|---|---|---|---|---|
| SPX0624 | 624 | 3285 | 1083 | 361 | 1016 | 1.20E-136 |

Description

[GI:2323341] [LN:AF014460] [AC:AF014460] [PN:PepQ] [FN:hydrolysis of Leu-Pro] [OR:Streptococcus mutans]

| ORF Name | NT ID | AA ID | NT/LN | AA/LN | Score | P-Value |
|---|---|---|---|---|---|---|
| SPX0625 | 625 | 3286 | 783 | 261 | 147 | 5.10E-36 |

Description

[LN:T31439] [AC:T31439] [PN:probable cobyric acid synthase CobQ] [OR:Heliobacillus mobilis]

| ORF Name | NT ID | AA ID | NT/LN | AA/LN | Score | P-Value |
|---|---|---|---|---|---|---|
| SPX0626 | 626 | 3287 | 1344 | 448 | 137 | 1.30E-46 |

Description

[LN:T31440] [AC:T31440] [PN:UDP-N-acetylmuramyl tripeptide synthetase homolog murC] [OR:Heliobacillus mobilis]

| ORF Name | NT ID | AA ID | NT/LN | AA/LN | Score | P-Value |
|---|---|---|---|---|---|---|
| SPX0627 | 627 | 3288 | 1317 | 439 | 797 | 4.80E-136 |

Description

[LN:YKGC_ECOLI] [AC:P77212] [GN:YKGC] [OR:Escherichia coli] [DE:INTERGENIC REGION] [SP:P77212]

| ORF Name | NT ID | AA ID | NT/LN | AA/LN | Score | P-Value |
|---|---|---|---|---|---|---|
| SPX0628 | 628 | 3289 | 873 | 291 | 711 | 3.70E-137 |

Description

[GI:7107009] [LN:AF168363] [AC:AF168363] [PN:oxalate:formate antiporter] [OR:Lactococcus lactis]

| ORF Name | NT ID | AA ID | NT/LN | AA/LN | Score | P-Value |
|---|---|---|---|---|---|---|
| SPX0629 | 629 | 3290 | 246 | 82 | 193 | 5.00E-21 |

Description

[GI:7107009] [LN:AF168363] [AC:AF168363] [PN:oxalate:formate antiporter] [OR:Lactococcus lactis]

| ORF Name | NT ID | AA ID | NT/LN | AA/LN | Score | P-Value |
|---|---|---|---|---|---|---|
| SPX0630 | 630 | 3291 | 1575 | 525 | 1329 | 1.80E-184 |

Description

[GI:4409804] [LN:AF091502] [AC:AF091502] [PN:autoaggregation-mediating protein] [GN:aggH] [OR:Lactobacillus reuteri]

| ORF Name | NT ID | AA ID | NT/LN | AA/LN | Score | P-Value |
|---|---|---|---|---|---|---|
| SPX0631 | 631 | 3292 | 789 | 263 | 547 | 3.10E-74 |

Description

[LN:CODY_BACSU] [AC:P39779] [GN:CODY] [OR:Bacillus subtilis] [DE:CODY PROTEIN (VEGETATIVE PROTEIN 286B) (VEG286B)] [SP:P39779]

| ORF Name | NT ID | AA ID | NT/LN | AA/LN | Score | P-Value |
|---|---|---|---|---|---|---|
| SPX0632 | 632 | 3293 | 207 | 69 | 174 | 1.30E-18 |

Description

[LN:C70008] [AC:C70008] [PN:pyrazinamidase/nicotinamidase homolog yueJ] [GN:yueJ] [CL:hypothetical protein b1011] [OR:Bacillus subtilis]

| ORF Name | NT ID | AA ID | NT/LN | AA/LN | Score | P-Value |
|---|---|---|---|---|---|---|
| SPX0633 | 633 | 3294 | 456 | 152 | 253 | 1.50E-30 |

Description

[LN:C70008] [AC:C70008] [PN:pyrazinamidase/nicotinamidase homolog yueJ] [GN:yueJ] [CL:hypothetical protein b1011] [OR:Bacillus subtilis]

| ORF Name | NT ID | AA ID | NT/LN | AA/LN | Score | P-Value |
|---|---|---|---|---|---|---|
| SPX0634 | 634 | 3295 | 234 | 78 | 328 | 1.70E-40 |

Description

[GI:600072] [LN:SEDEXB] [AC:X72832] [PN:ABC transporter] [GN:abc] [OR:Streptococcus equisimilis]

| ORF Name | NT ID | AA ID | NT/LN | AA/LN | Score | P-Value |
|---|---|---|---|---|---|---|
| SPX0635 | 635 | 3296 | 156 | 52 | 113 | 2.50E-10 |

Description

[LN:E72756] [AC:E72756] [PN:hypothetical protein APE0042] [GN:APE0042] [OR:Aeropyrum pernix]

| ORF Name | NT ID | AA ID | NT/LN | AA/LN | Score | P-Value |
|---|---|---|---|---|---|---|
| SPX0636 | 636 | 3297 | 855 | 285 | 731 | 1.70E-136 |

Description

[LN:MSMK_STRMU] [AC:Q00752] [GN:MSMK] [OR:Streptococcus mutans] [DE:MULTIPLE SUGAR-BINDING TRANSPORT ATP-BINDING PROTEIN MSMK] [SP:Q00752]

| ORF Name | NT ID | AA ID | NT/LN | AA/LN | Score | P-Value |
|---|---|---|---|---|---|---|
| SPX0637 | 637 | 3298 | 759 | 253 | 485 | 3.90E-95 |

Description

[LN:Y095_HAEIN] [AC:Q57060:O05007] [GN:HI0095] [OR:Haemophilus influenzae] [DE:HYPOTHETICAL PROTEIN HI0095] [SP:Q57060:O05007]

| ORF Name | NT ID | AA ID | NT/LN | AA/LN | Score | P-Value |
|---|---|---|---|---|---|---|
| SPX0638 | 638 | 3299 | 531 | 177 | 603 | 2.90E-79 |

Description

"[LN:B69587] [AC:B69587] [PN:adenine phosphoribosyltransferase,:AMP pyrophosphorylase:transphosphoribosidase] [GN:apt] [CL:adenine phosphoribosyltransferase] [OR:Bacillus subtilis] [EC:2.4.2.7]"

| ORF Name | NT ID | AA ID | NT/LN | AA/LN | Score | P-Value |
|---|---|---|---|---|---|---|
| SPX0639 | 639 | 3300 | 945 | 315 | 567 | 6.90E-116 |

Description

[LN:C72324] [AC:C72324] [PN:homoserine O-succinyltransferase] [GN:TM0881] [CL:homoserine succinyltransferase] [OR:Thermotoga maritima]

| ORF Name | NT ID | AA ID | NT LN | AA LN | Score | P-Value |
|---|---|---|---|---|---|---|
| SPX0640 | 640 | 3301 | 678 | 226 | 357 | 5.50E-90 |

Description

[GI:1813342] [LN:D78182] [AC:D78182] [GN:ORF2] [OR:Streptococcus mutans] [SR:Streptococcus mutans (strain:Xc) DNA]

| ORF Name | NT ID | AA ID | NT LN | AA LN | Score | P-Value |
|---|---|---|---|---|---|---|
| SPX0641 | 641 | 3302 | 375 | 125 | | |

Description

NO-HIT

| ORF Name | NT ID | AA ID | NT LN | AA LN | Score | P-Value |
|---|---|---|---|---|---|---|
| SPX0642 | 642 | 3303 | 759 | 253 | 864 | 1.30E-113 |

Description

"[LN:TPIS_LACDE] [AC:O32757] [GN:TPIA:TPI] [OR:Lactobacillus delbrueckii] [SR:,subspbulgaricus] [EC:5.3.1.1] [DE:TRIOSEPHOSPHATE ISOMERASE, (TIM)] [SP:O32757]"

| ORF Name | NT ID | AA ID | NT LN | AA LN | Score | P-Value |
|---|---|---|---|---|---|---|
| SPX0643 | 643 | 3304 | 1506 | 502 | 2728 | 0 |

Description

"[GI:4218526] [LN:SPAJ9639] [AC:AJ009639] [PN:1,4-beta-N-acetylmuramidase] [GN:lytC] [FN:lysis of cell wall peptidoglycan] [OR:Streptococcus pneumoniae]"

| ORF Name | NT ID | AA ID | NT LN | AA LN | Score | P-Value |
|---|---|---|---|---|---|---|
| SPX0644 | 644 | 3305 | 519 | 173 | 800 | 2.60E-105 |

Description

[GI:3513547] [LN:AF055720] [AC:AF055720] [PN:unknown] [OR:Streptococcus pneumoniae]

| ORF Name | NT ID | AA ID | NT LN | AA LN | Score | P-Value |
|---|---|---|---|---|---|---|
| SPX0645 | 645 | 3306 | 639 | 213 | | |

Description

NO-HIT

| ORF Name | NT ID | AA ID | NT LN | AA LN | Score | P-Value |
|---|---|---|---|---|---|---|
| SPX0646 | 646 | 3307 | 507 | 169 | 882 | 2.00E-118 |

Description

[GI:2196662] [LN:HSZ84379] [AC:Z84379] [PN:dihydrofolate reductase] [GN:dfr] [FN:trimethoprim resistance] [OR:Streptococcus pneumoniae]

| ORF Name | NT ID | AA ID | NT LN | AA LN | Score | P-Value |
|---|---|---|---|---|---|---|
| SPX0647 | 647 | 3308 | 207 | 69 | | |

Description

NO-HIT

| ORF Name | NT ID | AA ID | NT LN | AA LN | Score | P-Value |
|---|---|---|---|---|---|---|
| SPX0648 | 648 | 3309 | 1233 | 411 | 1251 | 4.80E-206 |

Description

[GI:7546983] [LN:AF236863] [AC:AF236863] [PN:protease ClpX] [GN:clpX] [OR:Lactococcus lactis]

| ORF Name | NT ID | AA ID | NT LN | AA LN | Score | P-Value |
|---|---|---|---|---|---|---|
| SPX0649 | 649 | 3310 | 588 | 196 | 807 | 9.70E-107 |

Description

[GI:7546984] [LN:AF236863] [AC:AF236863] [PN:hypothetical GTP-binding protein] [OR:Lactococcus lactis]

| ORF Name | NT ID | AA ID | NT LN | AA LN | Score | P-Value |
|---|---|---|---|---|---|---|
| SPX0650 | 650 | 3311 | 381 | 127 | 392 | 2.30E-49 |

Description

"[LN:ALDR_LACLA] [AC:O34133] [GN:ALDR] [OR:Lactococcus lactis] [SR:,subsplactis:Streptococcus lactis] [DE:PUTATIVE REGULATOR ALDR] [SP:O34133]"

| ORF Name | NT ID | AA ID | NT LN | AA LN | Score | P-Value |
|---|---|---|---|---|---|---|
| SPX0651 | 651 | 3312 | 891 | 297 | 337 | 2.00E-91 |

Description

[GI:7328270] [LN:SAY14324] [AC:Y14324] [PN:hypothetical protein] [OR:Staphylococcus aureus]

| ORF Name | NT ID | AA ID | NT LN | AA LN | Score | P-Value |
|---|---|---|---|---|---|---|
| SPX0652 | 652 | 3313 | 978 | 326 | 268 | 1.30E-62 |

Description

[LN:YVCK_BACSU] [AC:O06974] [GN:YVCK] [OR:Bacillus subtilis]
[DE:HYPOTHETICAL 34.7 KD PROTEIN IN CRH-TRXB INTERGENIC REGION] [SP:O06974]

| ORF Name | NT ID | AA ID | NT LN | AA LN | Score | P-Value |
|---|---|---|---|---|---|---|
| SPX0653 | 653 | 3314 | 912 | 304 | 424 | 5.50E-81 |

Description

[GI:7328272] [LN:SAY14324] [AC:Y14324] [OR:Staphylococcus aureus]

| ORF Name | NT ID | AA ID | NT LN | AA LN | Score | P-Value |
|---|---|---|---|---|---|---|
| SPX0654 | 654 | 3315 | 969 | 323 | 422 | 5.00E-99 |

Description

[LN:B70015] [AC:B70015] [PN:thioredoxin reductase homolog yumC] [GN:yumC]
[CL:thioredoxin reductase:thioredoxin reductase homology] [OR:Bacillus subtilis]

| ORF Name | NT ID | AA ID | NT LN | AA LN | Score | P-Value |
|---|---|---|---|---|---|---|
| SPX0655 | 655 | 3316 | 816 | 272 | 419 | 8.50E-81 |

Description

[LN:H69744] [AC:H69744] [PN:conserved hypothetical protein ybbP] [GN:ybbP]
[CL:hypothetical protein ybbP] [OR:Bacillus subtilis]

| ORF Name | NT ID | AA ID | NT LN | AA LN | Score | P-Value |
|---|---|---|---|---|---|---|
| SPX0656 | 656 | 3317 | 780 | 260 | 104 | 2.70E-10 |

Description

[LN:A69745] [AC:A69745] [PN:hypothetical protein ybbR] [GN:ybbR]
[OR:Bacillus subtilis]

| ORF Name | NT ID | AA ID | NT LN | AA LN | Score | P-Value |
|---|---|---|---|---|---|---|
| SPX0657 | 657 | 3318 | 192 | 64 | | |

Description

NO-HIT

| ORF Name | NT ID | AA ID | NT/LN | AA/LN | Score | P-Value |
|---|---|---|---|---|---|---|
| SPX0658 | 658 | 3319 | 1353 | 451 | 655 | 2.00E-180 |

Description

[GI:3892895] [LN:SAARGFEMD] [AC:Y15477] [PN:phosphoglucosamine-mutase] [GN:glmM] [OR:Staphylococcus aureus]

| ORF Name | NT ID | AA ID | NT/LN | AA/LN | Score | P-Value |
|---|---|---|---|---|---|---|
| SPX0659 | 659 | 3320 | 363 | 121 | | |

Description

NO-HIT

| ORF Name | NT ID | AA ID | NT/LN | AA/LN | Score | P-Value |
|---|---|---|---|---|---|---|
| SPX0660 | 660 | 3321 | 849 | 283 | 239 | 6.50E-25 |

Description

[LN:DEGV_BACSU] [AC:P32436] [GN:DEGV] [OR:Bacillus subtilis] [DE:DEGV PROTEIN] [SP:P32436]

| ORF Name | NT ID | AA ID | NT/LN | AA/LN | Score | P-Value |
|---|---|---|---|---|---|---|
| SPX0661 | 661 | 3322 | 768 | 256 | 614 | 6.50E-89 |

Description

"[LN:DAPB_BACSU] [AC:P42976] [GN:DAPB] [OR:Bacillus subtilis] [EC:1.3.1.26] [DE:DIHYDRODIPICOLINATE REDUCTASE,] [SP:P42976]"

| ORF Name | NT ID | AA ID | NT/LN | AA/LN | Score | P-Value |
|---|---|---|---|---|---|---|
| SPX0662 | 662 | 3323 | 1200 | 400 | 601 | 8.40E-92 |

Description

"[LN:PAPS_BACSU] [AC:P42977] [GN:PAPS] [OR:Bacillus subtilis] [EC:2.7.7.19] [DE:POLY(A) POLYMERASE, (PAP)] [SP:P42977]"

| ORF Name | NT ID | AA ID | NT/LN | AA/LN | Score | P-Value |
|---|---|---|---|---|---|---|
| SPX0663 | 663 | 3324 | 1872 | 624 | 669 | 1.80E-162 |

Description

[LN:A69814] [AC:A69814] [PN:ABC transporter (ATP-binding protein) homolog yfmR] [GN:yfmR] [CL:unassigned ATP-binding cassette proteins:ATP-binding cassette homology] [OR:Bacillus subtilis]

| ORF Name | NT ID | AA ID | NT/LN | AA/LN | Score | P-Value |
|---|---|---|---|---|---|---|
| SPX0664 | 664 | 3325 | 432 | 144 | | |

Description

NO-HIT

| ORF Name | NT ID | AA ID | NT/LN | AA/LN | Score | P-Value |
|---|---|---|---|---|---|---|
| SPX0665 | 665 | 3326 | 1182 | 394 | 629 | 1.90E-82 |

Description

[LN:YEAB_BACSU] [AC:P46348:O05001] [GN:YEAB] [OR:Bacillus subtilis] [DE:HYPOTHETICAL 31.8 KD PROTEIN IN GABP-GUAA INTERGENIC REGION (ORFX)] [SP:P46348:O05001]

| ORF Name | NT ID | AA ID | NT/LN | AA/LN | Score | P-Value |
|---|---|---|---|---|---|---|
| SPX0666 | 666 | 3327 | 2697 | 899 | 601 | 1.20E-189 |

Description

"[LN:S77052] [AC:S77052] [PN:cation-transporting ATPase, pacL-1:protein sll0672:protein sll0672] [GN:pacL-1] [CL:Na+/K+-transporting ATPase alpha chain:ATPase nucleotide-binding domain homology] [OR:Synechocystis sp.]"

| ORF Name | NT ID | AA ID | NT/LN | AA/LN | Score | P-Value |
|---|---|---|---|---|---|---|
| SPX0667 | 667 | 3328 | 291 | 97 | | |

Description

NO-HIT

| ORF Name | NT ID | AA ID | NT/LN | AA/LN | Score | P-Value |
|---|---|---|---|---|---|---|
| SPX0668 | 668 | 3329 | 249 | 83 | 73 | 0.00016 |

Description

[LN:H72624] [AC:H72624] [PN:hypothetical protein APE1456] [GN:APE1456] [OR:Aeropyrum pernix]

| ORF Name | NT ID | AA ID | NT/LN | AA/LN | Score | P-Value |
|---|---|---|---|---|---|---|
| SPX0669 | 669 | 3330 | 792 | 264 | 713 | 2.30E-105 |

Description

[LN:YGHU_ECOLI] [AC:Q46845] [GN:YGHU] [OR:Escherichia coli] [DE:HYPOTHETICAL 34.2 KD PROTEIN IN GSP-HYBG INTERGENIC REGION] [SP:Q46845]

| ORF Name | NT ID | AA ID | NT/LN | AA/LN | Score | P-Value |
|---|---|---|---|---|---|---|
| SPX0670 | 670 | 3331 | 456 | 152 | 368 | 3.30E-46 |

Description

"[LN:DEF_CLOBE] [AC:O08450] [GN:DEF:FMS] [OR:Clostridium beijerinckii] [SR:,Clostridium MP] [EC:3.5.1.31] [DE:DEFORMYLASE)] [SP:O08450]"

| ORF Name | NT ID | AA ID | NT/LN | AA/LN | Score | P-Value |
|---|---|---|---|---|---|---|
| SPX0671 | 671 | 3332 | 1596 | 532 | | |

Description

NO-HIT

| ORF Name | NT ID | AA ID | NT/LN | AA/LN | Score | P-Value |
|---|---|---|---|---|---|---|
| SPX0672 | 672 | 3333 | 180 | 60 | | |

Description

NO-HIT

| ORF Name | NT ID | AA ID | NT/LN | AA/LN | Score | P-Value |
|---|---|---|---|---|---|---|
| SPX0673 | 673 | 3334 | 729 | 243 | 473 | 1.20E-60 |

Description

[GI:4580623] [LN:AF118389] [AC:AF118389] [PN:unknown] [OR:Streptococcus suis]

| ORF Name | NT ID | AA ID | NT/LN | AA/LN | Score | P-Value |
|---|---|---|---|---|---|---|
| SPX0674 | 674 | 3335 | 630 | 210 | 111 | 2.10E-12 |

Description

[GI:6562870] [LN:SCM1] [AC:AL133422] [PN:putative secreted protein.] [GN:SCM1.21] [OR:Streptomyces coelicolor A3(2)]

| ORF Name | NT ID | AA ID | NT/LN | AA/LN | Score | P-Value |
|---|---|---|---|---|---|---|
| SPX0675 | 675 | 3336 | 489 | 163 | 68 | 0.00021 |

Description

[LN:YPMB_BACSU] [AC:P54396] [GN:YPMB] [OR:Bacillus subtilis]
[DE:HYPOTHETICAL 17.9 KD PROTEIN IN DING-ASPB INTERGENIC REGION] [SP:P54396]

| ORF Name | NT ID | AA ID | NT LN | AA LN | Score | P-Value |
|---|---|---|---|---|---|---|
| SPX0676 | 676 | 3337 | 1188 | 396 | 1400 | 2.80E-187 |

Description

[GI:6465901] [LN:AF035157] [AC:AF035157] [PN:aspartate aminotransferase] [GN:aspC] [OR:Lactococcus lactis]

| ORF Name | NT ID | AA ID | NT LN | AA LN | Score | P-Value |
|---|---|---|---|---|---|---|
| SPX0677 | 677 | 3338 | 372 | 124 | 178 | 1.90E-27 |

Description

[LN:T03486] [AC:T03486] [PN:conserved hypothetical protein] [OR:Rhodobacter capsulatus]

| ORF Name | NT ID | AA ID | NT LN | AA LN | Score | P-Value |
|---|---|---|---|---|---|---|
| SPX0678 | 678 | 3339 | 1344 | 448 | 703 | 1.60E-180 |

Description

[LN:SYN_BACSU] [AC:P39772] [GN:ASNS] [OR:Bacillus subtilis] [EC:6.1.1.22] [DE:(ASNRS)] [SP:P39772]

| ORF Name | NT ID | AA ID | NT LN | AA LN | Score | P-Value |
|---|---|---|---|---|---|---|
| SPX0679 | 679 | 3340 | 387 | 129 | | |

Description

NO-HIT

| ORF Name | NT ID | AA ID | NT LN | AA LN | Score | P-Value |
|---|---|---|---|---|---|---|
| SPX0680 | 680 | 3341 | 291 | 97 | 236 | 7.30E-39 |

Description

[LN:RS6_BACSU] [AC:P21468] [GN:RPSF] [OR:Bacillus subtilis] [DE:30S RIBOSOMAL PROTEIN S6 (BS9)] [SP:P21468]

| ORF Name | NT ID | AA ID | NT LN | AA LN | Score | P-Value |
|---|---|---|---|---|---|---|
| SPX0681 | 681 | 3342 | 471 | 157 | 481 | 5.20E-71 |

Description

[GI:6716352] [LN:AF145054] [AC:AF145054:AF001793:AF118440:U89246] [PN:ORF9] [GN:orf9] [OR:Streptococcus thermophilus bacteriophage 7201]

| ORF Name | NT ID | AA ID | NT/LN | AA/LN | Score | P-Value |
|---|---|---|---|---|---|---|
| SPX0682 | 682 | 3343 | 261 | 87 | 134 | 1.30E-13 |

Description

[LN:RS18_BACST] [AC:P10806] [GN:RPSR] [OR:Bacillus stearothermophilus]
[DE:30S RIBOSOMAL PROTEIN S18 (BS21)] [SP:P10806]

| ORF Name | NT ID | AA ID | NT/LN | AA/LN | Score | P-Value |
|---|---|---|---|---|---|---|
| SPX0683 | 683 | 3344 | 336 | 112 | | |

Description

NO-HIT

| ORF Name | NT ID | AA ID | NT/LN | AA/LN | Score | P-Value |
|---|---|---|---|---|---|---|
| SPX0684 | 684 | 3345 | 1401 | 467 | 270 | 7.50E-47 |

Description

[GI:4678225] [LN:AC007135] [AC:AC007135:AE002093] [PN:cyclophilin-like protein] [GN:At2g36130] [OR:Arabidopsis thaliana] [SR:thale cress]

| ORF Name | NT ID | AA ID | NT/LN | AA/LN | Score | P-Value |
|---|---|---|---|---|---|---|
| SPX0685 | 685 | 3346 | 252 | 84 | 172 | 6.10E-19 |

Description

[LN:YABR_BACSU] [AC:P37560] [GN:YABR] [OR:Bacillus subtilis]
[DE:HYPOTHETICAL 14.2 KD PROTEIN IN DIVIC-SPOIIE INTERGENIC REGION]
[SP:P37560]

| ORF Name | NT ID | AA ID | NT/LN | AA/LN | Score | P-Value |
|---|---|---|---|---|---|---|
| SPX0686 | 686 | 3347 | 261 | 87 | 96 | 1.40E-15 |

Description

[LN:YABB_BACSU] [AC:P37543] [GN:YABB] [OR:Bacillus subtilis]
[DE:HYPOTHETICAL 28.3 KD PROTEIN IN XPAC-ABRB INTERGENIC REGION] [SP:P37543]

| ORF Name | NT ID | AA ID | NT/LN | AA/LN | Score | P-Value |
|---|---|---|---|---|---|---|
| SPX0687 | 687 | 3348 | 201 | 67 | 109 | 3.00E-09 |

Description

[LN:YABB_BACSU] [AC:P37543] [GN:YABB] [OR:Bacillus subtilis]
[DE:HYPOTHETICAL 28.3 KD PROTEIN IN XPAC-ABRB INTERGENIC REGION] [SP:P37543]

| ORF Name | NT ID | AA ID | NT LN | AA LN | Score | P-Value |
|---|---|---|---|---|---|---|
| SPX0688 | 688 | 3349 | 387 | 129 | 267 | 1.40E-39 |

Description

[LN:YABB_BACSU] [AC:P37543] [GN:YABB] [OR:Bacillus subtilis]
[DE:HYPOTHETICAL 28.3 KD PROTEIN IN XPAC-ABRB INTERGENIC REGION] [SP:P37543]

| ORF Name | NT ID | AA ID | NT LN | AA LN | Score | P-Value |
|---|---|---|---|---|---|---|
| SPX0689 | 689 | 3350 | 279 | 93 | 224 | 1.50E-26 |

Description

[LN:A69742] [AC:A69742] [PN:conserved hypothetical protein yazA] [GN:yazA]
[CL:hypothetical protein 312] [OR:Bacillus subtilis]

| ORF Name | NT ID | AA ID | NT LN | AA LN | Score | P-Value |
|---|---|---|---|---|---|---|
| SPX0690 | 690 | 3351 | 180 | 60 | 143 | 5.60E-14 |

Description

[GI:1743856] [LN:SGU57759] [AC:U57759] [PN:intrageneric
coaggregation-relevant adhesin] [OR:Streptococcus gordonii]

| ORF Name | NT ID | AA ID | NT LN | AA LN | Score | P-Value |
|---|---|---|---|---|---|---|
| SPX0691 | 691 | 3352 | 666 | 222 | 955 | 2.60E-126 |

Description

[GI:1743856] [LN:SGU57759] [AC:U57759] [PN:intrageneric
coaggregation-relevant adhesin] [OR:Streptococcus gordonii]

| ORF Name | NT ID | AA ID | NT LN | AA LN | Score | P-Value |
|---|---|---|---|---|---|---|
| SPX0692 | 692 | 3353 | 513 | 171 | | |

Description

NO-HIT

| ORF Name | NT ID | AA ID | NT LN | AA LN | Score | P-Value |
|---|---|---|---|---|---|---|
| SPX0693 | 693 | 3354 | 315 | 105 | 140 | 1.80E-21 |

Description

[GI:2952534] [LN:AF051356] [AC:AF051356] [PN:unknown] [OR:Streptococcus mutans]

| ORF Name | NT ID | AA ID | NT/LN | AA/LN | Score | P-Value |
|---|---|---|---|---|---|---|
| SPX0694 | 694 | 3355 | 285 | 95 | | |
| Description | | | | | | |

NO-HIT

| ORF Name | NT ID | AA ID | NT/LN | AA/LN | Score | P-Value |
|---|---|---|---|---|---|---|
| SPX0695 | 695 | 3356 | 195 | 65 | 74 | 0.00038 |
| Description | | | | | | |

[GI:2772940] [LN:AF034574] [AC:AF034574] [PN:putative cruciform DNA binding protein] [GN:Gv1] [OR:Glomus versiforme]

| ORF Name | NT ID | AA ID | NT/LN | AA/LN | Score | P-Value |
|---|---|---|---|---|---|---|
| SPX0696 | 696 | 3357 | 1512 | 504 | 172 | 1.50E-35 |
| Description | | | | | | |

[LN:MURE_BACSU] [AC:Q03523] [GN:MURE] [OR:Bacillus subtilis] [EC:6.3.2.13] [DE:DIAMINOPIMELATE-ADDING ENZYME)] [SP:Q03523]

| ORF Name | NT ID | AA ID | NT/LN | AA/LN | Score | P-Value |
|---|---|---|---|---|---|---|
| SPX0697 | 697 | 3358 | 576 | 192 | 172 | 9.40E-16 |
| Description | | | | | | |

[LN:MURE_BACSU] [AC:Q03523] [GN:MURE] [OR:Bacillus subtilis] [EC:6.3.2.13] [DE:DIAMINOPIMELATE-ADDING ENZYME)] [SP:Q03523]

| ORF Name | NT ID | AA ID | NT/LN | AA/LN | Score | P-Value |
|---|---|---|---|---|---|---|
| SPX0698 | 698 | 3359 | 1623 | 541 | 187 | 2.90E-75 |
| Description | | | | | | |

[LN:G69992] [AC:G69992] [PN:spore cortex protein homolog ytgP] [GN:ytgP] [OR:Bacillus subtilis]

| ORF Name | NT ID | AA ID | NT/LN | AA/LN | Score | P-Value |
|---|---|---|---|---|---|---|
| SPX0699 | 699 | 3360 | 1959 | 653 | 3335 | 0 |
| Description | | | | | | |

[LN:ALIB_STRPN] [AC:Q51933] [GN:ALIB] [OR:Streptococcus pneumoniae] [DE:OLIGOPEPTIDE-BINDING PROTEIN ALIB PRECURSOR] [SP:Q51933]

| ORF Name | NT ID | AA ID | NT/LN | AA/LN | Score | P-Value |
|---|---|---|---|---|---|---|
| SPX0700 | 700 | 3361 | 555 | 185 | 282 | 2.00E-38 |

Description

[GI:1125685] [LN:SADNAS55] [AC:X87104] [GN:mdr] [FN:multiple grug resistance] [OR:Staphylococcus aureus]

| ORF Name | NT ID | AA ID | NT/LN | AA/LN | Score | P-Value |
|---|---|---|---|---|---|---|
| SPX0701 | 701 | 3362 | 540 | 180 | 179 | 9.60E-18 |

Description

[LN:S58356] [AC:S66651:S58356] [PN:pepT protein] [GN:pepT] [CL:unassigned ATP-binding cassette proteins:ATP-binding cassette homology] [OR:Staphylococcus epidermidis]

| ORF Name | NT ID | AA ID | NT/LN | AA/LN | Score | P-Value |
|---|---|---|---|---|---|---|
| SPX0702 | 702 | 3363 | 546 | 182 | 444 | 4.80E-55 |

Description

[GI:1262136] [LN:SAPBP4GEN] [AC:X91786] [PN:ATP-binding cassette transporter A] [GN:abcA] [OR:Staphylococcus aureus]

| ORF Name | NT ID | AA ID | NT/LN | AA/LN | Score | P-Value |
|---|---|---|---|---|---|---|
| SPX0703 | 703 | 3364 | 1095 | 365 | 681 | 2.80E-123 |

Description

[LN:A69847] [AC:A69847] [PN:cystathionine gamma-synthase homolog yjcI] [GN:yjcI] [CL:O-succinylhomoserine (thiol)-lyase] [OR:Bacillus subtilis]

| ORF Name | NT ID | AA ID | NT/LN | AA/LN | Score | P-Value |
|---|---|---|---|---|---|---|
| SPX0704 | 704 | 3365 | 1167 | 389 | 582 | 1.60E-99 |

Description

"[LN:PATB_BACSU] [AC:Q08432] [GN:PATB] [OR:Bacillus subtilis] [EC:2.6.1.-] [DE:PUTATIVE AMINOTRANSFERASE B,] [SP:Q08432]"

| ORF Name | NT ID | AA ID | NT/LN | AA/LN | Score | P-Value |
|---|---|---|---|---|---|---|
| SPX0705 | 705 | 3366 | 3099 | 1033 | 552 | 1.00E-129 |

Description

[GI:1769947] [LN:BCX98455] [AC:X98455] [GN:SNF] [OR:Bacillus cereus]

| ORF Name | NT ID | AA ID | NT/LN | AA/LN | Score | P-Value |
|---|---|---|---|---|---|---|
| SPX0706 | 706 | 3367 | 618 | 206 | | |

Description

NO-HIT

| ORF Name | NT ID | AA ID | NT/LN | AA/LN | Score | P-Value |
|---|---|---|---|---|---|---|
| SPX0707 | 707 | 3368 | 1335 | 445 | 491 | 2.00E-154 |

Description

[LN:MURC_BACSU] [AC:P40778] [GN:MURC] [OR:Bacillus subtilis] [EC:6.3.2.8] [DE:ACETYLMURANOYL-L-ALANINE SYNTHETASE)] [SP:P40778]

| ORF Name | NT ID | AA ID | NT/LN | AA/LN | Score | P-Value |
|---|---|---|---|---|---|---|
| SPX0708 | 708 | 3369 | 465 | 155 | | |

Description

NO-HIT

| ORF Name | NT ID | AA ID | NT/LN | AA/LN | Score | P-Value |
|---|---|---|---|---|---|---|
| SPX0709 | 709 | 3370 | 357 | 119 | 56 | 7.70E-05 |

Description

"[LN:A64491] [AC:A64491] [PN:N-terminal acetyltransferase complex, subunit ARD1 homolog] [CL:Escherichia coli ribosomal-protein-alanine N-acetyltransferase rimI] [OR:Methanococcus jannaschii]"

| ORF Name | NT ID | AA ID | NT/LN | AA/LN | Score | P-Value |
|---|---|---|---|---|---|---|
| SPX0710 | 710 | 3371 | 213 | 71 | | |

Description

NO-HIT

| ORF Name | NT ID | AA ID | NT/LN | AA/LN | Score | P-Value |
|---|---|---|---|---|---|---|
| SPX0711 | 711 | 3372 | 1506 | 502 | 185 | 2.10E-43 |

Description

[LN:E69979] [AC:E69979] [PN:folate metabolism homolog yrrL] [GN:yrrL] [CL:yceG protein] [OR:Bacillus subtilis]

| ORF Name | NT ID | AA ID | NT/LN | AA/LN | Score | P-Value |
|---|---|---|---|---|---|---|
| SPX0712 | 712 | 3373 | 483 | 161 | 271 | 3.60E-55 |

Description

[LN:GREA_BACSU] [AC:P80240] [GN:GREA] [OR:Bacillus subtilis] [DE:GREA) (GENERAL STRESS PROTEIN 20M) (GSP20M)] [SP:P80240]

| ORF Name | NT ID | AA ID | NT/LN | AA/LN | Score | P-Value |
|---|---|---|---|---|---|---|
| SPX0713 | 713 | 3374 | 183 | 61 | 121 | 2.50E-12 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX0714 | 714 | 3375 | 489 | 163 | 152 | 1.50E-24 |

Description

[LN:S31638] [AC:S31638] [PN:hypothetical protein] [OR:Lactobacillus curvatus]

| ORF Name | NT ID | AA ID | NT/LN | AA/LN | Score | P-Value |
|---|---|---|---|---|---|---|
| SPX0715 | 715 | 3376 | 198 | 66 | | |

Description

NO-HIT

| ORF Name | NT ID | AA ID | NT/LN | AA/LN | Score | P-Value |
|---|---|---|---|---|---|---|
| SPX0716 | 716 | 3377 | 210 | 70 | 89 | 0.0001 |

Description

[GI:4966270] [LN:CELK09H11] [AC:U97002] [GN:K09H11.1] [OR:Caenorhabditis elegans]

| ORF Name | NT ID | AA ID | NT/LN | AA/LN | Score | P-Value |
|---|---|---|---|---|---|---|
| SPX0717 | 717 | 3378 | 444 | 148 | 419 | 7.50E-56 |

Description

[GI:517210] [LN:SPU11799] [AC:U11799] [OR:Streptococcus pyogenes]

| ORF Name | NT ID | AA ID | NT LN | AA LN | Score | P-Value |
|---|---|---|---|---|---|---|
| SPX0718 | 718 | 3379 | 492 | 164 | 484 | 1.40E-63 |

Description

[GI:517210] [LN:SPU11799] [AC:U11799] [OR:Streptococcus pyogenes]

| ORF Name | NT ID | AA ID | NT LN | AA LN | Score | P-Value |
|---|---|---|---|---|---|---|
| SPX0719 | 719 | 3380 | 201 | 67 | 331 | 3.00E-44 |

Description

"[LN:S49404] [AC:S49404:S38206] [PN:H+-transporting ATP synthase, chain c] [GN:atpC] [CL:H+-transporting ATP synthase lipid-binding protein] [OR:Streptococcus pneumoniae] [EC:3.6.1.34]"

| ORF Name | NT ID | AA ID | NT LN | AA LN | Score | P-Value |
|---|---|---|---|---|---|---|
| SPX0720 | 720 | 3381 | 717 | 239 | 1205 | 5.00E-168 |

Description

"[LN:ATP6_STRPN] [AC:Q59954] [GN:ATPB:ATPA] [OR:Streptococcus pneumoniae] [EC:3.6.1.34] [DE:ATP SYNTHASE A CHAIN, (PROTEIN 6)] [SP:Q59954]"

| ORF Name | NT ID | AA ID | NT LN | AA LN | Score | P-Value |
|---|---|---|---|---|---|---|
| SPX0721 | 721 | 3382 | 495 | 165 | 769 | 2.90E-100 |

Description

"[LN:ATPF_STRPN] [AC:Q59952:Q59955] [GN:ATPF:ATPB] [OR:Streptococcus pneumoniae] [EC:3.6.1.34] [DE:ATP SYNTHASE B CHAIN, (SUBUNIT I)] [SP:Q59952:Q59955]"

| ORF Name | NT ID | AA ID | NT LN | AA LN | Score | P-Value |
|---|---|---|---|---|---|---|
| SPX0722 | 722 | 3383 | 537 | 179 | 509 | 8.40E-66 |

Description

[GI:4100654] [LN:AF001955] [AC:AF001955] [PN:proton-translocating ATPase delta subunit] [GN:uncH] [OR:Streptococcus sanguinis]

| ORF Name | NT ID | AA ID | NT LN | AA LN | Score | P-Value |
|---|---|---|---|---|---|---|
| SPX0723 | 723 | 3384 | 1506 | 502 | 2347 | 0 |

Description

[GI:4100655] [LN:AF001955] [AC:AF001955] [PN:proton-translocating ATPase alpha subunit] [GN:uncA] [OR:Streptococcus sanguinis]

| ORF Name | NT ID | AA ID | NT/LN | AA/LN | Score | P-Value |
|---|---|---|---|---|---|---|
| SPX0724 | 724 | 3385 | 879 | 293 | 1011 | 1.70E-169 |
| Description | | | | | | |

[GI:4100656] [LN:AF001955] [AC:AF001955] [PN:proton-translocating ATPase gamma subunit] [OR:Streptococcus sanguinis]

| ORF Name | NT ID | AA ID | NT/LN | AA/LN | Score | P-Value |
|---|---|---|---|---|---|---|
| SPX0725 | 725 | 3386 | 1407 | 469 | 2287 | 0 |
| Description | | | | | | |

[GI:4100657] [LN:AF001955] [AC:AF001955] [PN:proton-translocating ATPase beta subunit] [GN:uncD] [OR:Streptococcus sanguinis]

| ORF Name | NT ID | AA ID | NT/LN | AA/LN | Score | P-Value |
|---|---|---|---|---|---|---|
| SPX0726 | 726 | 3387 | 420 | 140 | 581 | 1.40E-76 |
| Description | | | | | | |

[GI:4100658] [LN:AF001955] [AC:AF001955] [PN:proton-translocating ATPase epsilon subunit] [GN:uncC] [OR:Streptococcus sanguinis]

| ORF Name | NT ID | AA ID | NT/LN | AA/LN | Score | P-Value |
|---|---|---|---|---|---|---|
| SPX0727 | 727 | 3388 | 753 | 251 | 175 | 2.70E-42 |
| Description | | | | | | |

[GI:6746427] [LN:AF179847] [AC:AF179847] [PN:putative transposase] [OR:Lactococcus lactis]

| ORF Name | NT ID | AA ID | NT/LN | AA/LN | Score | P-Value |
|---|---|---|---|---|---|---|
| SPX0728 | 728 | 3389 | 195 | 65 | | |
| Description | | | | | | |

NO-HIT

| ORF Name | NT ID | AA ID | NT/LN | AA/LN | Score | P-Value |
|---|---|---|---|---|---|---|
| SPX0729 | 729 | 3390 | 546 | 182 | 107 | 1.20E-15 |
| Description | | | | | | |

[GI:3849798] [LN:U91581] [AC:U91581:U04057] [PN:putative transposase] [GN:tpase] [OR:Lactococcus lactis subsp. lactis]

| ORF Name | NT ID | AA ID | NT LN | AA LN | Score | P-Value |
|---|---|---|---|---|---|---|
| SPX0730 | 730 | 3391 | 1014 | 338 | 444 | 1.50E-117 |

Description

[GI:3242228] [LN:LLCADHE] [AC:AJ001007] [GN:orfB] [OR:Lactococcus lactis]

| ORF Name | NT ID | AA ID | NT LN | AA LN | Score | P-Value |
|---|---|---|---|---|---|---|
| SPX0731 | 731 | 3392 | 234 | 78 | | |

Description

NO-HIT

| ORF Name | NT ID | AA ID | NT LN | AA LN | Score | P-Value |
|---|---|---|---|---|---|---|
| SPX0732 | 732 | 3393 | 1167 | 389 | 1141 | 1.60E-158 |

Description

[GI:4098497] [LN:SMU78604] [AC:U78604] [PN:putative membrane protein] [OR:Streptococcus mutans]

| ORF Name | NT ID | AA ID | NT LN | AA LN | Score | P-Value |
|---|---|---|---|---|---|---|
| SPX0733 | 733 | 3394 | 1230 | 410 | 457 | 6.20E-71 |

Description

"[GI:473901] [LN:LACALS] [AC:L16975] [OR:Lactococcus lactis] [SR:Lactococcus lactis (strain DSM 20384, sub_species lactis) DNA]"

| ORF Name | NT ID | AA ID | NT LN | AA LN | Score | P-Value |
|---|---|---|---|---|---|---|
| SPX0734 | 734 | 3395 | 642 | 214 | 351 | 1.70E-45 |

Description

"[LN:A72357] [AC:A72357] [PN:amino acid ABC transporter, permease protein] [GN:TM0592] [CL:histidine permease protein M] [OR:Thermotoga maritima]"

| ORF Name | NT ID | AA ID | NT LN | AA LN | Score | P-Value |
|---|---|---|---|---|---|---|
| SPX0735 | 735 | 3396 | 630 | 210 | 367 | 2.90E-65 |

Description

[GI:1649037] [LN:STU73111] [AC:U73111] [PN:glutamine transport ATP-binding protein GLNQ] [OR:Salmonella typhimurium]

| ORF Name | NT ID | AA ID | NT/LN | AA/LN | Score | P-Value |
|---|---|---|---|---|---|---|
| SPX0736 | 736 | 3397 | 837 | 279 | 1411 | 4.70E-188 |

Description

[GI:5929889] [LN:AF165218] [AC:AF165218] [PN:AatB] [GN:aatB]
[OR:Streptococcus pneumoniae]

| ORF Name | NT ID | AA ID | NT/LN | AA/LN | Score | P-Value |
|---|---|---|---|---|---|---|
| SPX0737 | 737 | 3398 | 348 | 116 | 578 | 1.80E-76 |

Description

[GI:5929888] [LN:AF165218] [AC:AF165218] [PN:Bta] [GN:bta] [OR:Streptococcus pneumoniae]

| ORF Name | NT ID | AA ID | NT/LN | AA/LN | Score | P-Value |
|---|---|---|---|---|---|---|
| SPX0738 | 738 | 3399 | 1719 | 573 | 2903 | 0 |

Description

[GI:5929887] [LN:AF165218] [AC:AF165218] [PN:Pgm] [GN:pgm] [OR:Streptococcus pneumoniae]

| ORF Name | NT ID | AA ID | NT/LN | AA/LN | Score | P-Value |
|---|---|---|---|---|---|---|
| SPX0739 | 739 | 3400 | 327 | 109 | 129 | 8.30E-12 |

Description

[GI:4200438] [LN:AF026471] [AC:AF026471] [PN:putative transposase]
[OR:Streptococcus pneumoniae]

| ORF Name | NT ID | AA ID | NT/LN | AA/LN | Score | P-Value |
|---|---|---|---|---|---|---|
| SPX0740 | 740 | 3401 | 300 | 100 | 245 | 5.10E-30 |

Description

[GI:5019553] [LN:SPN239004] [AC:AJ239004] [PN:putative transposase]
[OR:Streptococcus pneumoniae]

| ORF Name | NT ID | AA ID | NT/LN | AA/LN | Score | P-Value |
|---|---|---|---|---|---|---|
| SPX0741 | 741 | 3402 | 285 | 95 | | |

Description

NO-HIT

| ORF Name | NT ID | AA ID | NT/LN | AA/LN | Score | P-Value |
|---|---|---|---|---|---|---|
| SPX0742 | 742 | 3403 | 255 | 85 | | |

Description

NO-HIT

| ORF Name | NT ID | AA ID | NT/LN | AA/LN | Score | P-Value |
|---|---|---|---|---|---|---|
| SPX0743 | 743 | 3404 | 213 | 71 | | |

Description

NO-HIT

| ORF Name | NT ID | AA ID | NT/LN | AA/LN | Score | P-Value |
|---|---|---|---|---|---|---|
| SPX0744 | 744 | 3405 | 1113 | 371 | | |

Description

NO-HIT

| ORF Name | NT ID | AA ID | NT/LN | AA/LN | Score | P-Value |
|---|---|---|---|---|---|---|
| SPX0745 | 745 | 3406 | 522 | 174 | 72 | 1.10E-05 |

Description

"[LN:I38170] [AC:I38170] [PN:gene hr44 protein] [GN:hr44] [OR:Homo sapiens] [SR:, man]"

| ORF Name | NT ID | AA ID | NT/LN | AA/LN | Score | P-Value |
|---|---|---|---|---|---|---|
| SPX0746 | 746 | 3407 | 870 | 290 | 335 | 2.40E-72 |

Description

[LN:B72254] [AC:B72254] [PN:glycerol uptake facilitator protein] [GN:TM1429] [CL:glycerol facilitator protein] [OR:Thermotoga maritima]

| ORF Name | NT ID | AA ID | NT/LN | AA/LN | Score | P-Value |
|---|---|---|---|---|---|---|
| SPX0747 | 747 | 3408 | 1197 | 399 | 2022 | 6.40E-273 |

Description

[LN:EFTU_STROR] [AC:P33170] [GN:TUF] [OR:Streptococcus oralis] [DE:ELONGATION FACTOR TU (EF-TU)] [SP:P33170]

| ORF Name | NT ID | AA ID | NT/LN | AA/LN | Score | P-Value |
|---|---|---|---|---|---|---|
| SPX0748 | 748 | 3409 | 384 | 128 | 104 | 1.80E-06 |

Description

[LN:H71023] [AC:H71023] [PN:hypothetical protein PH1485] [GN:PH1485] [OR:Pyrococcus horikoshii]

| ORF Name | NT ID | AA ID | NT/LN | AA/LN | Score | P-Value |
|---|---|---|---|---|---|---|
| SPX0749 | 749 | 3410 | 414 | 138 | 99 | 6.40E-06 |

Description

[LN:S31840] [AC:S31840] [PN:probable transposase] [OR:Bacillus stearothermophilus]

| ORF Name | NT ID | AA ID | NT/LN | AA/LN | Score | P-Value |
|---|---|---|---|---|---|---|
| SPX0750 | 750 | 3411 | 186 | 62 | | |

Description

NO-HIT

| ORF Name | NT ID | AA ID | NT/LN | AA/LN | Score | P-Value |
|---|---|---|---|---|---|---|
| SPX0751 | 751 | 3412 | 654 | 218 | 163 | 3.90E-21 |

Description

[GI:722339] [LN:AXU22323] [AC:U22323] [PN:unknown] [OR:Acetobacter xylinus] [SR:Acetobacter xylinum]

| ORF Name | NT ID | AA ID | NT/LN | AA/LN | Score | P-Value |
|---|---|---|---|---|---|---|
| SPX0752 | 752 | 3413 | 1083 | 361 | 272 | 2.20E-72 |

Description

[LN:C69813] [AC:C69813] [PN:RNA helicase homolog yfmL] [GN:yfmL] [CL:unassigned DEAD/H box helicases:DEAD/H box helicase homology] [OR:Bacillus subtilis]

| ORF Name | NT ID | AA ID | NT/LN | AA/LN | Score | P-Value |
|---|---|---|---|---|---|---|
| SPX0753 | 753 | 3414 | 1062 | 354 | 197 | 3.10E-44 |

Description

[LN:YGJR_ECOLI] [AC:P42599:P42600:P76661] [GN:YGJR] [OR:Escherichia coli] [DE:HYPOTHETICAL 36.2 KD PROTEIN IN EBGC-UXAA INTERGENIC REGION] [SP:P42599:P42600:P76661]

| ORF Name | NT ID | AA ID | NT/LN | AA/LN | Score | P-Value |
|---|---|---|---|---|---|---|
| SPX0754 | 754 | 3415 | 186 | 62 | 77 | 0.00028 |

Description

"[LN:S67482] [AC:S67482:S52150] [PN:serine O-acetyltransferase,, cytosolic:serine acetyltransferase:serine acetyltransferase] [OR:Arabidopsis thaliana]"

| ORF Name | NT ID | AA ID | NT/LN | AA/LN | Score | P-Value |
|---|---|---|---|---|---|---|
| SPX0755 | 755 | 3416 | 378 | 126 | | |

Description

NO-HIT

| ORF Name | NT ID | AA ID | NT/LN | AA/LN | Score | P-Value |
|---|---|---|---|---|---|---|
| SPX0756 | 756 | 3417 | 1443 | 481 | 485 | 5.60E-59 |

Description

"[LN:G69849] [AC:G69849] [PN:endo-1,4-beta-xylanase homolog yjeA] [GN:yjeA] [CL:nodB homology] [OR:Bacillus subtilis]"

| ORF Name | NT ID | AA ID | NT/LN | AA/LN | Score | P-Value |
|---|---|---|---|---|---|---|
| SPX0757 | 757 | 3418 | 768 | 256 | 357 | 5.70E-83 |

Description

[LN:C70040] [AC:C70040] [PN:plant-metabolite dehydrogenase homolog yvgN] [GN:yvgN] [CL:aldehyde reductase] [OR:Bacillus subtilis]

| ORF Name | NT ID | AA ID | NT/LN | AA/LN | Score | P-Value |
|---|---|---|---|---|---|---|
| SPX0758 | 758 | 3419 | 231 | 77 | | |

Description

NO-HIT

| ORF Name | NT ID | AA ID | NT/LN | AA/LN | Score | P-Value |
|---|---|---|---|---|---|---|
| SPX0759 | 759 | 3420 | 762 | 254 | | |

Description

NO-HIT

| ORF Name | NT ID | AA ID | NT/LN | AA/LN | Score | P-Value |
|---|---|---|---|---|---|---|
| SPX0760 | 760 | 3421 | 918 | 306 | 1187 | 3.50E-159 |
| Description | | | | | | |

[LN:SYGA_BACSU] [AC:P54380] [GN:GLYQ] [OR:Bacillus subtilis] [EC:6.1.1.14] [DE:ALPHA CHAIN) (GLYRS)] [SP:P54380]

| ORF Name | NT ID | AA ID | NT/LN | AA/LN | Score | P-Value |
|---|---|---|---|---|---|---|
| SPX0761 | 761 | 3422 | 2037 | 679 | 1334 | 6.50E-179 |
| Description | | | | | | |

[LN:SYGB_BACSU] [AC:P54381] [GN:GLYS] [OR:Bacillus subtilis] [EC:6.1.1.14] [DE:BETA CHAIN) (GLYRS)] [SP:P54381]

| ORF Name | NT ID | AA ID | NT/LN | AA/LN | Score | P-Value |
|---|---|---|---|---|---|---|
| SPX0762 | 762 | 3423 | 258 | 86 | 218 | 1.20E-24 |
| Description | | | | | | |

[LN:E69894] [AC:E69894] [PN:hypothetical protein ynzC] [GN:ynzC] [OR:Bacillus subtilis]

| ORF Name | NT ID | AA ID | NT/LN | AA/LN | Score | P-Value |
|---|---|---|---|---|---|---|
| SPX0763 | 763 | 3424 | 1245 | 415 | 97 | 5.10E-08 |
| Description | | | | | | |

[LN:YIEF_ECOLI] [AC:P31465] [GN:YIEF] [OR:Escherichia coli] [DE:HYPOTHETICAL 20.4 KD PROTEIN IN TNAB-BGLB INTERGENIC REGION] [SP:P31465]

| ORF Name | NT ID | AA ID | NT/LN | AA/LN | Score | P-Value |
|---|---|---|---|---|---|---|
| SPX0764 | 764 | 3425 | 237 | 79 | | |
| Description | | | | | | |

NO-HIT

| ORF Name | NT ID | AA ID | NT/LN | AA/LN | Score | P-Value |
|---|---|---|---|---|---|---|
| SPX0765 | 765 | 3426 | 606 | 202 | 110 | 2.80E-13 |
| Description | | | | | | |

[LN:YIEF_ECOLI] [AC:P31465] [GN:YIEF] [OR:Escherichia coli] [DE:HYPOTHETICAL 20.4 KD PROTEIN IN TNAB-BGLB INTERGENIC REGION] [SP:P31465]

| ORF Name | NT ID | AA ID | NT/LN | AA/LN | Score | P-Value |
|---|---|---|---|---|---|---|
| SPX0766 | 766 | 3427 | 924 | 308 | 172 | 3.10E-41 |

Description

[LN:APBE_TREPA] [AC:O83774] [GN:APBE:TP0796] [OR:Treponema pallidum]
[DE:THIAMINE BIOSYNTHESIS LIPOPROTEIN APBE PRECURSOR] [SP:O83774]

| ORF Name | NT ID | AA ID | NT/LN | AA/LN | Score | P-Value |
|---|---|---|---|---|---|---|
| SPX0767 | 767 | 3428 | 273 | 91 | | |

Description

NO-HIT

| ORF Name | NT ID | AA ID | NT/LN | AA/LN | Score | P-Value |
|---|---|---|---|---|---|---|
| SPX0768 | 768 | 3429 | 1380 | 460 | 2342 | 0 |

Description

[GI:4416519] [LN:AF014458] [AC:AF014458] [PN:NADH oxidase] [OR:Streptococcus pneumoniae]

| ORF Name | NT ID | AA ID | NT/LN | AA/LN | Score | P-Value |
|---|---|---|---|---|---|---|
| SPX0769 | 769 | 3430 | 894 | 298 | 1411 | 3.40E-191 |

Description

[LN:YG47_HAEIN] [AC:P45293] [GN:HI1647] [OR:Haemophilus influenzae]
[DE:HYPOTHETICAL PROTEIN HI1647] [SP:P45293]

| ORF Name | NT ID | AA ID | NT/LN | AA/LN | Score | P-Value |
|---|---|---|---|---|---|---|
| SPX0770 | 770 | 3431 | 234 | 78 | 125 | 3.00E-12 |

Description

[LN:F71007] [AC:F71007] [PN:hypothetical protein PH1356] [GN:PH1356]
[CL:Pyrococcus horikoshii hypothetical protein PH1356] [OR:Pyrococcus horikoshii]

| ORF Name | NT ID | AA ID | NT/LN | AA/LN | Score | P-Value |
|---|---|---|---|---|---|---|
| SPX0771 | 771 | 3432 | 189 | 63 | 157 | 1.20E-15 |

Description

[LN:F72782] [AC:F72782] [PN:hypothetical protein APE0247] [GN:APE0247]
[OR:Aeropyrum pernix]

| ORF Name | NT ID | AA ID | NT LN | AA LN | Score | P-Value |
|---|---|---|---|---|---|---|
| SPX0772 | 772 | 3433 | 156 | 52 | 159 | 4.30E-16 |

Description

[LN:F72782] [AC:F72782] [PN:hypothetical protein APE0247] [GN:APE0247] [OR:Aeropyrum pernix]

| ORF Name | NT ID | AA ID | NT LN | AA LN | Score | P-Value |
|---|---|---|---|---|---|---|
| SPX0773 | 773 | 3434 | 582 | 194 | 720 | 2.40E-95 |

Description

[LN:YG48_HAEIN] [AC:P45294] [GN:HI1648] [OR:Haemophilus influenzae] [DE:HYPOTHETICAL PROTEIN HI1648] [SP:P45294]

| ORF Name | NT ID | AA ID | NT LN | AA LN | Score | P-Value |
|---|---|---|---|---|---|---|
| SPX0774 | 774 | 3435 | 648 | 216 | 183 | 5.00E-34 |

Description

[LN:YA37_TREPA] [AC:O84000] [GN:TP1037] [OR:Treponema pallidum] [DE:HYPOTHETICAL PROTEIN TP1037] [SP:O84000]

| ORF Name | NT ID | AA ID | NT LN | AA LN | Score | P-Value |
|---|---|---|---|---|---|---|
| SPX0775 | 775 | 3436 | 453 | 151 | | |

Description

NO-HIT

| ORF Name | NT ID | AA ID | NT LN | AA LN | Score | P-Value |
|---|---|---|---|---|---|---|
| SPX0776 | 776 | 3437 | 495 | 165 | 94 | 2.80E-12 |

Description

[LN:G81269] [AC:G81269] [PN:probable acetyltransferase Cj1715 [imported]] [GN:Cj1715] [OR:Campylobacter jejuni]

| ORF Name | NT ID | AA ID | NT LN | AA LN | Score | P-Value |
|---|---|---|---|---|---|---|
| SPX0777 | 777 | 3438 | 531 | 177 | 167 | 1.80E-29 |

Description

[GI:3694956] [LN:AF091508] [AC:AF091508] [PN:O-6-methylguanine DNA methyltransferase] [GN:ogt] [OR:Salmonella muenster]

| ORF Name | NT ID | AA ID | NT LN | AA LN | Score | P-Value |
|---|---|---|---|---|---|---|
| SPX0778 | 778 | 3439 | 357 | 119 | 272 | 2.10E-32 |

Description

[LN:B70021] [AC:B70021] [PN:arsenate reductase homolog yusI] [GN:yusI]
[CL:hypothetical protein yjbD] [OR:Bacillus subtilis]

| ORF Name | NT ID | AA ID | NT LN | AA LN | Score | P-Value |
|---|---|---|---|---|---|---|
| SPX0779 | 779 | 3440 | 378 | 126 | | |

Description

NO-HIT

| ORF Name | NT ID | AA ID | NT LN | AA LN | Score | P-Value |
|---|---|---|---|---|---|---|
| SPX0780 | 780 | 3441 | 801 | 267 | 284 | 2.10E-54 |

Description

[LN:YXEN_BACSU] [AC:P54953] [GN:YXEN:LP9F] [OR:Bacillus subtilis]
[DE:INTERGENIC REGION] [SP:P54953]

| ORF Name | NT ID | AA ID | NT LN | AA LN | Score | P-Value |
|---|---|---|---|---|---|---|
| SPX0781 | 781 | 3442 | 744 | 248 | 468 | 5.80E-82 |

Description

[GI:666983] [LN:BSPAAT] [AC:X77636] [PN:putative ATP binding subunit]
[GN:ORF3] [OR:Bacillus subtilis]

| ORF Name | NT ID | AA ID | NT LN | AA LN | Score | P-Value |
|---|---|---|---|---|---|---|
| SPX0782 | 782 | 3443 | 237 | 79 | | |

Description

NO-HIT

| ORF Name | NT ID | AA ID | NT LN | AA LN | Score | P-Value |
|---|---|---|---|---|---|---|
| SPX0783 | 783 | 3444 | 222 | 74 | | |

Description

NO-HIT

| ORF Name | NT ID | AA ID | NT LN | AA LN | Score | P-Value |
|---|---|---|---|---|---|---|
| SPX0784 | 784 | 3445 | 798 | 266 | 542 | 4.60E-98 |

Description

"[LN:TRXB_LISMO] [AC:O32823] [GN:TRXB] [OR:Listeria monocytogenes] [EC:1.6.4.5] [DE:THIOREDOXIN REDUCTASE,] [SP:O32823]"

| ORF Name | NT ID | AA ID | NT LN | AA LN | Score | P-Value |
|---|---|---|---|---|---|---|
| SPX0785 | 785 | 3446 | 762 | 254 | 322 | 1.30E-58 |

Description

"[LN:YACO_BACSU] [AC:Q06753] [GN:YACO] [OR:Bacillus subtilis] [EC:2.1.1.-] [DE:HYPOTHETICAL TRNA/RRNA METHYLTRANSFERASE YACO,] [SP:Q06753]"

| ORF Name | NT ID | AA ID | NT LN | AA LN | Score | P-Value |
|---|---|---|---|---|---|---|
| SPX0786 | 786 | 3447 | 612 | 204 | 394 | 4.10E-93 |

Description

"[GI:806487] [LN:LACLPAGAP] [AC:L36907] [FN:unknown] [OR:Lactococcus lactis] [SR:Lactococcus lactis (individual_isolate LM0230, sub_specie)"

| ORF Name | NT ID | AA ID | NT LN | AA LN | Score | P-Value |
|---|---|---|---|---|---|---|
| SPX0787 | 787 | 3448 | 252 | 84 | | |

Description

NO-HIT

| ORF Name | NT ID | AA ID | NT LN | AA LN | Score | P-Value |
|---|---|---|---|---|---|---|
| SPX0788 | 788 | 3449 | 483 | 161 | 136 | 6.00E-14 |

Description

[LN:H70069] [AC:H70069;JC7099] [PN:poly-gamma-glutamic synthesis PgsA protein] [GN:ywtB:pgsA] [OR:Bacillus subtilis]

| ORF Name | NT ID | AA ID | NT LN | AA LN | Score | P-Value |
|---|---|---|---|---|---|---|
| SPX0789 | 789 | 3450 | 378 | 126 | | |

Description

NO-HIT

| ORF Name | NT ID | AA ID | NT/LN | AA/LN | Score | P-Value |
|---|---|---|---|---|---|---|
| SPX0790 | 790 | 3451 | 828 | 276 | 242 | 8.80E-42 |

Description

[LN:F64819] [AC:F64819] [PN:hypothetical protein b0822] [CL:Methanobacterium thermoautotrophicum conserved hypothetical protein MTH1071] [OR:Escherichia coli]

| ORF Name | NT ID | AA ID | NT/LN | AA/LN | Score | P-Value |
|---|---|---|---|---|---|---|
| SPX0791 | 791 | 3452 | 636 | 212 | | |

Description

NO-HIT

| ORF Name | NT ID | AA ID | NT/LN | AA/LN | Score | P-Value |
|---|---|---|---|---|---|---|
| SPX0792 | 792 | 3453 | 726 | 242 | 1196 | 1.80E-160 |

Description

[GI:5001711] [LN:AF112358] [AC:AF112358] [PN:C3-degrading proteinase] [GN:cppA] [OR:Streptococcus pneumoniae]

| ORF Name | NT ID | AA ID | NT/LN | AA/LN | Score | P-Value |
|---|---|---|---|---|---|---|
| SPX0793 | 793 | 3454 | 936 | 312 | 117 | 4.00E-22 |

Description

[GI:6469268] [LN:SCC75A] [AC:AL133220] [PN:possible secreted esterase] [GN:SCC75A.29c] [OR:Streptomyces coelicolor A3(2)]

| ORF Name | NT ID | AA ID | NT/LN | AA/LN | Score | P-Value |
|---|---|---|---|---|---|---|
| SPX0794 | 794 | 3455 | 897 | 299 | 487 | 1.00E-64 |

Description

[LN:YICL_ECOLI] [AC:P31437] [GN:YICL] [OR:Escherichia coli] [DE:HYPOTHETICAL 33.1 KD PROTEIN IN SELC-NLPA INTERGENIC REGION] [SP:P31437]

| ORF Name | NT ID | AA ID | NT/LN | AA/LN | Score | P-Value |
|---|---|---|---|---|---|---|
| SPX0795 | 795 | 3456 | 699 | 233 | 294 | 7.80E-49 |

Description

[LN:D70044] [AC:D70044] [PN:transcription regulator GntR family homolog yvoA] [GN:yvoA] [CL:transcription regulator GntR] [OR:Bacillus subtilis]

| ORF Name | NT ID | AA ID | NT/LN | AA/LN | Score | P-Value |
|---|---|---|---|---|---|---|
| SPX0796 | 796 | 3457 | 1563 | 521 | 1721 | 3.40E-294 |

Description

[GI:4321715] [LN:AF058326] [AC:AF058326] [PN:GMP synthase] [GN:guaA] [OR:Lactococcus lactis]

| ORF Name | NT ID | AA ID | NT/LN | AA/LN | Score | P-Value |
|---|---|---|---|---|---|---|
| SPX0797 | 797 | 3458 | 186 | 62 | | |

Description

NO-HIT

| ORF Name | NT ID | AA ID | NT/LN | AA/LN | Score | P-Value |
|---|---|---|---|---|---|---|
| SPX0798 | 798 | 3459 | 288 | 96 | 204 | 2.90E-23 |

Description

"[LN:JC1151] [AC:JC1151] [PN:hypothetical protein, 20.3K] [OR:Agrobacterium tumefaciens]"

| ORF Name | NT ID | AA ID | NT/LN | AA/LN | Score | P-Value |
|---|---|---|---|---|---|---|
| SPX0799 | 799 | 3460 | 195 | 65 | | |

Description

NO-HIT

| ORF Name | NT ID | AA ID | NT/LN | AA/LN | Score | P-Value |
|---|---|---|---|---|---|---|
| SPX0800 | 800 | 3461 | 390 | 130 | 91 | 0.00062 |

Description

"[GI:5824139] [LN:POL245436] [AC:AJ245436:J04618:J04619:S50571:X52935:X65936] [PN:hypothetical protein, 57.8 kD] [OR:Pseudomonas putida]"

| ORF Name | NT ID | AA ID | NT/LN | AA/LN | Score | P-Value |
|---|---|---|---|---|---|---|
| SPX0801 | 801 | 3462 | 429 | 143 | 84 | 9.20E-08 |

Description

"[GI:6009407] [LN:AB024946] [AC:AB024946] [GN:orf31] [OR:Escherichia coli] [SR:Escherichia coli (sub_species:enteropathogenic, strain:B171]"

| ORF Name | NT ID | AA ID | NT LN | AA LN | Score | P-Value |
|---|---|---|---|---|---|---|
| SPX0802 | 802 | 3463 | 450 | 150 | 94 | 3.20E-15 |

Description

"[LN:Y4HP_RHISN] [AC:P50360] [GN:Y4HP] [OR:Rhizobium sp] [SR:,strain NGR234] [DE:HYPOTHETICAL 61.7 KD PROTEIN Y4HP] [SP:P50360]"

| ORF Name | NT ID | AA ID | NT LN | AA LN | Score | P-Value |
|---|---|---|---|---|---|---|
| SPX0803 | 803 | 3464 | 234 | 78 | 87 | 0.00033 |

Description

"[GI:5824139] [LN:POL245436] [AC:AJ245436:J04618:J04619:S50571:X52935:X65936] [PN:hypothetical protein, 57.8 kD] [OR:Pseudomonas putida]"

| ORF Name | NT ID | AA ID | NT LN | AA LN | Score | P-Value |
|---|---|---|---|---|---|---|
| SPX0804 | 804 | 3465 | 1365 | 455 | 253 | 2.70E-62 |

Description

"[LN:D69159] [AC:D69159] [PN:methyl coenzyme M reductase system, component A2 homolog] [GN:MTH454] [CL:unassigned ATP-binding cassette proteins:ATP-binding cassette homology] [OR:Methanobacterium thermoautotrophicum]"

| ORF Name | NT ID | AA ID | NT LN | AA LN | Score | P-Value |
|---|---|---|---|---|---|---|
| SPX0805 | 805 | 3466 | 222 | 74 | | |

Description

NO-HIT

| ORF Name | NT ID | AA ID | NT LN | AA LN | Score | P-Value |
|---|---|---|---|---|---|---|
| SPX0806 | 806 | 3467 | 696 | 232 | 88 | 1.90E-07 |

Description

[LN:E72202] [AC:E72202] [PN:conserved hypothetical protein] [GN:TM1868] [OR:Thermotoga maritima]

| ORF Name | NT ID | AA ID | NT LN | AA LN | Score | P-Value |
|---|---|---|---|---|---|---|
| SPX0807 | 807 | 3468 | 585 | 195 | | |

Description

NO-HIT

| ORF Name | NT ID | AA ID | NT/LN | AA/LN | Score | P-Value |
|---|---|---|---|---|---|---|
| SPX0808 | 808 | 3469 | 1746 | 582 | 554 | 3.00E-83 |

Description

[GI:4097162] [LN:PMU46488] [AC:U46488] [PN:NrpB] [GN:nrpB] [OR:Proteus mirabilis]

| ORF Name | NT ID | AA ID | NT/LN | AA/LN | Score | P-Value |
|---|---|---|---|---|---|---|
| SPX0809 | 809 | 3470 | 1761 | 587 | 526 | 2.60E-78 |

Description

[GI:4097161] [LN:PMU46488] [AC:U46488] [PN:NrpA] [GN:nrpA] [OR:Proteus mirabilis]

| ORF Name | NT ID | AA ID | NT/LN | AA/LN | Score | P-Value |
|---|---|---|---|---|---|---|
| SPX0810 | 810 | 3471 | 477 | 159 | 131 | 3.30E-12 |

Description

[LN:SOXS_ECOLI] [AC:P22539] [GN:SOXS] [OR:Escherichia coli] [DE:REGULATORY PROTEIN SOXS] [SP:P22539]

| ORF Name | NT ID | AA ID | NT/LN | AA/LN | Score | P-Value |
|---|---|---|---|---|---|---|
| SPX0811 | 811 | 3472 | 207 | 69 | | |

Description

NO-HIT

| ORF Name | NT ID | AA ID | NT/LN | AA/LN | Score | P-Value |
|---|---|---|---|---|---|---|
| SPX0812 | 812 | 3473 | 1191 | 397 | 889 | 2.70E-126 |

Description

[GI:2995646] [LN:AF051092] [AC:AF051092] [PN:DNA modification methyltransferase M.XbaI] [GN:xbaIM] [FN:recognizes ds DNA sequence TCTAGA; thought to] [OR:Xanthomonas campestris]

| ORF Name | NT ID | AA ID | NT/LN | AA/LN | Score | P-Value |
|---|---|---|---|---|---|---|
| SPX0813 | 813 | 3474 | 189 | 63 | 128 | 1.30E-17 |

Description

[GI:2995645] [LN:AF051092] [AC:AF051092] [PN:restriction endonuclease R.XbaI] [GN:xbaIR] [FN:recognizes ds DNA sequence TCTAGA; cleaves both] [OR:Xanthomonas campestris]

| ORF Name | NT ID | AA ID | NT/LN | AA/LN | Score | P-Value |
|---|---|---|---|---|---|---|
| SPX0814 | 814 | 3475 | 183 | 61 | 199 | 4.80E-22 |

Description

[GI:2995645] [LN:AF051092] [AC:AF051092] [PN:restriction endonuclease R.XbaI] [GN:xbaIR] [FN:recognizes ds DNA sequence TCTAGA; cleaves both] [OR:Xanthomonas campestris]

| ORF Name | NT ID | AA ID | NT/LN | AA/LN | Score | P-Value |
|---|---|---|---|---|---|---|
| SPX0815 | 815 | 3476 | 213 | 71 | | |

Description

NO-HIT

| ORF Name | NT ID | AA ID | NT/LN | AA/LN | Score | P-Value |
|---|---|---|---|---|---|---|
| SPX0816 | 816 | 3477 | 1287 | 429 | 681 | 4.70E-147 |

Description

[LN:H69979] [AC:H69979] [PN:proteinase homolog yrrO] [GN:yrrO] [CL:collagenase prtC] [OR:Bacillus subtilis]

| ORF Name | NT ID | AA ID | NT/LN | AA/LN | Score | P-Value |
|---|---|---|---|---|---|---|
| SPX0817 | 817 | 3478 | 729 | 243 | 251 | 6.20E-58 |

Description

[LN:H69979] [AC:H69979] [PN:proteinase homolog yrrO] [GN:yrrO] [CL:collagenase prtC] [OR:Bacillus subtilis]

| ORF Name | NT ID | AA ID | NT/LN | AA/LN | Score | P-Value |
|---|---|---|---|---|---|---|
| SPX0818 | 818 | 3479 | 723 | 241 | 225 | 4.40E-26 |

Description

[LN:YCBN_BACSU] [AC:P42246] [GN:YCBN] [OR:Bacillus subtilis]
[DE:HYPOTHETICAL 31.7 KD PROTEIN IN GLTP-CWLJ INTERGENIC REGION (ORF13)]
[SP:P42246]

| ORF Name | NT ID | AA ID | NT/LN | AA/LN | Score | P-Value |
|---|---|---|---|---|---|---|
| SPX0819 | 819 | 3480 | 729 | 243 | | |

Description

NO-HIT

| ORF_Name | NT_ID | AA_ID | NT/LN | AA/LN | Score | P-Value |
|---|---|---|---|---|---|---|
| SPX0820 | 820 | 3481 | 240 | 80 | 152 | 2.50E-16 |

Description

[GI:1536960] [LN:SOORFS] [AC:Z79691] [GN:yorfE] [FN:putative transcription regulator] [OR:Streptococcus pneumoniae]

| ORF_Name | NT_ID | AA_ID | NT/LN | AA/LN | Score | P-Value |
|---|---|---|---|---|---|---|
| SPX0821 | 821 | 3482 | 489 | 163 | | |

Description

NO-HIT

| ORF_Name | NT_ID | AA_ID | NT/LN | AA/LN | Score | P-Value |
|---|---|---|---|---|---|---|
| SPX0822 | 822 | 3483 | 1461 | 487 | 981 | 1.70E-215 |

Description

[LN:D70008] [AC:D70008] [PN:nicotinate phosphoribosyltransferase homolog yueK] [GN:yueK] [OR:Bacillus subtilis]

| ORF_Name | NT_ID | AA_ID | NT/LN | AA/LN | Score | P-Value |
|---|---|---|---|---|---|---|
| SPX0823 | 823 | 3484 | 825 | 275 | 923 | 1.70E-122 |

Description

[LN:NADE_ECOLI] [AC:P18843:P78235] [GN:NADE:EFG:NTRL] [OR:Escherichia coli] [EC:6.3.5.1] [DE:PROTEIN)] [SP:P18843:P78235]

| ORF_Name | NT_ID | AA_ID | NT/LN | AA/LN | Score | P-Value |
|---|---|---|---|---|---|---|
| SPX0824 | 824 | 3485 | 198 | 66 | | |

Description

NO-HIT

| ORF_Name | NT_ID | AA_ID | NT/LN | AA/LN | Score | P-Value |
|---|---|---|---|---|---|---|
| SPX0825 | 825 | 3486 | 552 | 184 | 135 | 1.80E-13 |

Description

[GI:7635982] [LN:SCE6] [AC:AL353832] [PN:putative acetyltransferase.] [GN:SCE6.13] [OR:Streptomyces coelicolor A3(2)]

| ORF Name | NT ID | AA ID | NT/LN | AA/LN | Score | P-Value |
|---|---|---|---|---|---|---|
| SPX0826 | 826 | 3487 | 750 | 250 | 66 | 0.00023 |

Description

[GI:4185565] [LN:AF115379] [AC:AF115379] [PN:surface protein Pls] [GN:pls] [OR:Staphylococcus aureus]

| ORF Name | NT ID | AA ID | NT/LN | AA/LN | Score | P-Value |
|---|---|---|---|---|---|---|
| SPX0827 | 827 | 3488 | 390 | 130 | 306 | 1.70E-36 |

Description

[LN:A41971] [AC:A41971:A60282:A33134] [PN:surface protein pspA precursor:pneumococcal surface protein A] [GN:pspA] [CL:cpl repeat homology] [OR:Streptococcus pneumoniae]

| ORF Name | NT ID | AA ID | NT/LN | AA/LN | Score | P-Value |
|---|---|---|---|---|---|---|
| SPX0828 | 828 | 3489 | 1041 | 347 | 1229 | 5.30E-166 |

Description

[LN:QUEA_BACSU] [AC:O32054] [GN:QUEA] [OR:Bacillus subtilis] [EC:5.-.-.-] [DE:(QUEUOSINE BIOSYNTHESIS PROTEIN QUEA)] [SP:O32054]

| ORF Name | NT ID | AA ID | NT/LN | AA/LN | Score | P-Value |
|---|---|---|---|---|---|---|
| SPX0829 | 829 | 3490 | 708 | 236 | 336 | 3.00E-66 |

Description

[LN:NAGB_BACSU] [AC:O35000] [GN:NAGB] [OR:Bacillus subtilis] [EC:5.3.1.10] [DE:PHOSPHATE DEAMINASE) (GNPDA) (GLCN6P DEAMINASE)] [SP:O35000]

| ORF Name | NT ID | AA ID | NT/LN | AA/LN | Score | P-Value |
|---|---|---|---|---|---|---|
| SPX0830 | 830 | 3491 | 201 | 67 | 248 | 1.00E-29 |

Description

[LN:T43742] [AC:T43742] [PN:ribosomal protein S21 [imported]] [OR:Listeria monocytogenes]

| ORF Name | NT ID | AA ID | NT/LN | AA/LN | Score | P-Value |
|---|---|---|---|---|---|---|
| SPX0831 | 831 | 3492 | 939 | 313 | 1224 | 7.60E-165 |

Description

[GI:4884536] [LN:AB027460] [AC:AB027460] [PN:Hpr kinase] [OR:Streptococcus bovis] [SR:Streptococcus bovis (strain:JB1) DNA]

| ORF Name | NT ID | AA ID | NT/LN | AA/LN | Score | P-Value |
|---|---|---|---|---|---|---|
| SPX0832 | 832 | 3493 | 576 | 192 | 608 | 1.30E-84 |

Description

"[LN:T11569] [AC:T11569] [PN:prolipoprotein diacylglyceryl transferase,] [GN:lgt] [CL:prolipoprotein diacylglyceryl transferase] [OR:Streptococcus mutans] [EC:2.4.99.-]"

| ORF Name | NT ID | AA ID | NT/LN | AA/LN | Score | P-Value |
|---|---|---|---|---|---|---|
| SPX0833 | 833 | 3494 | 384 | 128 | 333 | 1.50E-41 |

Description

[LN:T11570] [AC:T11570] [PN:hypothetical protein 1] [OR:Streptococcus mutans]

| ORF Name | NT ID | AA ID | NT/LN | AA/LN | Score | P-Value |
|---|---|---|---|---|---|---|
| SPX0834 | 834 | 3495 | 330 | 110 | | |

Description

NO-HIT

| ORF Name | NT ID | AA ID | NT/LN | AA/LN | Score | P-Value |
|---|---|---|---|---|---|---|
| SPX0835 | 835 | 3496 | 390 | 130 | 164 | 5.70E-17 |

Description

[LN:T11571] [AC:T11571] [PN:hypothetical protein 2] [OR:Streptococcus mutans]

| ORF Name | NT ID | AA ID | NT/LN | AA/LN | Score | P-Value |
|---|---|---|---|---|---|---|
| SPX0836 | 836 | 3497 | 1131 | 377 | 596 | 4.30E-126 |

Description

"[LN:B69640] [AC:B69640] [PN:coproporphyrinogen oxidase, III, oxygen-independent hemN] [GN:hemN] [CL:oxygen-independent coproporphyrinogen oxidase] [OR:Bacillus subtilis] [EC:1.3.3.3]"

| ORF Name | NT ID | AA ID | NT/LN | AA/LN | Score | P-Value |
|---|---|---|---|---|---|---|
| SPX0837 | 837 | 3498 | 498 | 166 | | |

Description

NO-HIT

| ORF Name | NT ID | AA ID | NT/LN | AA/LN | Score | P-Value |
|---|---|---|---|---|---|---|
| SPX0838 | 838 | 3499 | 738 | 246 | 96 | 7.20E-11 |

Description

[GI:4704640] [LN:AF110462] [AC:AF110462] [PN:oleoyl-ACP thioesterase] [OR:Elaeis guineensis]

| ORF Name | NT ID | AA ID | NT/LN | AA/LN | Score | P-Value |
|---|---|---|---|---|---|---|
| SPX0839 | 839 | 3500 | 609 | 203 | 466 | 3.10E-59 |

Description

[LN:H70023] [AC:H70023] [PN:N-acetyl-glucosamine catabolism homolog yutF] [GN:yutF] [CL:nagD protein] [OR:Bacillus subtilis]

| ORF Name | NT ID | AA ID | NT/LN | AA/LN | Score | P-Value |
|---|---|---|---|---|---|---|
| SPX0840 | 840 | 3501 | 651 | 217 | | |

Description

NO-HIT

| ORF Name | NT ID | AA ID | NT/LN | AA/LN | Score | P-Value |
|---|---|---|---|---|---|---|
| SPX0841 | 841 | 3502 | 324 | 108 | | |

Description

NO-HIT

| ORF Name | NT ID | AA ID | NT/LN | AA/LN | Score | P-Value |
|---|---|---|---|---|---|---|
| SPX0842 | 842 | 3503 | 402 | 134 | 447 | 5.60E-58 |

Description

[LN:D69843] [AC:D69843] [PN:conserved hypothetical protein yjbD] [GN:yjbD] [CL:hypothetical protein yjbD] [OR:Bacillus subtilis]

| ORF Name | NT ID | AA ID | NT/LN | AA/LN | Score | P-Value |
|---|---|---|---|---|---|---|
| SPX0843 | 843 | 3504 | 279 | 93 | 216 | 2.40E-24 |

Description

[LN:C69864] [AC:C69864] [PN:hypothetical protein yktA] [GN:yktA] [OR:Bacillus subtilis]

| ORF Name | NT ID | AA ID | NT LN | AA LN | Score | P-Value |
|---|---|---|---|---|---|---|
| SPX0844 | 844 | 3505 | 849 | 283 | 207 | 1.30E-46 |

Description

[LN:SUHB_BACSU] [AC:Q45499] [GN:SUHB] [OR:Bacillus subtilis] [DE:EXTRAGENIC SUPPRESSOR PROTEIN SUHB HOMOLOG] [SP:Q45499]

| ORF Name | NT ID | AA ID | NT LN | AA LN | Score | P-Value |
|---|---|---|---|---|---|---|
| SPX0845 | 845 | 3506 | 339 | 113 | | |

Description

NO-HIT

| ORF Name | NT ID | AA ID | NT LN | AA LN | Score | P-Value |
|---|---|---|---|---|---|---|
| SPX0846 | 846 | 3507 | 915 | 305 | 143 | 8.30E-21 |

Description

[LN:YEBU_ECOLI] [AC:P76273:O07980] [GN:YEBU] [OR:Escherichia coli] [DE:HYPOTHETICAL 53.2 KD PROTEIN IN PRC-PRPA INTERGENIC REGION] [SP:P76273:O07980]

| ORF Name | NT ID | AA ID | NT LN | AA LN | Score | P-Value |
|---|---|---|---|---|---|---|
| SPX0847 | 847 | 3508 | 228 | 76 | | |

Description

NO-HIT

| ORF Name | NT ID | AA ID | NT LN | AA LN | Score | P-Value |
|---|---|---|---|---|---|---|
| SPX0848 | 848 | 3509 | 168 | 56 | | |

Description

NO-HIT

| ORF Name | NT ID | AA ID | NT LN | AA LN | Score | P-Value |
|---|---|---|---|---|---|---|
| SPX0849 | 849 | 3510 | 234 | 78 | | |

Description

NO-HIT

| ORF Name | NT ID | AA ID | NT/LN | AA/LN | Score | P-Value |
|---|---|---|---|---|---|---|
| SPX0850 | 850 | 3511 | 879 | 293 | 465 | 1.40E-80 |

Description

[LN:YQGG_BACSU] [AC:P46338] [GN:YQGG] [OR:Bacillus subtilis] [DE:REGION PRECURSOR (ORF108)] [SP:P46338]

| ORF Name | NT ID | AA ID | NT/LN | AA/LN | Score | P-Value |
|---|---|---|---|---|---|---|
| SPX0851 | 851 | 3512 | 918 | 306 | 403 | 1.00E-99 |

Description

[LN:YQGH_BACSU] [AC:P46339] [GN:YQGH] [OR:Bacillus subtilis] [DE:REGION (ORF72)] [SP:P46339]

| ORF Name | NT ID | AA ID | NT/LN | AA/LN | Score | P-Value |
|---|---|---|---|---|---|---|
| SPX0852 | 852 | 3513 | 885 | 295 | 842 | 2.80E-114 |

Description

[LN:YQGI_BACSU] [AC:P46340] [GN:YQGI] [OR:Bacillus subtilis] [DE:REGION (ORF73)] [SP:P46340]

| ORF Name | NT ID | AA ID | NT/LN | AA/LN | Score | P-Value |
|---|---|---|---|---|---|---|
| SPX0853 | 853 | 3514 | 804 | 268 | 796 | 1.10E-105 |

Description

[LN:PSTB_METJA] [AC:Q58418] [GN:PSTB:MJ1012] [OR:Methanococcus jannaschii] [DE:PROBABLE PHOSPHATE TRANSPORT ATP-BINDING PROTEIN PSTB] [SP:Q58418]

| ORF Name | NT ID | AA ID | NT/LN | AA/LN | Score | P-Value |
|---|---|---|---|---|---|---|
| SPX0854 | 854 | 3515 | 759 | 253 | 763 | 7.10E-100 |

Description

[LN:T43868] [AC:T43868] [PN:phosphate transport system peripheral membrane protein B [imported]] [GN:pstB] [CL:inner membrane protein malK:ATP-binding cassette homology] [OR:Pseudomonas putida]

| ORF Name | NT ID | AA ID | NT/LN | AA/LN | Score | P-Value |
|---|---|---|---|---|---|---|
| SPX0855 | 855 | 3516 | 654 | 218 | 212 | 3.70E-40 |

Description

[GI:4530451] [LN:AF118229] [AC:AF118229] [PN:PhoU] [GN:phoU] [OR:Streptococcus pneumoniae]

| ORF Name | NT ID | AA ID | NT/LN | AA/LN | Score | P-Value |
|---|---|---|---|---|---|---|
| SPX0856 | 856 | 3517 | 816 | 272 | 190 | 2.40E-30 |

Description

"[LN:B72357] [AC:B72357] [PN:amino acid ABC transporter, periplasmic amino acid-binding protein] [GN:TM0593] [CL:lysine-arginine-ornithine-binding protein] [OR:Thermotoga maritima]"

| ORF Name | NT ID | AA ID | NT/LN | AA/LN | Score | P-Value |
|---|---|---|---|---|---|---|
| SPX0857 | 857 | 3518 | 1272 | 424 | 778 | 4.20E-129 |

Description

[GI:4580622] [LN:AF118389] [AC:AF118389] [PN:unknown] [OR:Streptococcus suis]

| ORF Name | NT ID | AA ID | NT/LN | AA/LN | Score | P-Value |
|---|---|---|---|---|---|---|
| SPX0858 | 858 | 3519 | 171 | 57 | | |

Description

NO-HIT

| ORF Name | NT ID | AA ID | NT/LN | AA/LN | Score | P-Value |
|---|---|---|---|---|---|---|
| SPX0859 | 859 | 3520 | 513 | 171 | 340 | 3.10E-77 |

Description

[GI:1524117] [LN:LLALDB] [AC:X82620] [PN:alpha-acetolactate decarboxylase] [GN:aldB] [OR:Lactococcus lactis]

| ORF Name | NT ID | AA ID | NT/LN | AA/LN | Score | P-Value |
|---|---|---|---|---|---|---|
| SPX0860 | 860 | 3521 | 201 | 67 | 265 | 2.40E-33 |

Description

[GI:1808671] [LN:SGCSHAG] [AC:X65164:S52427] [PN:putative alpha-acetolactate decarboxylase] [GN:aldB] [OR:Streptococcus gordonii]

| ORF Name | NT ID | AA ID | NT/LN | AA/LN | Score | P-Value |
|---|---|---|---|---|---|---|
| SPX0861 | 861 | 3522 | 729 | 243 | 106 | 1.50E-25 |

Description

[LN:A69830] [AC:A69830] [PN:hypothetical protein yhfC] [GN:yhfC] [OR:Bacillus subtilis]

| ORF Name | NT ID | AA ID | NT/LN | AA/LN | Score | P-Value |
|---|---|---|---|---|---|---|
| SPX0862 | 862 | 3523 | 906 | 302 | 212 | 5.60E-55 |

Description

[LN:MURB_BACSU] [AC:P18579:P16669:P37581] [GN:MURB] [OR:Bacillus subtilis]
[EC:1.1.1.158] [DE:ACETYLMURAMATE DEHYDROGENASE)] [SP:P18579:P16669:P37581]

| ORF Name | NT ID | AA ID | NT/LN | AA/LN | Score | P-Value |
|---|---|---|---|---|---|---|
| SPX0863 | 863 | 3524 | 1137 | 379 | 792 | 1.80E-114 |

Description

"[LN:A70180] [AC:A70180] [PN:spermidine/putrescine ABC transporter, ATP-binding protein (potA) homolog] [CL:unassigned ATP-binding cassette proteins:ATP-binding cassette homology] [OR:Borrelia burgdorferi] [SR:, Lyme disease spirochete]"

| ORF Name | NT ID | AA ID | NT/LN | AA/LN | Score | P-Value |
|---|---|---|---|---|---|---|
| SPX0864 | 864 | 3525 | 327 | 109 | | |

Description

NO-HIT

| ORF Name | NT ID | AA ID | NT/LN | AA/LN | Score | P-Value |
|---|---|---|---|---|---|---|
| SPX0865 | 865 | 3526 | 633 | 211 | 324 | 4.20E-44 |

Description

"[LN:H70179] [AC:H70179] [PN:spermidine/putrescine ABC transporter, permease protein (potB) homolog] [CL:spermidine/putrescine transport system permease protein potH] [OR:Borrelia burgdorferi] [SR:, Lyme disease spirochete]"

| ORF Name | NT ID | AA ID | NT/LN | AA/LN | Score | P-Value |
|---|---|---|---|---|---|---|
| SPX0866 | 866 | 3527 | 774 | 258 | 346 | 7.00E-66 |

Description

"[LN:G70179] [AC:G70179] [PN:spermidine/putrescine ABC transporter, permease protein (potC) homolog] [CL:spermidine/putrescine transport system permease protein potI] [OR:Borrelia burgdorferi] [SR:, Lyme disease spirochete]"

| ORF Name | NT ID | AA ID | NT/LN | AA/LN | Score | P-Value |
|---|---|---|---|---|---|---|
| SPX0867 | 867 | 3528 | 678 | 226 | 173 | 5.20E-48 |

Description

[LN:POTD_ECOLI] [AC:P23861] [GN:POTD] [OR:Escherichia coli]
[DE:SPERMIDINE/PUTRESCINE-BINDING PERIPLASMIC PROTEIN PRECURSOR (SPBP)]
[SP:P23861]

| ORF Name | NT ID | AA ID | NT/LN | AA/LN | Score | P-Value |
|---|---|---|---|---|---|---|
| SPX0868 | 868 | 3529 | 375 | 125 | 197 | 1.30E-20 |

Description

[LN:POTD_ECOLI] [AC:P23861] [GN:POTD] [OR:Escherichia coli]
[DE:SPERMIDINE/PUTRESCINE-BINDING PERIPLASMIC PROTEIN PRECURSOR (SPBP)]
[SP:P23861]

| ORF Name | NT ID | AA ID | NT/LN | AA/LN | Score | P-Value |
|---|---|---|---|---|---|---|
| SPX0869 | 869 | 3530 | 240 | 80 | | |

Description

NO-HIT

| ORF Name | NT ID | AA ID | NT/LN | AA/LN | Score | P-Value |
|---|---|---|---|---|---|---|
| SPX0870 | 870 | 3531 | 219 | 73 | | |

Description

NO-HIT

| ORF Name | NT ID | AA ID | NT/LN | AA/LN | Score | P-Value |
|---|---|---|---|---|---|---|
| SPX0871 | 871 | 3532 | 489 | 163 | 159 | 4.70E-15 |

Description

[LN:G70079] [AC:G70079] [PN:hypothetical protein yxjI] [GN:yxjI]
[CL:Bacillus subtilis hypothetical protein yxjI] [OR:Bacillus subtilis]

| ORF Name | NT ID | AA ID | NT/LN | AA/LN | Score | P-Value |
|---|---|---|---|---|---|---|
| SPX0872 | 872 | 3533 | 267 | 89 | 332 | 2.40E-39 |

Description

"[LN:SYA_BACSU] [AC:O34526] [GN:ALAS] [OR:Bacillus subtilis] [EC:6.1.1.7]
[DE:ALANYL-TRNA SYNTHETASE, (ALANINE--TRNA LIGASE) (ALARS)] [SP:O34526]"

| ORF Name | NT ID | AA ID | NT LN | AA LN | Score | P-Value |
|---|---|---|---|---|---|---|
| SPX0873 | 873 | 3534 | 2361 | 787 | 570 | 1.20E-202 |

Description

"[LN:SYA_BACSU] [AC:O34526] [GN:ALAS] [OR:Bacillus subtilis] [EC:6.1.1.7] [DE:ALANYL-TRNA SYNTHETASE, (ALANINE--TRNA LIGASE) (ALARS)] [SP:O34526]"

| ORF Name | NT ID | AA ID | NT LN | AA LN | Score | P-Value |
|---|---|---|---|---|---|---|
| SPX0874 | 874 | 3535 | 1455 | 485 | 1726 | 2.50E-257 |

Description

[GI:2760119] [LN:AB000830] [AC:AB000830] [PN:alpha-amylase precursor] [OR:Streptococcus bovis] [SR:Streptococcus bovis (strain:148) DNA]

| ORF Name | NT ID | AA ID | NT LN | AA LN | Score | P-Value |
|---|---|---|---|---|---|---|
| SPX0875 | 875 | 3536 | 192 | 64 | | |

Description

NO-HIT

| ORF Name | NT ID | AA ID | NT LN | AA LN | Score | P-Value |
|---|---|---|---|---|---|---|
| SPX0876 | 876 | 3537 | 750 | 250 | 489 | 1.10E-62 |

Description

"[LN:H75077] [AC:H75077] [PN:abc transporter, ATP-binding protein PAB1696] [GN:PAB1696] [CL:unassigned ATP-binding cassette proteins:ATP-binding cassette homology] [OR:Pyrococcus abyssi]"

| ORF Name | NT ID | AA ID | NT LN | AA LN | Score | P-Value |
|---|---|---|---|---|---|---|
| SPX0877 | 877 | 3538 | 1635 | 545 | | |

Description

NO-HIT

| ORF Name | NT ID | AA ID | NT LN | AA LN | Score | P-Value |
|---|---|---|---|---|---|---|
| SPX0878 | 878 | 3539 | 1164 | 388 | 468 | 2.20E-96 |

Description

[LN:YWBD_BACSU] [AC:P39587] [GN:YWBD:IPA-19D] [OR:Bacillus subtilis] [DE:HYPOTHETICAL 44.4 KD PROTEIN IN EPR-GALK INTERGENIC REGION] [SP:P39587]

| ORF Name | NT ID | AA ID | NT/LN | AA/LN | Score | P-Value |
|---|---|---|---|---|---|---|
| SPX0879 | 879 | 3540 | 678 | 226 | 165 | 6.60E-27 |

Description

[GI:5919207] [LN:AF184963] [AC:AF184963] [PN:3-dehydroquinase] [GN:aroD]
[OR:Salmonella enteritidis]

| ORF Name | NT ID | AA ID | NT/LN | AA/LN | Score | P-Value |
|---|---|---|---|---|---|---|
| SPX0880 | 880 | 3541 | 855 | 285 | 680 | 5.70E-89 |

Description

[GI:3821433] [LN:SPN232281] [AC:AJ232281] [PN:shikimate dehydrogenase]
[GN:aroE] [OR:Streptococcus pneumoniae]

| ORF Name | NT ID | AA ID | NT/LN | AA/LN | Score | P-Value |
|---|---|---|---|---|---|---|
| SPX0881 | 881 | 3542 | 1068 | 356 | 439 | 3.10E-84 |

Description

"[LN:AROB_SYNY3] [AC:P73997] [GN:AROB:SLR2130] [OR:Synechocystis sp]
[SR:,strain PCC 6803] [EC:4.6.1.3] [DE:3-DEHYDROQUINATE SYNTHASE,]
[SP:P73997]"

| ORF Name | NT ID | AA ID | NT/LN | AA/LN | Score | P-Value |
|---|---|---|---|---|---|---|
| SPX0882 | 882 | 3543 | 1167 | 389 | 790 | 1.40E-142 |

Description

[LN:AROC_BACSU] [AC:P31104] [GN:AROF] [OR:Bacillus subtilis] [EC:4.6.1.4]
[DE:PHOSPHOLYASE) (VEGETATIVE PROTEIN 216) (VEG216)] [SP:P31104]

| ORF Name | NT ID | AA ID | NT/LN | AA/LN | Score | P-Value |
|---|---|---|---|---|---|---|
| SPX0883 | 883 | 3544 | 1104 | 368 | 402 | 2.40E-127 |

Description

"[LN:TYRA_LACLA] [AC:P43901] [GN:TYRA] [OR:Lactococcus lactis]
[SR:,subsplactis:Streptococcus lactis] [EC:1.3.1.12] [DE:PREPHENATE
DEHYDROGENASE, (PDH)] [SP:P43901]"

| ORF Name | NT ID | AA ID | NT/LN | AA/LN | Score | P-Value |
|---|---|---|---|---|---|---|
| SPX0884 | 884 | 3545 | 339 | 113 | 152 | 7.80E-16 |

Description

[GI:3688819] [LN:AF084104] [AC:AF084104] [PN:hypothetical protein]
[OR:Bacillus firmus]

| ORF Name | NT ID | AA ID | NT/LN | AA/LN | Score | P-Value |
|---|---|---|---|---|---|---|
| SPX0885 | 885 | 3546 | 1284 | 428 | 2094 | 1.40E-284 |

Description

[GI:5616525] [LN:AF169483] [AC:AF169483]
[PN:5-enolpyruvylshikimate-3-phosphate synthase] [GN:aroA] [OR:Streptococcus pneumoniae]

| ORF Name | NT ID | AA ID | NT/LN | AA/LN | Score | P-Value |
|---|---|---|---|---|---|---|
| SPX0886 | 886 | 3547 | 477 | 159 | 262 | 3.60E-40 |

Description

"[LN:AROK_LACLA] [AC:P43906] [GN:AROK] [OR:Lactococcus lactis]
[SR:,subsplactis:Streptococcus lactis] [EC:2.7.1.71] [DE:SHIKIMATE KINASE, (SK)] [SP:P43906]"

| ORF Name | NT ID | AA ID | NT/LN | AA/LN | Score | P-Value |
|---|---|---|---|---|---|---|
| SPX0887 | 887 | 3548 | 846 | 282 | 707 | 3.20E-98 |

Description

"[LN:PHEA_LACLA] [AC:P43909] [OR:Lactococcus lactis]
[SR:,subsplactis:Streptococcus lactis] [EC:4.2.1.51] [DE:PREPHENATE DEHYDRATASE, (PDT)] [SP:P43909]"

| ORF Name | NT ID | AA ID | NT/LN | AA/LN | Score | P-Value |
|---|---|---|---|---|---|---|
| SPX0888 | 888 | 3549 | 693 | 231 | 91 | 7.60E-09 |

Description

[GI:7160813] [LN:EFA276231] [AC:AJ276231] [PN:PSR protein] [GN:psr]
[FN:unknown] [OR:Enterococcus faecalis]

| ORF Name | NT ID | AA ID | NT/LN | AA/LN | Score | P-Value |
|---|---|---|---|---|---|---|
| SPX0889 | 889 | 3550 | 600 | 200 | 268 | 9.10E-46 |

Description

[GI:7160813] [LN:EFA276231] [AC:AJ276231] [PN:PSR protein] [GN:psr]
[FN:unknown] [OR:Enterococcus faecalis]

| ORF Name | NT ID | AA ID | NT/LN | AA/LN | Score | P-Value |
|---|---|---|---|---|---|---|
| SPX0890 | 890 | 3551 | 846 | 282 | 172 | 1.10E-24 |

Description

[LN:LICD_HAEIN] [AC:P14184] [GN:LICD] [OR:Haemophilus influenzae] [DE:LICD PROTEIN] [SP:P14184]

| ORF Name | NT ID | AA ID | NT/LN | AA/LN | Score | P-Value |
|---|---|---|---|---|---|---|
| SPX0891 | 891 | 3552 | 402 | 134 | | |

Description

NO-HIT

| ORF Name | NT ID | AA ID | NT/LN | AA/LN | Score | P-Value |
|---|---|---|---|---|---|---|
| SPX0892 | 892 | 3553 | 1158 | 386 | 244 | 1.70E-28 |

Description

[LN:F70441] [AC:F70441] [PN:capsular polysaccharide biosynthsis protein] [GN:cap] [OR:Aquifex aeolicus]

| ORF Name | NT ID | AA ID | NT/LN | AA/LN | Score | P-Value |
|---|---|---|---|---|---|---|
| SPX0893 | 893 | 3554 | 987 | 329 | 327 | 4.10E-51 |

Description

[GI:3320393] [LN:AF030373] [AC:AF030373] [PN:galactosyl transferase] [GN:cps23FU] [OR:Streptococcus pneumoniae]

| ORF Name | NT ID | AA ID | NT/LN | AA/LN | Score | P-Value |
|---|---|---|---|---|---|---|
| SPX0894 | 894 | 3555 | 1434 | 478 | 96 | 0.00022 |

Description

[GI:5931973] [LN:AF125164] [AC:AF125164] [PN:putative polymerase] [GN:wzy] [OR:Bacteroides fragilis]

| ORF Name | NT ID | AA ID | NT/LN | AA/LN | Score | P-Value |
|---|---|---|---|---|---|---|
| SPX0895 | 895 | 3556 | 453 | 151 | | |

Description

NO-HIT

| ORF Name | NT ID | AA ID | NT/LN | AA/LN | Score | P-Value |
|---|---|---|---|---|---|---|
| SPX0896 | 896 | 3557 | 606 | 202 | | |

Description

NO-HIT

| ORF Name | NT ID | AA ID | NT/LN | AA/LN | Score | P-Value |
|---|---|---|---|---|---|---|
| SPX0897 | 897 | 3558 | 297 | 99 | | |

Description

NO-HIT

| ORF Name | NT ID | AA ID | NT/LN | AA/LN | Score | P-Value |
|---|---|---|---|---|---|---|
| SPX0898 | 898 | 3559 | 555 | 185 | 349 | 1.10E-42 |

Description

[GI:5360696] [LN:AB022909] [AC:AB022909] [PN:negative regulator of genetic competence] [GN:mecA] [OR:Streptococcus mutans] [SR:Streptococcus mutans (strain:Xc) DNA]

| ORF Name | NT ID | AA ID | NT/LN | AA/LN | Score | P-Value |
|---|---|---|---|---|---|---|
| SPX0899 | 899 | 3560 | 384 | 128 | | |

Description

NO-HIT

| ORF Name | NT ID | AA ID | NT/LN | AA/LN | Score | P-Value |
|---|---|---|---|---|---|---|
| SPX0900 | 900 | 3561 | 213 | 71 | 127 | 1.70E-11 |

Description

[GI:5360696] [LN:AB022909] [AC:AB022909] [PN:negative regulator of genetic competence] [GN:mecA] [OR:Streptococcus mutans] [SR:Streptococcus mutans (strain:Xc) DNA]

| ORF Name | NT ID | AA ID | NT/LN | AA/LN | Score | P-Value |
|---|---|---|---|---|---|---|
| SPX0901 | 901 | 3562 | 1287 | 429 | 1425 | 2.60E-191 |

Description

"[LN:DHOM_LACLA] [AC:P52985] [GN:HOM] [OR:Lactococcus lactis] [SR:,subsplactis:Streptococcus lactis] [EC:1.1.1.3] [DE:HOMOSERINE DEHYDROGENASE, (HDH)] [SP:P52985]"

| ORF Name | NT ID | AA ID | NT LN | AA LN | Score | P-Value |
|---|---|---|---|---|---|---|
| SPX0902 | 902 | 3563 | 870 | 290 | 1439 | 4.70E-194 |

Description

"[LN:KHSE_STRPN] [AC:P72535] [GN:THRB] [OR:Streptococcus pneumoniae] [EC:2.7.1.39] [DE:HOMOSERINE KINASE, (HK)] [SP:P72535]"

| ORF Name | NT ID | AA ID | NT LN | AA LN | Score | P-Value |
|---|---|---|---|---|---|---|
| SPX0903 | 903 | 3564 | 426 | 142 | | |

Description

NO-HIT

| ORF Name | NT ID | AA ID | NT LN | AA LN | Score | P-Value |
|---|---|---|---|---|---|---|
| SPX0904 | 904 | 3565 | 225 | 75 | 192 | 8.30E-23 |

Description

[LN:T30285] [AC:T30285] [PN:hypothetical protein] [OR:Streptococcus pneumoniae]

| ORF Name | NT ID | AA ID | NT LN | AA LN | Score | P-Value |
|---|---|---|---|---|---|---|
| SPX0905 | 905 | 3566 | 258 | 86 | 366 | 6.80E-46 |

Description

[LN:PMSR_STRPN] [AC:P35593] [GN:MSRA:EXP3] [OR:Streptococcus pneumoniae] [DE:(EXPORTED PROTEIN 3)] [SP:P35593]

| ORF Name | NT ID | AA ID | NT LN | AA LN | Score | P-Value |
|---|---|---|---|---|---|---|
| SPX0906 | 906 | 3567 | 768 | 256 | 1236 | 9.90E-167 |

Description

[LN:PMSR_STRPN] [AC:P35593] [GN:MSRA:EXP3] [OR:Streptococcus pneumoniae] [DE:(EXPORTED PROTEIN 3)] [SP:P35593]

| ORF Name | NT ID | AA ID | NT LN | AA LN | Score | P-Value |
|---|---|---|---|---|---|---|
| SPX0907 | 907 | 3568 | 309 | 103 | 123 | 6.70E-10 |

Description

"[LN:E72396] [AC:E72396] [PN:ABC transporter, ATP-binding protein] [GN:TM0287] [CL:unassigned ATP-binding cassette proteins:ATP-binding cassette homology] [OR:Thermotoga maritima]"

| ORF Name | NT ID | AA ID | NT/LN | AA/LN | Score | P-Value |
|---|---|---|---|---|---|---|
| SPX0908 | 908 | 3569 | 1464 | 488 | 472 | 3.40E-92 |

Description

"[LN:E72396] [AC:E72396] [PN:ABC transporter, ATP-binding protein] [GN:TM0287] [CL:unassigned ATP-binding cassette proteins:ATP-binding cassette homology] [OR:Thermotoga maritima]"

| ORF Name | NT ID | AA ID | NT/LN | AA/LN | Score | P-Value |
|---|---|---|---|---|---|---|
| SPX0909 | 909 | 3570 | 186 | 62 | | |

Description

NO-HIT

| ORF Name | NT ID | AA ID | NT/LN | AA/LN | Score | P-Value |
|---|---|---|---|---|---|---|
| SPX0910 | 910 | 3571 | 1752 | 584 | 722 | 7.90E-145 |

Description

[LN:Y08A_MYCTU] [AC:Q11047] [GN:MTCY50.10] [OR:Mycobacterium tuberculosis] [DE:HYPOTHETICAL ABC TRANSPORTER ATP-BINDING PROTEIN CY50.10] [SP:Q11047]

| ORF Name | NT ID | AA ID | NT/LN | AA/LN | Score | P-Value |
|---|---|---|---|---|---|---|
| SPX0911 | 911 | 3572 | 258 | 86 | 325 | 5.10E-41 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX0912 | 912 | 3573 | 387 | 129 | 95 | 8.00E-06 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX0913 | 913 | 3574 | 192 | 64 | | |

Description

NO-HIT

| ORF Name | NT ID | AA ID | NT LN | AA LN | Score | P-Value |
|---|---|---|---|---|---|---|
| SPX0914 | 914 | 3575 | 222 | 74 | | |
| Description | | | | | | |

NO-HIT

| ORF Name | NT ID | AA ID | NT LN | AA LN | Score | P-Value |
|---|---|---|---|---|---|---|
| SPX0915 | 915 | 3576 | 207 | 69 | | |
| Description | | | | | | |

NO-HIT

| ORF Name | NT ID | AA ID | NT LN | AA LN | Score | P-Value |
|---|---|---|---|---|---|---|
| SPX0916 | 916 | 3577 | 195 | 65 | | |
| Description | | | | | | |

NO-HIT

| ORF Name | NT ID | AA ID | NT LN | AA LN | Score | P-Value |
|---|---|---|---|---|---|---|
| SPX0917 | 917 | 3578 | 297 | 99 | | |
| Description | | | | | | |

NO-HIT

| ORF Name | NT ID | AA ID | NT LN | AA LN | Score | P-Value |
|---|---|---|---|---|---|---|
| SPX0918 | 918 | 3579 | 885 | 295 | 447 | 1.10E-56 |
| Description | | | | | | |

[LN:A70039] [AC:A70039] [PN:ABC transporter (ATP-binding protein) homolog yvfR] [GN:yvfR] [CL:unassigned ATP-binding cassette proteins:ATP-binding cassette homology] [OR:Bacillus subtilis]

| ORF Name | NT ID | AA ID | NT LN | AA LN | Score | P-Value |
|---|---|---|---|---|---|---|
| SPX0919 | 919 | 3580 | 738 | 246 | 289 | 1.00E-39 |
| Description | | | | | | |

[GI:6759480] [LN:BCE243712] [AC:AJ243712] [PN:YVFS protein] [GN:yvfS] [OR:Bacillus cereus]

| ORF Name | NT ID | AA ID | NT/LN | AA/LN | Score | P-Value |
|---|---|---|---|---|---|---|
| SPX0920 | 920 | 3581 | 1098 | 366 | 1715 | 5.40E-238 |

Description

[GI:5830547] [LN:SPAJ6400] [AC:AJ006400] [PN:histidine kinase] [GN:hk11]
[OR:Streptococcus pneumoniae]

| ORF Name | NT ID | AA ID | NT/LN | AA/LN | Score | P-Value |
|---|---|---|---|---|---|---|
| SPX0921 | 921 | 3582 | 600 | 200 | 932 | 2.00E-123 |

Description

[GI:5830548] [LN:SPAJ6400] [AC:AJ006400] [PN:response regulator] [GN:rr11]
[OR:Streptococcus pneumoniae]

| ORF Name | NT ID | AA ID | NT/LN | AA/LN | Score | P-Value |
|---|---|---|---|---|---|---|
| SPX0922 | 922 | 3583 | 1011 | 337 | 1328 | 1.10E-176 |

Description

[GI:7328454] [LN:AB028599] [AC:AB028599] [PN:catabolite control protein A]
[GN:ccpA] [OR:Streptococcus bovis] [SR:Streptococcus bovis (strain:JB1) DNA]

| ORF Name | NT ID | AA ID | NT/LN | AA/LN | Score | P-Value |
|---|---|---|---|---|---|---|
| SPX0923 | 923 | 3584 | 393 | 131 | 270 | 4.60E-32 |

Description

[LN:T30285] [AC:T30285] [PN:hypothetical protein] [OR:Streptococcus
pneumoniae]

| ORF Name | NT ID | AA ID | NT/LN | AA/LN | Score | P-Value |
|---|---|---|---|---|---|---|
| SPX0924 | 924 | 3585 | 339 | 113 | 89 | 5.70E-05 |

Description

[LN:T30285] [AC:T30285] [PN:hypothetical protein] [OR:Streptococcus
pneumoniae]

| ORF Name | NT ID | AA ID | NT/LN | AA/LN | Score | P-Value |
|---|---|---|---|---|---|---|
| SPX0925 | 925 | 3586 | 963 | 321 | 295 | 8.70E-56 |

Description

[LN:G75283] [AC:G75283] [PN:L-asparaginase] [GN:DR2353] [CL:asparaginase]
[OR:Deinococcus radiodurans]

| ORF Name | NT ID | AA ID | NT/LN | AA/LN | Score | P-Value |
|---|---|---|---|---|---|---|
| SPX0926 | 926 | 3587 | 1389 | 463 | 213 | 9.90E-43 |

Description

[LN:C69862] [AC:C69862] [PN:conserved hypothetical protein ykrA] [GN:ykrA] [CL:Methanobacterium thermoautotrophicum conserved hypothetical protein MTH1071] [OR:Bacillus subtilis]

| ORF Name | NT ID | AA ID | NT/LN | AA/LN | Score | P-Value |
|---|---|---|---|---|---|---|
| SPX0927 | 927 | 3588 | 453 | 151 | 127 | 6.20E-14 |

Description

[LN:A69220] [AC:A69220] [PN:conserved hypothetical protein MTH898] [GN:MTH898] [CL:Escherichia coli ybdQ protein] [OR:Methanobacterium thermoautotrophicum]

| ORF Name | NT ID | AA ID | NT/LN | AA/LN | Score | P-Value |
|---|---|---|---|---|---|---|
| SPX0928 | 928 | 3589 | 291 | 97 | | |

Description

NO-HIT

| ORF Name | NT ID | AA ID | NT/LN | AA/LN | Score | P-Value |
|---|---|---|---|---|---|---|
| SPX0929 | 929 | 3590 | 717 | 239 | 819 | 4.70E-109 |

Description

"[LN:YFBQ_HAEIN] [AC:P71348] [GN:HI0286] [OR:Haemophilus influenzae] [EC:2.6.1.-] [DE:PROBABLE AMINOTRANSFERASE HI0286,] [SP:P71348]"

| ORF Name | NT ID | AA ID | NT/LN | AA/LN | Score | P-Value |
|---|---|---|---|---|---|---|
| SPX0930 | 930 | 3591 | 333 | 111 | | |

Description

NO-HIT

| ORF Name | NT ID | AA ID | NT/LN | AA/LN | Score | P-Value |
|---|---|---|---|---|---|---|
| SPX0931 | 931 | 3592 | 375 | 125 | 385 | 1.70E-48 |

Description

"[LN:YFBQ_HAEIN] [AC:P71348] [GN:HI0286] [OR:Haemophilus influenzae] [EC:2.6.1.-] [DE:PROBABLE AMINOTRANSFERASE HI0286,] [SP:P71348]"

| ORF Name | NT ID | AA ID | NT LN | AA LN | Score | P-Value |
|---|---|---|---|---|---|---|
| SPX0932 | 932 | 3593 | 135 | 45 | 170 | 7.60E-20 |

Description

[LN:RL34_BACST] [AC:P23376] [GN:RPMH] [OR:Bacillus stearothermophilus]
[DE:50S RIBOSOMAL PROTEIN L34] [SP:P23376]

| ORF Name | NT ID | AA ID | NT LN | AA LN | Score | P-Value |
|---|---|---|---|---|---|---|
| SPX0933 | 933 | 3594 | 201 | 67 | | |

Description

NO-HIT

| ORF Name | NT ID | AA ID | NT LN | AA LN | Score | P-Value |
|---|---|---|---|---|---|---|
| SPX0934 | 934 | 3595 | 654 | 218 | 116 | 9.60E-07 |

Description

[GI:546643] [LN:S70345] [AC:S70345] [PN:SpaA] [GN:SpaA] [OR:Streptococcus sobrinus] [SR:Streptococcus sobrinus MUCOB 263]

| ORF Name | NT ID | AA ID | NT LN | AA LN | Score | P-Value |
|---|---|---|---|---|---|---|
| SPX0935 | 935 | 3596 | 225 | 75 | 180 | 6.20E-19 |

Description

[LN:YABD_BACSU] [AC:P37545] [GN:YABD] [OR:Bacillus subtilis]
[DE:HYPOTHETICAL 29.2 KD PROTEIN IN METS-KSGA INTERGENIC REGION] [SP:P37545]

| ORF Name | NT ID | AA ID | NT LN | AA LN | Score | P-Value |
|---|---|---|---|---|---|---|
| SPX0936 | 936 | 3597 | 543 | 181 | 469 | 3.60E-60 |

Description

[LN:YABD_BACSU] [AC:P37545] [GN:YABD] [OR:Bacillus subtilis]
[DE:HYPOTHETICAL 29.2 KD PROTEIN IN METS-KSGA INTERGENIC REGION] [SP:P37545]

| ORF Name | NT ID | AA ID | NT LN | AA LN | Score | P-Value |
|---|---|---|---|---|---|---|
| SPX0937 | 937 | 3598 | 561 | 187 | 235 | 2.70E-52 |

Description

[LN:YABF_BACSU] [AC:P37547] [GN:YABF] [OR:Bacillus subtilis]
[DE:HYPOTHETICAL 20.7 KD PROTEIN IN METS-KSGA INTERGENIC REGION] [SP:P37547]

| ORF Name | NT ID | AA ID | NT/LN | AA/LN | Score | P-Value |
|---|---|---|---|---|---|---|
| SPX0938 | 938 | 3599 | 912 | 304 | | |

Description

NO-HIT

| ORF Name | NT ID | AA ID | NT/LN | AA/LN | Score | P-Value |
|---|---|---|---|---|---|---|
| SPX0939 | 939 | 3600 | 297 | 99 | 149 | 3.30E-15 |

Description

[GI:7576923] [LN:AF242367] [AC:AF242367] [PN:lactococcin 972] [GN:lclA] [OR:Lactococcus lactis subsp. lactis]

| ORF Name | NT ID | AA ID | NT/LN | AA/LN | Score | P-Value |
|---|---|---|---|---|---|---|
| SPX0940 | 940 | 3601 | 807 | 269 | 65 | 5.50E-08 |

Description

[GI:3355783] [LN:LLJ002203] [AC:AJ002203] [PN:putative immunity] [GN:orf2] [OR:Lactococcus lactis]

| ORF Name | NT ID | AA ID | NT/LN | AA/LN | Score | P-Value |
|---|---|---|---|---|---|---|
| SPX0941 | 941 | 3602 | 1350 | 450 | 357 | 1.30E-89 |

Description

[GI:4009478] [LN:AF068902] [AC:AF068902] [PN:unknown] [OR:Streptococcus pneumoniae]

| ORF Name | NT ID | AA ID | NT/LN | AA/LN | Score | P-Value |
|---|---|---|---|---|---|---|
| SPX0942 | 942 | 3603 | 642 | 214 | 667 | 2.50E-87 |

Description

[GI:4009479] [LN:AF068902] [AC:AF068902] [PN:unknown] [OR:Streptococcus pneumoniae]

| ORF Name | NT ID | AA ID | NT/LN | AA/LN | Score | P-Value |
|---|---|---|---|---|---|---|
| SPX0943 | 943 | 3604 | 309 | 103 | | |

Description

NO-HIT

| ORF Name | NT ID | AA ID | NT LN | AA LN | Score | P-Value |
|---|---|---|---|---|---|---|
| SPX0944 | 944 | 3605 | 507 | 169 | | |

Description

NO-HIT

| ORF Name | NT ID | AA ID | NT LN | AA LN | Score | P-Value |
|---|---|---|---|---|---|---|
| SPX0945 | 945 | 3606 | 873 | 291 | 781 | 3.80E-104 |

Description

[LN:KSGA_BACSU] [AC:P37468] [GN:KSGA] [OR:Bacillus subtilis] [EC:2.1.1.-] [DE:DIMETHYLTRANSFERASE)] [SP:P37468]

| ORF Name | NT ID | AA ID | NT LN | AA LN | Score | P-Value |
|---|---|---|---|---|---|---|
| SPX0946 | 946 | 3607 | 879 | 293 | 394 | 5.10E-100 |

Description

[LN:A69879] [AC:A69879] [PN:conserved hypothetical protein yloQ] [GN:yloQ] [CL:conserved hypothetical protein HI1714] [OR:Bacillus subtilis]

| ORF Name | NT ID | AA ID | NT LN | AA LN | Score | P-Value |
|---|---|---|---|---|---|---|
| SPX0947 | 947 | 3608 | 903 | 301 | 460 | 1.20E-69 |

Description

"[LN:RPE_RHOCA] [AC:P51012] [GN:CBBE] [OR:Rhodobacter capsulatus] [SR:,Rhodopseudomonas capsulata] [EC:5.1.3.1] [DE:EPIMERASE) (PPE) (R5P3E)] [SP:P51012]"

| ORF Name | NT ID | AA ID | NT LN | AA LN | Score | P-Value |
|---|---|---|---|---|---|---|
| SPX0948 | 948 | 3609 | 663 | 221 | 143 | 3.50E-18 |

Description

[LN:C69879] [AC:C69879] [PN:hypothetical protein yloS] [GN:yloS] [OR:Bacillus subtilis]

| ORF Name | NT ID | AA ID | NT LN | AA LN | Score | P-Value |
|---|---|---|---|---|---|---|
| SPX0949 | 949 | 3610 | 1215 | 405 | 91 | 5.10E-07 |

Description

[LN:E81528] [AC:E81528] [PN:conserved hypothetical protein CP0874 [imported]] [GN:CP0874] [OR:Chlamydophila pneumoniae:Chlamydia pneumoniae]

| ORF Name | NT ID | AA ID | NT LN | AA LN | Score | P-Value |
|---|---|---|---|---|---|---|
| SPX0950 | 950 | 3611 | 942 | 314 | 453 | 1.00E-88 |

Description

[LN:G69818] [AC:G69818] [PN:CMP-binding factor homolog yhaM] [GN:yhaM] [OR:Bacillus subtilis]

| ORF Name | NT ID | AA ID | NT LN | AA LN | Score | P-Value |
|---|---|---|---|---|---|---|
| SPX0951 | 951 | 3612 | 828 | 276 | 498 | 2.80E-98 |

Description

[GI:2706406] [LN:LLAJ642] [AC:AJ222642] [GN:purR] [FN:activator of purine biosynthetic genes] [OR:Lactococcus lactis]

| ORF Name | NT ID | AA ID | NT LN | AA LN | Score | P-Value |
|---|---|---|---|---|---|---|
| SPX0952 | 952 | 3613 | 210 | 70 | 83 | 0.00046 |

Description

"[LN:TABA_PSESZ] [AC:P31851] [GN:TABA] [OR:Pseudomonas syringae] [SR:,pvtabaci] [DE:TABA PROTEIN] [SP:P31851]"

| ORF Name | NT ID | AA ID | NT LN | AA LN | Score | P-Value |
|---|---|---|---|---|---|---|
| SPX0953 | 953 | 3614 | 384 | 128 | 199 | 3.60E-21 |

Description

"[LN:TABA_PSESZ] [AC:P31851] [GN:TABA] [OR:Pseudomonas syringae] [SR:,pvtabaci] [DE:TABA PROTEIN] [SP:P31851]"

| ORF Name | NT ID | AA ID | NT LN | AA LN | Score | P-Value |
|---|---|---|---|---|---|---|
| SPX0954 | 954 | 3615 | 300 | 100 | | |

Description

NO-HIT

| ORF Name | NT ID | AA ID | NT LN | AA LN | Score | P-Value |
|---|---|---|---|---|---|---|
| SPX0955 | 955 | 3616 | 1005 | 335 | 371 | 8.10E-63 |

Description

"[LN:TABA_PSESZ] [AC:P31851] [GN:TABA] [OR:Pseudomonas syringae] [SR:,pvtabaci] [DE:TABA PROTEIN] [SP:P31851]"

| ORF Name | NT ID | AA ID | NT LN | AA LN | Score | P-Value |
|---|---|---|---|---|---|---|
| SPX0956 | 956 | 3617 | 795 | 265 | 1121 | 8.40E-152 |

Description

[LN:PFLA_STRMU] [AC:O68575] [GN:ACT:PFLC] [OR:Streptococcus mutans] [EC:1.97.1.4] [DE:ENZYME)] [SP:O68575]

| ORF Name | NT ID | AA ID | NT LN | AA LN | Score | P-Value |
|---|---|---|---|---|---|---|
| SPX0957 | 957 | 3618 | 927 | 309 | 140 | 6.90E-32 |

Description

[GI:6117974] [LN:AF139908] [AC:AF139908] [PN:membrane protein homolog] [OR:Listeria monocytogenes]

| ORF Name | NT ID | AA ID | NT LN | AA LN | Score | P-Value |
|---|---|---|---|---|---|---|
| SPX0958 | 958 | 3619 | 279 | 93 | 108 | 9.80E-09 |

Description

[LN:T35660] [AC:T35660] [PN:probable acylphosphatase] [GN:SC7A1.20] [OR:Streptomyces coelicolor]

| ORF Name | NT ID | AA ID | NT LN | AA LN | Score | P-Value |
|---|---|---|---|---|---|---|
| SPX0959 | 959 | 3620 | 759 | 253 | 217 | 1.10E-43 |

Description

[LN:G69984] [AC:G69984] [PN:rRNA methylase homolog ysgA] [GN:ysgA] [CL:conserved hypothetical protein HI0860] [OR:Bacillus subtilis]

| ORF Name | NT ID | AA ID | NT LN | AA LN | Score | P-Value |
|---|---|---|---|---|---|---|
| SPX0960 | 960 | 3621 | 684 | 228 | 433 | 1.10E-57 |

Description

[GI:3171165] [LN:AF064763] [AC:AF064763] [PN:putative membrane spanning protein] [OR:Lactococcus lactis subsp. cremoris]

| ORF Name | NT ID | AA ID | NT LN | AA LN | Score | P-Value |
|---|---|---|---|---|---|---|
| SPX0961 | 961 | 3622 | 216 | 72 | | |

Description

NO-HIT

| ORF Name | NT ID | AA ID | NT/LN | AA/LN | Score | P-Value |
|---|---|---|---|---|---|---|
| SPX0962 | 962 | 3623 | 993 | 331 | 1387 | 1.70E-186 |

Description

"[LN:ASNA_HAEIN] [AC:P44338] [GN:ASNA:HI0564] [OR:Haemophilus influenzae] [EC:6.3.1.1] [DE:ASPARTATE--AMMONIA LIGASE, (ASPARAGINE SYNTHETASE A)] [SP:P44338]"

| ORF Name | NT ID | AA ID | NT/LN | AA/LN | Score | P-Value |
|---|---|---|---|---|---|---|
| SPX0963 | 963 | 3624 | 540 | 180 | 279 | 1.30E-33 |

Description

[LN:E69874] [AC:E69874] [PN:conserved hypothetical protein ylbH] [GN:ylbH] [CL:Escherichia coli hypothetical 21.7K protein (ftsY-nikA intergenic region)] [OR:Bacillus subtilis]

| ORF Name | NT ID | AA ID | NT/LN | AA/LN | Score | P-Value |
|---|---|---|---|---|---|---|
| SPX0964 | 964 | 3625 | 369 | 123 | 184 | 3.00E-25 |

Description

[LN:G81347] [AC:G81347] [PN:3-deoxy-D-manno-octulosonic-acid transferase Cj0767c [imported]] [GN:kdtB:Cj0767c] [OR:Campylobacter jejuni]

| ORF Name | NT ID | AA ID | NT/LN | AA/LN | Score | P-Value |
|---|---|---|---|---|---|---|
| SPX0965 | 965 | 3626 | 717 | 239 | 184 | 7.20E-17 |

Description

[LN:A69875] [AC:A69875] [PN:hypothetical protein ylbL] [GN:ylbL] [OR:Bacillus subtilis]

| ORF Name | NT ID | AA ID | NT/LN | AA/LN | Score | P-Value |
|---|---|---|---|---|---|---|
| SPX0966 | 966 | 3627 | 234 | 78 | 101 | 1.90E-16 |

Description

[LN:A69875] [AC:A69875] [PN:hypothetical protein ylbL] [GN:ylbL] [OR:Bacillus subtilis]

| ORF Name | NT ID | AA ID | NT/LN | AA/LN | Score | P-Value |
|---|---|---|---|---|---|---|
| SPX0967 | 967 | 3628 | 285 | 95 | | |

Description

NO-HIT

| ORF Name | NT ID | AA ID | NT/LN | AA/LN | Score | P-Value |
|---|---|---|---|---|---|---|
| SPX0968 | 968 | 3629 | 1284 | 428 | 620 | 3.20E-133 |

Description

[LN:MURA_ACICA] [AC:P33986] [GN:MURA:MURZ] [OR:Acinetobacter calcoaceticus] [EC:2.5.1.7] [DE:TRANSFERASE) (EPT)] [SP:P33986]

| ORF Name | NT ID | AA ID | NT/LN | AA/LN | Score | P-Value |
|---|---|---|---|---|---|---|
| SPX0969 | 969 | 3630 | 225 | 75 | 320 | 4.60E-41 |

Description

[LN:EPUA_STRPN] [AC:Q03159] [GN:EPUA] [OR:Streptococcus pneumoniae] [DE:EPUA PROTEIN] [SP:Q03159]

| ORF Name | NT ID | AA ID | NT/LN | AA/LN | Score | P-Value |
|---|---|---|---|---|---|---|
| SPX0970 | 970 | 3631 | 825 | 275 | 1392 | 2.50E-182 |

Description

"[LN:NUCE_STRPN] [AC:Q03158] [GN:ENDA] [OR:Streptococcus pneumoniae] [EC:3.1.30.-] [DE:DNA-ENTRY NUCLEASE (COMPETENCE-SPECIFIC NUCLEASE),] [SP:Q03158]"

| ORF Name | NT ID | AA ID | NT/LN | AA/LN | Score | P-Value |
|---|---|---|---|---|---|---|
| SPX0971 | 971 | 3632 | 984 | 328 | 1168 | 4.20E-160 |

Description

[GI:2952527] [LN:AF051356] [AC:AF051356] [PN:putative hemolysin] [GN:hlyX] [OR:Streptococcus mutans]

| ORF Name | NT ID | AA ID | NT/LN | AA/LN | Score | P-Value |
|---|---|---|---|---|---|---|
| SPX0972 | 972 | 3633 | 285 | 95 | 266 | 6.50E-33 |

Description

[GI:2952527] [LN:AF051356] [AC:AF051356] [PN:putative hemolysin] [GN:hlyX] [OR:Streptococcus mutans]

| ORF Name | NT ID | AA ID | NT/LN | AA/LN | Score | P-Value |
|---|---|---|---|---|---|---|
| SPX0973 | 973 | 3634 | 3612 | 1204 | 1921 | 0 |

Description

[LN:T44375] [AC:T44375] [PN:rpoB protein [imported]] [CL:DNA-directed RNA polymerase beta chain] [OR:Bacillus halodurans]

| ORF_Name | NT ID | AA ID | NT/LN | AA/LN | Score | P-Value |
|---|---|---|---|---|---|---|
| SPX0974 | 974 | 3635 | 348 | 116 | | |
| Description | | | | | | |

NO-HIT

| ORF_Name | NT ID | AA ID | NT/LN | AA/LN | Score | P-Value |
|---|---|---|---|---|---|---|
| SPX0975 | 975 | 3636 | 171 | 57 | | |
| Description | | | | | | |

NO-HIT

| ORF_Name | NT ID | AA ID | NT/LN | AA/LN | Score | P-Value |
|---|---|---|---|---|---|---|
| SPX0976 | 976 | 3637 | 3678 | 1226 | 4009 | 0 |
| Description | | | | | | |

[LN:RPOC_STRPY] [AC:P95816] [GN:RPOC] [OR:Streptococcus pyogenes]
[EC:2.7.7.6] [DE:BETA' CHAIN) (RNA POLYMERASE BETA' SUBUNIT) (FRAGMENT)]
[SP:P95816]

| ORF_Name | NT ID | AA ID | NT/LN | AA/LN | Score | P-Value |
|---|---|---|---|---|---|---|
| SPX0977 | 977 | 3638 | 393 | 131 | | |
| Description | | | | | | |

NO-HIT

| ORF_Name | NT ID | AA ID | NT/LN | AA/LN | Score | P-Value |
|---|---|---|---|---|---|---|
| SPX0978 | 978 | 3639 | 414 | 138 | 192 | 4.30E-48 |
| Description | | | | | | |

[GI:1655704] [LN:XLNM23] [AC:X97899] [PN:NM23/nucleoside diphosphate kinase]
[OR:Xenopus laevis] [SR:African clawed frog]

| ORF_Name | NT ID | AA ID | NT/LN | AA/LN | Score | P-Value |
|---|---|---|---|---|---|---|
| SPX0979 | 979 | 3640 | 279 | 93 | | |
| Description | | | | | | |

NO-HIT

| ORF_Name | NT_ID | AA_ID | NT/LN | AA/LN | Score | P-Value |
|---|---|---|---|---|---|---|
| SPX0980 | 980 | 3641 | 633 | 211 | 472 | 1.50E-87 |

Description

[GI:4009479] [LN:AF068902] [AC:AF068902] [PN:unknown] [OR:Streptococcus pneumoniae]

| ORF_Name | NT_ID | AA_ID | NT/LN | AA/LN | Score | P-Value |
|---|---|---|---|---|---|---|
| SPX0981 | 981 | 3642 | 2016 | 672 | 277 | 4.50E-70 |

Description

[GI:4009478] [LN:AF068902] [AC:AF068902] [PN:unknown] [OR:Streptococcus pneumoniae]

| ORF_Name | NT_ID | AA_ID | NT/LN | AA/LN | Score | P-Value |
|---|---|---|---|---|---|---|
| SPX0982 | 982 | 3643 | 195 | 65 | | |

Description

NO-HIT

| ORF_Name | NT_ID | AA_ID | NT/LN | AA/LN | Score | P-Value |
|---|---|---|---|---|---|---|
| SPX0983 | 983 | 3644 | 864 | 288 | 110 | 2.30E-09 |

Description

[LN:JC6007] [AC:JC6007] [PN:transcription activator plcR] [GN:plcR] [CL:Bacillus thuringiensis transcription activator plcR] [OR:Bacillus thuringiensis]

| ORF_Name | NT_ID | AA_ID | NT/LN | AA/LN | Score | P-Value |
|---|---|---|---|---|---|---|
| SPX0984 | 984 | 3645 | 411 | 137 | | |

Description

NO-HIT

| ORF_Name | NT_ID | AA_ID | NT/LN | AA/LN | Score | P-Value |
|---|---|---|---|---|---|---|
| SPX0985 | 985 | 3646 | 477 | 159 | 166 | 2.20E-36 |

Description

[LN:C69786] [AC:C69786] [PN:conserved hypothetical protein ydiB] [GN:ydiB] [CL:hypothetical protein HI0065] [OR:Bacillus subtilis]

| ORF Name | NT ID | AA ID | NT/LN | AA/LN | Score | P-Value |
|---|---|---|---|---|---|---|
| SPX0986 | 986 | 3647 | 519 | 173 | 149 | 7.60E-28 |

Description

[LN:D72360] [AC:D72360] [PN:conserved hypothetical protein] [GN:TM0577]
[OR:Thermotoga maritima]

| ORF Name | NT ID | AA ID | NT/LN | AA/LN | Score | P-Value |
|---|---|---|---|---|---|---|
| SPX0987 | 987 | 3648 | 1017 | 339 | 182 | 6.50E-46 |

Description

[LN:LYTR_BACSU] [AC:Q02115] [GN:LYTR] [OR:Bacillus subtilis]
[DE:MEMBRANE-BOUND PROTEIN LYTR] [SP:Q02115]

| ORF Name | NT ID | AA ID | NT/LN | AA/LN | Score | P-Value |
|---|---|---|---|---|---|---|
| SPX0988 | 988 | 3649 | 1257 | 419 | 2015 | 1.70E-272 |

Description

[LN:CINA_STRPN] [AC:P54184:Q54853] [GN:CINA:EXP10] [OR:Streptococcus pneumoniae] [DE:PUTATIVE COMPETENCE-DAMAGE PROTEIN (EXPORTED PROTEIN 10)]
[SP:P54184:Q54853]

| ORF Name | NT ID | AA ID | NT/LN | AA/LN | Score | P-Value |
|---|---|---|---|---|---|---|
| SPX0989 | 989 | 3650 | 1167 | 389 | 1928 | 6.10E-256 |

Description

[LN:RECA_STRPN] [AC:P30758] [GN:RECA] [OR:Streptococcus pneumoniae] [DE:RECA PROTEIN] [SP:P30758]

| ORF Name | NT ID | AA ID | NT/LN | AA/LN | Score | P-Value |
|---|---|---|---|---|---|---|
| SPX0990 | 990 | 3651 | 1371 | 457 | 2252 | 0 |

Description

[GI:2398825] [LN:SPCINREC] [AC:Z34303] [PN:DinF protein] [GN:dinF]
[OR:Streptococcus pneumoniae]

| ORF Name | NT ID | AA ID | NT/LN | AA/LN | Score | P-Value |
|---|---|---|---|---|---|---|
| SPX0991 | 991 | 3652 | 957 | 319 | 1786 | 1.50E-240 |

Description

[LN:ALYS_STRPN] [AC:P06653] [GN:LYTA] [OR:Streptococcus pneumoniae]
[EC:3.5.1.28] [DE:HYDROLASE) (MUCOPEPTIDE AMINOHYDROLASE) (CELL WALL HYDROLASE)] [SP:P06653]

| ORF Name | NT ID | AA ID | NT/LN | AA/LN | Score | P-Value |
|---|---|---|---|---|---|---|
| SPX0992 | 992 | 3653 | 237 | 79 | | |

Description

NO-HIT

| ORF Name | NT ID | AA ID | NT/LN | AA/LN | Score | P-Value |
|---|---|---|---|---|---|---|
| SPX0993 | 993 | 3654 | 243 | 81 | | |

Description

NO-HIT

| ORF Name | NT ID | AA ID | NT/LN | AA/LN | Score | P-Value |
|---|---|---|---|---|---|---|
| SPX0994 | 994 | 3655 | 360 | 120 | | |

Description

NO-HIT

| ORF Name | NT ID | AA ID | NT/LN | AA/LN | Score | P-Value |
|---|---|---|---|---|---|---|
| SPX0995 | 995 | 3656 | 426 | 142 | | |

Description

NO-HIT

| ORF Name | NT ID | AA ID | NT/LN | AA/LN | Score | P-Value |
|---|---|---|---|---|---|---|
| SPX0996 | 996 | 3657 | 225 | 75 | | |

Description

NO-HIT

| ORF Name | NT ID | AA ID | NT/LN | AA/LN | Score | P-Value |
|---|---|---|---|---|---|---|
| SPX0997 | 997 | 3658 | 996 | 332 | 676 | 4.50E-129 |

Description

[GI:2398827] [LN:SPCINREC] [AC:Z34303] [PN:hypothetical protein] [OR:Streptococcus pneumoniae]

| ORF Name | NT ID | AA ID | NT/LN | AA/LN | Score | P-Value |
|---|---|---|---|---|---|---|
| SPX0998 | 998 | 3659 | 246 | 82 | | |

Description

NO-HIT

| ORF Name | NT ID | AA ID | NT LN | AA LN | Score | P-Value |
|---|---|---|---|---|---|---|
| SPX0999 | 999 | 3660 | 270 | 90 | | |

Description

NO-HIT

| ORF Name | NT ID | AA ID | NT LN | AA LN | Score | P-Value |
|---|---|---|---|---|---|---|
| SPX1000 | 1000 | 3661 | 261 | 87 | | |

Description

NO-HIT

| ORF Name | NT ID | AA ID | NT LN | AA LN | Score | P-Value |
|---|---|---|---|---|---|---|
| SPX1001 | 1001 | 3662 | 303 | 101 | 296 | 7.00E-36 |

Description

[LN:S52544] [AC:S52544] [PN:ISL2 protein] [OR:Lactobacillus helveticus]

| ORF Name | NT ID | AA ID | NT LN | AA LN | Score | P-Value |
|---|---|---|---|---|---|---|
| SPX1002 | 1002 | 3663 | 132 | 44 | 108 | 5.70E-09 |

Description

[LN:S52544] [AC:S52544] [PN:ISL2 protein] [OR:Lactobacillus helveticus]

| ORF Name | NT ID | AA ID | NT LN | AA LN | Score | P-Value |
|---|---|---|---|---|---|---|
| SPX1003 | 1003 | 3664 | 459 | 153 | | |

Description

NO-HIT

| ORF Name | NT ID | AA ID | NT LN | AA LN | Score | P-Value |
|---|---|---|---|---|---|---|
| SPX1004 | 1004 | 3665 | 609 | 203 | | |

Description

NO-HIT

| ORF Name | NT ID | AA ID | NT LN | AA LN | Score | P-Value |
|---|---|---|---|---|---|---|
| SPX1005 | 1005 | 3666 | 411 | 137 | | |

Description

NO-HIT

| ORF Name | NT ID | AA ID | NT LN | AA LN | Score | P-Value |
|---|---|---|---|---|---|---|
| SPX1006 | 1006 | 3667 | 1416 | 472 | 2426 | 0 |

Description

[LN:A28568] [AC:A28568:S12829] [PN:pneumolysin] [CL:dipeptide transport protein] [OR:Streptococcus pneumoniae]

| ORF Name | NT ID | AA ID | NT LN | AA LN | Score | P-Value |
|---|---|---|---|---|---|---|
| SPX1007 | 1007 | 3668 | 717 | 239 | 915 | 1.30E-119 |

Description

[LN:A64963] [AC:A64963] [PN:conserved hypothetical protein b1983] [CL:hypothetical protein MG332] [OR:Escherichia coli]

| ORF Name | NT ID | AA ID | NT LN | AA LN | Score | P-Value |
|---|---|---|---|---|---|---|
| SPX1008 | 1008 | 3669 | 450 | 150 | 104 | 9.20E-07 |

Description

[LN:C72329] [AC:C72329] [PN:hypothetical protein TM0816] [GN:TM0816] [OR:Thermotoga maritima]

| ORF Name | NT ID | AA ID | NT LN | AA LN | Score | P-Value |
|---|---|---|---|---|---|---|
| SPX1009 | 1009 | 3670 | 873 | 291 | 309 | 1.20E-35 |

Description

[GI:6759558] [LN:SC7A8] [AC:AL137187] [PN:putative ABC transporter] [GN:SC7A8.02] [OR:Streptomyces coelicolor A3(2)]

| ORF Name | NT ID | AA ID | NT LN | AA LN | Score | P-Value |
|---|---|---|---|---|---|---|
| SPX1010 | 1010 | 3671 | 1032 | 344 | 335 | 7.80E-76 |

Description

[GI:6759559] [LN:SC7A8] [AC:AL137187] [PN:putative ABC transporter] [GN:SC7A8.03] [OR:Streptomyces coelicolor A3(2)]

| ORF Name | NT ID | AA ID | NT LN | AA LN | Score | P-Value |
|---|---|---|---|---|---|---|
| SPX1011 | 1011 | 3672 | 363 | 121 | | |

Description

NO-HIT

| ORF Name | NT ID | AA ID | NT/LN | AA/LN | Score | P-Value |
|---|---|---|---|---|---|---|
| SPX1012 | 1012 | 3673 | 504 | 168 | 130 | 2.10E-10 |

Description

[LN:Y374_METJA] [AC:Q57819] [GN:MJ0374] [OR:Methanococcus jannaschii] [DE:HYPOTHETICAL PROTEIN MJ0374] [SP:Q57819]

| ORF Name | NT ID | AA ID | NT/LN | AA/LN | Score | P-Value |
|---|---|---|---|---|---|---|
| SPX1013 | 1013 | 3674 | 450 | 150 | | |

Description

NO-HIT

| ORF Name | NT ID | AA ID | NT/LN | AA/LN | Score | P-Value |
|---|---|---|---|---|---|---|
| SPX1014 | 1014 | 3675 | 675 | 225 | | |

Description

NO-HIT

| ORF Name | NT ID | AA ID | NT/LN | AA/LN | Score | P-Value |
|---|---|---|---|---|---|---|
| SPX1015 | 1015 | 3676 | 222 | 74 | 125 | 8.00E-13 |

Description

[GI:1914870] [LN:SPZ82001] [AC:Z82001] [PN:unknown] [OR:Streptococcus pneumoniae]

| ORF Name | NT ID | AA ID | NT/LN | AA/LN | Score | P-Value |
|---|---|---|---|---|---|---|
| SPX1016 | 1016 | 3677 | 300 | 100 | | |

Description

NO-HIT

| ORF Name | NT ID | AA ID | NT/LN | AA/LN | Score | P-Value |
|---|---|---|---|---|---|---|
| SPX1017 | 1017 | 3678 | 318 | 106 | 276 | 6.70E-34 |

Description

[LN:G69998] [AC:G69998] [PN:thioredoxin H1 homolog ytpP] [GN:ytpP] [CL:thioredoxin:thioredoxin homology] [OR:Bacillus subtilis]

| ORF Name | NT ID | AA ID | NT LN | AA LN | Score | P-Value |
|---|---|---|---|---|---|---|
| SPX1018 | 1018 | 3679 | 378 | 126 | | |

Description

NO-HIT

| ORF Name | NT ID | AA ID | NT LN | AA LN | Score | P-Value |
|---|---|---|---|---|---|---|
| SPX1019 | 1019 | 3680 | 627 | 209 | 217 | 5.30E-44 |

Description

[LN:A69999] [AC:A69999] [PN:phenylalanyl-tRNA synthetase (beta subunit) homolog ytpR] [GN:ytpR] [CL:Mycoplasma genitalium hypothetical protein MG449] [OR:Bacillus subtilis]

| ORF Name | NT ID | AA ID | NT LN | AA LN | Score | P-Value |
|---|---|---|---|---|---|---|
| SPX1020 | 1020 | 3681 | 762 | 254 | 354 | 4.20E-67 |

Description

[GI:2425123] [LN:AF019986] [AC:AF019986] [PN:PksB] [GN:pksB] [OR:Dictyostelium discoideum]

| ORF Name | NT ID | AA ID | NT LN | AA LN | Score | P-Value |
|---|---|---|---|---|---|---|
| SPX1021 | 1021 | 3682 | 396 | 132 | 227 | 1.20E-34 |

Description

[GI:6716352] [LN:AF145054] [AC:AF145054:AF001793:AF118440:U89246] [PN:ORF9] [GN:orf9] [OR:Streptococcus thermophilus bacteriophage 7201]

| ORF Name | NT ID | AA ID | NT LN | AA LN | Score | P-Value |
|---|---|---|---|---|---|---|
| SPX1022 | 1022 | 3683 | 285 | 95 | 460 | 1.90E-58 |

Description

[GI:4566772] [LN:AF117741] [AC:AF117741] [PN:cochaperonin GroES] [GN:groES] [OR:Streptococcus pneumoniae]

| ORF Name | NT ID | AA ID | NT LN | AA LN | Score | P-Value |
|---|---|---|---|---|---|---|
| SPX1023 | 1023 | 3684 | 609 | 203 | 344 | 8.20E-43 |

Description

[GI:1196510] [LN:MSGTCWPA] [AC:M15467] [PN:unknown protein] [OR:Mycobacterium tuberculosis] [SR:Mycobacterium tuberculosis (strain Erdman) DNA]

| ORF Name | NT ID | AA ID | NT/LN | AA/LN | Score | P-Value |
|---|---|---|---|---|---|---|
| SPX1024 | 1024 | 3685 | 1623 | 541 | 2611 | 0 |
| Description | | | | | | |

[GI:4566773] [LN:AF117741] [AC:AF117741] [PN:chaperonin GroEL] [GN:groEL]
[OR:Streptococcus pneumoniae]

| ORF Name | NT ID | AA ID | NT/LN | AA/LN | Score | P-Value |
|---|---|---|---|---|---|---|
| SPX1025 | 1025 | 3686 | 210 | 70 | 70 | 3.30E-06 |
| Description | | | | | | |

[LN:C71647] [AC:C71647] [PN:hypothetical protein RP851] [GN:RP851]
[OR:Rickettsia prowazekii]

| ORF Name | NT ID | AA ID | NT/LN | AA/LN | Score | P-Value |
|---|---|---|---|---|---|---|
| SPX1026 | 1026 | 3687 | 252 | 84 | 139 | 1.80E-13 |
| Description | | | | | | |

[LN:F72338] [AC:F72338] [PN:conserved hypothetical protein] [GN:TM0731]
[OR:Thermotoga maritima]

| ORF Name | NT ID | AA ID | NT/LN | AA/LN | Score | P-Value |
|---|---|---|---|---|---|---|
| SPX1027 | 1027 | 3688 | 192 | 64 | | |
| Description | | | | | | |

NO-HIT

| ORF Name | NT ID | AA ID | NT/LN | AA/LN | Score | P-Value |
|---|---|---|---|---|---|---|
| SPX1028 | 1028 | 3689 | 774 | 258 | 129 | 6.70E-09 |
| Description | | | | | | |

[LN:T33885] [AC:T33885] [PN:hypothetical protein H14E04.1] [GN:H14E04.1]
[CL:24-sterol C-methyltransferase:bioC homology] [OR:Caenorhabditis elegans]

| ORF Name | NT ID | AA ID | NT/LN | AA/LN | Score | P-Value |
|---|---|---|---|---|---|---|
| SPX1029 | 1029 | 3690 | 339 | 113 | 133 | 1.50E-11 |
| Description | | | | | | |

[LN:AB025228] [AC:AB025228] [GN:rgg] [OR:Streptococcus oralis]
[SR:Streptococcus oralis (strain:ATCC10557) DNA]

| ORF Name | NT ID | AA ID | NT/LN | AA/LN | Score | P-Value |
|---|---|---|---|---|---|---|
| SPX1030 | 1030 | 3691 | 348 | 116 | 90 | 8.90E-06 |

Description

[LN:AB025228] [AC:AB025228] [GN:rgg] [OR:Streptococcus oralis]
[SR:Streptococcus oralis (strain:ATCC10557) DNA]

| ORF Name | NT ID | AA ID | NT/LN | AA/LN | Score | P-Value |
|---|---|---|---|---|---|---|
| SPX1031 | 1031 | 3692 | 534 | 178 | 294 | 4.90E-36 |

Description

[LN:F69815] [AC:F69815] [PN:hypothetical protein ygaC] [GN:ygaC]
[CL:Bacillus subtilis hypothetical protein ygaC] [OR:Bacillus subtilis]

| ORF Name | NT ID | AA ID | NT/LN | AA/LN | Score | P-Value |
|---|---|---|---|---|---|---|
| SPX1032 | 1032 | 3693 | 180 | 60 | | |

Description

NO-HIT

| ORF Name | NT ID | AA ID | NT/LN | AA/LN | Score | P-Value |
|---|---|---|---|---|---|---|
| SPX1033 | 1033 | 3694 | 861 | 287 | 226 | 3.30E-32 |

Description

[LN:H69800] [AC:H69800] [PN:hypothetical protein yfhG] [GN:yfhG]
[OR:Bacillus subtilis]

| ORF Name | NT ID | AA ID | NT/LN | AA/LN | Score | P-Value |
|---|---|---|---|---|---|---|
| SPX1034 | 1034 | 3695 | 1356 | 452 | 606 | 1.00E-145 |

Description

[LN:F69806] [AC:F69806] [PN:RNA methyltransferase homolog yfjO] [GN:yfjO]
[CL:hypothetical protein HI0333] [OR:Bacillus subtilis]

| ORF Name | NT ID | AA ID | NT/LN | AA/LN | Score | P-Value |
|---|---|---|---|---|---|---|
| SPX1035 | 1035 | 3696 | 246 | 82 | | |

Description

NO-HIT

| ORF Name | NT ID | AA ID | NT/LN | AA/LN | Score | P-Value |
|---|---|---|---|---|---|---|
| SPX1036 | 1036 | 3697 | 150 | 50 | 82 | 7.60E-06 |

Description

[LN:G71244] [AC:G71244] [PN:hypothetical protein PH0217] [GN:PH0217] [OR:Pyrococcus horikoshii]

| ORF Name | NT ID | AA ID | NT/LN | AA/LN | Score | P-Value |
|---|---|---|---|---|---|---|
| SPX1037 | 1037 | 3698 | 186 | 62 | | |

Description

NO-HIT

| ORF Name | NT ID | AA ID | NT/LN | AA/LN | Score | P-Value |
|---|---|---|---|---|---|---|
| SPX1038 | 1038 | 3699 | 261 | 87 | 136 | 3.90E-14 |

Description

[LN:G81516] [AC:G81516] [PN:hypothetical protein CP0988 [imported]] [GN:CP0988] [OR:Chlamydophila pneumoniae:Chlamydia pneumoniae]

| ORF Name | NT ID | AA ID | NT/LN | AA/LN | Score | P-Value |
|---|---|---|---|---|---|---|
| SPX1039 | 1039 | 3700 | 228 | 76 | 190 | 1.00E-21 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX1040 | 1040 | 3701 | 237 | 79 | | |

Description

NO-HIT

| ORF Name | NT ID | AA ID | NT/LN | AA/LN | Score | P-Value |
|---|---|---|---|---|---|---|
| SPX1041 | 1041 | 3702 | 282 | 94 | 301 | 2.00E-35 |

Description

[LN:DHAS_STRMU] [AC:P10539] [GN:ASD] [OR:Streptococcus mutans] [EC:1.2.1.11] [DE:DEHYDROGENASE)] [SP:P10539]

| ORF Name | NT ID | AA ID | NT/LN | AA/LN | Score | P-Value |
|---|---|---|---|---|---|---|
| SPX1042 | 1042 | 3703 | 276 | 92 | 325 | 3.80E-40 |
| Description | | | | | | |

[LN:DHAS_STRMU] [AC:P10539] [GN:ASD] [OR:Streptococcus mutans] [EC:1.2.1.11] [DE:DEHYDROGENASE)] [SP:P10539]

| ORF Name | NT ID | AA ID | NT/LN | AA/LN | Score | P-Value |
|---|---|---|---|---|---|---|
| SPX1043 | 1043 | 3704 | 666 | 222 | 590 | 1.20E-108 |
| Description | | | | | | |

[LN:DHAS_STRMU] [AC:P10539] [GN:ASD] [OR:Streptococcus mutans] [EC:1.2.1.11] [DE:DEHYDROGENASE)] [SP:P10539]

| ORF Name | NT ID | AA ID | NT/LN | AA/LN | Score | P-Value |
|---|---|---|---|---|---|---|
| SPX1044 | 1044 | 3705 | 936 | 312 | 192 | 2.60E-55 |
| Description | | | | | | |

"[LN:B72246] [AC:B72246] [PN:dihydrodipicolinate synthase, TM1521 [similarity]] [GN:TM1521] [CL:Pseudomonas 5-dehydro-4-deoxyglucarate dehydratase] [OR:Thermotoga maritima] [EC:4.2.1.52]"

| ORF Name | NT ID | AA ID | NT/LN | AA/LN | Score | P-Value |
|---|---|---|---|---|---|---|
| SPX1045 | 1045 | 3706 | 1374 | 458 | 1312 | 1.10E-249 |
| Description | | | | | | |

[GI:6448626] [LN:SAG251564] [AC:AJ251564] [PN:thiophene degradation protein F] [GN:thdF] [FN:putative thiophene and furan oxidation gene] [OR:Streptococcus agalactiae]

| ORF Name | NT ID | AA ID | NT/LN | AA/LN | Score | P-Value |
|---|---|---|---|---|---|---|
| SPX1046 | 1046 | 3707 | 225 | 75 | 127 | 1.30E-12 |
| Description | | | | | | |

"[LN:A43397] [AC:A43397:S35225] [PN:4-oxalocrotonate tautomerase, xylH] [GN:xylH] [CL:4-oxalocrotonate tautomerase] [OR:Pseudomonas putida] [EC:5.3.2.-]"

| ORF Name | NT ID | AA ID | NT LN | AA LN | Score | P-Value |
|---|---|---|---|---|---|---|
| SPX1047 | 1047 | 3708 | 492 | 164 | 724 | 7.00E-97 |

Description

"[LN:KITH_STRGC] [AC:P47848] [GN:TDK] [OR:Streptococcus gordonii challis] [EC:2.7.1.21] [DE:THYMIDINE KINASE,] [SP:P47848]"

| ORF Name | NT ID | AA ID | NT LN | AA LN | Score | P-Value |
|---|---|---|---|---|---|---|
| SPX1048 | 1048 | 3709 | 843 | 281 | 642 | 2.20E-103 |

Description

[LN:RF1_BACSU] [AC:P45872] [GN:PRFA] [OR:Bacillus subtilis] [DE:PEPTIDE CHAIN RELEASE FACTOR 1 (RF-1)] [SP:P45872]

| ORF Name | NT ID | AA ID | NT LN | AA LN | Score | P-Value |
|---|---|---|---|---|---|---|
| SPX1049 | 1049 | 3710 | 429 | 143 | 350 | 2.60E-43 |

Description

[LN:RF1_BACSU] [AC:P45872] [GN:PRFA] [OR:Bacillus subtilis] [DE:PEPTIDE CHAIN RELEASE FACTOR 1 (RF-1)] [SP:P45872]

| ORF Name | NT ID | AA ID | NT LN | AA LN | Score | P-Value |
|---|---|---|---|---|---|---|
| SPX1050 | 1050 | 3711 | 840 | 280 | 183 | 8.00E-41 |

Description

[LN:HEMK_BACSU] [AC:P45873] [GN:YWKE] [OR:Bacillus subtilis] [DE:HEMK PROTEIN HOMOLOG] [SP:P45873]

| ORF Name | NT ID | AA ID | NT LN | AA LN | Score | P-Value |
|---|---|---|---|---|---|---|
| SPX1051 | 1051 | 3712 | 603 | 201 | 244 | 1.80E-32 |

Description

[GI:6015811] [LN:SSU18930] [AC:Y18930] [PN:hypothetical protein] [GN:ORF-c09_003] [OR:Sulfolobus solfataricus]

| ORF Name | NT ID | AA ID | NT LN | AA LN | Score | P-Value |
|---|---|---|---|---|---|---|
| SPX1052 | 1052 | 3713 | 432 | 144 | 97 | 1.30E-05 |

Description

[LN:PHNO_ECOLI] [AC:P16691] [GN:PHNO] [OR:Escherichia coli] [DE:PHNO PROTEIN] [SP:P16691]

| ORF Name | NT ID | AA ID | NT/LN | AA/LN | Score | P-Value |
|---|---|---|---|---|---|---|
| SPX1053 | 1053 | 3714 | 1257 | 419 | 858 | 7.90E-176 |

Description

[LN:GLYA_BACSU] [AC:P39148] [GN:GLYA:GLYC:IPC-34D] [OR:Bacillus subtilis]
[EC:2.1.2.1] [DE:(SHMT)] [SP:P39148]

| ORF Name | NT ID | AA ID | NT/LN | AA/LN | Score | P-Value |
|---|---|---|---|---|---|---|
| SPX1054 | 1054 | 3715 | 1008 | 336 | 130 | 3.90E-11 |

Description

[GI:6899993] [LN:CST130879] [AC:AJ130879] [PN:hypothetical protein]
[FN:unknown] [OR:Clostridium sticklandii]

| ORF Name | NT ID | AA ID | NT/LN | AA/LN | Score | P-Value |
|---|---|---|---|---|---|---|
| SPX1055 | 1055 | 3716 | 615 | 205 | 243 | 1.60E-27 |

Description

[LN:F69900] [AC:F69900] [PN:transposon-related protein homolog yocA]
[GN:yocA] [OR:Bacillus subtilis]

| ORF Name | NT ID | AA ID | NT/LN | AA/LN | Score | P-Value |
|---|---|---|---|---|---|---|
| SPX1056 | 1056 | 3717 | 975 | 325 | 104 | 7.60E-08 |

Description

[LN:YPUA_BACSU] [AC:P31847:P37951] [GN:YPUA] [OR:Bacillus subtilis]
[DE:HYPOTHETICAL 31.3 KD PROTEIN IN LYSA-PPIB INTERGENIC REGION (ORFX19)]
[SP:P31847:P37951]

| ORF Name | NT ID | AA ID | NT/LN | AA/LN | Score | P-Value |
|---|---|---|---|---|---|---|
| SPX1057 | 1057 | 3718 | 1644 | 548 | 767 | 5.90E-131 |

Description

[LN:E69793] [AC:E69793] [PN:RNA methyltransferase homolog yefA] [GN:yefA]
[CL:hypothetical protein HI0333] [OR:Bacillus subtilis]

| ORF Name | NT ID | AA ID | NT/LN | AA/LN | Score | P-Value |
|---|---|---|---|---|---|---|
| SPX1058 | 1058 | 3719 | 294 | 98 | | |

Description

NO-HIT

| ORF Name | NT ID | AA ID | NT/LN | AA/LN | Score | P-Value |
|---|---|---|---|---|---|---|
| SPX1059 | 1059 | 3720 | 249 | 83 | | |

Description

NO-HIT

| ORF Name | NT ID | AA ID | NT/LN | AA/LN | Score | P-Value |
|---|---|---|---|---|---|---|
| SPX1060 | 1060 | 3721 | 195 | 65 | 81 | 3.20E-08 |

Description

[LN:C69931] [AC:C69931] [PN:transcription regulator homolog yozG] [GN:yozG] [OR:Bacillus subtilis]

| ORF Name | NT ID | AA ID | NT/LN | AA/LN | Score | P-Value |
|---|---|---|---|---|---|---|
| SPX1061 | 1061 | 3722 | 240 | 80 | | |

Description

NO-HIT

| ORF Name | NT ID | AA ID | NT/LN | AA/LN | Score | P-Value |
|---|---|---|---|---|---|---|
| SPX1062 | 1062 | 3723 | 1035 | 345 | 276 | 3.80E-70 |

Description

[GI:2276374] [LN:CDU02617] [AC:U02617] [PN:DtxR/iron regulated lipoprotein precursor] [GN:irp1] [FN:iron transport] [OR:Corynebacterium diphtheriae]

| ORF Name | NT ID | AA ID | NT/LN | AA/LN | Score | P-Value |
|---|---|---|---|---|---|---|
| SPX1063 | 1063 | 3724 | 636 | 212 | | |

Description

NO-HIT

| ORF Name | NT ID | AA ID | NT/LN | AA/LN | Score | P-Value |
|---|---|---|---|---|---|---|
| SPX1064 | 1064 | 3725 | 1008 | 336 | 643 | 1.40E-86 |

Description

[LN:T44797] [AC:T44797] [PN:iron transport membrane protein irp1B [imported]] [GN:irp1B] [CL:vitamin B12 transport protein btuC] [OR:Corynebacterium diphtheriae]

| ORF Name | NT ID | AA ID | NT LN | AA LN | Score | P-Value |
|---|---|---|---|---|---|---|
| SPX1065 | 1065 | 3726 | 1008 | 336 | 484 | 1.10E-82 |

Description

[LN:T44798] [AC:T44798] [PN:iron transport membrane protein irp1C [imported]] [GN:irp1C] [CL:vitamin B12 transport protein btuC] [OR:Corynebacterium diphtheriae]

| ORF Name | NT ID | AA ID | NT LN | AA LN | Score | P-Value |
|---|---|---|---|---|---|---|
| SPX1066 | 1066 | 3727 | 222 | 74 | | |

Description

NO-HIT

| ORF Name | NT ID | AA ID | NT LN | AA LN | Score | P-Value |
|---|---|---|---|---|---|---|
| SPX1067 | 1067 | 3728 | 414 | 138 | | |

Description

NO-HIT

| ORF Name | NT ID | AA ID | NT LN | AA LN | Score | P-Value |
|---|---|---|---|---|---|---|
| SPX1068 | 1068 | 3729 | 795 | 265 | 694 | 6.10E-91 |

Description

[LN:G70022] [AC:G70022] [PN:iron(III) dicitrate transport permease homolog yusV] [GN:yusV] [CL:inner membrane protein malK:ATP-binding cassette homology] [OR:Bacillus subtilis]

| ORF Name | NT ID | AA ID | NT LN | AA LN | Score | P-Value |
|---|---|---|---|---|---|---|
| SPX1069 | 1069 | 3730 | 261 | 87 | 151 | 1.30E-14 |

Description

[GI:2467226] [LN:LLLPK214] [AC:X92946:Y10522] [PN:transposase] [GN:tnpA] [OR:Lactococcus lactis]

| ORF Name | NT ID | AA ID | NT LN | AA LN | Score | P-Value |
|---|---|---|---|---|---|---|
| SPX1070 | 1070 | 3731 | 456 | 152 | 137 | 1.10E-10 |

Description

"[LN:T4BB_BACCO] [AC:Q07606] [GN:BCGIB] [OR:Bacillus coagulans] [EC:3.1.21.-] [DE:RESTRICTION ENZYME BGCI BETA SUBUNIT,] [SP:Q07606]"

| ORF Name | NT ID | AA ID | NT LN | AA LN | Score | P-Value |
|---|---|---|---|---|---|---|
| SPX1071 | 1071 | 3732 | 276 | 92 | | |

Description

NO-HIT

| ORF Name | NT ID | AA ID | NT LN | AA LN | Score | P-Value |
|---|---|---|---|---|---|---|
| SPX1072 | 1072 | 3733 | 249 | 83 | | |

Description

NO-HIT

| ORF Name | NT ID | AA ID | NT LN | AA LN | Score | P-Value |
|---|---|---|---|---|---|---|
| SPX1073 | 1073 | 3734 | 210 | 70 | | |

Description

NO-HIT

| ORF Name | NT ID | AA ID | NT LN | AA LN | Score | P-Value |
|---|---|---|---|---|---|---|
| SPX1074 | 1074 | 3735 | 1680 | 560 | 138 | 3.40E-35 |

Description

[GI:6681569] [LN:AB014436] [AC:AB014436] [PN:cassette chromosome recombinase B] [GN:ccrB] [OR:Staphylococcus aureus] [SR:Staphylococcus aureus (strain:85/2082) DNA]

| ORF Name | NT ID | AA ID | NT LN | AA LN | Score | P-Value |
|---|---|---|---|---|---|---|
| SPX1075 | 1075 | 3736 | 612 | 204 | | |

Description

NO-HIT

| ORF Name | NT ID | AA ID | NT LN | AA LN | Score | P-Value |
|---|---|---|---|---|---|---|
| SPX1076 | 1076 | 3737 | 189 | 63 | | |

Description

NO-HIT

| ORF Name | NT ID | AA ID | NT/LN | AA/LN | Score | P-Value |
|---|---|---|---|---|---|---|
| SPX1077 | 1077 | 3738 | 759 | 253 | | |

Description

NO-HIT

| ORF Name | NT ID | AA ID | NT/LN | AA/LN | Score | P-Value |
|---|---|---|---|---|---|---|
| SPX1078 | 1078 | 3739 | 855 | 285 | 70 | 4.40E-09 |

Description

[GI:7020551] [LN:AK000453] [AC:AK000453] [OR:Homo sapiens] [SR:Homo sapiens signet-ring cell carcinoma cell_line:KATO III cDNA t]

| ORF Name | NT ID | AA ID | NT/LN | AA/LN | Score | P-Value |
|---|---|---|---|---|---|---|
| SPX1079 | 1079 | 3740 | 885 | 295 | 192 | 4.90E-36 |

Description

[LN:F69795] [AC:F69795] [PN:conserved hypothetical protein yerQ] [GN:yerQ] [OR:Bacillus subtilis]

| ORF Name | NT ID | AA ID | NT/LN | AA/LN | Score | P-Value |
|---|---|---|---|---|---|---|
| SPX1080 | 1080 | 3741 | 279 | 93 | 124 | 1.30E-19 |

Description

"[LN:JS0673] [AC:JS0673] [PN:neopullulanase,] [CL:neopullulanase:alpha-amylase core homology] [OR:Bacillus sp.] [EC:3.2.1.135]"

| ORF Name | NT ID | AA ID | NT/LN | AA/LN | Score | P-Value |
|---|---|---|---|---|---|---|
| SPX1081 | 1081 | 3742 | 1455 | 485 | 683 | 3.10E-176 |

Description

"[LN:F70033] [AC:F70033] [PN:glucan 1,4-alpha-maltohydrolase homolog yvdF] [GN:yvdF] [CL:neopullulanase:alpha-amylase core homology] [OR:Bacillus subtilis]"

| ORF Name | NT ID | AA ID | NT/LN | AA/LN | Score | P-Value |
|---|---|---|---|---|---|---|
| SPX1082 | 1082 | 3743 | 303 | 101 | | |

Description

NO-HIT

| ORF Name | NT ID | AA ID | NT/LN | AA/LN | Score | P-Value |
|---|---|---|---|---|---|---|
| SPX1083 | 1083 | 3744 | 429 | 143 | 249 | 9.00E-30 |
| Description | | | | | | |

[GI:6102604] [LN:AF144880] [AC:AF144880] [PN:aminoglycoside 6'-N-acetyltransferase] [GN:aac(6')-Iy] [OR:Salmonella enteritidis]

| ORF Name | NT ID | AA ID | NT/LN | AA/LN | Score | P-Value |
|---|---|---|---|---|---|---|
| SPX1084 | 1084 | 3745 | 570 | 190 | | |
| Description | | | | | | |

NO-HIT

| ORF Name | NT ID | AA ID | NT/LN | AA/LN | Score | P-Value |
|---|---|---|---|---|---|---|
| SPX1085 | 1085 | 3746 | 213 | 71 | | |
| Description | | | | | | |

NO-HIT

| ORF Name | NT ID | AA ID | NT/LN | AA/LN | Score | P-Value |
|---|---|---|---|---|---|---|
| SPX1086 | 1086 | 3747 | 282 | 94 | | |
| Description | | | | | | |

NO-HIT

| ORF Name | NT ID | AA ID | NT/LN | AA/LN | Score | P-Value |
|---|---|---|---|---|---|---|
| SPX1087 | 1087 | 3748 | 195 | 65 | 184 | 8.80E-20 |
| Description | | | | | | |

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1088 | 1088 | 3749 | 1230 | 410 | 419 | 1.50E-74 |
| Description | | | | | | |

[LN:FTSW_ENTHR] [AC:Q47866] [GN:FTSW] [OR:Enterococcus hirae] [DE:PROBABLE CELL DIVISION PROTEIN FTSW] [SP:Q47866]

| ORF Name | NT ID | AA ID | NT LN | AA LN | Score | P-Value |
|---|---|---|---|---|---|---|
| SPX1089 | 1089 | 3750 | 2697 | 899 | 418 | 1.60E-169 |

Description

[GI:144985] [LN:CORPEPC] [AC:M25819] [PN:phosphoenolpyruvate carboxylase] [OR:Corynebacterium glutamicum] [SR:Corynebacterium glutamicum (clone: pTG1200.) (tissue library: ATC]

| ORF Name | NT ID | AA ID | NT LN | AA LN | Score | P-Value |
|---|---|---|---|---|---|---|
| SPX1090 | 1090 | 3751 | 306 | 102 | | |

Description

NO-HIT

| ORF Name | NT ID | AA ID | NT LN | AA LN | Score | P-Value |
|---|---|---|---|---|---|---|
| SPX1091 | 1091 | 3752 | 630 | 210 | 105 | 2.60E-05 |

Description

[LN:H71693] [AC:H71693] [PN:hypothetical protein RP367] [GN:RP367] [OR:Rickettsia prowazekii]

| ORF Name | NT ID | AA ID | NT LN | AA LN | Score | P-Value |
|---|---|---|---|---|---|---|
| SPX1092 | 1092 | 3753 | 669 | 223 | 163 | 6.00E-23 |

Description

[LN:A71694] [AC:A71694] [PN:hypothetical protein RP368] [GN:RP368] [OR:Rickettsia prowazekii]

| ORF Name | NT ID | AA ID | NT LN | AA LN | Score | P-Value |
|---|---|---|---|---|---|---|
| SPX1093 | 1093 | 3754 | 759 | 253 | 365 | 1.80E-45 |

Description

[GI:1661179] [LN:SMU75471] [AC:U75471] [PN:high affinity branched chain amino acid] [GN:livG] [OR:Streptococcus mutans]

| ORF Name | NT ID | AA ID | NT LN | AA LN | Score | P-Value |
|---|---|---|---|---|---|---|
| SPX1094 | 1094 | 3755 | 192 | 64 | 82 | 2.10E-05 |

Description

[LN:A71007] [AC:A71007] [PN:hypothetical protein PH1351] [GN:PH1351] [OR:Pyrococcus horikoshii]

| ORF Name | NT ID | AA ID | NT/LN | AA/LN | Score | P-Value |
|---|---|---|---|---|---|---|
| SPX1095 | 1095 | 3756 | 1776 | 592 | 694 | 1.40E-161 |

Description

"[LN:PRIM_LACLA] [AC:Q04505] [GN:DNAG:DNAE] [OR:Lactococcus lactis] [SR:,subsplactis:Streptococcus lactis] [EC:2.7.7.-] [DE:DNA PRIMASE,] [SP:Q04505]"

| ORF Name | NT ID | AA ID | NT/LN | AA/LN | Score | P-Value |
|---|---|---|---|---|---|---|
| SPX1096 | 1096 | 3757 | 915 | 305 | 1452 | 2.30E-194 |

Description

[LN:RPOD_STRPN] [AC:O08388] [GN:RPOD] [OR:Streptococcus pneumoniae] [DE:RNA POLYMERASE SIGMA FACTOR RPOD] [SP:O08388]

| ORF Name | NT ID | AA ID | NT/LN | AA/LN | Score | P-Value |
|---|---|---|---|---|---|---|
| SPX1097 | 1097 | 3758 | 198 | 66 | 290 | 2.40E-35 |

Description

[LN:RPOD_STRPN] [AC:O08388] [GN:RPOD] [OR:Streptococcus pneumoniae] [DE:RNA POLYMERASE SIGMA FACTOR RPOD] [SP:O08388]

| ORF Name | NT ID | AA ID | NT/LN | AA/LN | Score | P-Value |
|---|---|---|---|---|---|---|
| SPX1098 | 1098 | 3759 | 330 | 110 | 556 | 5.10E-73 |

Description

[GI:2108332] [LN:SPDNAGCPO] [AC:Y11463] [OR:Streptococcus pneumoniae]

| ORF Name | NT ID | AA ID | NT/LN | AA/LN | Score | P-Value |
|---|---|---|---|---|---|---|
| SPX1099 | 1099 | 3760 | 207 | 69 | | |

Description

NO-HIT

| ORF Name | NT ID | AA ID | NT/LN | AA/LN | Score | P-Value |
|---|---|---|---|---|---|---|
| SPX1100 | 1100 | 3761 | 801 | 267 | 1357 | 1.40E-186 |

Description

[GI:2108333] [LN:SPDNAGCPO] [AC:Y11463] [GN:cpoA] [OR:Streptococcus pneumoniae]

| ORF Name | NT ID | AA ID | NT/LN | AA/LN | Score | P-Value |
|---|---|---|---|---|---|---|
| SPX1101 | 1101 | 3762 | 198 | 66 | 318 | 4.00E-38 |

Description

[GI:2108333] [LN:SPDNAGCPO] [AC:Y11463] [GN:cpoA] [OR:Streptococcus pneumoniae]

| ORF Name | NT ID | AA ID | NT/LN | AA/LN | Score | P-Value |
|---|---|---|---|---|---|---|
| SPX1102 | 1102 | 3763 | 1326 | 442 | 1475 | 1.70E-200 |

Description

[GI:2108334] [LN:SPDNAGCPO] [AC:Y11463] [OR:Streptococcus pneumoniae]

| ORF Name | NT ID | AA ID | NT/LN | AA/LN | Score | P-Value |
|---|---|---|---|---|---|---|
| SPX1103 | 1103 | 3764 | 177 | 59 | 151 | 3.70E-16 |

Description

[LN:B72287] [AC:B72287] [PN:conserved hypothetical protein] [GN:TM1156] [OR:Thermotoga maritima]

| ORF Name | NT ID | AA ID | NT/LN | AA/LN | Score | P-Value |
|---|---|---|---|---|---|---|
| SPX1104 | 1104 | 3765 | 1176 | 392 | 1021 | 5.10E-184 |

Description

[LN:OBG_BACSU] [AC:P20964] [GN:OBG] [OR:Bacillus subtilis] [DE:SPO0B-ASSOCIATED GTP-BINDING PROTEIN] [SP:P20964]

| ORF Name | NT ID | AA ID | NT/LN | AA/LN | Score | P-Value |
|---|---|---|---|---|---|---|
| SPX1105 | 1105 | 3766 | 1260 | 420 | 424 | 9.00E-142 |

Description

[LN:MURA_BACSU] [AC:P19670:Q03225] [GN:MURA:MURZ] [OR:Bacillus subtilis] [EC:2.5.1.7] [DE:ENOLPYRUVYL TRANSFERASE) (EPT)] [SP:P19670:Q03225]

| ORF Name | NT ID | AA ID | NT/LN | AA/LN | Score | P-Value |
|---|---|---|---|---|---|---|
| SPX1106 | 1106 | 3767 | 528 | 176 | 156 | 1.00E-17 |

Description

[LN:C69895] [AC:C69895] [PN:conserved hypothetical protein yoaA] [GN:yoaA] [CL:Escherichia coli ribosomal-protein-alanine N-acetyltransferase rimJ] [OR:Bacillus subtilis]

| ORF Name | NT ID | AA ID | NT/LN | AA/LN | Score | P-Value |
|---|---|---|---|---|---|---|
| SPX1107 | 1107 | 3768 | 1278 | 426 | 425 | 4.20E-85 |
| Description | | | | | | |

[LN:A69998] [AC:A69998] [PN:hypothetical protein ytoI] [GN:ytoI] [OR:Bacillus subtilis]

| ORF Name | NT ID | AA ID | NT/LN | AA/LN | Score | P-Value |
|---|---|---|---|---|---|---|
| SPX1108 | 1108 | 3769 | 861 | 287 | 345 | 3.30E-65 |
| Description | | | | | | |

"[LN:T44405] [AC:T44405] [PN:methionyl aminopeptidase, map [imported]] [CL:Escherichia coli methionyl aminopeptidase] [OR:Bacillus halodurans] [EC:3.4.11.18]"

| ORF Name | NT ID | AA ID | NT/LN | AA/LN | Score | P-Value |
|---|---|---|---|---|---|---|
| SPX1109 | 1109 | 3770 | 543 | 181 | 307 | 2.50E-38 |
| Description | | | | | | |

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1110 | 1110 | 3771 | 225 | 75 | 104 | 5.80E-08 |
| Description | | | | | | |

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1111 | 1111 | 3772 | 390 | 130 | 384 | 4.80E-49 |
| Description | | | | | | |

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1112 | 1112 | 3773 | 2292 | 764 | 1351 | 7.70E-282 |
| Description | | | | | | |

[LN:E69794] [AC:E69794] [PN:ATP-dependent DNA helicase homolog yerF] [GN:yerF] [CL:helicase II] [OR:Bacillus subtilis]

| ORF Name | NT ID | AA ID | NT/LN | AA/LN | Score | P-Value |
|---|---|---|---|---|---|---|
| SPX1113 | 1113 | 3774 | 720 | 240 | 488 | 2.80E-62 |

Description

[LN:RADC_BACSU] [AC:Q02170] [GN:YSXA] [OR:Bacillus subtilis] [DE:DNA REPAIR PROTEIN RADC HOMOLOG (ORFB)] [SP:Q02170]

| ORF Name | NT ID | AA ID | NT/LN | AA/LN | Score | P-Value |
|---|---|---|---|---|---|---|
| SPX1114 | 1114 | 3775 | 690 | 230 | 237 | 6.50E-27 |

Description

"[LN:YDP3_LACLA] [AC:P22347] [OR:Lactococcus lactis]
[SR:,subsplactis:Streptococcus lactis] [DE:HYPOTHETICAL 18.7 KD PROTEIN IN PEPX 3'REGION (ORF3)] [SP:P22347]"

| ORF Name | NT ID | AA ID | NT/LN | AA/LN | Score | P-Value |
|---|---|---|---|---|---|---|
| SPX1115 | 1115 | 3776 | 642 | 214 | 339 | 2.60E-68 |

Description

[LN:A69787] [AC:A69787] [PN:hypothetical protein ydiH] [GN:ydiH]
[OR:Bacillus subtilis]

| ORF Name | NT ID | AA ID | NT/LN | AA/LN | Score | P-Value |
|---|---|---|---|---|---|---|
| SPX1116 | 1116 | 3777 | 252 | 84 | | |

Description

NO-HIT

| ORF Name | NT ID | AA ID | NT/LN | AA/LN | Score | P-Value |
|---|---|---|---|---|---|---|
| SPX1117 | 1117 | 3778 | 348 | 116 | | |

Description

NO-HIT

| ORF Name | NT ID | AA ID | NT/LN | AA/LN | Score | P-Value |
|---|---|---|---|---|---|---|
| SPX1118 | 1118 | 3779 | 795 | 265 | 288 | 2.40E-63 |

Description

[LN:E69981] [AC:E69981] [PN:iron-sulfur cofactor synthesis protein yrvO]
[GN:yrvO] [CL:nitrogen fixation protein nifS] [OR:Bacillus subtilis]

| ORF Name | NT ID | AA ID | NT/LN | AA/LN | Score | P-Value |
|---|---|---|---|---|---|---|
| SPX1119 | 1119 | 3780 | 435 | 145 | 149 | 4.90E-18 |
| Description | | | | | | |

[GI:2289093] [LN:CAU76387] [AC:U76387] [PN:PRPP synthetase] [GN:prs]
[OR:Corynebacterium ammoniagenes]

| ORF Name | NT ID | AA ID | NT/LN | AA/LN | Score | P-Value |
|---|---|---|---|---|---|---|
| SPX1120 | 1120 | 3781 | 549 | 183 | 547 | 6.60E-75 |
| Description | | | | | | |

[GI:2289093] [LN:CAU76387] [AC:U76387] [PN:PRPP synthetase] [GN:prs]
[OR:Corynebacterium ammoniagenes]

| ORF Name | NT ID | AA ID | NT/LN | AA/LN | Score | P-Value |
|---|---|---|---|---|---|---|
| SPX1121 | 1121 | 3782 | 570 | 190 | 164 | 1.20E-26 |
| Description | | | | | | |

[LN:C69844] [AC:C69844] [PN:hypothetical protein yjbK] [GN:yjbK]
[CL:Bacillus subtilis hypothetical protein yjbK] [OR:Bacillus subtilis]

| ORF Name | NT ID | AA ID | NT/LN | AA/LN | Score | P-Value |
|---|---|---|---|---|---|---|
| SPX1122 | 1122 | 3783 | 504 | 168 | 338 | 6.80E-68 |
| Description | | | | | | |

[LN:E69844] [AC:E69844] [PN:GTP pyrophosphokinase homolog yjbM] [GN:yjbM]
[CL:GTP pyrophosphokinase related protein] [OR:Bacillus subtilis]

| ORF Name | NT ID | AA ID | NT/LN | AA/LN | Score | P-Value |
|---|---|---|---|---|---|---|
| SPX1123 | 1123 | 3784 | 213 | 71 | 90 | 6.20E-06 |
| Description | | | | | | |

[LN:E69844] [AC:E69844] [PN:GTP pyrophosphokinase homolog yjbM] [GN:yjbM]
[CL:GTP pyrophosphokinase related protein] [OR:Bacillus subtilis]

| ORF Name | NT ID | AA ID | NT/LN | AA/LN | Score | P-Value |
|---|---|---|---|---|---|---|
| SPX1124 | 1124 | 3785 | 789 | 263 | 309 | 4.70E-67 |
| Description | | | | | | |

[LN:F69844] [AC:F69844] [PN:conserved hypothetical protein yjbN] [GN:yjbN]
[CL:conserved hypothetical protein HI0072] [OR:Bacillus subtilis]

| ORF Name | NT ID | AA ID | NT/LN | AA/LN | Score | P-Value |
|---|---|---|---|---|---|---|
| SPX1125 | 1125 | 3786 | 897 | 299 | 286 | 3.40E-66 |
| Description | | | | | | |

[LN:YJBO_BACSU] [AC:O31613] [GN:YJBO] [OR:Bacillus subtilis]
[DE:HYPOTHETICAL 31.5 KD PROTEIN IN MECA-TENA INTERGENIC REGION] [SP:O31613]

| ORF Name | NT ID | AA ID | NT/LN | AA/LN | Score | P-Value |
|---|---|---|---|---|---|---|
| SPX1126 | 1126 | 3787 | 975 | 325 | 867 | 5.10E-115 |
| Description | | | | | | |

[LN:PTA_BACSU] [AC:P39646] [GN:PTA:IPA-88D] [OR:Bacillus subtilis]
[EC:2.3.1.8] [DE:(PHOSPHOTRANSACETYLASE) (VEGETATIVE PROTEIN 43) (VEG43)]
[SP:P39646]

| ORF Name | NT ID | AA ID | NT/LN | AA/LN | Score | P-Value |
|---|---|---|---|---|---|---|
| SPX1127 | 1127 | 3788 | 237 | 79 | | |
| Description | | | | | | |

NO-HIT

| ORF Name | NT ID | AA ID | NT/LN | AA/LN | Score | P-Value |
|---|---|---|---|---|---|---|
| SPX1128 | 1128 | 3789 | 597 | 199 | 472 | 3.10E-122 |
| Description | | | | | | |

[GI:663279] [LN:STRCOMAA] [AC:M36180:L15190] [PN:transposase]
[OR:Streptococcus pneumoniae] [SR:Streptococcus pneumoniae (strain RX1) DNA]

| ORF Name | NT ID | AA ID | NT/LN | AA/LN | Score | P-Value |
|---|---|---|---|---|---|---|
| SPX1129 | 1129 | 3790 | 327 | 109 | 280 | 2.00E-34 |
| Description | | | | | | |

[GI:2804700] [LN:AF030361] [AC:AF030361] [PN:transposase] [OR:Streptococcus pneumoniae]

| ORF Name | NT ID | AA ID | NT/LN | AA/LN | Score | P-Value |
|---|---|---|---|---|---|---|
| SPX1130 | 1130 | 3791 | 519 | 173 | 875 | 3.10E-119 |
| Description | | | | | | |

[GI:663278] [LN:STRCOMAA] [AC:M36180:L15190] [PN:transposase]
[OR:Streptococcus pneumoniae] [SR:Streptococcus pneumoniae (strain RX1) DNA]

| ORF_Name | NT_ID | AA_ID | NT/LN | AA/LN | Score | P-Value |
|---|---|---|---|---|---|---|
| SPX1131 | 1131 | 3792 | 324 | 108 | 190 | 3.90E-21 |

Description

[LN:YAAK_BACSU] [AC:P24281] [GN:YAAK] [OR:Bacillus subtilis]
[DE:HYPOTHETICAL 11.8 KD PROTEIN IN DNAZ-RECR INTERGENIC REGION] [SP:P24281]

| ORF_Name | NT_ID | AA_ID | NT/LN | AA/LN | Score | P-Value |
|---|---|---|---|---|---|---|
| SPX1132 | 1132 | 3793 | 693 | 231 | 89 | 1.90E-05 |

Description

[LN:E69896] [AC:E69896] [PN:hypothetical protein yoaK] [GN:yoaK]
[OR:Bacillus subtilis]

| ORF_Name | NT_ID | AA_ID | NT/LN | AA/LN | Score | P-Value |
|---|---|---|---|---|---|---|
| SPX1133 | 1133 | 3794 | 315 | 105 | 360 | 3.20E-44 |

Description

[LN:RL21_BACSU] [AC:P26908] [GN:RPLU] [OR:Bacillus subtilis] [DE:50S
RIBOSOMAL PROTEIN L21 (BL20)] [SP:P26908]

| ORF_Name | NT_ID | AA_ID | NT/LN | AA/LN | Score | P-Value |
|---|---|---|---|---|---|---|
| SPX1134 | 1134 | 3795 | 441 | 147 | | |

Description

NO-HIT

| ORF_Name | NT_ID | AA_ID | NT/LN | AA/LN | Score | P-Value |
|---|---|---|---|---|---|---|
| SPX1135 | 1135 | 3796 | 345 | 115 | 152 | 1.30E-22 |

Description

[LN:YSXB_BACSU] [AC:P26942:Q45629] [GN:YSXB] [OR:Bacillus subtilis]
[DE:HYPOTHETICAL 12.3 KD PROTEIN IN RPLU-RPMA INTERGENIC REGION (ORF X)]
[SP:P26942:Q45629]

| ORF_Name | NT_ID | AA_ID | NT/LN | AA/LN | Score | P-Value |
|---|---|---|---|---|---|---|
| SPX1136 | 1136 | 3797 | 294 | 98 | 372 | 1.10E-46 |

Description

[LN:RL27_BACSU] [AC:P05657] [GN:RPMA] [OR:Bacillus subtilis] [DE:50S
RIBOSOMAL PROTEIN L27 (BL30) (BL24)] [SP:P05657]

| ORF Name | NT ID | AA ID | NT/LN | AA/LN | Score | P-Value |
|---|---|---|---|---|---|---|
| SPX1137 | 1137 | 3798 | 165 | 55 | 77 | 4.70E-09 |

Description

[GI:1914870] [LN:SPZ82001] [AC:Z82001] [PN:unknown] [OR:Streptococcus pneumoniae]

| ORF Name | NT ID | AA ID | NT/LN | AA/LN | Score | P-Value |
|---|---|---|---|---|---|---|
| SPX1138 | 1138 | 3799 | 918 | 306 | 808 | 1.30E-107 |

Description

[GI:2289231] [LN:SAU92073] [AC:U92073] [PN:macrolide-efflux protein] [GN:mreA] [FN:resistance to 14- and 15-membered macrolides] [OR:Streptococcus agalactiae]

| ORF Name | NT ID | AA ID | NT/LN | AA/LN | Score | P-Value |
|---|---|---|---|---|---|---|
| SPX1139 | 1139 | 3800 | 849 | 283 | 531 | 2.80E-71 |

Description

[LN:YPJC_BACSU] [AC:P42978] [GN:YPJC:JOJC] [OR:Bacillus subtilis] [DE:HYPOTHETICAL 23.6 KD PROTEIN IN QCRC-DAPB INTERGENIC REGION] [SP:P42978]

| ORF Name | NT ID | AA ID | NT/LN | AA/LN | Score | P-Value |
|---|---|---|---|---|---|---|
| SPX1140 | 1140 | 3801 | 840 | 280 | 252 | 9.50E-36 |

Description

[GI:671632] [LN:SADIRED] [AC:Z16422] [PN:unknown] [GN:ORF2] [OR:Staphylococcus aureus]

| ORF Name | NT ID | AA ID | NT/LN | AA/LN | Score | P-Value |
|---|---|---|---|---|---|---|
| SPX1141 | 1141 | 3802 | 276 | 92 | 397 | 9.60E-50 |

Description

[GI:5209334] [LN:L40356] [AC:L40356] [PN:histone-like DNA-binding protein] [GN:hlpA] [OR:Streptococcus gordonii]

| ORF Name | NT ID | AA ID | NT/LN | AA/LN | Score | P-Value |
|---|---|---|---|---|---|---|
| SPX1142 | 1142 | 3803 | 1902 | 634 | 905 | 2.00E-202 |

Description

[LN:YDIF_BACSU] [AC:O05519] [GN:YDIF] [OR:Bacillus subtilis] [DE:HYPOTHETICAL ABC TRANSPORTER ATP-BINDING PROTEIN YDIF] [SP:O05519]

| ORF Name | NT ID | AA ID | NT/LN | AA/LN | Score | P-Value |
|---|---|---|---|---|---|---|
| SPX1143 | 1143 | 3804 | 894 | 298 | 204 | 8.40E-33 |

Description

[GI:4102023] [LN:AF007761] [AC:AF007761] [PN:MutR] [GN:mutR] [FN:positive transcriptional regulator of mutA] [OR:Streptococcus mutans]

| ORF Name | NT ID | AA ID | NT/LN | AA/LN | Score | P-Value |
|---|---|---|---|---|---|---|
| SPX1144 | 1144 | 3805 | 1179 | 393 | 113 | 5.30E-22 |

Description

[LN:H72265] [AC:H72265] [PN:hypothetical protein TM1336] [GN:TM1336] [OR:Thermotoga maritima]

| ORF Name | NT ID | AA ID | NT/LN | AA/LN | Score | P-Value |
|---|---|---|---|---|---|---|
| SPX1145 | 1145 | 3806 | 1968 | 656 | 521 | 1.40E-217 |

Description

"[LN:F69794] [AC:F69794] [PN:DNA ligase (NAD+),] [GN:yerG] [CL:polydeoxyribonucleotide synthase (NAD+)] [OR:Bacillus subtilis] [EC:6.5.1.2]"

| ORF Name | NT ID | AA ID | NT/LN | AA/LN | Score | P-Value |
|---|---|---|---|---|---|---|
| SPX1146 | 1146 | 3807 | 2280 | 760 | 620 | 2.20E-109 |

Description

[GI:3089609] [LN:AF060205] [AC:AF060205] [PN:pullulanase] [GN:pul] [OR:Thermus sp. IM6501]

| ORF Name | NT ID | AA ID | NT/LN | AA/LN | Score | P-Value |
|---|---|---|---|---|---|---|
| SPX1147 | 1147 | 3808 | 1425 | 475 | 1818 | 2.70E-245 |

Description

[LN:GAPN_STRMU] [AC:Q59931] [GN:GAPN] [OR:Streptococcus mutans] [EC:1.2.1.9] [DE:DEHYDROGENASE)] [SP:Q59931]

| ORF Name | NT ID | AA ID | NT/LN | AA/LN | Score | P-Value |
|---|---|---|---|---|---|---|
| SPX1148 | 1148 | 3809 | 1929 | 643 | 658 | 6.60E-176 |

Description

"[LN:S18599] [AC:S18599] [PN:1,4-alpha-glucan branching enzyme,:glycogen branching enzyme] [CL:1,4-alpha-glucan branching enzyme] [OR:Bacillus stearothermophilus] [EC:2.4.1.18]"

| ORF Name | NT ID | AA ID | NT/LN | AA/LN | Score | P-Value |
|---|---|---|---|---|---|---|
| SPX1149 | 1149 | 3810 | 1143 | 381 | 187 | 6.00E-19 |

Description

[LN:CCE277601] [AC:AJ277601] [PN:ADP-glucose pyrophosphorylase] [GN:glgD] [OR:Clostridium cellulolyticum]

| ORF Name | NT ID | AA ID | NT/LN | AA/LN | Score | P-Value |
|---|---|---|---|---|---|---|
| SPX1150 | 1150 | 3811 | 1140 | 380 | 324 | 4.80E-53 |

Description

[LN:GLGD_BACST] [AC:O08327] [GN:GLGD] [OR:Bacillus stearothermophilus] [DE:GLYCOGEN BIOSYNTHESIS PROTEIN GLGD] [SP:O08327]

| ORF Name | NT ID | AA ID | NT/LN | AA/LN | Score | P-Value |
|---|---|---|---|---|---|---|
| SPX1151 | 1151 | 3812 | 1434 | 478 | 813 | 6.80E-159 |

Description

[LN:GLGA_BACSU] [AC:P39125] [GN:GLGA] [OR:Bacillus subtilis] [EC:2.4.1.21] [DE:SYNTHASE)] [SP:P39125]

| ORF Name | NT ID | AA ID | NT/LN | AA/LN | Score | P-Value |
|---|---|---|---|---|---|---|
| SPX1152 | 1152 | 3813 | 372 | 124 | 214 | 7.80E-24 |

Description

[LN:B69517] [AC:B69517] [PN:phosphoserine phosphatase (serB) homolog] [OR:Archaeoglobus fulgidus]

| ORF Name | NT ID | AA ID | NT/LN | AA/LN | Score | P-Value |
|---|---|---|---|---|---|---|
| SPX1153 | 1153 | 3814 | 330 | 110 | 213 | 6.30E-24 |

Description

"[LN:A64499] [AC:A64499] [PN:phosphoserine phosphatase,] [CL:phosphoserine phosphatase] [OR:Methanococcus jannaschii] [EC:3.1.3.3]"

| ORF Name | NT ID | AA ID | NT/LN | AA/LN | Score | P-Value |
|---|---|---|---|---|---|---|
| SPX1154 | 1154 | 3815 | 1116 | 372 | 1670 | 1.30E-226 |

Description

[GI:7380122] [LN:NMA5Z2491] [AC:AL162756:AL157959] [PN:hypothetical protein NMA1473] [GN:NMA1473] [OR:Neisseria meningitidis]

| ORF Name | NT ID | AA ID | NT LN | AA LN | Score | P-Value |
|---|---|---|---|---|---|---|
| SPX1155 | 1155 | 3816 | 447 | 149 | | |

Description

NO-HIT

| ORF Name | NT ID | AA ID | NT LN | AA LN | Score | P-Value |
|---|---|---|---|---|---|---|
| SPX1156 | 1156 | 3817 | 1305 | 435 | 2119 | 6.30E-286 |

Description

[GI:5263171] [LN:AB029313] [AC:AB029313] [PN:enolase] [GN:eno]
[OR:Streptococcus intermedius] [SR:Streptococcus intermedius (strain:ATCC 27335) DNA]

| ORF Name | NT ID | AA ID | NT LN | AA LN | Score | P-Value |
|---|---|---|---|---|---|---|
| SPX1157 | 1157 | 3818 | 468 | 156 | 74 | 6.80E-09 |

Description

"[LN:T45116] [AC:T45116] [PN:phosphopyruvate hydratase, [imported]]
[OR:Schizosaccharomyces pombe] [EC:4.2.1.11]"

| ORF Name | NT ID | AA ID | NT LN | AA LN | Score | P-Value |
|---|---|---|---|---|---|---|
| SPX1158 | 1158 | 3819 | 132 | 44 | 75 | 2.00E-06 |

Description

[LN:B72477] [AC:B72477] [PN:hypothetical protein APE2459] [GN:APE2459]
[OR:Aeropyrum pernix]

| ORF Name | NT ID | AA ID | NT LN | AA LN | Score | P-Value |
|---|---|---|---|---|---|---|
| SPX1159 | 1159 | 3820 | 507 | 169 | 174 | 3.60E-16 |

Description

[GI:6782411] [LN:STH243106] [AC:AJ243106] [PN:integrase] [GN:int]
[OR:Streptococcus thermophilus]

| ORF Name | NT ID | AA ID | NT LN | AA LN | Score | P-Value |
|---|---|---|---|---|---|---|
| SPX1160 | 1160 | 3821 | 339 | 113 | 556 | 6.20E-74 |

Description

[GI:5019553] [LN:SPN239004] [AC:AJ239004] [PN:putative transposase]
[OR:Streptococcus pneumoniae]

| ORF_Name | NT ID | AA ID | NT/LN | AA/LN | Score | P-Value |
|---|---|---|---|---|---|---|
| SPX1161 | 1161 | 3822 | 348 | 116 | 573 | 1.80E-75 |

Description

[GI:4200438] [LN:AF026471] [AC:AF026471] [PN:putative transposase] [OR:Streptococcus pneumoniae]

| ORF_Name | NT ID | AA ID | NT/LN | AA/LN | Score | P-Value |
|---|---|---|---|---|---|---|
| SPX1162 | 1162 | 3823 | 3276 | 1092 | 315 | 2.90E-101 |

Description

[LN:T30307] [AC:T30307] [PN:rexB protein] [GN:rexB] [OR:Lactococcus lactis]

| ORF_Name | NT ID | AA ID | NT/LN | AA/LN | Score | P-Value |
|---|---|---|---|---|---|---|
| SPX1163 | 1163 | 3824 | 3651 | 1217 | 517 | 1.80E-246 |

Description

[LN:T30308] [AC:T30308] [PN:rexA protein] [OR:Lactococcus lactis]

| ORF_Name | NT ID | AA ID | NT/LN | AA/LN | Score | P-Value |
|---|---|---|---|---|---|---|
| SPX1164 | 1164 | 3825 | 237 | 79 | | |

Description

NO-HIT

| ORF_Name | NT ID | AA ID | NT/LN | AA/LN | Score | P-Value |
|---|---|---|---|---|---|---|
| SPX1165 | 1165 | 3826 | 192 | 64 | 205 | 2.00E-24 |

Description

[LN:T30285] [AC:T30285] [PN:hypothetical protein] [OR:Streptococcus pneumoniae]

| ORF_Name | NT ID | AA ID | NT/LN | AA/LN | Score | P-Value |
|---|---|---|---|---|---|---|
| SPX1166 | 1166 | 3827 | 1179 | 393 | | |

Description

NO-HIT

| ORF Name | NT ID | AA ID | NT LN | AA LN | Score | P-Value |
|---|---|---|---|---|---|---|
| SPX1167 | 1167 | 3828 | 333 | 111 | | |

Description

NO-HIT

| ORF Name | NT ID | AA ID | NT LN | AA LN | Score | P-Value |
|---|---|---|---|---|---|---|
| SPX1168 | 1168 | 3829 | 5898 | 1966 | 7485 | 0 |

Description

[GI:1213494] [LN:SPU47687] [AC:U47687] [PN:immunoglobulin A1 protease] [GN:iga] [OR:Streptococcus pneumoniae] [SR:Streptococcus pneumoniae strain=R6]

| ORF Name | NT ID | AA ID | NT LN | AA LN | Score | P-Value |
|---|---|---|---|---|---|---|
| SPX1169 | 1169 | 3830 | 228 | 76 | 138 | 8.00E-12 |

Description

[GI:6911257] [LN:AF221126] [AC:AF221126] [PN:putative zinc metalloprotease] [GN:zmpB] [OR:Streptococcus pneumoniae]

| ORF Name | NT ID | AA ID | NT LN | AA LN | Score | P-Value |
|---|---|---|---|---|---|---|
| SPX1170 | 1170 | 3831 | 852 | 284 | 707 | 2.50E-96 |

Description

[LN:F69880] [AC:F69880] [PN:conserved hypothetical protein ylqF] [GN:ylqF] [CL:conserved hypothetical protein MG442] [OR:Bacillus subtilis]

| ORF Name | NT ID | AA ID | NT LN | AA LN | Score | P-Value |
|---|---|---|---|---|---|---|
| SPX1171 | 1171 | 3832 | 780 | 260 | 615 | 3.40E-79 |

Description

[LN:C69693] [AC:C69693] [PN:ribonuclease H rnh] [GN:rnh] [CL:ribonuclease HII] [OR:Bacillus subtilis]

| ORF Name | NT ID | AA ID | NT LN | AA LN | Score | P-Value |
|---|---|---|---|---|---|---|
| SPX1172 | 1172 | 3833 | 1551 | 517 | 261 | 1.40E-51 |

Description

[LN:YADQ_ECOLI] [AC:P37019:P77394] [GN:YADQ] [OR:Escherichia coli] [DE:HYPOTHETICAL 46.0 KD PROTEIN IN HEML-PFS INTERGENIC REGION] [SP:P37019:P77394]

| ORF Name | NT ID | AA ID | NT/LN | AA/LN | Score | P-Value |
|---|---|---|---|---|---|---|
| SPX1173 | 1173 | 3834 | 1071 | 357 | 1529 | 9.60E-206 |
| Description | | | | | | |

[GI:3152920] [LN:AF065141] [AC:AF065141] [PN:unknown] [OR:Streptococcus mutans]

| ORF Name | NT ID | AA ID | NT/LN | AA/LN | Score | P-Value |
|---|---|---|---|---|---|---|
| SPX1174 | 1174 | 3835 | 990 | 330 | 577 | 6.60E-108 |
| Description | | | | | | |

[LN:G69830] [AC:G69830] [PN:lipoate-protein ligase homolog yhfJ] [GN:yhfJ] [CL:lipoate-protein ligase] [OR:Bacillus subtilis]

| ORF Name | NT ID | AA ID | NT/LN | AA/LN | Score | P-Value |
|---|---|---|---|---|---|---|
| SPX1175 | 1175 | 3836 | 1704 | 568 | 334 | 6.80E-104 |
| Description | | | | | | |

[LN:I40794] [AC:I40794] [PN:dihydrolipoamide dehydrogenase] [OR:Clostridium magnum] [EC:1.8.1.4]

| ORF Name | NT ID | AA ID | NT/LN | AA/LN | Score | P-Value |
|---|---|---|---|---|---|---|
| SPX1176 | 1176 | 3837 | 1128 | 376 | 366 | 8.20E-70 |
| Description | | | | | | |

"[LN:I40793] [AC:I40793] [PN:dihydrolipoamide S-acetyltransferase,] [CL:dihydrolipoamide acetyltransferase:lipoyl/biotin-binding homology] [OR:Clostridium magnum] [EC:2.3.1.12]"

| ORF Name | NT ID | AA ID | NT/LN | AA/LN | Score | P-Value |
|---|---|---|---|---|---|---|
| SPX1177 | 1177 | 3838 | 993 | 331 | 550 | 5.00E-108 |
| Description | | | | | | |

"[LN:I40791] [AC:I40791] [PN:acetoin dehydrogenase (TPP-dependent), beta chain] [CL:pyruvate dehydrogenase (lipoamide) beta chain] [OR:Clostridium magnum] [EC:1.-.-.-]"

| ORF Name | NT ID | AA ID | NT/LN | AA/LN | Score | P-Value |
|---|---|---|---|---|---|---|
| SPX1178 | 1178 | 3839 | 438 | 146 | | |
| Description | | | | | | |

NO-HIT

| ORF Name | NT ID | AA ID | NT/LN | AA/LN | Score | P-Value |
|---|---|---|---|---|---|---|
| SPX1179 | 1179 | 3840 | 312 | 104 | 136 | 6.90E-13 |

Description

[LN:G72548] [AC:G72548] [PN:hypothetical protein APE1675] [GN:APE1675] [OR:Aeropyrum pernix]

| ORF Name | NT ID | AA ID | NT/LN | AA/LN | Score | P-Value |
|---|---|---|---|---|---|---|
| SPX1180 | 1180 | 3841 | 969 | 323 | 554 | 6.20E-107 |

Description

"[LN:I40790] [AC:I40790] [PN:acetoin dehydrogenase (TPP-dependent), alpha chain] [CL:pyruvate dehydrogenase (lipoamide) alpha chain:thiamin pyrophosphate-binding domain homology] [OR:Clostridium magnum] [EC:1.-.-.-]"

| ORF Name | NT ID | AA ID | NT/LN | AA/LN | Score | P-Value |
|---|---|---|---|---|---|---|
| SPX1181 | 1181 | 3842 | 1362 | 454 | 482 | 2.40E-117 |

Description

[LN:F69906] [AC:F69906] [PN:conserved hypothetical protein yojI] [GN:yojI] [CL:conserved hypothetical protein HI1612] [OR:Bacillus subtilis]

| ORF Name | NT ID | AA ID | NT/LN | AA/LN | Score | P-Value |
|---|---|---|---|---|---|---|
| SPX1182 | 1182 | 3843 | 261 | 87 | | |

Description

NO-HIT

| ORF Name | NT ID | AA ID | NT/LN | AA/LN | Score | P-Value |
|---|---|---|---|---|---|---|
| SPX1183 | 1183 | 3844 | 1269 | 423 | 351 | 1.70E-86 |

Description

"[LN:PYRC_LACLE] [AC:P48795] [GN:PYRC] [OR:Lactobacillus leichmannii] [EC:3.5.2.3] [DE:DIHYDROOROTASE, (DHOASE)] [SP:P48795]"

| ORF Name | NT ID | AA ID | NT/LN | AA/LN | Score | P-Value |
|---|---|---|---|---|---|---|
| SPX1184 | 1184 | 3845 | 465 | 155 | 845 | 7.70E-113 |

Description

"[LN:MUTX_STRPN] [AC:P41354] [GN:MUTX] [OR:Streptococcus pneumoniae] [EC:3.6.1.-] [DE:(8-OXO-DGTPASE), (DGTP PYROPHOSPHOHYDROLASE)] [SP:P41354]"

| ORF_Name | NT_ID | AA_ID | NT/LN | AA/LN | Score | P-Value |
|---|---|---|---|---|---|---|
| SPX1185 | 1185 | 3846 | 666 | 222 | 1123 | 8.50E-151 |

Description

"[LN:UNG_STRPN] [AC:P23379] [GN:UNG] [OR:Streptococcus pneumoniae] [EC:3.2.2.-] [DE:URACIL-DNA GLYCOSYLASE, (UDG)] [SP:P23379]"

| ORF_Name | NT_ID | AA_ID | NT/LN | AA/LN | Score | P-Value |
|---|---|---|---|---|---|---|
| SPX1186 | 1186 | 3847 | 603 | 201 | | |

Description

NO-HIT

| ORF_Name | NT_ID | AA_ID | NT/LN | AA/LN | Score | P-Value |
|---|---|---|---|---|---|---|
| SPX1187 | 1187 | 3848 | 714 | 238 | 260 | 5.40E-57 |

Description

[LN:E69814] [AC:E69814] [PN:conserved hypothetical protein yfnB] [GN:yfnB] [CL:Alcaligenes eutrophus phosphoglycolate phosphatase] [OR:Bacillus subtilis]

| ORF_Name | NT_ID | AA_ID | NT/LN | AA/LN | Score | P-Value |
|---|---|---|---|---|---|---|
| SPX1188 | 1188 | 3849 | 228 | 76 | 66 | 1.60E-05 |

Description

[LN:H75623] [AC:H75623] [PN:conserved hypothetical protein] [GN:DRB0052] [OR:Deinococcus radiodurans]

| ORF_Name | NT_ID | AA_ID | NT/LN | AA/LN | Score | P-Value |
|---|---|---|---|---|---|---|
| SPX1189 | 1189 | 3850 | 2556 | 852 | 412 | 3.10E-104 |

Description

[LN:T46758] [AC:T46758] [PN:hypothetical protein [imported]] [OR:Streptococcus agalactiae]

| ORF_Name | NT_ID | AA_ID | NT/LN | AA/LN | Score | P-Value |
|---|---|---|---|---|---|---|
| SPX1190 | 1190 | 3851 | 2490 | 830 | 397 | 3.60E-100 |

Description

[LN:T46758] [AC:T46758] [PN:hypothetical protein [imported]] [OR:Streptococcus agalactiae]

| ORF Name | NT ID | AA ID | NT LN | AA LN | Score | P-Value |
|---|---|---|---|---|---|---|
| SPX1191 | 1191 | 3852 | 1233 | 411 | 1763 | 4.80E-237 |

Description

[GI:4958916] [LN:AB027569] [AC:AB027569] [PN:phosphoenolpyruvate-protein phosphotransferase] [GN:ptsI] [OR:Streptococcus bovis] [SR:Streptococcus bovis (strain:JB1) DNA]

| ORF Name | NT ID | AA ID | NT LN | AA LN | Score | P-Value |
|---|---|---|---|---|---|---|
| SPX1192 | 1192 | 3853 | 138 | 46 | 144 | 1.50E-15 |

Description

[LN:YKXH_BACSU] [AC:P08876] [GN:YKXH] [OR:Bacillus subtilis]
[DE:HYPOTHETICAL 7.4 KD PROTEIN IN PTSX OPERON (PROTEIN K)] [SP:P08876]

| ORF Name | NT ID | AA ID | NT LN | AA LN | Score | P-Value |
|---|---|---|---|---|---|---|
| SPX1193 | 1193 | 3854 | 264 | 88 | 402 | 2.30E-50 |

Description

[LN:PTHP_STRMU] [AC:P45596] [GN:PTSH] [OR:Streptococcus mutans]
[DE:PHOSPHOCARRIER PROTEIN HPR (HISTIDINE-CONTAINING PROTEIN)] [SP:P45596]

| ORF Name | NT ID | AA ID | NT LN | AA LN | Score | P-Value |
|---|---|---|---|---|---|---|
| SPX1194 | 1194 | 3855 | 219 | 73 | 233 | 1.50E-27 |

Description

"[LN:NRDH_LACLC] [AC:Q48708] [GN:NRDH] [OR:Lactococcus lactis]
[SR:,subspcremoris:Streptococcus cremoris] [DE:GLUTAREDOXIN-LIKE PROTEIN NRDH] [SP:Q48708]"

| ORF Name | NT ID | AA ID | NT LN | AA LN | Score | P-Value |
|---|---|---|---|---|---|---|
| SPX1195 | 1195 | 3856 | 2160 | 720 | 1042 | 2.20E-255 |

Description

[GI:3077613] [LN:CANRDFGEN] [AC:Y09572] [PN:ribonucleotide reductase subunit R1E] [GN:nrdE] [OR:Corynebacterium ammoniagenes]

| ORF Name | NT ID | AA ID | NT LN | AA LN | Score | P-Value |
|---|---|---|---|---|---|---|
| SPX1196 | 1196 | 3857 | 189 | 63 | | |

Description

NO-HIT

| ORF Name | NT ID | AA ID | NT/LN | AA/LN | Score | P-Value |
|---|---|---|---|---|---|---|
| SPX1197 | 1197 | 3858 | 963 | 321 | 818 | 2.90E-116 |

Description

[GI:3068719] [LN:AF050168] [AC:AF050168] [PN:ribonucleoside diphosphate reductase small] [GN:nrdF] [OR:Corynebacterium ammoniagenes]

| ORF Name | NT ID | AA ID | NT/LN | AA/LN | Score | P-Value |
|---|---|---|---|---|---|---|
| SPX1198 | 1198 | 3859 | 762 | 254 | 371 | 2.50E-80 |

Description

"[LN:LACR_LACLA] [AC:P18816] [GN:LACR] [OR:Lactococcus lactis] [SR:,subsplactis:Streptococcus lactis] [DE:LACTOSE PHOSPHOTRANSFERASE SYSTEM REPRESSOR] [SP:P18816]"

| ORF Name | NT ID | AA ID | NT/LN | AA/LN | Score | P-Value |
|---|---|---|---|---|---|---|
| SPX1199 | 1199 | 3860 | 252 | 84 | | |

Description

NO-HIT

| ORF Name | NT ID | AA ID | NT/LN | AA/LN | Score | P-Value |
|---|---|---|---|---|---|---|
| SPX1200 | 1200 | 3861 | 1416 | 472 | 2452 | 0 |

Description

"[LN:LACG_LACLA] [AC:P11546] [GN:LACG] [OR:Lactococcus lactis] [SR:,subsplactis:Streptococcus lactis] [EC:3.2.1.85] [DE:GALACTOHYDROLASE) (PGALASE) (P-BETA-GAL) (PBG)] [SP:P11546]"

| ORF Name | NT ID | AA ID | NT/LN | AA/LN | Score | P-Value |
|---|---|---|---|---|---|---|
| SPX1201 | 1201 | 3862 | 1695 | 565 | 1628 | 4.50E-299 |

Description

"[LN:PTLB_LACLA] [AC:P23531] [GN:LACE] [OR:Lactococcus lactis] [SR:,subsplactis:Streptococcus lactis] [EC:2.7.1.69] [DE:(EC 2.7.1.69) (EII-LAC)] [SP:P23531]"

| ORF Name | NT ID | AA ID | NT/LN | AA/LN | Score | P-Value |
|---|---|---|---|---|---|---|
| SPX1202 | 1202 | 3863 | 318 | 106 | 454 | 2.90E-58 |愉

Description

"[LN:PTLA_LACLA] [AC:P23532] [GN:LACF] [OR:Lactococcus lactis]
[SR:,subsplactis:Streptococcus lactis] [EC:2.7.1.69] [DE:(EC 2.7.1.69)
(EIII-LAC)] [SP:P23532]"

| ORF Name | NT ID | AA ID | NT/LN | AA/LN | Score | P-Value |
|---|---|---|---|---|---|---|
| SPX1203 | 1203 | 3864 | 837 | 279 | 487 | 1.40E-75 |

Description

[LN:LACT_LACCA] [AC:P24401] [GN:LACT] [OR:Lactobacillus casei]
[DE:TRANSCRIPTION ANTITERMINATOR LACT] [SP:P24401]

| ORF Name | NT ID | AA ID | NT/LN | AA/LN | Score | P-Value |
|---|---|---|---|---|---|---|
| SPX1204 | 1204 | 3865 | 810 | 270 | 1232 | 1.10E-164 |

Description

"[LN:LACD_LACLA] [AC:P26593] [GN:LACD] [OR:Lactococcus lactis]
[SR:,subsplactis:Streptococcus lactis] [EC:4.1.2.40] [DE:ALDOLASE)
(D-TAGATOSE-1,6-BISPHOSPHATE ALDOLASE)] [SP:P26593]"

| ORF Name | NT ID | AA ID | NT/LN | AA/LN | Score | P-Value |
|---|---|---|---|---|---|---|
| SPX1205 | 1205 | 3866 | 819 | 273 | 810 | 9.10E-118 |

Description

"[LN:LACC_LACLA] [AC:P23391] [GN:LACC] [OR:Lactococcus lactis]
[SR:,subsplactis:Streptococcus lactis] [EC:2.7.1.144]
[DE:TAGATOSE-6-PHOSPHATE KINASE, (PHOSPHOTAGATOKINASE)] [SP:P23391]"

| ORF Name | NT ID | AA ID | NT/LN | AA/LN | Score | P-Value |
|---|---|---|---|---|---|---|
| SPX1206 | 1206 | 3867 | 489 | 163 | | |

Description

NO-HIT

| ORF Name | NT ID | AA ID | NT/LN | AA/LN | Score | P-Value |
|---|---|---|---|---|---|---|
| SPX1207 | 1207 | 3868 | 516 | 172 | 810 | 5.00E-108 |

Description

"[LN:LACB_LACLA] [AC:P23495] [GN:LACB] [OR:Lactococcus lactis]
[SR:,subsplactis:Streptococcus lactis] [EC:5.3.1.26]
[DE:GALACTOSE-6-PHOSPHATE ISOMERASE LACB SUBUNIT,] [SP:P23495]"

| ORF Name | NT ID | AA ID | NT/LN | AA/LN | Score | P-Value |
|---|---|---|---|---|---|---|
| SPX1208 | 1208 | 3869 | 426 | 142 | 612 | 2.90E-80 |

Description

"[LN:LACA_LACLA] [AC:P23494] [GN:LACA] [OR:Lactococcus lactis]
[SR:,subsplactis:Streptococcus lactis] [EC:5.3.1.26]
[DE:GALACTOSE-6-PHOSPHATE ISOMERASE LACA SUBUNIT,] [SP:P23494]"

| ORF Name | NT ID | AA ID | NT/LN | AA/LN | Score | P-Value |
|---|---|---|---|---|---|---|
| SPX1209 | 1209 | 3870 | 291 | 97 | 57 | 0.00024 |

Description

[GI:712785] [LN:S74218] [AC:S74218] [GN:E9] [OR:reindeer papillomavirus]

| ORF Name | NT ID | AA ID | NT/LN | AA/LN | Score | P-Value |
|---|---|---|---|---|---|---|
| SPX1210 | 1210 | 3871 | 477 | 159 | 507 | 1.70E-65 |

Description

"[LN:LAXP_LACLA] [AC:P23496] [GN:LACX] [OR:Lactococcus lactis]
[SR:,subsplactis:Streptococcus lactis] [DE:LACX PROTEIN, PLASMID]
[SP:P23496]"

| ORF Name | NT ID | AA ID | NT/LN | AA/LN | Score | P-Value |
|---|---|---|---|---|---|---|
| SPX1211 | 1211 | 3872 | 621 | 207 | 374 | 1.20E-65 |

Description

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1212 | 1212 | 3873 | 321 | 107 | 193 | 4.90E-21 |

Description

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1213 | 1213 | 3874 | 303 | 101 | | |
| Description | | | | | | |

NO-HIT

| ORF Name | NT ID | AA ID | NT/LN | AA/LN | Score | P-Value |
|---|---|---|---|---|---|---|
| SPX1214 | 1214 | 3875 | 444 | 148 | 88 | 1.30E-10 |
| Description | | | | | | |

"[GI:4512375] [LN:AB011837] [AC:AB011837] [PN:phosphotransferase system (PTS)] [GN:fruA] [OR:Bacillus halodurans] [SR:Bacillus halodurans (strain:C-125) DNA, clone_lib:lambda no.9]"

| ORF Name | NT ID | AA ID | NT/LN | AA/LN | Score | P-Value |
|---|---|---|---|---|---|---|
| SPX1215 | 1215 | 3876 | 1293 | 431 | 2159 | 2.90E-302 |
| Description | | | | | | |

[GI:2804700] [LN:AF030361] [AC:AF030361] [PN:transposase] [OR:Streptococcus pneumoniae]

| ORF Name | NT ID | AA ID | NT/LN | AA/LN | Score | P-Value |
|---|---|---|---|---|---|---|
| SPX1216 | 1216 | 3877 | 189 | 63 | 120 | 2.10E-12 |
| Description | | | | | | |

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX1217 | 1217 | 3878 | 1251 | 417 | 1395 | 2.00E-200 |
| Description | | | | | | |

"[LN:THD1_LACLA] [AC:Q02145] [GN:ILVA] [OR:Lactococcus lactis] [SR:,subsplactis:Streptococcus lactis] [EC:4.2.1.16] [DE:DEAMINASE)] [SP:Q02145]"

| ORF Name | NT ID | AA ID | NT/LN | AA/LN | Score | P-Value |
|---|---|---|---|---|---|---|
| SPX1218 | 1218 | 3879 | 357 | 119 | | |
| Description | | | | | | |

NO-HIT

| ORF Name | NT ID | AA ID | NT LN | AA LN | Score | P-Value |
|---|---|---|---|---|---|---|
| SPX1219 | 1219 | 3880 | 234 | 78 | | |谢
| Description | | | | | | |

NO-HIT

| ORF Name | NT ID | AA ID | NT LN | AA LN | Score | P-Value |
|---|---|---|---|---|---|---|
| SPX1220 | 1220 | 3881 | 267 | 89 | | |
| Description | | | | | | |

NO-HIT

| ORF Name | NT ID | AA ID | NT LN | AA LN | Score | P-Value |
|---|---|---|---|---|---|---|
| SPX1221 | 1221 | 3882 | 1023 | 341 | 1329 | 9.50E-179 |
| Description | | | | | | |

"[LN:ILVC_LACLA] [AC:Q02138] [GN:ILVC] [OR:Lactococcus lactis]
[SR:,subsplactis:Streptococcus lactis] [EC:1.1.1.86] [DE:ISOMEROREDUCTASE)
(ALPHA-KETO-BETA-HYDROXYLACIL REDUCTOISOMERASE)] [SP:Q02138]"

| ORF Name | NT ID | AA ID | NT LN | AA LN | Score | P-Value |
|---|---|---|---|---|---|---|
| SPX1222 | 1222 | 3883 | 501 | 167 | 477 | 4.10E-62 |
| Description | | | | | | |

"[LN:ILVN_LACLA] [AC:Q02140] [GN:ILVN] [OR:Lactococcus lactis]
[SR:,subsplactis:Streptococcus lactis] [EC:4.1.3.18] [DE:(ACETOHYDROXY-ACID
SYNTHASE SMALL SUBUNIT) (ALS)] [SP:Q02140]"

| ORF Name | NT ID | AA ID | NT LN | AA LN | Score | P-Value |
|---|---|---|---|---|---|---|
| SPX1223 | 1223 | 3884 | 1701 | 567 | 1207 | 2.30E-266 |
| Description | | | | | | |

"[LN:ILVB_LACLA] [AC:Q02137] [GN:ILVB] [OR:Lactococcus lactis]
[SR:,subsplactis:Streptococcus lactis] [EC:4.1.3.18] [DE:(ACETOHYDROXY-ACID
SYNTHASE LARGE SUBUNIT) (ALS)] [SP:Q02137]"

| ORF Name | NT ID | AA ID | NT LN | AA LN | Score | P-Value |
|---|---|---|---|---|---|---|
| SPX1224 | 1224 | 3885 | 2037 | 679 | 565 | 7.80E-167 |
| Description | | | | | | |

[LN:E69879] [AC:E69879] [PN:conserved hypothetical protein yloV] [GN:yloV]
[CL:Mycoplasma genitalium hypothetical protein MG369] [OR:Bacillus subtilis]

| ORF Name | NT ID | AA ID | NT/LN | AA/LN | Score | P-Value |
|---|---|---|---|---|---|---|
| SPX1225 | 1225 | 3886 | 189 | 63 | 222 | 4.40E-26 |

Description

[LN:RL28_BACSU] [AC:P37807] [GN:RPMB] [OR:Bacillus subtilis] [DE:50S RIBOSOMAL PROTEIN L28] [SP:P37807]

| ORF Name | NT ID | AA ID | NT/LN | AA/LN | Score | P-Value |
|---|---|---|---|---|---|---|
| SPX1226 | 1226 | 3887 | 246 | 82 | 123 | 5.10E-19 |

Description

[GI:6760462] [LN:AF224467] [AC:AF224467] [PN:putative glycosyl transferase] [OR:Haemophilus ducreyi]

| ORF Name | NT ID | AA ID | NT/LN | AA/LN | Score | P-Value |
|---|---|---|---|---|---|---|
| SPX1227 | 1227 | 3888 | 198 | 66 | 157 | 8.80E-16 |

Description

[GI:6760462] [LN:AF224467] [AC:AF224467] [PN:putative glycosyl transferase] [OR:Haemophilus ducreyi]

| ORF Name | NT ID | AA ID | NT/LN | AA/LN | Score | P-Value |
|---|---|---|---|---|---|---|
| SPX1228 | 1228 | 3889 | 1545 | 515 | 771 | 2.70E-216 |

Description

[GI:3256222] [LN:SAY14370] [AC:Y14370] [PN:peptide chain release factor 3] [GN:RF3] [OR:Staphylococcus aureus]

| ORF Name | NT ID | AA ID | NT/LN | AA/LN | Score | P-Value |
|---|---|---|---|---|---|---|
| SPX1229 | 1229 | 3890 | 303 | 101 | 190 | 4.90E-21 |

Description

[LN:A69795] [AC:A69795] [PN:conserved hypothetical protein yerL] [GN:yerL] [CL:probable glu-tRNA amidotransferase C chain] [OR:Bacillus subtilis]

| ORF Name | NT ID | AA ID | NT/LN | AA/LN | Score | P-Value |
|---|---|---|---|---|---|---|
| SPX1230 | 1230 | 3891 | 1467 | 489 | 1333 | 1.60E-186 |

Description

[LN:B69795] [AC:B69795] [PN:amidase homolog yerM] [GN:yerM] [CL:indoleacetamide hydrolase] [OR:Bacillus subtilis]

| ORF Name | NT ID | AA ID | NT LN | AA LN | Score | P-Value |
|---|---|---|---|---|---|---|
| SPX1231 | 1231 | 3892 | 639 | 213 | 414 | 4.30E-94 |

Description

[LN:T44293] [AC:T44293] [PN:hypothetical protein yerN [imported]] [CL:PET112 protein] [OR:Bacillus halodurans]

| ORF Name | NT ID | AA ID | NT LN | AA LN | Score | P-Value |
|---|---|---|---|---|---|---|
| SPX1232 | 1232 | 3893 | 807 | 269 | 744 | 4.60E-97 |

Description

[LN:C69795] [AC:C69795] [PN:pet112-like protein homolog yerN] [GN:yerN] [CL:PET112 protein] [OR:Bacillus subtilis]

| ORF Name | NT ID | AA ID | NT LN | AA LN | Score | P-Value |
|---|---|---|---|---|---|---|
| SPX1233 | 1233 | 3894 | 1044 | 348 | 719 | 1.70E-145 |

Description

"[LN:H69789] [AC:H69789] [PN:L-iditol 2-dehydrogenase, homolog ydjL:sorbitol dehydrogenase homolog] [GN:ydjL] [CL:alcohol dehydrogenase:long-chain alcohol dehydrogenase homology] [OR:Bacillus subtilis] [EC:1.1.1.14]"

| ORF Name | NT ID | AA ID | NT LN | AA LN | Score | P-Value |
|---|---|---|---|---|---|---|
| SPX1234 | 1234 | 3895 | 201 | 67 | 138 | 4.80E-14 |

Description

[LN:T30285] [AC:T30285] [PN:hypothetical protein] [OR:Streptococcus pneumoniae]

| ORF Name | NT ID | AA ID | NT LN | AA LN | Score | P-Value |
|---|---|---|---|---|---|---|
| SPX1235 | 1235 | 3896 | 561 | 187 | 430 | 7.10E-54 |

Description

[LN:EFP_BACSU] [AC:P49778] [GN:EFP] [OR:Bacillus subtilis] [DE:ELONGATION FACTOR P (EF-P)] [SP:P49778]

| ORF Name | NT ID | AA ID | NT LN | AA LN | Score | P-Value |
|---|---|---|---|---|---|---|
| SPX1236 | 1236 | 3897 | 390 | 130 | 139 | 8.30E-19 |

Description

[LN:YQHY_BACSU] [AC:P54519] [GN:YQHY] [OR:Bacillus subtilis] [DE:HYPOTHETICAL 14.7 KD PROTEIN IN ACCC-FOLD INTERGENIC REGION] [SP:P54519]

| ORF Name | NT ID | AA ID | NT LN | AA LN | Score | P-Value |
|---|---|---|---|---|---|---|
| SPX1237 | 1237 | 3898 | 423 | 141 | 105 | 1.00E-12 |

Description

[GI:6580774] [LN:AF088897] [AC:AF088897:AF034613:AF086792:U63733]
[PN:N-utilization substance protein B] [GN:nusB] [OR:Zymomonas mobilis]

| ORF Name | NT ID | AA ID | NT LN | AA LN | Score | P-Value |
|---|---|---|---|---|---|---|
| SPX1238 | 1238 | 3899 | 570 | 190 | 948 | 7.40E-131 |

Description

[GI:663279] [LN:STRCOMAA] [AC:M36180:L15190] [PN:transposase]
[OR:Streptococcus pneumoniae] [SR:Streptococcus pneumoniae (strain RX1) DNA]

| ORF Name | NT ID | AA ID | NT LN | AA LN | Score | P-Value |
|---|---|---|---|---|---|---|
| SPX1239 | 1239 | 3900 | 783 | 261 | 1075 | 1.10E-148 |

Description

[GI:2804700] [LN:AF030361] [AC:AF030361] [PN:transposase] [OR:Streptococcus pneumoniae]

| ORF Name | NT ID | AA ID | NT LN | AA LN | Score | P-Value |
|---|---|---|---|---|---|---|
| SPX1240 | 1240 | 3901 | 834 | 278 | 80 | 9.90E-07 |

Description

[LN:E69787] [AC:E69787] [PN:hypothetical protein ydiL] [GN:ydiL]
[OR:Bacillus subtilis]

| ORF Name | NT ID | AA ID | NT LN | AA LN | Score | P-Value |
|---|---|---|---|---|---|---|
| SPX1241 | 1241 | 3902 | 252 | 84 | | |

Description

NO-HIT

| ORF Name | NT ID | AA ID | NT LN | AA LN | Score | P-Value |
|---|---|---|---|---|---|---|
| SPX1242 | 1242 | 3903 | 768 | 256 | 653 | 4.10E-90 |

Description

[GI:285621] [LN:BACPK] [AC:D13095] [PN:undefined open reading frame]
[OR:Bacillus stearothermophilus] [SR:Bacillus stearothermophilus
(strain:NCA1503) DNA]

| ORF Name | NT ID | AA ID | NT/LN | AA/LN | Score | P-Value |
|---|---|---|---|---|---|---|
| SPX1243 | 1243 | 3904 | 864 | 288 | 602 | 2.20E-92 |

Description

"[LN:ACCD_SYNP7] [AC:Q54776] [GN:ACCD] [OR:Synechococcus sp] [SR:,strain PCC 7942:Anacystis nidulans R2] [EC:6.4.1.2] [DE:(EC 6.4.1.2) (ACCASE BETA CHAIN)] [SP:Q54776]"

| ORF Name | NT ID | AA ID | NT/LN | AA/LN | Score | P-Value |
|---|---|---|---|---|---|---|
| SPX1244 | 1244 | 3905 | 1368 | 456 | 1101 | 1.50E-181 |

Description

[LN:A69581] [AC:A69581] [PN:acetyl-CoA carboxylase (biotin carboxylase subunit) accC] [GN:accC] [CL:biotin carboxylase:biotin carboxylase homology] [OR:Bacillus subtilis]

| ORF Name | NT ID | AA ID | NT/LN | AA/LN | Score | P-Value |
|---|---|---|---|---|---|---|
| SPX1245 | 1245 | 3906 | 423 | 141 | 299 | 1.60E-49 |

Description

"[LN:D70065] [AC:D70065] [PN:(3R)-hydroxymyristoyl-[acyl carrier protein] dehydratase, ywpB] [GN:ywpB] [CL:(3R)-hydroxymyristoyl-[acyl carrier protein] dehydratase] [OR:Bacillus subtilis] [EC:4.2.1.-]"

| ORF Name | NT ID | AA ID | NT/LN | AA/LN | Score | P-Value |
|---|---|---|---|---|---|---|
| SPX1246 | 1246 | 3907 | 486 | 162 | 248 | 1.10E-34 |

Description

"[LN:C75558] [AC:C75558] [PN:acetyl-CoA carboxylase, bitoin carboxyl carrier protein] [GN:DR0118] [CL:biotin carboxyl carrier protein:lipoyl/biotin-binding homology] [OR:Deinococcus radiodurans]"

| ORF Name | NT ID | AA ID | NT/LN | AA/LN | Score | P-Value |
|---|---|---|---|---|---|---|
| SPX1247 | 1247 | 3908 | 279 | 93 | 134 | 1.30E-13 |

Description

[LN:FAB2_MYCTU] [AC:Q10525] [GN:RV2246:MTCY427.27] [OR:Mycobacterium tuberculosis] [EC:2.3.1.41] [DE:(BETA-KETOACYL-ACP SYNTHASE 2) (KAS 2)] [SP:Q10525]

| ORF Name | NT ID | AA ID | NT/LN | AA/LN | Score | P-Value |
|---|---|---|---|---|---|---|
| SPX1248 | 1248 | 3909 | 1080 | 360 | 477 | 2.60E-113 |

Description

"[LN:S77464] [AC:S77464] [PN:3-oxoacyl-[acyl-carrier-protein] synthase, beta chain:beta ketoacyl-acyl carrier protein synthase:protein sll1069:beta ketoacyl-acyl carrier protein synthase:protein sll1069] [GN:fabF] [OR:Synechocystis sp.]"

| ORF Name | NT ID | AA ID | NT/LN | AA/LN | Score | P-Value |
|---|---|---|---|---|---|---|
| SPX1249 | 1249 | 3910 | 732 | 244 | 482 | 2.10E-76 |

Description

[LN:FABG_CUPLA] [AC:P28643] [GN:CLKR27] [OR:Cuphea lanceolata] [EC:1.1.1.100] [DE:(3-KETOACYL-ACYL CARRIER PROTEIN REDUCTASE)] [SP:P28643]

| ORF Name | NT ID | AA ID | NT/LN | AA/LN | Score | P-Value |
|---|---|---|---|---|---|---|
| SPX1250 | 1250 | 3911 | 222 | 74 | 81 | 9.50E-05 |

Description

[LN:H72482] [AC:H72482] [PN:hypothetical protein APE2504] [GN:APE2504] [OR:Aeropyrum pernix]

| ORF Name | NT ID | AA ID | NT/LN | AA/LN | Score | P-Value |
|---|---|---|---|---|---|---|
| SPX1251 | 1251 | 3912 | 921 | 307 | 374 | 1.00E-85 |

Description

"[LN:B41856] [AC:B41856:A42147:S20443:A64853] [PN:[acyl-carrier-protein] S-malonyltransferase,] [GN:fabD:tfpA] [CL:[acyl-carrier-protein] S-malonyltransferase:[acyl-carrier-protein] S-malonyltransferase homology] [OR:Escherichia coli] [EC:2.3.1.39]"

| ORF Name | NT ID | AA ID | NT/LN | AA/LN | Score | P-Value |
|---|---|---|---|---|---|---|
| SPX1252 | 1252 | 3913 | 975 | 325 | 681 | 5.90E-101 |

Description

[LN:A72335] [AC:A72335] [PN:conserved hypothetical protein] [GN:TM0800] [OR:Thermotoga maritima]

| ORF Name | NT ID | AA ID | NT/LN | AA/LN | Score | P-Value |
|---|---|---|---|---|---|---|
| SPX1253 | 1253 | 3914 | 225 | 75 | 80 | 1.80E-12 |

Description

[LN:ACP_BACSU] [AC:P80643:P51832] [GN:ACPA:ACPP] [OR:Bacillus subtilis]
[DE:ACYL CARRIER PROTEIN (ACP)] [SP:P80643:P51832]

| ORF Name | NT ID | AA ID | NT/LN | AA/LN | Score | P-Value |
|---|---|---|---|---|---|---|
| SPX1254 | 1254 | 3915 | 567 | 189 | 202 | 6.90E-38 |

Description

"[LN:S75457] [AC:S75457] [PN:beta-ketoacyl-acyl carrier protein synthase III:protein slr1511:protein slr1511] [GN:fabH]
[CL:3-oxoacyl-[acyl-carrier-protein] synthase III] [OR:Synechocystis sp.]
[SR:PCC 6803, , PCC 6803] [SR:PCC 6803, ]"

| ORF Name | NT ID | AA ID | NT/LN | AA/LN | Score | P-Value |
|---|---|---|---|---|---|---|
| SPX1255 | 1255 | 3916 | 420 | 140 | 269 | 1.30E-46 |

Description

[GI:7416010] [LN:AB025973] [AC:AB025973]
[PN:3-oxoacyl-[acyl-carrier-protein] synthase III] [GN:accS]
[OR:Lactobacillus plantarum] [SR:Lactobacillus plantarum (strain:L137) DNA]

| ORF Name | NT ID | AA ID | NT/LN | AA/LN | Score | P-Value |
|---|---|---|---|---|---|---|
| SPX1256 | 1256 | 3917 | 198 | 66 | | |

Description

NO-HIT

| ORF Name | NT ID | AA ID | NT/LN | AA/LN | Score | P-Value |
|---|---|---|---|---|---|---|
| SPX1257 | 1257 | 3918 | 435 | 145 | 139 | 5.00E-12 |

Description

[GI:4139249] [LN:AF110185] [AC:AF110185] [PN:unknown] [OR:Burkholderia pseudomallei]

| ORF Name | NT ID | AA ID | NT/LN | AA/LN | Score | P-Value |
|---|---|---|---|---|---|---|
| SPX1258 | 1258 | 3919 | 198 | 66 | | |

Description

NO-HIT

| ORF Name | NT ID | AA ID | NT/LN | AA/LN | Score | P-Value |
|---|---|---|---|---|---|---|
| SPX1259 | 1259 | 3920 | 294 | 98 | 138 | 7.10E-13 |

Description

[GI:3253198] [LN:AF029714] [AC:AF029714:Z71175] [PN:PhaB] [GN:phaB]
[OR:Pseudomonas putida]

| ORF Name | NT ID | AA ID | NT/LN | AA/LN | Score | P-Value |
|---|---|---|---|---|---|---|
| SPX1260 | 1260 | 3921 | 228 | 76 | 156 | 9.00E-18 |

Description

[GI:1914870] [LN:SPZ82001] [AC:Z82001] [PN:unknown] [OR:Streptococcus pneumoniae]

| ORF Name | NT ID | AA ID | NT/LN | AA/LN | Score | P-Value |
|---|---|---|---|---|---|---|
| SPX1261 | 1261 | 3922 | 1365 | 455 | 1240 | 6.10E-166 |

Description

[LN:A69763] [AC:A69763] [PN:homoserine dehydrogenase homolog yclM] [GN:yclM]
[CL:aspartate kinase:aspartate kinase homology] [OR:Bacillus subtilis]

| ORF Name | NT ID | AA ID | NT/LN | AA/LN | Score | P-Value |
|---|---|---|---|---|---|---|
| SPX1262 | 1262 | 3923 | 372 | 124 | 493 | 2.80E-64 |

Description

[GI:5669858] [LN:AF130465] [AC:AF130465] [PN:unknown] [GN:manO]
[OR:Streptococcus salivarius]

| ORF Name | NT ID | AA ID | NT/LN | AA/LN | Score | P-Value |
|---|---|---|---|---|---|---|
| SPX1263 | 1263 | 3924 | 1125 | 375 | 564 | 8.90E-141 |

Description

"[LN:SYS_BACSU] [AC:P37464] [GN:SERS] [OR:Bacillus subtilis] [EC:6.1.1.11]
[DE:SERYL-TRNA SYNTHETASE, (SERINE--TRNA LIGASE) (SERRS)] [SP:P37464]"

| ORF Name | NT ID | AA ID | NT/LN | AA/LN | Score | P-Value |
|---|---|---|---|---|---|---|
| SPX1264 | 1264 | 3925 | 273 | 91 | 101 | 6.30E-08 |

Description

"[LN:SYS_MYCGE] [AC:P47251] [GN:SERS:MG005] [OR:Mycoplasma genitalium]
[EC:6.1.1.11] [DE:SERYL-TRNA SYNTHETASE, (SERINE--TRNA LIGASE) (SERRS)]
[SP:P47251]"

| ORF Name | NT ID | AA ID | NT/LN | AA/LN | Score | P-Value |
|---|---|---|---|---|---|---|
| SPX1265 | 1265 | 3926 | 912 | 304 | | |

Description

NO-HIT

| ORF Name | NT ID | AA ID | NT/LN | AA/LN | Score | P-Value |
|---|---|---|---|---|---|---|
| SPX1266 | 1266 | 3927 | 207 | 69 | | |

Description

NO-HIT

| ORF Name | NT ID | AA ID | NT/LN | AA/LN | Score | P-Value |
|---|---|---|---|---|---|---|
| SPX1267 | 1267 | 3928 | 549 | 183 | 217 | 2.40E-57 |

Description

[GI:7379894] [LN:NMA4Z2491] [AC:AL162755:AL157959] [PN:hypothetical protein NMA1203] [GN:NMA1203] [OR:Neisseria meningitidis]

| ORF Name | NT ID | AA ID | NT/LN | AA/LN | Score | P-Value |
|---|---|---|---|---|---|---|
| SPX1268 | 1268 | 3929 | 1323 | 441 | 611 | 6.80E-118 |

Description

"[LN:D71327] [AC:D71327] [PN:probable D-alanine glycine permease (dagA)] [GN:TP0414] [CL:sodium-dependent D-alanine/glycine transport protein] [OR:Treponema pallidum subsp. pallidum] [SR:, syphilis spirochete]"

| ORF Name | NT ID | AA ID | NT/LN | AA/LN | Score | P-Value |
|---|---|---|---|---|---|---|
| SPX1269 | 1269 | 3930 | 2337 | 779 | 671 | 5.70E-155 |

Description

[LN:MUS2_BACSU] [AC:P94545] [GN:MUTS2] [OR:Bacillus subtilis] [DE:MUTS2 PROTEIN] [SP:P94545]

| ORF Name | NT ID | AA ID | NT/LN | AA/LN | Score | P-Value |
|---|---|---|---|---|---|---|
| SPX1270 | 1270 | 3931 | 753 | 251 | 175 | 7.10E-43 |

Description

[GI:6746427] [LN:AF179847] [AC:AF179847] [PN:putative transposase] [OR:Lactococcus lactis]

| ORF Name | NT ID | AA ID | NT LN | AA LN | Score | P-Value |
|---|---|---|---|---|---|---|
| SPX1271 | 1271 | 3932 | 195 | 65 | | |
| Description | | | | | | |

NO-HIT

| ORF Name | NT ID | AA ID | NT LN | AA LN | Score | P-Value |
|---|---|---|---|---|---|---|
| SPX1272 | 1272 | 3933 | 546 | 182 | 107 | 1.20E-15 |
| Description | | | | | | |

[GI:3849798] [LN:U91581] [AC:U91581:U04057] [PN:putative transposase]
[GN:tpase] [OR:Lactococcus lactis subsp. lactis]

| ORF Name | NT ID | AA ID | NT LN | AA LN | Score | P-Value |
|---|---|---|---|---|---|---|
| SPX1273 | 1273 | 3934 | 549 | 183 | 95 | 4.30E-13 |
| Description | | | | | | |

[LN:B69985] [AC:B69985] [PN:hypothetical protein yshB] [GN:yshB]
[OR:Bacillus subtilis]

| ORF Name | NT ID | AA ID | NT LN | AA LN | Score | P-Value |
|---|---|---|---|---|---|---|
| SPX1274 | 1274 | 3935 | 312 | 104 | | |
| Description | | | | | | |

NO-HIT

| ORF Name | NT ID | AA ID | NT LN | AA LN | Score | P-Value |
|---|---|---|---|---|---|---|
| SPX1275 | 1275 | 3936 | 882 | 294 | 1444 | 8.00E-194 |
| Description | | | | | | |

"[LN:RNH2_STRPN] [AC:O07874] [GN:RNHB] [OR:Streptococcus pneumoniae]
[EC:3.1.26.4] [DE:RIBONUCLEASE HII, (RNASE HII)] [SP:O07874]"

| ORF Name | NT ID | AA ID | NT LN | AA LN | Score | P-Value |
|---|---|---|---|---|---|---|
| SPX1276 | 1276 | 3937 | 615 | 205 | 1065 | 6.70E-145 |
| Description | | | | | | |

"[LN:LEP_STRPN] [AC:O07344] [GN:LEPB:SPI] [OR:Streptococcus pneumoniae]
[EC:3.4.21.89] [DE:SIGNAL PEPTIDASE I, (SPASE I) (LEADER PEPTIDASE I)]
[SP:O07344]"

| ORF Name | NT ID | AA ID | NT LN | AA LN | Score | P-Value |
|---|---|---|---|---|---|---|
| SPX1277 | 1277 | 3938 | 279 | 93 | | |

Description

NO-HIT

| ORF Name | NT ID | AA ID | NT LN | AA LN | Score | P-Value |
|---|---|---|---|---|---|---|
| SPX1278 | 1278 | 3939 | 2367 | 789 | 738 | 5.80E-165 |

Description

[LN:A69979] [AC:A69979] [PN:conjugation transfer protein homolog yrrC]
[GN:yrrC] [OR:Bacillus subtilis]

| ORF Name | NT ID | AA ID | NT LN | AA LN | Score | P-Value |
|---|---|---|---|---|---|---|
| SPX1279 | 1279 | 3940 | 1284 | 428 | 1691 | 1.40E-223 |

Description

[GI:3549287] [LN:AF073922] [AC:AF073922] [PN:RopA] [GN:ropA]
[OR:Streptococcus pyogenes]

| ORF Name | NT ID | AA ID | NT LN | AA LN | Score | P-Value |
|---|---|---|---|---|---|---|
| SPX1280 | 1280 | 3941 | 1137 | 379 | 1350 | 2.20E-182 |

Description

"[LN:MTLD_STRMU] [AC:Q02418] [GN:MTLD] [OR:Streptococcus mutans]
[EC:1.1.1.17] [DE:MANNITOL-1-PHOSPHATE 5-DEHYDROGENASE,] [SP:Q02418]"

| ORF Name | NT ID | AA ID | NT LN | AA LN | Score | P-Value |
|---|---|---|---|---|---|---|
| SPX1281 | 1281 | 3942 | 438 | 146 | 544 | 5.30E-71 |

Description

[LN:PTMA_STRMU] [AC:Q02420] [GN:MTLF] [OR:Streptococcus mutans]
[EC:2.7.1.69] [DE:(EC 2.7.1.69) (EIII-MTL)] [SP:Q02420]

| ORF Name | NT ID | AA ID | NT LN | AA LN | Score | P-Value |
|---|---|---|---|---|---|---|
| SPX1282 | 1282 | 3943 | 1956 | 652 | 392 | 1.00E-47 |

Description

[LN:YMTF_STRMU] [AC:Q02425] [OR:Streptococcus mutans] [DE:HYPOTHETICAL
PROTEIN IN MTLF 5'REGION (ORFX) (FRAGMENT)] [SP:Q02425]

| ORF Name | NT ID | AA ID | NT/LN | AA/LN | Score | P-Value |
|---|---|---|---|---|---|---|
| SPX1283 | 1283 | 3944 | 1788 | 596 | 1099 | 4.90E-194 |

Description

[LN:PTMB_BACST] [AC:P50852] [GN:MTLA] [OR:Bacillus stearothermophilus]
[EC:2.7.1.69] [DE:(EC 2.7.1.69) (EII-MTL)] [SP:P50852]

| ORF Name | NT ID | AA ID | NT/LN | AA/LN | Score | P-Value |
|---|---|---|---|---|---|---|
| SPX1284 | 1284 | 3945 | 201 | 67 | | |

Description

NO-HIT

| ORF Name | NT ID | AA ID | NT/LN | AA/LN | Score | P-Value |
|---|---|---|---|---|---|---|
| SPX1285 | 1285 | 3946 | 573 | 191 | 422 | 2.30E-53 |

Description

[LN:B30868] [AC:B30868] [PN:hypothetical protein 1] [OR:Streptococcus agalactiae]

| ORF Name | NT ID | AA ID | NT/LN | AA/LN | Score | P-Value |
|---|---|---|---|---|---|---|
| SPX1286 | 1286 | 3947 | 834 | 278 | 582 | 1.50E-140 |

Description

[LN:A33595] [AC:A33595:A30868] [PN:probable transposase] [CL:transposase IS3] [OR:Streptococcus agalactiae]

| ORF Name | NT ID | AA ID | NT/LN | AA/LN | Score | P-Value |
|---|---|---|---|---|---|---|
| SPX1287 | 1287 | 3948 | 1023 | 341 | 1142 | 5.00E-219 |

Description

[GI:1914875] [LN:SPZ82002] [AC:Z82002] [PN:PCPC] [GN:pcpC] [FN:unknown]
[OR:Streptococcus pneumoniae]

| ORF Name | NT ID | AA ID | NT/LN | AA/LN | Score | P-Value |
|---|---|---|---|---|---|---|
| SPX1288 | 1288 | 3949 | 294 | 98 | 194 | 3.40E-25 |

Description

[GI:4586910] [LN:AB017447] [AC:AB017447] [PN:protective antigen SpaA.1]
[OR:Erysipelothrix rhusiopathiae] [SR:Erysipelothrix rhusiopathiae
(strain:Fujisawa) DNA]

| ORF Name | NT ID | AA ID | NT/LN | AA/LN | Score | P-Value |
|---|---|---|---|---|---|---|
| SPX1289 | 1289 | 3950 | 657 | 219 | 104 | 1.50E-08 |

Description

[LN:S25140] [AC:S25140] [PN:serine proteinase homolog] [CL:staphylococcal serine proteinase] [OR:Enterococcus faecalis]

| ORF Name | NT ID | AA ID | NT/LN | AA/LN | Score | P-Value |
|---|---|---|---|---|---|---|
| SPX1290 | 1290 | 3951 | 240 | 80 | 296 | 8.20E-35 |

Description

[GI:1914874] [LN:SPZ82002] [AC:Z82002] [PN:unknown] [OR:Streptococcus pneumoniae]

| ORF Name | NT ID | AA ID | NT/LN | AA/LN | Score | P-Value |
|---|---|---|---|---|---|---|
| SPX1291 | 1291 | 3952 | 273 | 91 | 146 | 3.20E-14 |

Description

[GI:4584089] [LN:BAJ10128] [AC:AJ010128] [PN:DNA alkylation repair enzyme] [GN:alkD] [FN:complements DNA alkylation repair deficiency] [OR:Bacillus cereus]

| ORF Name | NT ID | AA ID | NT/LN | AA/LN | Score | P-Value |
|---|---|---|---|---|---|---|
| SPX1292 | 1292 | 3953 | 255 | 85 | 102 | 2.90E-08 |

Description

[GI:4584089] [LN:BAJ10128] [AC:AJ010128] [PN:DNA alkylation repair enzyme] [GN:alkD] [FN:complements DNA alkylation repair deficiency] [OR:Bacillus cereus]

| ORF Name | NT ID | AA ID | NT/LN | AA/LN | Score | P-Value |
|---|---|---|---|---|---|---|
| SPX1293 | 1293 | 3954 | 633 | 211 | 1040 | 1.50E-139 |

Description

[GI:5830527] [LN:SPAJ6393] [AC:AJ006393] [PN:response regulator] [GN:rr03] [OR:Streptococcus pneumoniae]

| ORF Name | NT ID | AA ID | NT/LN | AA/LN | Score | P-Value |
|---|---|---|---|---|---|---|
| SPX1294 | 1294 | 3955 | 996 | 332 | 1603 | 3.60E-220 |

Description

[GI:5830526] [LN:SPAJ6393] [AC:AJ006393] [PN:histidine kinase] [GN:hk03] [OR:Streptococcus pneumoniae]

| ORF Name | NT ID | AA ID | NT LN | AA LN | Score | P-Value |
|---|---|---|---|---|---|---|
| SPX1295 | 1295 | 3956 | 699 | 233 | 104 | 1.50E-11 |

Description

[LN:G70045] [AC:G70045] [PN:hypothetical protein yvqF] [GN:yvqF]
[OR:Bacillus subtilis]

| ORF Name | NT ID | AA ID | NT LN | AA LN | Score | P-Value |
|---|---|---|---|---|---|---|
| SPX1296 | 1296 | 3957 | 1011 | 337 | 151 | 6.20E-42 |

Description

[LN:D75084] [AC:D75084] [PN:carotenoid biosynthetic gene erwcrts related PAB1662] [GN:PAB1662] [CL:carotenoid biosynthesis protein homolog]
[OR:Pyrococcus abyssi]

| ORF Name | NT ID | AA ID | NT LN | AA LN | Score | P-Value |
|---|---|---|---|---|---|---|
| SPX1297 | 1297 | 3958 | 1008 | 336 | 67 | 0.00053 |

Description

"[LN:KIME_METJA] [AC:Q58487] [GN:MJ1087] [OR:Methanococcus jannaschii]
[EC:2.7.1.36] [DE:MEVALONATE KINASE, (MK)] [SP:Q58487]"

| ORF Name | NT ID | AA ID | NT LN | AA LN | Score | P-Value |
|---|---|---|---|---|---|---|
| SPX1298 | 1298 | 3959 | 1035 | 345 | 141 | 5.90E-28 |

Description

[GI:6625790] [LN:AF203779] [AC:AF203779] [PN:diphosphomevalonate decarboxylase MVD1] [GN:MVD1] [OR:Candida albicans]

| ORF Name | NT ID | AA ID | NT LN | AA LN | Score | P-Value |
|---|---|---|---|---|---|---|
| SPX1299 | 1299 | 3960 | 879 | 293 | 134 | 1.60E-20 |

Description

[LN:F72474] [AC:F72474] [PN:probable mevalonate kinase APE2439] [GN:APE2439]
[OR:Aeropyrum pernix]

| ORF Name | NT ID | AA ID | NT LN | AA LN | Score | P-Value |
|---|---|---|---|---|---|---|
| SPX1300 | 1300 | 3961 | 330 | 110 | 193 | 8.50E-21 |

Description

[GI:1914875] [LN:SPZ82002] [AC:Z82002] [PN:PCPC] [GN:pcpC] [FN:unknown]
[OR:Streptococcus pneumoniae]

| ORF Name | NT ID | AA ID | NT LN | AA LN | Score | P-Value |
|---|---|---|---|---|---|---|
| SPX1301 | 1301 | 3962 | 876 | 292 | | |

Description

NO-HIT

| ORF Name | NT ID | AA ID | NT LN | AA LN | Score | P-Value |
|---|---|---|---|---|---|---|
| SPX1302 | 1302 | 3963 | 1233 | 411 | 97 | 4.90E-10 |

Description

[GI:3582221] [LN:AE001272] [AC:AE001272] [PN:conserved hypothetical protein] [GN:ORF00049] [OR:Lactococcus lactis]

| ORF Name | NT ID | AA ID | NT LN | AA LN | Score | P-Value |
|---|---|---|---|---|---|---|
| SPX1303 | 1303 | 3964 | 999 | 333 | 402 | 1.50E-124 |

Description

[GI:1914875] [LN:SPZ82002] [AC:Z82002] [PN:PCPC] [GN:pcpC] [FN:unknown] [OR:Streptococcus pneumoniae]

| ORF Name | NT ID | AA ID | NT LN | AA LN | Score | P-Value |
|---|---|---|---|---|---|---|
| SPX1304 | 1304 | 3965 | 1113 | 371 | 289 | 1.70E-89 |

Description

[GI:1914875] [LN:SPZ82002] [AC:Z82002] [PN:PCPC] [GN:pcpC] [FN:unknown] [OR:Streptococcus pneumoniae]

| ORF Name | NT ID | AA ID | NT LN | AA LN | Score | P-Value |
|---|---|---|---|---|---|---|
| SPX1305 | 1305 | 3966 | 690 | 230 | 212 | 7.30E-56 |

Description

[GI:3599371] [LN:AF082668] [AC:AF082668] [PN:CsrR] [GN:csrR] [FN:negative regulator of hyaluronic acid capsule] [OR:Streptococcus pyogenes]

| ORF Name | NT ID | AA ID | NT LN | AA LN | Score | P-Value |
|---|---|---|---|---|---|---|
| SPX1306 | 1306 | 3967 | 1374 | 458 | 801 | 5.10E-226 |

Description

[GI:3033358] [LN:LLU74322] [AC:U74322] [PN:6-phosphogluconate dehydrogenase] [OR:Lactococcus lactis]

| ORF_Name | NT_ID | AA_ID | NT/LN | AA/LN | Score | P-Value |
|---|---|---|---|---|---|---|
| SPX1307 | 1307 | 3968 | 1395 | 465 | 109 | 1.10E-06 |

Description

[GI:1684847] [LN:HSU77718] [AC:U77718] [PN:pinin] [OR:Homo sapiens] [SR:human]

| ORF_Name | NT_ID | AA_ID | NT/LN | AA/LN | Score | P-Value |
|---|---|---|---|---|---|---|
| SPX1308 | 1308 | 3969 | 1158 | 386 | 678 | 1.20E-133 |

Description

[LN:YPSC_BACSU] [AC:P50840] [GN:YPSC] [OR:Bacillus subtilis]
[DE:HYPOTHETICAL 43.5 KD PROTEIN IN COTD-KDUD INTERGENIC REGION PRECURSOR]
[SP:P50840]

| ORF_Name | NT_ID | AA_ID | NT/LN | AA/LN | Score | P-Value |
|---|---|---|---|---|---|---|
| SPX1309 | 1309 | 3970 | 330 | 110 | 166 | 6.70E-18 |

Description

[LN:YPSB_BACSU] [AC:P50839] [GN:YPSB] [OR:Bacillus subtilis]
[DE:HYPOTHETICAL 11.6 KD PROTEIN IN COTD-KDUD INTERGENIC REGION] [SP:P50839]

| ORF_Name | NT_ID | AA_ID | NT/LN | AA/LN | Score | P-Value |
|---|---|---|---|---|---|---|
| SPX1310 | 1310 | 3971 | 528 | 176 | 147 | 8.20E-19 |

Description

[LN:YPSA_BACSU] [AC:P50838] [GN:YPSA] [OR:Bacillus subtilis]
[DE:HYPOTHETICAL 21.1 KD PROTEIN IN COTD-KDUD INTERGENIC REGION] [SP:P50838]

| ORF_Name | NT_ID | AA_ID | NT/LN | AA/LN | Score | P-Value |
|---|---|---|---|---|---|---|
| SPX1311 | 1311 | 3972 | 597 | 199 | 1043 | 3.40E-141 |

Description

[LN:YPOA_STRPN] [AC:P38034] [OR:Streptococcus pneumoniae] [DE:HYPOTHETICAL
23.1 KD PROTEIN IN PONA 5'REGION] [SP:P38034]

| ORF_Name | NT_ID | AA_ID | NT/LN | AA/LN | Score | P-Value |
|---|---|---|---|---|---|---|
| SPX1312 | 1312 | 3973 | 2160 | 720 | 3734 | 0 |

Description

[GI:6563337] [LN:AF210745] [AC:AF210745] [PN:penicillin-binding protein 1A]
[GN:pbp1a] [OR:Streptococcus pneumoniae]

| ORF Name | NT ID | AA ID | NT LN | AA LN | Score | P-Value |
|---|---|---|---|---|---|---|
| SPX1313 | 1313 | 3974 | 204 | 68 | | |

Description

NO-HIT

| ORF Name | NT ID | AA ID | NT LN | AA LN | Score | P-Value |
|---|---|---|---|---|---|---|
| SPX1314 | 1314 | 3975 | 5304 | 1768 | 1762 | 9.10E-232 |

Description

[GI:1658320] [LN:SPDEXCAP] [AC:Z47210] [GN:orf] [OR:Streptococcus pneumoniae]

| ORF Name | NT ID | AA ID | NT LN | AA LN | Score | P-Value |
|---|---|---|---|---|---|---|
| SPX1315 | 1315 | 3976 | 1983 | 661 | 3378 | 0 |

Description

[LN:ALIA_STRPN] [AC:P35592:Q54782:O54620:O52228] [GN:ALIA:EXP1:PLPA]
[OR:Streptococcus pneumoniae] [DE:OLIGOPEPTIDE-BINDING PROTEIN ALIA
PRECURSOR (EXPORTED PROTEIN 1)] [SP:P35592:Q54782:O54620:O52228]

| ORF Name | NT ID | AA ID | NT LN | AA LN | Score | P-Value |
|---|---|---|---|---|---|---|
| SPX1316 | 1316 | 3977 | 234 | 78 | 87 | 0.00034 |

Description

"[GI:5824139] [LN:POL245436]
[AC:AJ245436:J04618:J04619:S50571:X52935:X65936] [PN:hypothetical protein,
57.8 kD] [OR:Pseudomonas putida]"

| ORF Name | NT ID | AA ID | NT LN | AA LN | Score | P-Value |
|---|---|---|---|---|---|---|
| SPX1317 | 1317 | 3978 | 450 | 150 | 94 | 3.20E-15 |

Description

"[LN:Y4HP_RHISN] [AC:P50360] [GN:Y4HP] [OR:Rhizobium sp] [SR:,strain NGR234]
[DE:HYPOTHETICAL 61.7 KD PROTEIN Y4HP] [SP:P50360]"

| ORF Name | NT ID | AA ID | NT LN | AA LN | Score | P-Value |
|---|---|---|---|---|---|---|
| SPX1318 | 1318 | 3979 | 174 | 58 | | |

Description

NO-HIT

| ORF Name | NT ID | AA ID | NT/LN | AA/LN | Score | P-Value |
|---|---|---|---|---|---|---|
| SPX1319 | 1319 | 3980 | 258 | 86 | 80 | 8.90E-06 |

Description

"[LN:Y4HP_RHISN] [AC:P50360] [GN:Y4HP] [OR:Rhizobium sp] [SR:,strain NGR234] [DE:HYPOTHETICAL 61.7 KD PROTEIN Y4HP] [SP:P50360]"

| ORF Name | NT ID | AA ID | NT/LN | AA/LN | Score | P-Value |
|---|---|---|---|---|---|---|
| SPX1320 | 1320 | 3981 | 429 | 143 | 84 | 9.20E-08 |

Description

"[GI:6009407] [LN:AB024946] [AC:AB024946] [GN:orf31] [OR:Escherichia coli] [SR:Escherichia coli (sub_species:enteropathogenic, strain:B171]"

| ORF Name | NT ID | AA ID | NT/LN | AA/LN | Score | P-Value |
|---|---|---|---|---|---|---|
| SPX1321 | 1321 | 3982 | 852 | 284 | 1480 | 1.00E-198 |

Description

[GI:2804705] [LN:AF030362] [AC:AF030362] [PN:dTDP-L-rhamnose synthase] [GN:cpsO] [OR:Streptococcus pneumoniae]

| ORF Name | NT ID | AA ID | NT/LN | AA/LN | Score | P-Value |
|---|---|---|---|---|---|---|
| SPX1322 | 1322 | 3983 | 1050 | 350 | 1853 | 2.90E-249 |

Description

[GI:4200435] [LN:AF026471] [AC:AF026471] [PN:Cps2N] [GN:cps2N] [OR:Streptococcus pneumoniae]

| ORF Name | NT ID | AA ID | NT/LN | AA/LN | Score | P-Value |
|---|---|---|---|---|---|---|
| SPX1323 | 1323 | 3984 | 597 | 199 | 1027 | 4.50E-137 |

Description

"[GI:3907611] [LN:AF094575] [AC:AF094575] [PN:dTDP-4-keto-6-deoxyglucose-3,5-epimerase] [GN:cps19aM] [OR:Streptococcus pneumoniae]"

| ORF Name | NT ID | AA ID | NT/LN | AA/LN | Score | P-Value |
|---|---|---|---|---|---|---|
| SPX1324 | 1324 | 3985 | 870 | 290 | 1430 | 7.20E-193 |

Description

[GI:4406249] [LN:AF105113] [AC:AF105113] [PN:glucose-1-phosphate thymidylyl transferase] [GN:cps19AL] [OR:Streptococcus pneumoniae]

| ORF Name | NT ID | AA ID | NT/LN | AA/LN | Score | P-Value |
|---|---|---|---|---|---|---|
| SPX1325 | 1325 | 3986 | 1428 | 476 | 2017 | 3.10E-287 |

Description

[GI:3907608] [LN:AF094575] [AC:AF094575] [PN:putative repeat unit transporter Cps19aJ] [GN:cps19aJ] [OR:Streptococcus pneumoniae]

| ORF Name | NT ID | AA ID | NT/LN | AA/LN | Score | P-Value |
|---|---|---|---|---|---|---|
| SPX1326 | 1326 | 3987 | 285 | 95 | | |

Description

NO-HIT

| ORF Name | NT ID | AA ID | NT/LN | AA/LN | Score | P-Value |
|---|---|---|---|---|---|---|
| SPX1327 | 1327 | 3988 | 1344 | 448 | 148 | 6.90E-31 |

Description

[GI:3907607] [LN:AF094575] [AC:AF094575] [PN:polysaccharide polymerase Cps19aI] [GN:cps19aI] [OR:Streptococcus pneumoniae]

| ORF Name | NT ID | AA ID | NT/LN | AA/LN | Score | P-Value |
|---|---|---|---|---|---|---|
| SPX1328 | 1328 | 3989 | 987 | 329 | 178 | 2.00E-31 |

Description

[LN:T00087] [AC:T00087] [PN:rhamnosyltransferase] [GN:rgpBc] [OR:Streptococcus mutans]

| ORF Name | NT ID | AA ID | NT/LN | AA/LN | Score | P-Value |
|---|---|---|---|---|---|---|
| SPX1329 | 1329 | 3990 | 726 | 242 | 93 | 1.90E-06 |

Description

[LN:T35395] [AC:T35395] [PN:probable transferase] [GN:SC6A5.04] [OR:Streptomyces coelicolor]

| ORF Name | NT ID | AA ID | NT/LN | AA/LN | Score | P-Value |
|---|---|---|---|---|---|---|
| SPX1330 | 1330 | 3991 | 558 | 186 | 154 | 3.00E-14 |

Description

[GI:2209209] [LN:AF004325] [AC:AF004325] [PN:unknown] [GN:cps19bG] [OR:Streptococcus pneumoniae]

| ORF Name | NT ID | AA ID | NT LN | AA LN | Score | P-Value |
|---|---|---|---|---|---|---|
| SPX1331 | 1331 | 3992 | 945 | 315 | 96 | 6.50E-16 |

Description

[GI:3132871] [LN:AF019375] [AC:AF019375] [PN:UDP-glucose:(glucosyl) LPS] [GN:waaR] [OR:Escherichia coli]

| ORF Name | NT ID | AA ID | NT LN | AA LN | Score | P-Value |
|---|---|---|---|---|---|---|
| SPX1332 | 1332 | 3993 | 1368 | 456 | 1141 | 0 |

Description

[GI:3907603] [LN:AF094575] [AC:AF094575] [PN:glucosyl-1-phosphate transferase Cps19aE] [GN:cps19aE] [OR:Streptococcus pneumoniae]

| ORF Name | NT ID | AA ID | NT LN | AA LN | Score | P-Value |
|---|---|---|---|---|---|---|
| SPX1333 | 1333 | 3994 | 681 | 227 | 1055 | 4.60E-145 |

Description

[GI:3907602] [LN:AF094575] [AC:AF094575] [PN:Cps19aD] [GN:cps19aD] [FN:chain length regulation and export] [OR:Streptococcus pneumoniae]

| ORF Name | NT ID | AA ID | NT LN | AA LN | Score | P-Value |
|---|---|---|---|---|---|---|
| SPX1334 | 1334 | 3995 | 696 | 232 | 1061 | 2.00E-141 |

Description

[GI:3907601] [LN:AF094575] [AC:AF094575] [PN:Cps19aC] [GN:cps19aC] [FN:chain length regulation and export] [OR:Streptococcus pneumoniae]

| ORF Name | NT ID | AA ID | NT LN | AA LN | Score | P-Value |
|---|---|---|---|---|---|---|
| SPX1335 | 1335 | 3996 | 780 | 260 | 1195 | 2.90E-162 |

Description

[GI:3907600] [LN:AF094575] [AC:AF094575] [PN:Cps19aB] [GN:cps19aB] [OR:Streptococcus pneumoniae]

| ORF Name | NT ID | AA ID | NT LN | AA LN | Score | P-Value |
|---|---|---|---|---|---|---|
| SPX1336 | 1336 | 3997 | 1455 | 485 | 2238 | 0 |

Description

[GI:3550627] [LN:SPAJ6986] [AC:AJ006986] [GN:cap33fA] [OR:Streptococcus pneumoniae]

| ORF Name | NT ID | AA ID | NT/LN | AA/LN | Score | P-Value |
|---|---|---|---|---|---|---|
| SPX1337 | 1337 | 3998 | 1074 | 358 | 1690 | 9.20E-228 |
| Description | | | | | | |

[LN:TRA2_STRPN] [AC:Q54513] [OR:Streptococcus pneumoniae] [DE:TRANSPOSASE FOR INSERTION SEQUENCE IS1202] [SP:Q54513]

| ORF Name | NT ID | AA ID | NT/LN | AA/LN | Score | P-Value |
|---|---|---|---|---|---|---|
| SPX1338 | 1338 | 3999 | 360 | 120 | 581 | 6.60E-75 |
| Description | | | | | | |

[LN:TRA2_STRPN] [AC:Q54513] [OR:Streptococcus pneumoniae] [DE:TRANSPOSASE FOR INSERTION SEQUENCE IS1202] [SP:Q54513]

| ORF Name | NT ID | AA ID | NT/LN | AA/LN | Score | P-Value |
|---|---|---|---|---|---|---|
| SPX1339 | 1339 | 4000 | 951 | 317 | 267 | 3.80E-61 |
| Description | | | | | | |

"[GI:6332767] [LN:AB033763] [AC:AB033763:AB014419:AB014429:AB014439] [PN:hypothetical protein] [OR:Staphylococcus aureus] [SR:Staphylococcus aureus (strain:NCTC10442) DNA, clone_lib:Lambda das]"

| ORF Name | NT ID | AA ID | NT/LN | AA/LN | Score | P-Value |
|---|---|---|---|---|---|---|
| SPX1340 | 1340 | 4001 | 537 | 179 | 551 | 1.10E-70 |
| Description | | | | | | |

[LN:B30868] [AC:B30868] [PN:hypothetical protein 1] [OR:Streptococcus agalactiae]

| ORF Name | NT ID | AA ID | NT/LN | AA/LN | Score | P-Value |
|---|---|---|---|---|---|---|
| SPX1341 | 1341 | 4002 | 483 | 161 | 550 | 2.00E-80 |
| Description | | | | | | |

[LN:A33595] [AC:A33595:A30868] [PN:probable transposase] [CL:transposase IS3] [OR:Streptococcus agalactiae]

| ORF Name | NT ID | AA ID | NT/LN | AA/LN | Score | P-Value |
|---|---|---|---|---|---|---|
| SPX1342 | 1342 | 4003 | 834 | 278 | 587 | 1.60E-140 |
| Description | | | | | | |

[LN:A33595] [AC:A33595:A30868] [PN:probable transposase] [CL:transposase IS3] [OR:Streptococcus agalactiae]

| ORF Name | NT ID | AA ID | NT LN | AA LN | Score | P-Value |
|---|---|---|---|---|---|---|
| SPX1343 | 1343 | 4004 | 1611 | 537 | 2499 | 0 |

Description

"[GI:3320387] [LN:AF030373] [AC:AF030373] [PN:alpha, 1-6-glucosidase] [GN:dexB] [OR:Streptococcus pneumoniae]"

| ORF Name | NT ID | AA ID | NT LN | AA LN | Score | P-Value |
|---|---|---|---|---|---|---|
| SPX1344 | 1344 | 4005 | 1485 | 495 | | |

Description

NO-HIT

| ORF Name | NT ID | AA ID | NT LN | AA LN | Score | P-Value |
|---|---|---|---|---|---|---|
| SPX1345 | 1345 | 4006 | 483 | 161 | 288 | 9.40E-46 |

Description

[LN:D75280] [AC:D75280] [PN:conserved hypothetical protein] [GN:DR2387] [CL:conserved hypothetical protein HI0491] [OR:Deinococcus radiodurans]

| ORF Name | NT ID | AA ID | NT LN | AA LN | Score | P-Value |
|---|---|---|---|---|---|---|
| SPX1346 | 1346 | 4007 | 2106 | 702 | 2049 | 0 |

Description

[GI:871784] [LN:BOVCLPAB] [AC:L34677] [PN:Clp-like ATP-dependent protease binding subunit] [OR:Bos taurus] [SR:Bos taurus calf thymus cDNA to mRNA]

| ORF Name | NT ID | AA ID | NT LN | AA LN | Score | P-Value |
|---|---|---|---|---|---|---|
| SPX1347 | 1347 | 4008 | 240 | 80 | | |

Description

NO-HIT

| ORF Name | NT ID | AA ID | NT LN | AA LN | Score | P-Value |
|---|---|---|---|---|---|---|
| SPX1348 | 1348 | 4009 | 981 | 327 | 1619 | 8.40E-229 |

Description

[GI:4009489] [LN:AF068903] [AC:AF068903]
[PN:undecaprenyl-phosphate-UDP-MurNAc-pentapeptide] [GN:mraY]
[OR:Streptococcus pneumoniae]

| ORF Name | NT ID | AA ID | NT/LN | AA/LN | Score | P-Value |
|---|---|---|---|---|---|---|
| SPX1349 | 1349 | 4010 | 2253 | 751 | 3812 | 0 |

Description

[LN:PBPX_STRPN] [AC:P14677] [GN:PBPX] [OR:Streptococcus pneumoniae]
[DE:PENICILLIN-BINDING PROTEIN 2X (PBP-2X) (PBP2X)] [SP:P14677]

| ORF Name | NT ID | AA ID | NT/LN | AA/LN | Score | P-Value |
|---|---|---|---|---|---|---|
| SPX1350 | 1350 | 4011 | 318 | 106 | 505 | 1.40E-65 |

Description

[GI:4009487] [LN:AF068903] [AC:AF068903] [PN:Yl1D] [GN:yl1D]
[OR:Streptococcus pneumoniae]

| ORF Name | NT ID | AA ID | NT/LN | AA/LN | Score | P-Value |
|---|---|---|---|---|---|---|
| SPX1351 | 1351 | 4012 | 951 | 317 | 1604 | 2.70E-217 |

Description

[GI:4009486] [LN:AF068903] [AC:AF068903] [PN:Yl1C] [GN:yl1C]
[OR:Streptococcus pneumoniae]

| ORF Name | NT ID | AA ID | NT/LN | AA/LN | Score | P-Value |
|---|---|---|---|---|---|---|
| SPX1352 | 1352 | 4013 | 195 | 65 | 323 | 1.20E-40 |

Description

[GI:1536960] [LN:SOORFS] [AC:Z79691] [GN:yorfE] [FN:putative transcription regulator] [OR:Streptococcus pneumoniae]

| ORF Name | NT ID | AA ID | NT/LN | AA/LN | Score | P-Value |
|---|---|---|---|---|---|---|
| SPX1353 | 1353 | 4014 | 426 | 142 | 291 | 1.40E-36 |

Description

[GI:1524349] [LN:SOORFS] [AC:Z79691] [PN:OrfC] [GN:yorfC] [OR:Streptococcus pneumoniae]

| ORF Name | NT ID | AA ID | NT/LN | AA/LN | Score | P-Value |
|---|---|---|---|---|---|---|
| SPX1354 | 1354 | 4015 | 282 | 94 | | |

Description

NO-HIT

| ORF Name | NT ID | AA ID | NT LN | AA LN | Score | P-Value |
|---|---|---|---|---|---|---|
| SPX1355 | 1355 | 4016 | 255 | 85 | 178 | 5.70E-20 |
| Description | | | | | | |

[GI:1536959] [LN:SOORFS] [AC:Z79691] [PN:OrfB] [GN:yorfb] [OR:Streptococcus pneumoniae]

| ORF Name | NT ID | AA ID | NT LN | AA LN | Score | P-Value |
|---|---|---|---|---|---|---|
| SPX1356 | 1356 | 4017 | 243 | 81 | 391 | 2.00E-51 |
| Description | | | | | | |

[GI:1536959] [LN:SOORFS] [AC:Z79691] [PN:OrfB] [GN:yorfb] [OR:Streptococcus pneumoniae]

| ORF Name | NT ID | AA ID | NT LN | AA LN | Score | P-Value |
|---|---|---|---|---|---|---|
| SPX1357 | 1357 | 4018 | 336 | 112 | 219 | 4.90E-27 |
| Description | | | | | | |

[GI:1536959] [LN:SOORFS] [AC:Z79691] [PN:OrfB] [GN:yorfb] [OR:Streptococcus pneumoniae]

| ORF Name | NT ID | AA ID | NT LN | AA LN | Score | P-Value |
|---|---|---|---|---|---|---|
| SPX1358 | 1358 | 4019 | 192 | 64 | 111 | 4.30E-10 |
| Description | | | | | | |

[GI:1536959] [LN:SOORFS] [AC:Z79691] [PN:OrfB] [GN:yorfb] [OR:Streptococcus pneumoniae]

| ORF Name | NT ID | AA ID | NT LN | AA LN | Score | P-Value |
|---|---|---|---|---|---|---|
| SPX1359 | 1359 | 4020 | 1002 | 334 | 1703 | 2.00E-229 |
| Description | | | | | | |

"[GI:1536958] [LN:SOORFS] [AC:Z79691] [PN:RegR] [GN:regR] [FN:putative transcription regulator, member GalR] [OR:Streptococcus pneumoniae]"

| ORF Name | NT ID | AA ID | NT LN | AA LN | Score | P-Value |
|---|---|---|---|---|---|---|
| SPX1360 | 1360 | 4021 | 1902 | 634 | 1094 | 3.90E-148 |
| Description | | | | | | |

[GI:1524347] [LN:SOORFS] [AC:Z79691] [PN:OrfA] [GN:yorfA] [OR:Streptococcus pneumoniae]

| ORF Name | NT ID | AA ID | NT/LN | AA/LN | Score | P-Value |
|---|---|---|---|---|---|---|
| SPX1361 | 1361 | 4022 | 294 | 98 | 96 | 7.80E-07 |

Description

[LN:D70408] [AC:D70408] [PN:conserved hypothetical protein aq_1254]
[GN:aq_1254] [CL:yajC protein] [OR:Aquifex aeolicus]

| ORF Name | NT ID | AA ID | NT/LN | AA/LN | Score | P-Value |
|---|---|---|---|---|---|---|
| SPX1362 | 1362 | 4023 | 819 | 273 | 268 | 3.50E-51 |

Description

"[LN:PTPD_ECOLI] [AC:P42911] [GN:AGAD] [OR:Escherichia coli] [DE:ENZYME II, D COMPONENT)] [SP:P42911]"

| ORF Name | NT ID | AA ID | NT/LN | AA/LN | Score | P-Value |
|---|---|---|---|---|---|---|
| SPX1363 | 1363 | 4024 | 780 | 260 | 170 | 4.30E-27 |

Description

[GI:1732200] [LN:VFU65015] [AC:U65015] [PN:PTS permease for mannose subunit IIPMan] [GN:manY] [OR:Vibrio furnissii]

| ORF Name | NT ID | AA ID | NT/LN | AA/LN | Score | P-Value |
|---|---|---|---|---|---|---|
| SPX1364 | 1364 | 4025 | 492 | 164 | 286 | 3.40E-44 |

Description

"[LN:PTPV_ECOLI] [AC:P42904:P76669] [GN:AGAV] [OR:Escherichia coli]
[EC:2.7.1.69] [DE:ENZYME II, B COMPONENT 2),] [SP:P42904:P76669]"

| ORF Name | NT ID | AA ID | NT/LN | AA/LN | Score | P-Value |
|---|---|---|---|---|---|---|
| SPX1365 | 1365 | 4026 | 1008 | 336 | 475 | 2.70E-95 |

Description

[GI:5869507] [LN:AB019619] [AC:AB019619] [PN:unsaturated glucuronyl hydrolase] [GN:ugl] [OR:Bacillus sp. GL1] [SR:Bacillus sp. GL1 (strain:GL1) DNA]

| ORF Name | NT ID | AA ID | NT/LN | AA/LN | Score | P-Value |
|---|---|---|---|---|---|---|
| SPX1366 | 1366 | 4027 | 438 | 146 | | |

Description

NO-HIT

| ORF Name | NT ID | AA ID | NT/LN | AA/LN | Score | P-Value |
|---|---|---|---|---|---|---|
| SPX1367 | 1367 | 4028 | 435 | 145 | 129 | 3.30E-17 |

Description

[GI:5669855] [LN:AF130465] [AC:AF130465] [PN:mannose-specific phosphotransferase system] [GN:manL] [OR:Streptococcus salivarius]

| ORF Name | NT ID | AA ID | NT/LN | AA/LN | Score | P-Value |
|---|---|---|---|---|---|---|
| SPX1368 | 1368 | 4029 | 654 | 218 | 436 | 1.40E-55 |

Description

[LN:YJGU_ECOLI] [AC:P39345] [GN:YJGU] [OR:Escherichia coli] [EC:1.-.-.-] [DE:(EC 1.-.-.-)] [SP:P39345]

| ORF Name | NT ID | AA ID | NT/LN | AA/LN | Score | P-Value |
|---|---|---|---|---|---|---|
| SPX1369 | 1369 | 4030 | 375 | 125 | | |

Description

NO-HIT

| ORF Name | NT ID | AA ID | NT/LN | AA/LN | Score | P-Value |
|---|---|---|---|---|---|---|
| SPX1370 | 1370 | 4031 | 294 | 98 | 169 | 2.50E-19 |

Description

[LN:YJGU_ECOLI] [AC:P39345] [GN:YJGU] [OR:Escherichia coli] [EC:1.-.-.-] [DE:(EC 1.-.-.-)] [SP:P39345]

| ORF Name | NT ID | AA ID | NT/LN | AA/LN | Score | P-Value |
|---|---|---|---|---|---|---|
| SPX1371 | 1371 | 4032 | 642 | 214 | | |

Description

NO-HIT

| ORF Name | NT ID | AA ID | NT/LN | AA/LN | Score | P-Value |
|---|---|---|---|---|---|---|
| SPX1372 | 1372 | 4033 | 1002 | 334 | 317 | 1.00E-46 |

Description

[LN:G72422] [AC:G72422] [PN:2-keto-3-deoxygluconate kinase] [GN:TM0067] [CL:ribokinase] [OR:Thermotoga maritima]

| ORF Name | NT ID | AA ID | NT/LN | AA/LN | Score | P-Value |
|---|---|---|---|---|---|---|
| SPX1373 | 1373 | 4034 | 630 | 210 | 271 | 6.10E-46 |

Description

[LN:F72422] [AC:F72422] [PN:2-dehydro-3-deoxyphosphogluconate aldolase/4-hydroxy-2-oxoglutarate aldolase] [GN:TM0066] [CL:2-dehydro-3-deoxyphosphogluconate aldolase] [OR:Thermotoga maritima]

| ORF Name | NT ID | AA ID | NT/LN | AA/LN | Score | P-Value |
|---|---|---|---|---|---|---|
| SPX1374 | 1374 | 4035 | 354 | 118 | 264 | 1.50E-50 |

Description

[GI:1841332] [LN:D64071] [AC:D64071] [PN:putative protein of unknown function] [OR:Actinobacillus actinomycetemcomitans] [SR:Actinobacillus actinomycetemcomitans (strain:Y4) DNA]

| ORF Name | NT ID | AA ID | NT/LN | AA/LN | Score | P-Value |
|---|---|---|---|---|---|---|
| SPX1375 | 1375 | 4036 | 3237 | 1079 | 4863 | 0 |

Description

"[LN:HYSA_STRPN] [AC:Q54873:Q54874] [OR:Streptococcus pneumoniae] [EC:4.2.2.1] [DE:HYALURONATE LYASE PRECURSOR, (HYALURONIDASE) (HYASE)] [SP:Q54873:Q54874]"

| ORF Name | NT ID | AA ID | NT/LN | AA/LN | Score | P-Value |
|---|---|---|---|---|---|---|
| SPX1376 | 1376 | 4037 | 477 | 159 | 482 | 1.90E-62 |

Description

[GI:2598550] [LN:LLAJ109] [AC:AJ000109] [PN:gluthatione peroxidase] [GN:gpo] [OR:Lactococcus lactis]

| ORF Name | NT ID | AA ID | NT/LN | AA/LN | Score | P-Value |
|---|---|---|---|---|---|---|
| SPX1377 | 1377 | 4038 | 2214 | 738 | 181 | 4.50E-33 |

Description

[GI:6686567] [LN:AAC252161] [AC:AJ252161] [PN:putative alpha-glucosidase] [GN:glcA] [OR:Alicyclobacillus acidocaldarius]

| ORF Name | NT ID | AA ID | NT/LN | AA/LN | Score | P-Value |
|---|---|---|---|---|---|---|
| SPX1378 | 1378 | 4039 | 183 | 61 | | |

Description

NO-HIT

| ORF Name | NT ID | AA ID | NT LN | AA LN | Score | P-Value |
|---|---|---|---|---|---|---|
| SPX1379 | 1379 | 4040 | 1347 | 449 | 231 | 3.40E-63 |

Description

"[LN:PTCC_BACST] [AC:Q45400] [GN:CELB] [OR:Bacillus stearothermophilus] [DE:PERMEASE IIC COMPONENT) (PHOSPHOTRANSFERASE ENZYME II, C COMPONENT)] [SP:Q45400]"

| ORF Name | NT ID | AA ID | NT LN | AA LN | Score | P-Value |
|---|---|---|---|---|---|---|
| SPX1380 | 1380 | 4041 | 507 | 169 | | |

Description

NO-HIT

| ORF Name | NT ID | AA ID | NT LN | AA LN | Score | P-Value |
|---|---|---|---|---|---|---|
| SPX1381 | 1381 | 4042 | 315 | 105 | 234 | 2.00E-27 |

Description

[LN:PTCA_BACSU] [AC:P46319] [GN:CELC:LICA] [OR:Bacillus subtilis] [EC:2.7.1.69] [DE:(EC 2.7.1.69) (EIII-CEL)] [SP:P46319]

| ORF Name | NT ID | AA ID | NT LN | AA LN | Score | P-Value |
|---|---|---|---|---|---|---|
| SPX1382 | 1382 | 4043 | 1980 | 660 | 138 | 9.20E-51 |

Description

[LN:CELR_BACSU] [AC:P46321] [GN:CELR:LICR] [OR:Bacillus subtilis] [DE:PUTATIVE CEL OPERON REGULATOR] [SP:P46321]

| ORF Name | NT ID | AA ID | NT LN | AA LN | Score | P-Value |
|---|---|---|---|---|---|---|
| SPX1383 | 1383 | 4044 | 342 | 114 | 84 | 2.40E-08 |

Description

[LN:PTCB_BACST] [AC:Q45399] [GN:CELA] [OR:Bacillus stearothermophilus] [EC:2.7.1.69] [DE:(EC 2.7.1.69)] [SP:Q45399]

| ORF Name | NT ID | AA ID | NT LN | AA LN | Score | P-Value |
|---|---|---|---|---|---|---|
| SPX1384 | 1384 | 4045 | 240 | 80 | 142 | 1.20E-15 |

Description

[LN:Y110_METJA] [AC:Q57574] [GN:MJ0110] [OR:Methanococcus jannaschii] [DE:HYPOTHETICAL PROTEIN MJ0110] [SP:Q57574]

| ORF Name | NT ID | AA ID | NT/LN | AA/LN | Score | P-Value |
|---|---|---|---|---|---|---|
| SPX1385 | 1385 | 4046 | 1479 | 493 | 797 | 2.50E-225 |

Description

[LN:JE0395] [AC:JE0395] [PN:phospho-beta-galactosidase I] [CL:Agrobacterium beta-glucosidase] [OR:Lactobacillus gasseri]

| ORF Name | NT ID | AA ID | NT/LN | AA/LN | Score | P-Value |
|---|---|---|---|---|---|---|
| SPX1386 | 1386 | 4047 | 366 | 122 | | |

Description

NO-HIT

| ORF Name | NT ID | AA ID | NT/LN | AA/LN | Score | P-Value |
|---|---|---|---|---|---|---|
| SPX1387 | 1387 | 4048 | 207 | 69 | 359 | 2.90E-46 |

Description

[GI:5019553] [LN:SPN239004] [AC:AJ239004] [PN:putative transposase] [OR:Streptococcus pneumoniae]

| ORF Name | NT ID | AA ID | NT/LN | AA/LN | Score | P-Value |
|---|---|---|---|---|---|---|
| SPX1388 | 1388 | 4049 | 393 | 131 | 456 | 1.30E-58 |

Description

[LN:RS9_BACST] [AC:P07842] [GN:RPSI] [OR:Bacillus stearothermophilus] [DE:30S RIBOSOMAL PROTEIN S9 (BS10)] [SP:P07842]

| ORF Name | NT ID | AA ID | NT/LN | AA/LN | Score | P-Value |
|---|---|---|---|---|---|---|
| SPX1389 | 1389 | 4050 | 447 | 149 | 487 | 2.30E-62 |

Description

[LN:RL13_STACA] [AC:Q00990] [GN:RPLM] [OR:Staphylococcus carnosus] [DE:50S RIBOSOMAL PROTEIN L13] [SP:Q00990]

| ORF Name | NT ID | AA ID | NT/LN | AA/LN | Score | P-Value |
|---|---|---|---|---|---|---|
| SPX1390 | 1390 | 4051 | 366 | 122 | | |

Description

NO-HIT

| ORF Name | NT ID | AA ID | NT LN | AA LN | Score | P-Value |
|---|---|---|---|---|---|---|
| SPX1391 | 1391 | 4052 | 318 | 106 | | |

Description

NO-HIT

| ORF Name | NT ID | AA ID | NT LN | AA LN | Score | P-Value |
|---|---|---|---|---|---|---|
| SPX1392 | 1392 | 4053 | 393 | 131 | 630 | 8.40E-84 |

Description

"[LN:SULD_STRPN] [AC:P22291:O33697] [GN:SULD] [OR:Streptococcus pneumoniae] [EC:4.1.2.25:2.7.6.3] [DE:HYDROXYMETHYL-7,8-DIHYDROPTERIN PYROPHOSPHOKINASE) (PPPK)]] [SP:P22291:O33697]"

| ORF Name | NT ID | AA ID | NT LN | AA LN | Score | P-Value |
|---|---|---|---|---|---|---|
| SPX1393 | 1393 | 4054 | 510 | 170 | 834 | 1.40E-111 |

Description

"[LN:A36704] [AC:A36704] [PN:bifunctional folate biosynthesis enzyme sulD:6-hydroxymethyl-7,8-dihydropterin pyrophosphokinase:7, 8-dihydro-6-hydroxymethylpterin pyrophosphokinase] [GN:sulD] [OR:Streptococcus pneumoniae]"

| ORF Name | NT ID | AA ID | NT LN | AA LN | Score | P-Value |
|---|---|---|---|---|---|---|
| SPX1394 | 1394 | 4055 | 555 | 185 | 938 | 4.90E-127 |

Description

"[LN:GCH1_STRPN] [AC:P51595] [GN:SULC] [OR:Streptococcus pneumoniae] [EC:3.5.4.16] [DE:GTP CYCLOHYDROLASE I, (GTP-CH-I)] [SP:P51595]"

| ORF Name | NT ID | AA ID | NT LN | AA LN | Score | P-Value |
|---|---|---|---|---|---|---|
| SPX1395 | 1395 | 4056 | 1323 | 441 | 2219 | 0 |

Description

[GI:564018] [LN:SPU16156] [AC:U16156:M17362:M58706] [PN:dihydrofolate synthetase] [GN:sulB] [FN:folate biosynthesis] [OR:Streptococcus pneumoniae]

| ORF Name | NT ID | AA ID | NT LN | AA LN | Score | P-Value |
|---|---|---|---|---|---|---|
| SPX1396 | 1396 | 4057 | 981 | 327 | 1485 | 7.00E-201 |

Description

[LN:DHPS_STRPN] [AC:P05382] [GN:SULA] [OR:Streptococcus pneumoniae] [EC:2.5.1.15] [DE:PYROPHOSPHORYLASE)] [SP:P05382]

| ORF Name | NT ID | AA ID | NT LN | AA LN | Score | P-Value |
|---|---|---|---|---|---|---|
| SPX1397 | 1397 | 4058 | 708 | 236 | 143 | 3.00E-13 |

Description

[GI:1402529] [LN:D78257] [AC:D78257] [PN:ORF8] [GN:orf8] [OR:Enterococcus faecalis] [SR:Enterococcus faecalis plasmid:pYI17 DNA]

| ORF Name | NT ID | AA ID | NT LN | AA LN | Score | P-Value |
|---|---|---|---|---|---|---|
| SPX1398 | 1398 | 4059 | 186 | 62 | | |

Description

NO-HIT

| ORF Name | NT ID | AA ID | NT LN | AA LN | Score | P-Value |
|---|---|---|---|---|---|---|
| SPX1399 | 1399 | 4060 | 1482 | 494 | 447 | 1.70E-116 |

Description

[GI:6624219] [LN:AB023289] [AC:AB023289] [GN:ORFX] [OR:Pseudomonas fluorescens] [SR:Pseudomonas fluorescens (strain:No.33) DNA]

| ORF Name | NT ID | AA ID | NT LN | AA LN | Score | P-Value |
|---|---|---|---|---|---|---|
| SPX1400 | 1400 | 4061 | 813 | 271 | 199 | 8.70E-36 |

Description

[LN:F69841] [AC:F69841] [PN:conserved hypothetical protein yitU] [GN:yitU] [CL:Methanobacterium thermoautotrophicum conserved hypothetical protein MTH1071] [OR:Bacillus subtilis]

| ORF Name | NT ID | AA ID | NT LN | AA LN | Score | P-Value |
|---|---|---|---|---|---|---|
| SPX1401 | 1401 | 4062 | 933 | 311 | 861 | 2.70E-156 |

Description

[GI:7379448] [LN:NMA3Z2491] [AC:AL162754:AL157959] [PN:putative alcohol dehydrogenase] [GN:adhA] [OR:Neisseria meningitidis]

| ORF Name | NT ID | AA ID | NT LN | AA LN | Score | P-Value |
|---|---|---|---|---|---|---|
| SPX1402 | 1402 | 4063 | 999 | 333 | 795 | 2.40E-188 |

Description

[GI:5669855] [LN:AF130465] [AC:AF130465] [PN:mannose-specific phosphotransferase system] [GN:manL] [OR:Streptococcus salivarius]

| ORF Name | NT ID | AA ID | NT LN | AA LN | Score | P-Value |
|---|---|---|---|---|---|---|
| SPX1403 | 1403 | 4064 | 804 | 268 | 974 | 1.10E-144 |

Description

[GI:5669856] [LN:AF130465] [AC:AF130465] [PN:mannose-specific phosphotransferase system] [GN:manM] [OR:Streptococcus salivarius]

| ORF Name | NT ID | AA ID | NT LN | AA LN | Score | P-Value |
|---|---|---|---|---|---|---|
| SPX1404 | 1404 | 4065 | 912 | 304 | 1157 | 3.60E-158 |

Description

[GI:5669857] [LN:AF130465] [AC:AF130465] [PN:mannose-specific phosphotransferase system] [GN:manN] [OR:Streptococcus salivarius]

| ORF Name | NT ID | AA ID | NT LN | AA LN | Score | P-Value |
|---|---|---|---|---|---|---|
| SPX1405 | 1405 | 4066 | 1335 | 445 | 1900 | 4.00E-256 |

Description

"[LN:PEPC_STRTR] [AC:Q56115] [GN:PEPC] [OR:Streptococcus thermophilus] [EC:3.4.22.-] [DE:AMINOPEPTIDASE C,] [SP:Q56115]"

| ORF Name | NT ID | AA ID | NT LN | AA LN | Score | P-Value |
|---|---|---|---|---|---|---|
| SPX1406 | 1406 | 4067 | 723 | 241 | 223 | 1.50E-59 |

Description

[GI:7328274] [LN:SAY14816] [AC:Y14816] [PN:hypothetical protein] [GN:ORF231] [OR:Staphylococcus aureus]

| ORF Name | NT ID | AA ID | NT LN | AA LN | Score | P-Value |
|---|---|---|---|---|---|---|
| SPX1407 | 1407 | 4068 | 411 | 137 | 328 | 2.80E-41 |

Description

[LN:T30285] [AC:T30285] [PN:hypothetical protein] [OR:Streptococcus pneumoniae]

| ORF Name | NT ID | AA ID | NT LN | AA LN | Score | P-Value |
|---|---|---|---|---|---|---|
| SPX1408 | 1408 | 4069 | 231 | 77 | | |

Description

NO-HIT

| ORF Name | NT ID | AA ID | NT LN | AA LN | Score | P-Value |
|---|---|---|---|---|---|---|
| SPX1409 | 1409 | 4070 | 231 | 77 | 154 | 1.90E-17 |

Description

[LN:B69770] [AC:B69770] [PN:conserved hypothetical protein ydaS] [GN:ydaS] [OR:Bacillus subtilis]

| ORF Name | NT ID | AA ID | NT LN | AA LN | Score | P-Value |
|---|---|---|---|---|---|---|
| SPX1410 | 1410 | 4071 | 1242 | 414 | 1792 | 6.20E-241 |

Description

[GI:4731022] [LN:AF102860] [AC:AF102860] [PN:aminopeptidase PepS] [GN:pepS] [OR:Streptococcus thermophilus]

| ORF Name | NT ID | AA ID | NT LN | AA LN | Score | P-Value |
|---|---|---|---|---|---|---|
| SPX1411 | 1411 | 4072 | 180 | 60 | | |

Description

NO-HIT

| ORF Name | NT ID | AA ID | NT LN | AA LN | Score | P-Value |
|---|---|---|---|---|---|---|
| SPX1412 | 1412 | 4073 | 231 | 77 | | |

Description

NO-HIT

| ORF Name | NT ID | AA ID | NT LN | AA LN | Score | P-Value |
|---|---|---|---|---|---|---|
| SPX1413 | 1413 | 4074 | 279 | 93 | 110 | 1.90E-19 |

Description

"[LN:B71883] [AC:B71883] [PN:hypothetical protein jhp0831] [GN:jhp0831] [CL:conserved hypothetical protein HI0711] [OR:Helicobacter pylori] [SR:strain J99, , strain J99] [SR:strain J99, ]"

| ORF Name | NT ID | AA ID | NT LN | AA LN | Score | P-Value |
|---|---|---|---|---|---|---|
| SPX1414 | 1414 | 4075 | 264 | 88 | 80 | 0.00012 |

Description

[LN:DINJ_ECOLI] [AC:Q47150] [GN:DINJ] [OR:Escherichia coli] [DE:DNA-DAMAGE-INDUCIBLE PROTEIN J] [SP:Q47150]

| ORF Name | NT ID | AA ID | NT/LN | AA/LN | Score | P-Value |
|---|---|---|---|---|---|---|
| SPX1415 | 1415 | 4076 | 4392 | 1464 | 1689 | 0 |

Description

"[GI:143342] [LN:BACPOLC] [AC:M22996] [GN:polC] [OR:Bacillus subtilis] [SR:B.subtilis SB19 DNA, clone PRO10]"

| ORF Name | NT ID | AA ID | NT/LN | AA/LN | Score | P-Value |
|---|---|---|---|---|---|---|
| SPX1416 | 1416 | 4077 | 2082 | 694 | 2833 | 0 |

Description

[LN:T44380] [AC:T44380] [PN:translation elongation factor EF-G fus [imported]] [GN:fus] [CL:translation elongation factor G:translation elongation factor Tu homology] [OR:Bacillus halodurans]

| ORF Name | NT ID | AA ID | NT/LN | AA/LN | Score | P-Value |
|---|---|---|---|---|---|---|
| SPX1417 | 1417 | 4078 | 357 | 119 | 86 | 5.20E-10 |

Description

[LN:YHA2_EIKCO] [AC:P35649] [OR:Eikenella corrodens] [DE:HYPOTHETICAL 66.3 KD PROTEIN IN HAG2 5'REGION] [SP:P35649]

| ORF Name | NT ID | AA ID | NT/LN | AA/LN | Score | P-Value |
|---|---|---|---|---|---|---|
| SPX1418 | 1418 | 4079 | 450 | 150 | 88 | 1.30E-08 |

Description

[LN:YHA2_EIKCO] [AC:P35649] [OR:Eikenella corrodens] [DE:HYPOTHETICAL 66.3 KD PROTEIN IN HAG2 5'REGION] [SP:P35649]

| ORF Name | NT ID | AA ID | NT/LN | AA/LN | Score | P-Value |
|---|---|---|---|---|---|---|
| SPX1419 | 1419 | 4080 | 432 | 144 | 173 | 1.90E-17 |

Description

[GI:7576785] [LN:AF214675] [AC:AF214675] [PN:unknown in vivo-induced protein 131-19] [OR:Pseudomonas aeruginosa]

| ORF Name | NT ID | AA ID | NT/LN | AA/LN | Score | P-Value |
|---|---|---|---|---|---|---|
| SPX1420 | 1420 | 4081 | 471 | 157 | 633 | 1.10E-83 |

Description

[LN:F69699] [AC:F69699:S11357] [PN:ribosomal protein S7 (rpsG):ribosomal protein BS7] [GN:rpsG] [CL:Escherichia coli ribosomal protein S7] [OR:Bacillus subtilis]

| ORF Name | NT ID | AA ID | NT/LN | AA/LN | Score | P-Value |
|---|---|---|---|---|---|---|
| SPX1421 | 1421 | 4082 | 414 | 138 | 699 | 1.70E-91 |

Description

[LN:RS12_STRPN] [AC:P30891] [GN:RPSL:STR] [OR:Streptococcus pneumoniae] [DE:30S RIBOSOMAL PROTEIN S12] [SP:P30891]

| ORF Name | NT ID | AA ID | NT/LN | AA/LN | Score | P-Value |
|---|---|---|---|---|---|---|
| SPX1422 | 1422 | 4083 | 3615 | 1205 | 1478 | 0 |

Description

[GI:1665738] [LN:D78258] [AC:D78258] [PN:alkaline amylopullulanase] [OR:Bacillus sp.] [SR:Bacillus sp. (strain:KSM-1378) DNA]

| ORF Name | NT ID | AA ID | NT/LN | AA/LN | Score | P-Value |
|---|---|---|---|---|---|---|
| SPX1423 | 1423 | 4084 | 924 | 308 | 655 | 1.70E-115 |

Description

"[GI:2735505] [LN:SCU96107] [AC:U96107] [PN:N5,N10-methylenetetrahydromethanopterin] [OR:Staphylococcus carnosus]"

| ORF Name | NT ID | AA ID | NT/LN | AA/LN | Score | P-Value |
|---|---|---|---|---|---|---|
| SPX1424 | 1424 | 4085 | 1809 | 603 | 963 | 3.70E-194 |

Description

"[LN:B69633] [AC:B69633] [PN:glutamine--fructose-6-phosphate transaminase (isomerizing), glmS] [GN:glmS] [CL:glutamine--fructose-6-phosphate aminotransferase (isomerizing)] [OR:Bacillus subtilis] [EC:2.6.1.16]"

| ORF Name | NT ID | AA ID | NT/LN | AA/LN | Score | P-Value |
|---|---|---|---|---|---|---|
| SPX1425 | 1425 | 4086 | 1380 | 460 | 851 | 2.00E-207 |

Description

[LN:D69785] [AC:D69785] [PN:beta-glucosidase homolog ydhP] [GN:ydhP] [CL:Agrobacterium beta-glucosidase] [OR:Bacillus subtilis]

| ORF Name | NT ID | AA ID | NT/LN | AA/LN | Score | P-Value |
|---|---|---|---|---|---|---|
| SPX1426 | 1426 | 4087 | 1041 | 347 | 298 | 1.30E-82 |

Description

"[LN:G69682] [AC:G69682] [PN:proline--tRNA ligase, proS:prolyl-tRNA synthetase] [GN:proS] [CL:proline--tRNA ligase] [OR:Bacillus subtilis] [EC:6.1.1.15]"

| ORF Name | NT ID | AA ID | NT/LN | AA/LN | Score | P-Value |
|---|---|---|---|---|---|---|
| SPX1427 | 1427 | 4088 | 1008 | 336 | 691 | 5.20E-109 |

Description

"[LN:G69682] [AC:G69682] [PN:proline--tRNA ligase, proS:prolyl-tRNA synthetase] [GN:proS] [CL:proline--tRNA ligase] [OR:Bacillus subtilis] [EC:6.1.1.15]"

| ORF Name | NT ID | AA ID | NT/LN | AA/LN | Score | P-Value |
|---|---|---|---|---|---|---|
| SPX1428 | 1428 | 4089 | 1260 | 420 | 436 | 8.50E-136 |

Description

[GI:5714510] [LN:AF152237] [AC:AF152237] [PN:Eep] [GN:eep] [FN:determinant for enhanced expression of] [OR:Enterococcus faecalis]

| ORF Name | NT ID | AA ID | NT/LN | AA/LN | Score | P-Value |
|---|---|---|---|---|---|---|
| SPX1429 | 1429 | 4090 | 804 | 268 | 202 | 1.20E-51 |

Description

[LN:CDSA_BACSU] [AC:O31752] [GN:CDSA] [OR:Bacillus subtilis] [EC:2.7.7.41] [DE:SYNTHASE)] [SP:O31752]

| ORF Name | NT ID | AA ID | NT/LN | AA/LN | Score | P-Value |
|---|---|---|---|---|---|---|
| SPX1430 | 1430 | 4091 | 777 | 259 | 490 | 2.80E-90 |

Description

[LN:UPPS_BACSU] [AC:O31751] [GN:UPPS] [OR:Bacillus subtilis] [EC:2.5.1.31] [DE:(DI-TRANS-POLY-CIS-DECAPRENYLCISTRANSFERASE)] [SP:O31751]

| ORF Name | NT ID | AA ID | NT/LN | AA/LN | Score | P-Value |
|---|---|---|---|---|---|---|
| SPX1431 | 1431 | 4092 | 573 | 191 | 127 | 1.50E-11 |

Description

[LN:S70841] [AC:S70841] [PN:hypothetical transmembrane protein (sipS 3' region)] [CL:Bradyrhizobium japonicum hypothetical transmembrane protein (sipS 3' region)] [OR:Bradyrhizobium japonicum]

| ORF Name | NT ID | AA ID | NT/LN | AA/LN | Score | P-Value |
|---|---|---|---|---|---|---|
| SPX1432 | 1432 | 4093 | 999 | 333 | 1045 | 1.50E-140 |

Description

[LN:H81105] [AC:H81105] [PN:Holliday junction DNA helicase RuvB NMB1243 [imported]] [GN:NMB1243] [OR:Neisseria meningitidis]

| ORF Name | NT ID | AA ID | NT LN | AA LN | Score | P-Value |
|---|---|---|---|---|---|---|
| SPX1433 | 1433 | 4094 | 105 | 35 | 76 | 0.00015 |

Description

[LN:H72613] [AC:H72613] [PN:hypothetical protein APE1371] [GN:APE1371] [OR:Aeropyrum pernix]

| ORF Name | NT ID | AA ID | NT LN | AA LN | Score | P-Value |
|---|---|---|---|---|---|---|
| SPX1434 | 1434 | 4095 | 417 | 139 | 103 | 1.50E-06 |

Description

[GI:5616248] [LN:AF158628] [AC:AF158628] [PN:hypothetical protein] [OR:Prochlorococcus PCC9511]

| ORF Name | NT ID | AA ID | NT LN | AA LN | Score | P-Value |
|---|---|---|---|---|---|---|
| SPX1435 | 1435 | 4096 | 696 | 232 | 482 | 1.50E-73 |

Description

"[LN:YIW2_YEAST] [AC:P40586] [GN:YIR042C] [OR:Saccharomyces cerevisiae] [SR:,Baker's yeast] [DE:HYPOTHETICAL 27.4 KD PROTEIN IN HYR1 3'REGION] [SP:P40586]"

| ORF Name | NT ID | AA ID | NT LN | AA LN | Score | P-Value |
|---|---|---|---|---|---|---|
| SPX1436 | 1436 | 4097 | 192 | 64 | | |

Description

NO-HIT

| ORF Name | NT ID | AA ID | NT LN | AA LN | Score | P-Value |
|---|---|---|---|---|---|---|
| SPX1437 | 1437 | 4098 | 2502 | 834 | 944 | 0 |

Description

"[LN:C70131] [AC:C70131] [PN:leucine--tRNA ligase, leuS:leucyl-tRNA synthetase:leucyl-tRNA synthetase] [CL:leucine--tRNA ligase] [OR:Borrelia burgdorferi] [SR:, Lyme disease spirochete] [EC:6.1.1.4]"

| ORF Name | NT ID | AA ID | NT LN | AA LN | Score | P-Value |
|---|---|---|---|---|---|---|
| SPX1438 | 1438 | 4099 | 1089 | 363 | 998 | 1.00E-137 |

Description

"[LN:GLDA_BACST] [AC:P32816] [GN:GLDA:GLD] [OR:Bacillus stearothermophilus] [EC:1.1.1.6] [DE:GLYCEROL DEHYDROGENASE, (GLDH)] [SP:P32816]"

| ORF Name | NT ID | AA ID | NT/LN | AA/LN | Score | P-Value |
|---|---|---|---|---|---|---|
| SPX1439 | 1439 | 4100 | 669 | 223 | 356 | 8.20E-53 |

Description

[GI:2582658] [LN:CBAJ2527] [AC:AJ002527] [PN:OrfX] [GN:orfX] [FN:putative transaldolase (37.4% identity to talC)] [OR:Clostridium beijerinckii]

| ORF Name | NT ID | AA ID | NT/LN | AA/LN | Score | P-Value |
|---|---|---|---|---|---|---|
| SPX1440 | 1440 | 4101 | 2448 | 816 | 992 | 1.80E-275 |

Description

[LN:PFLF_ECOLI] [AC:P75793] [GN:YBIW] [OR:Escherichia coli] [EC:2.3.1.54] [DE:LYASE 3)] [SP:P75793]

| ORF Name | NT ID | AA ID | NT/LN | AA/LN | Score | P-Value |
|---|---|---|---|---|---|---|
| SPX1441 | 1441 | 4102 | 1281 | 427 | 337 | 4.90E-89 |

Description

"[LN:PTCC_BACST] [AC:Q45400] [GN:CELB] [OR:Bacillus stearothermophilus] [DE:PERMEASE IIC COMPONENT) (PHOSPHOTRANSFERASE ENZYME II, C COMPONENT)] [SP:Q45400]"

| ORF Name | NT ID | AA ID | NT/LN | AA/LN | Score | P-Value |
|---|---|---|---|---|---|---|
| SPX1442 | 1442 | 4103 | 309 | 103 | 194 | 3.50E-22 |

Description

[LN:A69785] [AC:A69785] [PN:cellobiose phosphotransferase system enzym homolog ydhM] [GN:ydhM] [CL:phosphotransferase system enzyme II cellobiose-specific factor IIB] [OR:Bacillus subtilis]

| ORF Name | NT ID | AA ID | NT/LN | AA/LN | Score | P-Value |
|---|---|---|---|---|---|---|
| SPX1443 | 1443 | 4104 | 321 | 107 | 186 | 5.70E-21 |

Description

[LN:PTCA_BACSU] [AC:P46319] [GN:CELC:LICA] [OR:Bacillus subtilis] [EC:2.7.1.69] [DE:(EC 2.7.1.69) (EIII-CEL)] [SP:P46319]

| ORF Name | NT ID | AA ID | NT/LN | AA/LN | Score | P-Value |
|---|---|---|---|---|---|---|
| SPX1444 | 1444 | 4105 | 981 | 327 | 265 | 2.80E-49 |

Description

[LN:SORC_KLEPN] [AC:P37078] [GN:SORC] [OR:Klebsiella pneumoniae] [DE:SORBITOL OPERON REGULATOR (SOR OPERON ACTIVATOR)] [SP:P37078]

| ORF Name | NT ID | AA ID | NT/LN | AA/LN | Score | P-Value |
|---|---|---|---|---|---|---|
| SPX1445 | 1445 | 4106 | 747 | 249 | 252 | 6.10E-57 |

Description

[LN:YCIT_ECOLI] [AC:P76034] [GN:YCIT] [OR:Escherichia coli] [DE:HYPOTHETICAL TRANSCRIPTIONAL REGULATOR IN OSMB-RNB INTERGENIC REGION] [SP:P76034]

| ORF Name | NT ID | AA ID | NT/LN | AA/LN | Score | P-Value |
|---|---|---|---|---|---|---|
| SPX1446 | 1446 | 4107 | 777 | 259 | 266 | 4.40E-55 |

Description

"[LN:PFLE_ECOLI] [AC:P75794] [GN:YBIY] [OR:Escherichia coli] [EC:1.97.1.4] [DE:PUTATIVE PYRUVATE FORMATE-LYASE 3 ACTIVATING ENZYME,] [SP:P75794]"

| ORF Name | NT ID | AA ID | NT/LN | AA/LN | Score | P-Value |
|---|---|---|---|---|---|---|
| SPX1447 | 1447 | 4108 | 249 | 83 | 105 | 3.60E-08 |

Description

[GI:7331182] [LN:AF235048] [AC:AF235048] [PN:AgpT] [GN:agpT] [OR:Sinorhizobium meliloti]

| ORF Name | NT ID | AA ID | NT/LN | AA/LN | Score | P-Value |
|---|---|---|---|---|---|---|
| SPX1448 | 1448 | 4109 | 195 | 65 | 177 | 4.60E-18 |

Description

[GI:6127225] [LN:SHU75349] [AC:U75349] [PN:periplasmic-iron-binding protein BitA] [GN:bit operon] [OR:Brachyspira hyodysenteriae]

| ORF Name | NT ID | AA ID | NT/LN | AA/LN | Score | P-Value |
|---|---|---|---|---|---|---|
| SPX1449 | 1449 | 4110 | 369 | 123 | 242 | 1.10E-26 |

Description

[GI:6127225] [LN:SHU75349] [AC:U75349] [PN:periplasmic-iron-binding protein BitA] [GN:bit operon] [OR:Brachyspira hyodysenteriae]

| ORF Name | NT ID | AA ID | NT/LN | AA/LN | Score | P-Value |
|---|---|---|---|---|---|---|
| SPX1450 | 1450 | 4111 | 954 | 318 | 799 | 1.70E-113 |

Description

[GI:2766194] [LN:SHU75349] [AC:U75349] [PN:putative ABC transporter BitD] [GN:bit operon] [OR:Brachyspira hyodysenteriae]

| ORF Name | NT ID | AA ID | NT/LN | AA/LN | Score | P-Value |
|---|---|---|---|---|---|---|
| SPX1451 | 1451 | 4112 | 627 | 209 | 283 | 2.70E-40 |

Description

[GI:2766195] [LN:SHU75349] [AC:U75349] [PN:putative permease BitE] [GN:bit operon] [OR:Brachyspira hyodysenteriae]

| ORF Name | NT ID | AA ID | NT/LN | AA/LN | Score | P-Value |
|---|---|---|---|---|---|---|
| SPX1452 | 1452 | 4113 | 771 | 257 | 295 | 1.50E-68 |

Description

[GI:2766196] [LN:SHU75349] [AC:U75349] [PN:putative permease BitF] [GN:bit operon] [OR:Brachyspira hyodysenteriae]

| ORF Name | NT ID | AA ID | NT/LN | AA/LN | Score | P-Value |
|---|---|---|---|---|---|---|
| SPX1453 | 1453 | 4114 | 198 | 66 | 164 | 3.20E-17 |

Description

[GI:2766196] [LN:SHU75349] [AC:U75349] [PN:putative permease BitF] [GN:bit operon] [OR:Brachyspira hyodysenteriae]

| ORF Name | NT ID | AA ID | NT/LN | AA/LN | Score | P-Value |
|---|---|---|---|---|---|---|
| SPX1454 | 1454 | 4115 | 750 | 250 | 137 | 3.20E-10 |

Description

[LN:PMGY_TREPA] [AC:P96121] [GN:GPM:PGM:TP0168] [OR:Treponema pallidum] [EC:5.4.2.1] [DE:(BPG-DEPENDENT PGAM)] [SP:P96121]

| ORF Name | NT ID | AA ID | NT/LN | AA/LN | Score | P-Value |
|---|---|---|---|---|---|---|
| SPX1455 | 1455 | 4116 | 1338 | 446 | 855 | 6.60E-196 |

Description

[GI:7380543] [LN:NMA6Z2491] [AC:AL162757:AL157959] [PN:conserved hypothetical protein] [GN:NMA1908] [OR:Neisseria meningitidis]

| ORF Name | NT ID | AA ID | NT/LN | AA/LN | Score | P-Value |
|---|---|---|---|---|---|---|
| SPX1456 | 1456 | 4117 | 360 | 120 | 123 | 9.30E-21 |

Description

[LN:E64494] [AC:E64494] [PN:hypothetical protein MJ1558] [OR:Methanococcus jannaschii]

| ORF Name | NT ID | AA ID | NT/LN | AA/LN | Score | P-Value |
|---|---|---|---|---|---|---|
| SPX1457 | 1457 | 4118 | 387 | 129 | 282 | 2.20E-58 |

Description

[LN:T44411] [AC:T44411] [PN:ribosomal protein L17 [imported]] [GN:rplQ]
[CL:Escherichia coli ribosomal protein L17] [OR:Bacillus halodurans]

| ORF Name | NT ID | AA ID | NT/LN | AA/LN | Score | P-Value |
|---|---|---|---|---|---|---|
| SPX1458 | 1458 | 4119 | 936 | 312 | 963 | 6.70E-130 |

Description

[LN:RPOA_BACSU] [AC:P20429] [GN:RPOA] [OR:Bacillus subtilis] [EC:2.7.7.6]
[DE:ALPHA CHAIN) (RNA POLYMERASE ALPHA SUBUNIT)] [SP:P20429]

| ORF Name | NT ID | AA ID | NT/LN | AA/LN | Score | P-Value |
|---|---|---|---|---|---|---|
| SPX1459 | 1459 | 4120 | 402 | 134 | | |

Description

NO-HIT

| ORF Name | NT ID | AA ID | NT/LN | AA/LN | Score | P-Value |
|---|---|---|---|---|---|---|
| SPX1460 | 1460 | 4121 | 423 | 141 | 494 | 1.80E-63 |

Description

[LN:RS11_BACSU] [AC:P04969] [GN:RPSK] [OR:Bacillus subtilis] [DE:30S
RIBOSOMAL PROTEIN S11 (BS11)] [SP:P04969]

| ORF Name | NT ID | AA ID | NT/LN | AA/LN | Score | P-Value |
|---|---|---|---|---|---|---|
| SPX1461 | 1461 | 4122 | 366 | 122 | 433 | 1.70E-55 |

Description

[GI:1044989] [LN:BACRPLP] [AC:L47971] [PN:ribosomal protein S13] [GN:rpsM]
[OR:Bacillus subtilis]

| ORF Name | NT ID | AA ID | NT/LN | AA/LN | Score | P-Value |
|---|---|---|---|---|---|---|
| SPX1462 | 1462 | 4123 | 168 | 56 | 237 | 1.10E-28 |

Description

[LN:S17988] [AC:S17988] [PN:translation initiation factor IF-1] [GN:infA]
[CL:translation initiation factor IF-1] [OR:Lactococcus lactis subsp.
lactis]

| ORF Name | NT ID | AA ID | NT/LN | AA/LN | Score | P-Value |
|---|---|---|---|---|---|---|
| SPX1463 | 1463 | 4124 | 639 | 213 | 560 | 8.10E-95 |
| Description | | | | | | |

"[LN:KAD_LACLA] [AC:P27143] [GN:ADK] [OR:Lactococcus lactis]
[SR:,subsplactis:Streptococcus lactis] [EC:2.7.4.3] [DE:ADENYLATE KINASE,
(ATP-AMP TRANSPHOSPHORYLASE)] [SP:P27143]"

| ORF Name | NT ID | AA ID | NT/LN | AA/LN | Score | P-Value |
|---|---|---|---|---|---|---|
| SPX1464 | 1464 | 4125 | 1311 | 437 | 927 | 4.30E-126 |
| Description | | | | | | |

"[LN:SECY_LACLA] [AC:P27148] [GN:SECY] [OR:Lactococcus lactis]
[SR:,subsplactis:Streptococcus lactis] [DE:PREPROTEIN TRANSLOCASE SECY
SUBUNIT] [SP:P27148]"

| ORF Name | NT ID | AA ID | NT/LN | AA/LN | Score | P-Value |
|---|---|---|---|---|---|---|
| SPX1465 | 1465 | 4126 | 441 | 147 | 614 | 7.90E-79 |
| Description | | | | | | |

[LN:RL15_STAAU] [AC:O06445] [GN:RPLO] [OR:Staphylococcus aureus] [DE:50S
RIBOSOMAL PROTEIN L15] [SP:O06445]

| ORF Name | NT ID | AA ID | NT/LN | AA/LN | Score | P-Value |
|---|---|---|---|---|---|---|
| SPX1466 | 1466 | 4127 | 183 | 61 | 185 | 6.90E-21 |
| Description | | | | | | |

[LN:RL30_STAAU] [AC:O06444] [GN:RPMD] [OR:Staphylococcus aureus] [DE:50S
RIBOSOMAL PROTEIN L30] [SP:O06444]

| ORF Name | NT ID | AA ID | NT/LN | AA/LN | Score | P-Value |
|---|---|---|---|---|---|---|
| SPX1467 | 1467 | 4128 | 495 | 165 | 621 | 8.70E-81 |
| Description | | | | | | |

[LN:RS5_BACST] [AC:P02357] [GN:RPSE] [OR:Bacillus stearothermophilus]
[DE:30S RIBOSOMAL PROTEIN S5 (BS5)] [SP:P02357]

| ORF Name | NT ID | AA ID | NT/LN | AA/LN | Score | P-Value |
|---|---|---|---|---|---|---|
| SPX1468 | 1468 | 4129 | 357 | 119 | 232 | 2.60E-53 |
| Description | | | | | | |

[LN:RL18_BACSU] [AC:P46899:P70969] [GN:RPLR] [OR:Bacillus subtilis] [DE:50S
RIBOSOMAL PROTEIN L18] [SP:P46899:P70969]

| ORF Name | NT ID | AA ID | NT/LN | AA/LN | Score | P-Value |
|---|---|---|---|---|---|---|
| SPX1469 | 1469 | 4130 | 525 | 175 | 478 | 2.00E-66 |

Description

[LN:B69695] [AC:B69695] [PN:ribosomal protein L6 (BL8) rplF] [GN:rplF]
[CL:Escherichia coli ribosomal protein L6] [OR:Bacillus subtilis]

| ORF Name | NT ID | AA ID | NT/LN | AA/LN | Score | P-Value |
|---|---|---|---|---|---|---|
| SPX1470 | 1470 | 4131 | 399 | 133 | 521 | 2.60E-67 |

Description

[GI:1044978] [LN:BACRPLP] [AC:L47971] [PN:ribosomal protein S8] [GN:rpsH]
[OR:Bacillus subtilis]

| ORF Name | NT ID | AA ID | NT/LN | AA/LN | Score | P-Value |
|---|---|---|---|---|---|---|
| SPX1471 | 1471 | 4132 | 237 | 79 | | |

Description

NO-HIT

| ORF Name | NT ID | AA ID | NT/LN | AA/LN | Score | P-Value |
|---|---|---|---|---|---|---|
| SPX1472 | 1472 | 4133 | 270 | 90 | 325 | 8.80E-41 |

Description

[LN:F69835] [AC:F69835] [PN:ribosomal protein S14 homolog yhzA] [GN:yhzA]
[CL:Escherichia coli ribosomal protein S14] [OR:Bacillus subtilis]

| ORF Name | NT ID | AA ID | NT/LN | AA/LN | Score | P-Value |
|---|---|---|---|---|---|---|
| SPX1473 | 1473 | 4134 | 543 | 181 | 728 | 6.40E-96 |

Description

[LN:T44395] [AC:T44395] [PN:ribosomal protein L5 [imported]] [GN:rplE]
[CL:Escherichia coli ribosomal protein L5] [OR:Bacillus halodurans]

| ORF Name | NT ID | AA ID | NT/LN | AA/LN | Score | P-Value |
|---|---|---|---|---|---|---|
| SPX1474 | 1474 | 4135 | 306 | 102 | 508 | 2.80E-65 |

Description

[GI:4927751] [LN:AF126059] [AC:AF126059] [PN:RpL24] [GN:rplX]
[OR:Streptococcus pneumoniae]

| ORF Name | NT ID | AA ID | NT/LN | AA/LN | Score | P-Value |
|---|---|---|---|---|---|---|
| SPX1475 | 1475 | 4136 | 369 | 123 | 597 | 2.20E-78 |

Description

[GI:4927750] [LN:AF126059] [AC:AF126059] [PN:RpL14] [GN:rplN]
[OR:Streptococcus pneumoniae]

| ORF Name | NT ID | AA ID | NT/LN | AA/LN | Score | P-Value |
|---|---|---|---|---|---|---|
| SPX1476 | 1476 | 4137 | 330 | 110 | 100 | 4.40E-07 |

Description

[LN:E71186] [AC:E71186] [PN:hypothetical protein PH1769] [GN:PH1769]
[CL:Pyrococcus horikoshii hypothetical protein PH1769] [OR:Pyrococcus horikoshii]

| ORF Name | NT ID | AA ID | NT/LN | AA/LN | Score | P-Value |
|---|---|---|---|---|---|---|
| SPX1477 | 1477 | 4138 | 261 | 87 | 430 | 3.10E-55 |

Description

[GI:4927749] [LN:AF126059] [AC:AF126059] [PN:RpS17] [GN:rpsQ]
[OR:Streptococcus pneumoniae]

| ORF Name | NT ID | AA ID | NT/LN | AA/LN | Score | P-Value |
|---|---|---|---|---|---|---|
| SPX1478 | 1478 | 4139 | 399 | 133 | | |

Description

NO-HIT

| ORF Name | NT ID | AA ID | NT/LN | AA/LN | Score | P-Value |
|---|---|---|---|---|---|---|
| SPX1479 | 1479 | 4140 | 207 | 69 | 324 | 8.90E-40 |

Description

[GI:4927748] [LN:AF126059] [AC:AF126059] [PN:RpL29] [GN:rpmC]
[OR:Streptococcus pneumoniae]

| ORF Name | NT ID | AA ID | NT/LN | AA/LN | Score | P-Value |
|---|---|---|---|---|---|---|
| SPX1480 | 1480 | 4141 | 414 | 138 | 708 | 1.30E-94 |

Description

[GI:4927747] [LN:AF126059] [AC:AF126059] [PN:RpL16] [GN:rplP]
[OR:Streptococcus pneumoniae]

| ORF Name | NT ID | AA ID | NT LN | AA LN | Score | P-Value |
|---|---|---|---|---|---|---|
| SPX1481 | 1481 | 4142 | 627 | 209 | 1063 | 2.10E-142 |

Description

[GI:4927746] [LN:AF126059] [AC:AF126059] [PN:RpS3] [GN:rpsC]
[OR:Streptococcus pneumoniae]

| ORF Name | NT ID | AA ID | NT LN | AA LN | Score | P-Value |
|---|---|---|---|---|---|---|
| SPX1482 | 1482 | 4143 | 225 | 75 | 356 | 1.60E-44 |

Description

[GI:4927745] [LN:AF126059] [AC:AF126059] [PN:RpL22] [GN:rplV]
[OR:Streptococcus pneumoniae]

| ORF Name | NT ID | AA ID | NT LN | AA LN | Score | P-Value |
|---|---|---|---|---|---|---|
| SPX1483 | 1483 | 4144 | 246 | 82 | | |

Description

NO-HIT

| ORF Name | NT ID | AA ID | NT LN | AA LN | Score | P-Value |
|---|---|---|---|---|---|---|
| SPX1484 | 1484 | 4145 | 282 | 94 | 492 | 5.20E-64 |

Description

[GI:4927744] [LN:AF126059] [AC:AF126059] [PN:RpS19] [GN:rpsS]
[OR:Streptococcus pneumoniae]

| ORF Name | NT ID | AA ID | NT LN | AA LN | Score | P-Value |
|---|---|---|---|---|---|---|
| SPX1485 | 1485 | 4146 | 834 | 278 | 1144 | 2.80E-152 |

Description

[LN:RL2_BACST] [AC:P04257] [GN:RPLB] [OR:Bacillus stearothermophilus]
[DE:50S RIBOSOMAL PROTEIN L2] [SP:P04257]

| ORF Name | NT ID | AA ID | NT LN | AA LN | Score | P-Value |
|---|---|---|---|---|---|---|
| SPX1486 | 1486 | 4147 | 297 | 99 | 162 | 1.30E-30 |

Description

[GI:3273331] [LN:AB015722] [AC:AB015722] [PN:ribosomal protrein L23]
[OR:Bacillus stearothermophilus] [SR:Bacillus stearothermophilus DNA]

| ORF Name | NT ID | AA ID | NT/LN | AA/LN | Score | P-Value |
|---|---|---|---|---|---|---|
| SPX1487 | 1487 | 4148 | 624 | 208 | 696 | 6.80E-91 |
| Description | | | | | | |

[LN:RL4_BACST] [AC:P28601] [GN:RPLD] [OR:Bacillus stearothermophilus] [DE:50S RIBOSOMAL PROTEIN L4] [SP:P28601]

| ORF Name | NT ID | AA ID | NT/LN | AA/LN | Score | P-Value |
|---|---|---|---|---|---|---|
| SPX1488 | 1488 | 4149 | 627 | 209 | 496 | 6.60E-110 |
| Description | | | | | | |

[LN:RL3_BACSU] [AC:P42920] [GN:RPLC] [OR:Bacillus subtilis] [DE:50S RIBOSOMAL PROTEIN L3 (BL3)] [SP:P42920]

| ORF Name | NT ID | AA ID | NT/LN | AA/LN | Score | P-Value |
|---|---|---|---|---|---|---|
| SPX1489 | 1489 | 4150 | 309 | 103 | 494 | 3.40E-64 |
| Description | | | | | | |

[LN:RS10_STRMU] [AC:P48853] [GN:RPSJ] [OR:Streptococcus mutans] [DE:30S RIBOSOMAL PROTEIN S10] [SP:P48853]

| ORF Name | NT ID | AA ID | NT/LN | AA/LN | Score | P-Value |
|---|---|---|---|---|---|---|
| SPX1490 | 1490 | 4151 | 618 | 206 | 71 | 0.00018 |
| Description | | | | | | |

[GI:7302797] [LN:AE003803] [AC:AE003803:AE002787] [GN:CG4798] [OR:Drosophila melanogaster] [SR:fruit fly]

| ORF Name | NT ID | AA ID | NT/LN | AA/LN | Score | P-Value |
|---|---|---|---|---|---|---|
| SPX1491 | 1491 | 4152 | 591 | 197 | 843 | 3.60E-112 |
| Description | | | | | | |

[GI:4098082] [LN:LLU73336] [AC:U73336] [PN:anaerobic ribonucleotide reductase activator] [GN:nrdG] [FN:activation of anaerobic] [OR:Lactococcus lactis subsp. cremoris]

| ORF Name | NT ID | AA ID | NT/LN | AA/LN | Score | P-Value |
|---|---|---|---|---|---|---|
| SPX1492 | 1492 | 4153 | 207 | 69 | | |
| Description | | | | | | |

NO-HIT

| ORF Name | NT ID | AA ID | NT/LN | AA/LN | Score | P-Value |
|---|---|---|---|---|---|---|
| SPX1493 | 1493 | 4154 | 507 | 169 | 187 | 4.50E-19 |

Description

[LN:G75479] [AC:G75479] [PN:hypothetical protein] [GN:DR0763] [OR:Deinococcus radiodurans]

| ORF Name | NT ID | AA ID | NT/LN | AA/LN | Score | P-Value |
|---|---|---|---|---|---|---|
| SPX1494 | 1494 | 4155 | 465 | 155 | | |

Description

NO-HIT

| ORF Name | NT ID | AA ID | NT/LN | AA/LN | Score | P-Value |
|---|---|---|---|---|---|---|
| SPX1495 | 1495 | 4156 | 2214 | 738 | 1123 | 1.10E-231 |

Description

[GI:4098081] [LN:LLU73336] [AC:U73336] [PN:anaerobic ribonucleotide reductase] [GN:nrdD] [OR:Lactococcus lactis subsp. cremoris]

| ORF Name | NT ID | AA ID | NT/LN | AA/LN | Score | P-Value |
|---|---|---|---|---|---|---|
| SPX1496 | 1496 | 4157 | 1557 | 519 | | |

Description

NO-HIT

| ORF Name | NT ID | AA ID | NT/LN | AA/LN | Score | P-Value |
|---|---|---|---|---|---|---|
| SPX1497 | 1497 | 4158 | 1476 | 492 | 519 | 3.70E-97 |

Description

[LN:YWAP_STRMU] [AC:P34001] [OR:Streptococcus mutans] [DE:HYPOTHETICAL PROTEIN IN WAPA 3'REGION (FRAGMENT)] [SP:P34001]

| ORF Name | NT ID | AA ID | NT/LN | AA/LN | Score | P-Value |
|---|---|---|---|---|---|---|
| SPX1498 | 1498 | 4159 | 558 | 186 | 93 | 0.00012 |

Description

"[LN:A26892] [AC:A26892] [PN:Mopa box protein] [OR:Mus musculus] [SR:, house mouse]"

| ORF Name | NT ID | AA ID | NT LN | AA LN | Score | P-Value |
|---|---|---|---|---|---|---|
| SPX1499 | 1499 | 4160 | 210 | 70 | | |
| Description | | | | | | |

NO-HIT

| ORF Name | NT ID | AA ID | NT LN | AA LN | Score | P-Value |
|---|---|---|---|---|---|---|
| SPX1500 | 1500 | 4161 | 390 | 130 | 66 | 7.30E-09 |
| Description | | | | | | |

[GI:1119198] [LN:BACCOMC] [AC:M30805] [PN:unknown protein] [OR:Bacillus subtilis] [SR:Bacillus subtilis (strain IS75) DNA]

| ORF Name | NT ID | AA ID | NT LN | AA LN | Score | P-Value |
|---|---|---|---|---|---|---|
| SPX1501 | 1501 | 4162 | 483 | 161 | 119 | 5.10E-16 |
| Description | | | | | | |

[LN:FOLC_LACCA] [AC:P15925] [GN:FGS] [OR:Lactobacillus casei] [EC:6.3.2.17] [DE:SYNTHETASE) (FPGS)] [SP:P15925]

| ORF Name | NT ID | AA ID | NT LN | AA LN | Score | P-Value |
|---|---|---|---|---|---|---|
| SPX1502 | 1502 | 4163 | 492 | 164 | 251 | 2.00E-38 |
| Description | | | | | | |

[LN:FOLC_BACSU] [AC:Q05865] [GN:FOLC] [OR:Bacillus subtilis] [EC:6.3.2.17] [DE:SYNTHETASE) (FPGS)] [SP:Q05865]

| ORF Name | NT ID | AA ID | NT LN | AA LN | Score | P-Value |
|---|---|---|---|---|---|---|
| SPX1503 | 1503 | 4164 | 306 | 102 | 87 | 5.90E-11 |
| Description | | | | | | |

[LN:A69982] [AC:A69982] [PN:hypothetical protein yrzB] [GN:yrzB] [OR:Bacillus subtilis]

| ORF Name | NT ID | AA ID | NT LN | AA LN | Score | P-Value |
|---|---|---|---|---|---|---|
| SPX1504 | 1504 | 4165 | 420 | 140 | 327 | 2.00E-40 |
| Description | | | | | | |

[LN:D69979] [AC:D69979] [PN:conserved hypothetical protein yrrK] [GN:yrrK] [CL:Haemophilus influenzae conserved hypothetical protein HI0305] [OR:Bacillus subtilis]

| ORF Name | NT ID | AA ID | NT/LN | AA/LN | Score | P-Value |
|---|---|---|---|---|---|---|
| SPX1505 | 1505 | 4166 | 267 | 89 | | |
| Description | | | | | | |

NO-HIT

| ORF Name | NT ID | AA ID | NT/LN | AA/LN | Score | P-Value |
|---|---|---|---|---|---|---|
| SPX1506 | 1506 | 4167 | 570 | 190 | | |
| Description | | | | | | |

NO-HIT

| ORF Name | NT ID | AA ID | NT/LN | AA/LN | Score | P-Value |
|---|---|---|---|---|---|---|
| SPX1507 | 1507 | 4168 | 399 | 133 | 315 | 1.80E-38 |
| Description | | | | | | |

[GI:6650536] [LN:AF103794] [AC:AF103794] [PN:unknown] [OR:Listeria monocytogenes]

| ORF Name | NT ID | AA ID | NT/LN | AA/LN | Score | P-Value |
|---|---|---|---|---|---|---|
| SPX1508 | 1508 | 4169 | 378 | 126 | 333 | 1.60E-40 |
| Description | | | | | | |

[GI:517210] [LN:SPU11799] [AC:U11799] [OR:Streptococcus pyogenes]

| ORF Name | NT ID | AA ID | NT/LN | AA/LN | Score | P-Value |
|---|---|---|---|---|---|---|
| SPX1509 | 1509 | 4170 | 393 | 131 | 340 | 3.70E-41 |
| Description | | | | | | |

[GI:517210] [LN:SPU11799] [AC:U11799] [OR:Streptococcus pyogenes]

| ORF Name | NT ID | AA ID | NT/LN | AA/LN | Score | P-Value |
|---|---|---|---|---|---|---|
| SPX1510 | 1510 | 4171 | 888 | 296 | 1035 | 8.50E-139 |
| Description | | | | | | |

[GI:6318592] [LN:AF146529] [AC:AF146529] [PN:aromatic amino acid aminotransferase] [GN:araT] [FN:catalyzes the last reaction in the biosynthesis] [OR:Lactococcus lactis subsp. cremoris]

| ORF Name | NT ID | AA ID | NT/LN | AA/LN | Score | P-Value |
|---|---|---|---|---|---|---|
| SPX1511 | 1511 | 4172 | 186 | 62 | | |

Description

NO-HIT

| ORF Name | NT ID | AA ID | NT/LN | AA/LN | Score | P-Value |
|---|---|---|---|---|---|---|
| SPX1512 | 1512 | 4173 | 771 | 257 | 297 | 2.20E-40 |

Description

[LN:YQXN_BACSU] [AC:P42095] [GN:YQXN:YQFI] [OR:Bacillus subtilis]
[DE:(ORF3)] [SP:P42095]

| ORF Name | NT ID | AA ID | NT/LN | AA/LN | Score | P-Value |
|---|---|---|---|---|---|---|
| SPX1513 | 1513 | 4174 | 993 | 331 | 623 | 6.80E-120 |

Description

[LN:H69679] [AC:H69679] [PN:involved in fatty acid/phospholipid synthesis plsX] [GN:plsX] [CL:phospholipid synthesis protein] [OR:Bacillus subtilis]

| ORF Name | NT ID | AA ID | NT/LN | AA/LN | Score | P-Value |
|---|---|---|---|---|---|---|
| SPX1514 | 1514 | 4175 | 336 | 112 | | |

Description

NO-HIT

| ORF Name | NT ID | AA ID | NT/LN | AA/LN | Score | P-Value |
|---|---|---|---|---|---|---|
| SPX1515 | 1515 | 4176 | 234 | 78 | 129 | 1.40E-17 |

Description

[LN:C72349] [AC:C72349] [PN:acyl carrier protein] [GN:TM0662] [CL:acyl carrier protein:acyl carrier protein homology] [OR:Thermotoga maritima]

| ORF Name | NT ID | AA ID | NT/LN | AA/LN | Score | P-Value |
|---|---|---|---|---|---|---|
| SPX1516 | 1516 | 4177 | 294 | 98 | 320 | 4.80E-40 |

Description

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1517 | 1517 | 4178 | 231 | 77 | 64 | 3.00E-06 |

Description

[GI:2695624] [LN:STU93029] [AC:U93029] [PN:amphipathic pore-forming peptide precursor] [GN:thmA] [OR:Streptococcus thermophilus]

| ORF Name | NT ID | AA ID | NT/LN | AA/LN | Score | P-Value |
|---|---|---|---|---|---|---|
| SPX1518 | 1518 | 4179 | 207 | 69 | | |

Description

NO-HIT

| ORF Name | NT ID | AA ID | NT/LN | AA/LN | Score | P-Value |
|---|---|---|---|---|---|---|
| SPX1519 | 1519 | 4180 | 2160 | 720 | 3571 | 0 |

Description

[LN:COMA_STRPN] [AC:Q03727] [GN:COMA] [OR:Streptococcus pneumoniae] [DE:TRANSPORT ATP-BINDING PROTEIN COMA] [SP:Q03727]

| ORF Name | NT ID | AA ID | NT/LN | AA/LN | Score | P-Value |
|---|---|---|---|---|---|---|
| SPX1520 | 1520 | 4181 | 1350 | 450 | 2184 | 8.20E-289 |

Description

[LN:COMB_STRPN] [AC:P36498] [GN:COMB] [OR:Streptococcus pneumoniae] [DE:TRANSPORT PROTEIN COMB] [SP:P36498]

| ORF Name | NT ID | AA ID | NT/LN | AA/LN | Score | P-Value |
|---|---|---|---|---|---|---|
| SPX1521 | 1521 | 4182 | 750 | 250 | 1189 | 1.40E-160 |

Description

[LN:PUR7_STRPN] [AC:Q07296] [GN:PURC] [OR:Streptococcus pneumoniae] [EC:6.3.2.6] [DE:(SAICAR SYNTHETASE)] [SP:Q07296]

| ORF Name | NT ID | AA ID | NT/LN | AA/LN | Score | P-Value |
|---|---|---|---|---|---|---|
| SPX1522 | 1522 | 4183 | 762 | 254 | 127 | 2.80E-08 |

Description

"[LN:C69492] [AC:C69492] [PN:phosphoribosylformylglycinamidine synthase, component II:formylglycinamide ribotide amidotransferase:phosphoribosylformylglycinamidine synthetase] [OR:Archaeoglobus fulgidus] [EC:6.3.5.3]"

| ORF Name | NT ID | AA ID | NT/LN | AA/LN | Score | P-Value |
|---|---|---|---|---|---|---|
| SPX1523 | 1523 | 4184 | 285 | 95 | 155 | 3.80E-15 |

Description

[GI:4928281] [LN:AF132127] [AC:AF132127] [PN:glucose-6-phosphate isomerase] [GN:gpi] [OR:Streptococcus mutans]

| ORF Name | NT ID | AA ID | NT/LN | AA/LN | Score | P-Value |
|---|---|---|---|---|---|---|
| SPX1524 | 1524 | 4185 | 1371 | 457 | 1764 | 1.20E-238 |

Description

[GI:4928281] [LN:AF132127] [AC:AF132127] [PN:glucose-6-phosphate isomerase] [GN:gpi] [OR:Streptococcus mutans]

| ORF Name | NT ID | AA ID | NT/LN | AA/LN | Score | P-Value |
|---|---|---|---|---|---|---|
| SPX1525 | 1525 | 4186 | 738 | 246 | 246 | 3.10E-28 |

Description

"[LN:YDP3_LACLA] [AC:P22347] [OR:Lactococcus lactis] [SR:,subsplactis:Streptococcus lactis] [DE:HYPOTHETICAL 18.7 KD PROTEIN IN PEPX 3'REGION (ORF3)] [SP:P22347]"

| ORF Name | NT ID | AA ID | NT/LN | AA/LN | Score | P-Value |
|---|---|---|---|---|---|---|
| SPX1526 | 1526 | 4187 | 1812 | 604 | 1001 | 2.10E-222 |

Description

[GI:4104142] [LN:AF033015] [AC:AF033015] [PN:ABC transporter homolog Z] [OR:Listeria monocytogenes]

| ORF Name | NT ID | AA ID | NT/LN | AA/LN | Score | P-Value |
|---|---|---|---|---|---|---|
| SPX1527 | 1527 | 4188 | 216 | 72 | | |

Description

NO-HIT

| ORF Name | NT ID | AA ID | NT/LN | AA/LN | Score | P-Value |
|---|---|---|---|---|---|---|
| SPX1528 | 1528 | 4189 | 324 | 108 | 105 | 1.60E-07 |

Description

[GI:6015958] [LN:SSU18930] [AC:Y18930] [PN:hypothetical protein] [GN:ORF-c22_037] [OR:Sulfolobus solfataricus]

| ORF Name | NT ID | AA ID | NT/LN | AA/LN | Score | P-Value |
|---|---|---|---|---|---|---|
| SPX1529 | 1529 | 4190 | 588 | 196 | 455 | 7.30E-58 |

Description

[GI:4104141] [LN:AF033015] [AC:AF033015] [PN:ABC transporter homolog Y] [OR:Listeria monocytogenes]

| ORF Name | NT ID | AA ID | NT/LN | AA/LN | Score | P-Value |
|---|---|---|---|---|---|---|
| SPX1530 | 1530 | 4191 | 1083 | 361 | 422 | 2.80E-66 |

Description

[GI:4104140] [LN:AF033015] [AC:AF033015] [PN:ABC transporter homolog X] [OR:Listeria monocytogenes]

| ORF Name | NT ID | AA ID | NT/LN | AA/LN | Score | P-Value |
|---|---|---|---|---|---|---|
| SPX1531 | 1531 | 4192 | 1965 | 655 | 3290 | 0 |

Description

[LN:HEXA_STRPN] [AC:P10564] [GN:HEXA] [OR:Streptococcus pneumoniae] [DE:DNA MISMATCH REPAIR PROTEIN HEXA] [SP:P10564]

| ORF Name | NT ID | AA ID | NT/LN | AA/LN | Score | P-Value |
|---|---|---|---|---|---|---|
| SPX1532 | 1532 | 4193 | 546 | 182 | 859 | 6.40E-114 |

Description

[LN:HEXA_STRPN] [AC:P10564] [GN:HEXA] [OR:Streptococcus pneumoniae] [DE:DNA MISMATCH REPAIR PROTEIN HEXA] [SP:P10564]

| ORF Name | NT ID | AA ID | NT/LN | AA/LN | Score | P-Value |
|---|---|---|---|---|---|---|
| SPX1533 | 1533 | 4194 | 447 | 149 | 740 | 7.50E-99 |

Description

[LN:ARGR_STRPN] [AC:Q54870] [GN:ARGR] [OR:Streptococcus pneumoniae] [DE:PROBABLE ARGININE REPRESSOR] [SP:Q54870]

| ORF Name | NT ID | AA ID | NT/LN | AA/LN | Score | P-Value |
|---|---|---|---|---|---|---|
| SPX1534 | 1534 | 4195 | 1692 | 564 | 365 | 3.20E-102 |

Description

"[LN:SYRC_YEAST] [AC:Q05506] [GN:YDR341C:D9651.10] [OR:Saccharomyces cerevisiae] [SR:,Baker's yeast] [EC:6.1.1.19] [DE:-TRNA LIGASE) (ARGRS)] [SP:Q05506]"

| ORF Name | NT ID | AA ID | NT/LN | AA/LN | Score | P-Value |
|---|---|---|---|---|---|---|
| SPX1535 | 1535 | 4196 | 450 | 150 | 398 | 6.20E-51 |
| Description | | | | | | |

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1536 | 1536 | 4197 | 204 | 68 | | |
| Description | | | | | | |

NO-HIT

| ORF Name | NT ID | AA ID | NT/LN | AA/LN | Score | P-Value |
|---|---|---|---|---|---|---|
| SPX1537 | 1537 | 4198 | 285 | 95 | 102 | 6.20E-17 |
| Description | | | | | | |

"[LN:S74709] [AC:S74709] [PN:hypothetical protein sll1188] [OR:Synechocystis sp.] [SR:PCC 6803, , PCC 6803] [SR:PCC 6803, ]"

| ORF Name | NT ID | AA ID | NT/LN | AA/LN | Score | P-Value |
|---|---|---|---|---|---|---|
| SPX1538 | 1538 | 4199 | 708 | 236 | 1209 | 4.90E-164 |
| Description | | | | | | |

[GI:5830529] [LN:SPAJ6394] [AC:AJ006394] [PN:response regulator] [GN:phoP] [OR:Streptococcus pneumoniae]

| ORF Name | NT ID | AA ID | NT/LN | AA/LN | Score | P-Value |
|---|---|---|---|---|---|---|
| SPX1539 | 1539 | 4200 | 1332 | 444 | 2196 | 4.10E-300 |
| Description | | | | | | |

[GI:5830530] [LN:SPAJ6394] [AC:AJ006394] [PN:histidine kinase] [GN:phoR] [OR:Streptococcus pneumoniae]

| ORF Name | NT ID | AA ID | NT/LN | AA/LN | Score | P-Value |
|---|---|---|---|---|---|---|
| SPX1540 | 1540 | 4201 | 876 | 292 | 1435 | 1.70E-188 |
| Description | | | | | | |

[GI:4530447] [LN:AF118229] [AC:AF118229] [PN:phosphate binding protein PstS] [GN:pstS] [OR:Streptococcus pneumoniae]

| ORF Name | NT ID | AA ID | NT LN | AA LN | Score | P-Value |
|---|---|---|---|---|---|---|
| SPX1541 | 1541 | 4202 | 816 | 272 | 1333 | 2.80E-185 |
| Description | | | | | | |

[GI:4530448] [LN:AF118229] [AC:AF118229] [PN:transmembrane protein PstC] [GN:pstC] [OR:Streptococcus pneumoniae]

| ORF Name | NT ID | AA ID | NT LN | AA LN | Score | P-Value |
|---|---|---|---|---|---|---|
| SPX1542 | 1542 | 4203 | 816 | 272 | 1312 | 1.10E-182 |
| Description | | | | | | |

[GI:4530449] [LN:AF118229] [AC:AF118229] [PN:transmembrane protein PstA] [GN:PstA] [OR:Streptococcus pneumoniae]

| ORF Name | NT ID | AA ID | NT LN | AA LN | Score | P-Value |
|---|---|---|---|---|---|---|
| SPX1543 | 1543 | 4204 | 753 | 251 | 1284 | 2.00E-174 |
| Description | | | | | | |

[GI:4530450] [LN:AF118229] [AC:AF118229] [PN:ATP-binding cassette protein PstB] [GN:pstB] [OR:Streptococcus pneumoniae]

| ORF Name | NT ID | AA ID | NT LN | AA LN | Score | P-Value |
|---|---|---|---|---|---|---|
| SPX1544 | 1544 | 4205 | 651 | 217 | 1067 | 8.20E-144 |
| Description | | | | | | |

[GI:4530451] [LN:AF118229] [AC:AF118229] [PN:PhoU] [GN:phoU] [OR:Streptococcus pneumoniae]

| ORF Name | NT ID | AA ID | NT LN | AA LN | Score | P-Value |
|---|---|---|---|---|---|---|
| SPX1545 | 1545 | 4206 | 426 | 142 | 131 | 2.90E-10 |
| Description | | | | | | |

[GI:5822769] [LN:AB024553] [AC:AB024553] [OR:Bacillus halodurans] [SR:Bacillus halodurans (strain:C-125) DNA]

| ORF Name | NT ID | AA ID | NT LN | AA LN | Score | P-Value |
|---|---|---|---|---|---|---|
| SPX1546 | 1546 | 4207 | 219 | 73 | | |
| Description | | | | | | |

NO-HIT

| ORF Name | NT ID | AA ID | NT/LN | AA/LN | Score | P-Value |
|---|---|---|---|---|---|---|
| SPX1547 | 1547 | 4208 | 459 | 153 | | |

Description

NO-HIT

| ORF Name | NT ID | AA ID | NT/LN | AA/LN | Score | P-Value |
|---|---|---|---|---|---|---|
| SPX1548 | 1548 | 4209 | 1017 | 339 | 921 | 6.40E-122 |

Description

[LN:GPDA_BACSU] [AC:P46919] [GN:GPSA:GLYC] [OR:Bacillus subtilis]
[EC:1.1.1.94] [DE:DEPENDENT DIHYDROXYACETONE-PHOSPHATE REDUCTASE)]
[SP:P46919]

| ORF Name | NT ID | AA ID | NT/LN | AA/LN | Score | P-Value |
|---|---|---|---|---|---|---|
| SPX1549 | 1549 | 4210 | 900 | 300 | 1481 | 1.60E-199 |

Description

[GI:3550619] [LN:SPAJ4869] [AC:AJ004869] [PN:UTP-glucose-1-phosphate
uridylyltransferase] [GN:galU] [FN:synthesis of UDP-glucose]
[OR:Streptococcus pneumoniae]

| ORF Name | NT ID | AA ID | NT/LN | AA/LN | Score | P-Value |
|---|---|---|---|---|---|---|
| SPX1550 | 1550 | 4211 | 675 | 225 | | |

Description

NO-HIT

| ORF Name | NT ID | AA ID | NT/LN | AA/LN | Score | P-Value |
|---|---|---|---|---|---|---|
| SPX1551 | 1551 | 4212 | 681 | 227 | 520 | 1.90E-70 |

Description

[LN:SUB400707] [AC:AJ400707] [PN:hypothetical protein] [OR:Streptococcus uberis]

| ORF Name | NT ID | AA ID | NT/LN | AA/LN | Score | P-Value |
|---|---|---|---|---|---|---|
| SPX1552 | 1552 | 4213 | 546 | 182 | 236 | 1.30E-55 |

Description

[GI:3192049] [LN:AB001562] [AC:AB001562] [OR:Streptococcus mutans]
[SR:Streptococcus mutans (strain:Xc) DNA]

| ORF Name | NT ID | AA ID | NT/LN | AA/LN | Score | P-Value |
|---|---|---|---|---|---|---|
| SPX1553 | 1553 | 4214 | 1131 | 377 | 622 | 4.50E-119 |
| Description | | | | | | |

[LN:G69866] [AC:G69866] [PN:hippurate hydrolase homolog ykuR] [GN:ykuR]
[CL:hippurate hydrolase] [OR:Bacillus subtilis]

| ORF Name | NT ID | AA ID | NT/LN | AA/LN | Score | P-Value |
|---|---|---|---|---|---|---|
| SPX1554 | 1554 | 4215 | 699 | 233 | 578 | 1.10E-86 |
| Description | | | | | | |

"[LN:H72245] [AC:H72245] [PN:2,3,4,5-tetrahydropyridine-2-carboxylate
N-succinyltransferase-related protein] [GN:TM1519] [OR:Thermotoga maritima]"

| ORF Name | NT ID | AA ID | NT/LN | AA/LN | Score | P-Value |
|---|---|---|---|---|---|---|
| SPX1555 | 1555 | 4216 | 459 | 153 | 75 | 5.50E-08 |
| Description | | | | | | |

[GI:6103625] [LN:AF172095] [AC:AF172095] [PN:unknown] [OR:Picea rubens]

| ORF Name | NT ID | AA ID | NT/LN | AA/LN | Score | P-Value |
|---|---|---|---|---|---|---|
| SPX1556 | 1556 | 4217 | 216 | 72 | | |
| Description | | | | | | |

NO-HIT

| ORF Name | NT ID | AA ID | NT/LN | AA/LN | Score | P-Value |
|---|---|---|---|---|---|---|
| SPX1557 | 1557 | 4218 | 834 | 278 | 214 | 2.60E-30 |
| Description | | | | | | |

[LN:YDED_BACSU] [AC:P96661] [GN:YDED] [OR:Bacillus subtilis]
[DE:HYPOTHETICAL 35.3 KD PROTEIN IN CSPC-NAP INTERGENIC REGION] [SP:P96661]

| ORF Name | NT ID | AA ID | NT/LN | AA/LN | Score | P-Value |
|---|---|---|---|---|---|---|
| SPX1558 | 1558 | 4219 | 2463 | 821 | 4147 | 0 |
| Description | | | | | | |

[GI:6165962] [LN:AF101781] [AC:AF101781] [PN:penicillin-binding protein 1b]
[GN:pbp1b] [OR:Streptococcus pneumoniae]

| ORF Name | NT ID | AA ID | NT LN | AA LN | Score | P-Value |
|---|---|---|---|---|---|---|
| SPX1559 | 1559 | 4220 | 1257 | 419 | 697 | 1.90E-174 |

Description

[LN:SYY1_BACSU] [AC:P22326] [GN:TYRS] [OR:Bacillus subtilis] [EC:6.1.1.1] [DE:(TYRRS 1)] [SP:P22326]

| ORF Name | NT ID | AA ID | NT LN | AA LN | Score | P-Value |
|---|---|---|---|---|---|---|
| SPX1560 | 1560 | 4221 | 2073 | 691 | 218 | 1.60E-63 |

Description

"[LN:COPA_ENTHR] [AC:P32113:Q47841] [GN:COPA] [OR:Enterococcus hirae] [EC:3.6.1.36] [DE:COPPER/POTASSIUM-TRANSPORTING ATPASE A,] [SP:P32113:Q47841]"

| ORF Name | NT ID | AA ID | NT LN | AA LN | Score | P-Value |
|---|---|---|---|---|---|---|
| SPX1561 | 1561 | 4222 | 195 | 65 | | |

Description

NO-HIT

| ORF Name | NT ID | AA ID | NT LN | AA LN | Score | P-Value |
|---|---|---|---|---|---|---|
| SPX1562 | 1562 | 4223 | 264 | 88 | 109 | 2.90E-08 |

Description

[LN:RRMA_ECOLI] [AC:P36999] [GN:RRMA] [OR:Escherichia coli] [EC:2.1.1.51] [DE:METHYLTRANSFERASE)] [SP:P36999]

| ORF Name | NT ID | AA ID | NT LN | AA LN | Score | P-Value |
|---|---|---|---|---|---|---|
| SPX1563 | 1563 | 4224 | 591 | 197 | 192 | 1.90E-25 |

Description

[LN:YXJB_BACSU] [AC:P42313] [GN:YXJB:N15I] [OR:Bacillus subtilis] [DE:HYPOTHETICAL 31.5 KD PROTEIN IN KATB 3'REGION] [SP:P42313]

| ORF Name | NT ID | AA ID | NT LN | AA LN | Score | P-Value |
|---|---|---|---|---|---|---|
| SPX1564 | 1564 | 4225 | 171 | 57 | | |

Description

NO-HIT

| ORF Name | NT ID | AA ID | NT/LN | AA/LN | Score | P-Value |
|---|---|---|---|---|---|---|
| SPX1565 | 1565 | 4226 | 573 | 191 | | |

Description

NO-HIT

| ORF Name | NT ID | AA ID | NT/LN | AA/LN | Score | P-Value |
|---|---|---|---|---|---|---|
| SPX1566 | 1566 | 4227 | 2259 | 753 | 473 | 5.80E-165 |

Description

"[LN:PHSG_BACSU] [AC:P39123] [GN:GLGP] [OR:Bacillus subtilis] [EC:2.4.1.1] [DE:GLYCOGEN PHOSPHORYLASE,] [SP:P39123]"

| ORF Name | NT ID | AA ID | NT/LN | AA/LN | Score | P-Value |
|---|---|---|---|---|---|---|
| SPX1567 | 1567 | 4228 | 1518 | 506 | 2687 | 0 |

Description

[LN:MALQ_STRPN] [AC:P29851] [GN:MALM] [OR:Streptococcus pneumoniae] [EC:2.4.1.25] [DE:(DISPROPORTIONATING ENZYME) (D-ENZYME)] [SP:P29851]

| ORF Name | NT ID | AA ID | NT/LN | AA/LN | Score | P-Value |
|---|---|---|---|---|---|---|
| SPX1568 | 1568 | 4229 | 1272 | 424 | 2167 | 3.30E-288 |

Description

[LN:MALX_STRPN] [AC:P29850] [GN:MALX] [OR:Streptococcus pneumoniae] [DE:MALTOSE/MALTODEXTRIN-BINDING PROTEIN PRECURSOR] [SP:P29850]

| ORF Name | NT ID | AA ID | NT/LN | AA/LN | Score | P-Value |
|---|---|---|---|---|---|---|
| SPX1569 | 1569 | 4230 | 1293 | 431 | 2176 | 0 |

Description

[LN:MALC_STRPN] [AC:Q04698] [GN:MALC] [OR:Streptococcus pneumoniae] [DE:MALTODEXTRIN TRANSPORT SYSTEM PERMEASE PROTEIN MALC] [SP:Q04698]

| ORF Name | NT ID | AA ID | NT/LN | AA/LN | Score | P-Value |
|---|---|---|---|---|---|---|
| SPX1570 | 1570 | 4231 | 843 | 281 | 1265 | 2.40E-177 |

Description

[LN:MALD_STRPN] [AC:Q04699] [GN:MALD] [OR:Streptococcus pneumoniae] [DE:MALTODEXTRIN TRANSPORT SYSTEM PERMEASE PROTEIN MALD] [SP:Q04699]

| ORF Name | NT ID | AA ID | NT/LN | AA/LN | Score | P-Value |
|---|---|---|---|---|---|---|
| SPX1571 | 1571 | 4232 | 801 | 267 | 540 | 1.70E-145 |

Description

[LN:MALA_STRPN] [AC:Q08510] [GN:MALA] [OR:Streptococcus pneumoniae] [DE:MALA PROTEIN] [SP:Q08510]

| ORF Name | NT ID | AA ID | NT/LN | AA/LN | Score | P-Value |
|---|---|---|---|---|---|---|
| SPX1572 | 1572 | 4233 | 987 | 329 | 1668 | 7.30E-227 |

Description

[GI:2656094] [LN:STRMALR] [AC:L21856] [PN:repressor protein] [GN:malR] [FN:maltose operon transcriptional repressor] [OR:Streptococcus pneumoniae]

| ORF Name | NT ID | AA ID | NT/LN | AA/LN | Score | P-Value |
|---|---|---|---|---|---|---|
| SPX1573 | 1573 | 4234 | 342 | 114 | | |

Description

NO-HIT

| ORF Name | NT ID | AA ID | NT/LN | AA/LN | Score | P-Value |
|---|---|---|---|---|---|---|
| SPX1574 | 1574 | 4235 | 381 | 127 | 378 | 8.30E-48 |

Description

[LN:T30285] [AC:T30285] [PN:hypothetical protein] [OR:Streptococcus pneumoniae]

| ORF Name | NT ID | AA ID | NT/LN | AA/LN | Score | P-Value |
|---|---|---|---|---|---|---|
| SPX1575 | 1575 | 4236 | 942 | 314 | 463 | 6.90E-73 |

Description

[GI:1620924] [LN:BS168NPRB] [AC:Z79580] [OR:Bacillus subtilis]

| ORF Name | NT ID | AA ID | NT/LN | AA/LN | Score | P-Value |
|---|---|---|---|---|---|---|
| SPX1576 | 1576 | 4237 | 1764 | 588 | 701 | 1.30E-229 |

Description

[LN:SYD_BACSU] [AC:O32038] [GN:ASPS] [OR:Bacillus subtilis] [EC:6.1.1.12] [DE:(ASPRS)] [SP:O32038]

| ORF Name | NT ID | AA ID | NT LN | AA LN | Score | P-Value |
|---|---|---|---|---|---|---|
| SPX1577 | 1577 | 4238 | 432 | 144 | | |

Description

NO-HIT

| ORF Name | NT ID | AA ID | NT LN | AA LN | Score | P-Value |
|---|---|---|---|---|---|---|
| SPX1578 | 1578 | 4239 | 192 | 64 | | |

Description

NO-HIT

| ORF Name | NT ID | AA ID | NT LN | AA LN | Score | P-Value |
|---|---|---|---|---|---|---|
| SPX1579 | 1579 | 4240 | 231 | 77 | | |

Description

NO-HIT

| ORF Name | NT ID | AA ID | NT LN | AA LN | Score | P-Value |
|---|---|---|---|---|---|---|
| SPX1580 | 1580 | 4241 | 642 | 214 | 120 | 9.80E-14 |

Description

[GI:1402529] [LN:D78257] [AC:D78257] [PN:ORF8] [GN:orf8] [OR:Enterococcus faecalis] [SR:Enterococcus faecalis plasmid:pYI17 DNA]

| ORF Name | NT ID | AA ID | NT LN | AA LN | Score | P-Value |
|---|---|---|---|---|---|---|
| SPX1581 | 1581 | 4242 | 741 | 247 | | |

Description

NO-HIT

| ORF Name | NT ID | AA ID | NT LN | AA LN | Score | P-Value |
|---|---|---|---|---|---|---|
| SPX1582 | 1582 | 4243 | 201 | 67 | | |

Description

NO-HIT

| ORF Name | NT ID | AA ID | NT LN | AA LN | Score | P-Value |
|---|---|---|---|---|---|---|
| SPX1583 | 1583 | 4244 | 465 | 155 | 78 | 0.00011 |

Description

[LN:T07291] [AC:T07291] [PN:hypothetical protein 42c] [OR:chloroplast Chlorella vulgaris]

| ORF Name | NT ID | AA ID | NT LN | AA LN | Score | P-Value |
|---|---|---|---|---|---|---|
| SPX1584 | 1584 | 4245 | 186 | 62 | | |

Description

NO-HIT

| ORF Name | NT ID | AA ID | NT LN | AA LN | Score | P-Value |
|---|---|---|---|---|---|---|
| SPX1585 | 1585 | 4246 | 192 | 64 | | |

Description

NO-HIT

| ORF Name | NT ID | AA ID | NT LN | AA LN | Score | P-Value |
|---|---|---|---|---|---|---|
| SPX1586 | 1586 | 4247 | 189 | 63 | 200 | 7.00E-24 |

Description

[LN:T30285] [AC:T30285] [PN:hypothetical protein] [OR:Streptococcus pneumoniae]

| ORF Name | NT ID | AA ID | NT LN | AA LN | Score | P-Value |
|---|---|---|---|---|---|---|
| SPX1587 | 1587 | 4248 | 1290 | 430 | 1740 | 7.50E-236 |

Description

[LN:SYH_STREQ] [AC:P30053] [GN:HISS] [OR:Streptococcus equisimilis] [EC:6.1.1.21] [DE:(HISRS)] [SP:P30053]

| ORF Name | NT ID | AA ID | NT LN | AA LN | Score | P-Value |
|---|---|---|---|---|---|---|
| SPX1588 | 1588 | 4249 | 921 | 307 | | |

Description

NO-HIT

| ORF_Name | NT_ID | AA_ID | NT LN | AA LN | Score | P-Value |
|---|---|---|---|---|---|---|
| SPX1589 | 1589 | 4250 | 1248 | 416 | 334 | 2.10E-57 |
| Description | | | | | | |

[GI:3582221] [LN:AE001272] [AC:AE001272] [PN:conserved hypothetical protein] [GN:ORF00049] [OR:Lactococcus lactis]

| ORF_Name | NT_ID | AA_ID | NT LN | AA LN | Score | P-Value |
|---|---|---|---|---|---|---|
| SPX1590 | 1590 | 4251 | 399 | 133 | | |
| Description | | | | | | |

NO-HIT

| ORF_Name | NT_ID | AA_ID | NT LN | AA LN | Score | P-Value |
|---|---|---|---|---|---|---|
| SPX1591 | 1591 | 4252 | 852 | 284 | 301 | 1.70E-34 |
| Description | | | | | | |

[LN:RGG_STRGC] [AC:P49330] [GN:RGG] [OR:Streptococcus gordonii challis] [DE:RGG PROTEIN] [SP:P49330]

| ORF_Name | NT_ID | AA_ID | NT LN | AA LN | Score | P-Value |
|---|---|---|---|---|---|---|
| SPX1592 | 1592 | 4253 | 342 | 114 | 227 | 6.60E-27 |
| Description | | | | | | |

[GI:2258088] [LN:AB000631] [AC:AB000631] [OR:Streptococcus mutans] [SR:Streptococcus mutans DNA]

| ORF_Name | NT_ID | AA_ID | NT LN | AA LN | Score | P-Value |
|---|---|---|---|---|---|---|
| SPX1593 | 1593 | 4254 | 1704 | 568 | 994 | 1.30E-207 |
| Description | | | | | | |

"[LN:S76895] [AC:S76895] [PN:hypothetical protein] [CL:dihydroxy-acid dehydratase] [OR:Synechocystis sp.] [SR:PCC 6803, , PCC 6803] [SR:PCC 6803, ]"

| ORF_Name | NT_ID | AA_ID | NT LN | AA LN | Score | P-Value |
|---|---|---|---|---|---|---|
| SPX1594 | 1594 | 4255 | 933 | 311 | 272 | 2.40E-45 |
| Description | | | | | | |

"[LN:TKTC_METJA] [AC:Q58092] [GN:MJ0679] [OR:Methanococcus jannaschii] [EC:2.2.1.1] [DE:PUTATIVE TRANSKETOLASE C-TERMINAL SECTION, (TK)] [SP:Q58092]"

| ORF Name | NT ID | AA ID | NT/LN | AA/LN | Score | P-Value |
|---|---|---|---|---|---|---|
| SPX1595 | 1595 | 4256 | 858 | 286 | 347 | 7.70E-66 |

Description

"[LN:TKTN_METJA] [AC:Q58094] [GN:MJ0681] [OR:Methanococcus jannaschii] [EC:2.2.1.1] [DE:PUTATIVE TRANSKETOLASE N-TERMINAL SECTION, (TK)] [SP:Q58094]"

| ORF Name | NT ID | AA ID | NT/LN | AA/LN | Score | P-Value |
|---|---|---|---|---|---|---|
| SPX1596 | 1596 | 4257 | 1347 | 449 | 535 | 9.90E-132 |

Description

[LN:T37066] [AC:T37066] [PN:probable integral membrane protein] [GN:SCJ21.17c] [OR:Streptomyces coelicolor]

| ORF Name | NT ID | AA ID | NT/LN | AA/LN | Score | P-Value |
|---|---|---|---|---|---|---|
| SPX1597 | 1597 | 4258 | 285 | 95 | | |

Description

NO-HIT

| ORF Name | NT ID | AA ID | NT/LN | AA/LN | Score | P-Value |
|---|---|---|---|---|---|---|
| SPX1598 | 1598 | 4259 | 2031 | 677 | 197 | 8.80E-31 |

Description

"[GI:4512373] [LN:AB011837] [AC:AB011837] [GN:yjdC] [OR:Bacillus halodurans] [SR:Bacillus halodurans (strain:C-125) DNA, clone_lib:lambda no.9]"

| ORF Name | NT ID | AA ID | NT/LN | AA/LN | Score | P-Value |
|---|---|---|---|---|---|---|
| SPX1599 | 1599 | 4260 | 1008 | 336 | 133 | 1.30E-18 |

Description

[GI:6689167] [LN:SCE20] [AC:AL136058] [PN:putative membrane protein] [GN:SCE20.08c] [OR:Streptomyces coelicolor A3(2)]

| ORF Name | NT ID | AA ID | NT/LN | AA/LN | Score | P-Value |
|---|---|---|---|---|---|---|
| SPX1600 | 1600 | 4261 | 201 | 67 | | |

Description

NO-HIT

| ORF Name | NT ID | AA ID | NT/LN | AA/LN | Score | P-Value |
|---|---|---|---|---|---|---|
| SPX1601 | 1601 | 4262 | 183 | 61 | 240 | 3.00E-28 |
| Description | | | | | | |

"[LN:RL32_LACLC] [AC:O34101] [GN:RPMF] [OR:Lactococcus lactis] [SR:,subspcremoris:Streptococcus cremoris] [DE:50S RIBOSOMAL PROTEIN L32] [SP:O34101]"

| ORF Name | NT ID | AA ID | NT/LN | AA/LN | Score | P-Value |
|---|---|---|---|---|---|---|
| SPX1602 | 1602 | 4263 | 1926 | 642 | 1320 | 0 |
| Description | | | | | | |

[GI:1914872] [LN:SPZ82001] [AC:Z82001] [PN:PCPA] [GN:pcpA] [OR:Streptococcus pneumoniae]

| ORF Name | NT ID | AA ID | NT/LN | AA/LN | Score | P-Value |
|---|---|---|---|---|---|---|
| SPX1603 | 1603 | 4264 | 228 | 76 | | |
| Description | | | | | | |

NO-HIT

| ORF Name | NT ID | AA ID | NT/LN | AA/LN | Score | P-Value |
|---|---|---|---|---|---|---|
| SPX1604 | 1604 | 4265 | 576 | 192 | 429 | 4.10E-54 |
| Description | | | | | | |

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1605 | 1605 | 4266 | 378 | 126 | 303 | 4.10E-37 |
| Description | | | | | | |

[LN:S52544] [AC:S52544] [PN:ISL2 protein] [OR:Lactobacillus helveticus]

| ORF Name | NT ID | AA ID | NT/LN | AA/LN | Score | P-Value |
|---|---|---|---|---|---|---|
| SPX1606 | 1606 | 4267 | 327 | 109 | 495 | 7.70E-65 |
| Description | | | | | | |

[GI:1914871] [LN:SPZ82001] [AC:Z82001] [PN:unknown] [OR:Streptococcus pneumoniae]

| ORF Name | NT ID | AA ID | NT/LN | AA/LN | Score | P-Value |
|---|---|---|---|---|---|---|
| SPX1607 | 1607 | 4268 | 1881 | 627 | 95 | 0.00073 |
| Description | | | | | | |

[LN:T27355] [AC:T27355] [PN:hypothetical protein Y70D2A.2] [GN:Y70D2A.2] [OR:Caenorhabditis elegans]

| ORF Name | NT ID | AA ID | NT/LN | AA/LN | Score | P-Value |
|---|---|---|---|---|---|---|
| SPX1608 | 1608 | 4269 | 870 | 290 | 108 | 2.70E-22 |
| Description | | | | | | |

"[LN:F70203] [AC:F70203] [PN:xylose operon regulatory protein (xylR-2) homolog] [CL:glucose kinase:glucose kinase homology] [OR:Borrelia burgdorferi] [SR:, Lyme disease spirochete]"

| ORF Name | NT ID | AA ID | NT/LN | AA/LN | Score | P-Value |
|---|---|---|---|---|---|---|
| SPX1609 | 1609 | 4270 | 2661 | 887 | 345 | 6.30E-65 |
| Description | | | | | | |

[LN:YBGG_ECOLI] [AC:P54746:P75753] [GN:YBGG] [OR:Escherichia coli] [DE:HYPOTHETICAL 100.0 KD PROTEIN IN HRSA-CYDA INTERGENIC REGION] [SP:P54746:P75753]

| ORF Name | NT ID | AA ID | NT/LN | AA/LN | Score | P-Value |
|---|---|---|---|---|---|---|
| SPX1610 | 1610 | 4271 | 1305 | 435 | 409 | 6.20E-106 |
| Description | | | | | | |

[LN:T37125] [AC:T37125] [PN:hypothetical protein SCJ4.42c] [GN:SCJ4.42c] [OR:Streptomyces coelicolor]

| ORF Name | NT ID | AA ID | NT/LN | AA/LN | Score | P-Value |
|---|---|---|---|---|---|---|
| SPX1611 | 1611 | 4272 | 2085 | 695 | 408 | 9.50E-105 |
| Description | | | | | | |

[GI:5759293] [LN:AF175722] [AC:AF175722] [PN:immunoreactive 89kD antigen PG87] [OR:Porphyromonas gingivalis]

| ORF Name | NT ID | AA ID | NT/LN | AA/LN | Score | P-Value |
|---|---|---|---|---|---|---|
| SPX1612 | 1612 | 4273 | 1680 | 560 | 249 | 2.20E-63 |

Description

"[GI:4096756] [LN:SSU39394] [AC:U39394] [PN:alpha-1,3/4-fucosidase precursor] [FN:alpha-fucosidase specific for alpha-1,3 and] [OR:Streptomyces sp.] [SR:Streptomyces sp]"

| ORF Name | NT ID | AA ID | NT/LN | AA/LN | Score | P-Value |
|---|---|---|---|---|---|---|
| SPX1613 | 1613 | 4274 | 1230 | 410 | 942 | 1.30E-244 |

Description

[LN:SAGP_STRPY] [AC:P16962] [GN:SAGP] [OR:Streptococcus pyogenes] [DE:STREPTOCOCCAL ACID GLYCOPROTEIN] [SP:P16962]

| ORF Name | NT ID | AA ID | NT/LN | AA/LN | Score | P-Value |
|---|---|---|---|---|---|---|
| SPX1614 | 1614 | 4275 | 1017 | 339 | 897 | 3.80E-184 |

Description

[GI:2764612] [LN:LSAJ1330] [AC:AJ001330] [PN:ornithine transcarbamoylase] [GN:arcB] [OR:Lactobacillus sakei]

| ORF Name | NT ID | AA ID | NT/LN | AA/LN | Score | P-Value |
|---|---|---|---|---|---|---|
| SPX1615 | 1615 | 4276 | 948 | 316 | 465 | 3.40E-129 |

Description

[GI:2894540] [LN:EFAJ3331] [AC:AJ223331] [PN:carbamate kinase] [GN:arcC] [FN:synthesis of ATP from carbamylphosphate] [OR:Enterococcus faecium]

| ORF Name | NT ID | AA ID | NT/LN | AA/LN | Score | P-Value |
|---|---|---|---|---|---|---|
| SPX1616 | 1616 | 4277 | 1512 | 504 | 426 | 4.50E-106 |

Description

[GI:2697115] [LN:AF008219] [AC:AF008219] [PN:unknown] [OR:Borrelia afzelii]

| ORF Name | NT ID | AA ID | NT/LN | AA/LN | Score | P-Value |
|---|---|---|---|---|---|---|
| SPX1617 | 1617 | 4278 | 1332 | 444 | 277 | 8.20E-67 |

Description

[LN:S43914] [AC:S43914] [PN:hypothetical protein 1] [CL:peptidase V] [OR:Bacillus stearothermophilus]

| ORF Name | NT ID | AA ID | NT LN | AA LN | Score | P-Value |
|---|---|---|---|---|---|---|
| SPX1618 | 1618 | 4279 | 192 | 64 | | |

Description

NO-HIT

| ORF Name | NT ID | AA ID | NT LN | AA LN | Score | P-Value |
|---|---|---|---|---|---|---|
| SPX1619 | 1619 | 4280 | 237 | 79 | | |

Description

NO-HIT

| ORF Name | NT ID | AA ID | NT LN | AA LN | Score | P-Value |
|---|---|---|---|---|---|---|
| SPX1620 | 1620 | 4281 | 267 | 89 | | |

Description

NO-HIT

| ORF Name | NT ID | AA ID | NT LN | AA LN | Score | P-Value |
|---|---|---|---|---|---|---|
| SPX1621 | 1621 | 4282 | 153 | 51 | | |

Description

NO-HIT

| ORF Name | NT ID | AA ID | NT LN | AA LN | Score | P-Value |
|---|---|---|---|---|---|---|
| SPX1622 | 1622 | 4283 | 216 | 72 | 176 | 4.20E-20 |

Description

[LN:T30285] [AC:T30285] [PN:hypothetical protein] [OR:Streptococcus pneumoniae]

| ORF Name | NT ID | AA ID | NT LN | AA LN | Score | P-Value |
|---|---|---|---|---|---|---|
| SPX1623 | 1623 | 4284 | 165 | 55 | | |

Description

NO-HIT

| ORF Name | NT ID | AA ID | NT/LN | AA/LN | Score | P-Value |
|---|---|---|---|---|---|---|
| SPX1624 | 1624 | 4285 | 900 | 300 | 560 | 2.70E-78 |

Description

[GI:6714460] [LN:ATAC008261] [AC:AC008261] [GN:T4P13.3] [OR:Arabidopsis thaliana] [SR:thale cress]

| ORF Name | NT ID | AA ID | NT/LN | AA/LN | Score | P-Value |
|---|---|---|---|---|---|---|
| SPX1625 | 1625 | 4286 | 192 | 64 | | |

Description

NO-HIT

| ORF Name | NT ID | AA ID | NT/LN | AA/LN | Score | P-Value |
|---|---|---|---|---|---|---|
| SPX1626 | 1626 | 4287 | 1152 | 384 | 840 | 1.50E-119 |

Description

"[LN:ADH2_ECOLI] [AC:P37686] [GN:YIAY] [OR:Escherichia coli] [EC:1.1.1.1] [DE:PROBABLE ALCOHOL DEHYDROGENASE,] [SP:P37686]"

| ORF Name | NT ID | AA ID | NT/LN | AA/LN | Score | P-Value |
|---|---|---|---|---|---|---|
| SPX1627 | 1627 | 4288 | 1767 | 589 | 874 | 7.80E-287 |

Description

[GI:6015981] [LN:AF137263] [AC:AF137263] [PN:L-fucose isomerase] [GN:fucI] [OR:Bacteroides thetaiotaomicron]

| ORF Name | NT ID | AA ID | NT/LN | AA/LN | Score | P-Value |
|---|---|---|---|---|---|---|
| SPX1628 | 1628 | 4289 | 729 | 243 | 201 | 8.40E-20 |

Description

"[LN:B70645] [AC:B70645] [PN:L-fuculose-phosphate aldolase,] [GN:fucA] [CL:L-ribulose-phosphate 4-epimerase] [OR:Mycobacterium tuberculosis] [EC:4.1.2.17]"

| ORF Name | NT ID | AA ID | NT/LN | AA/LN | Score | P-Value |
|---|---|---|---|---|---|---|
| SPX1629 | 1629 | 4290 | 3087 | 1029 | | |

Description

NO-HIT

SEQUENCE LISTING

The patent contains a lengthy "Sequence Listing" section. A copy of the "Sequence Listing" is available in electronic form from the USPTO web site (http://seqdata.uspto.gov/sequence.html?DocID=6699703B1). An electronic copy of the "Sequence Listing" will also be available from the USPTO upon request and payment of the fee set forth in 37 CFR 1.19(b)(3).

What is claimed is:

1. An isolated nucleic acid encoding a *S. pneumoniae* polypeptide of SEQ ID NO: 5225.

2. A recombinant expression vector comprising the nucleic acid of claim 1 operably linked to a transcription regulatory element.

3. A cell comprising a recombinant expression vector of claim 2.

4. An isolated nucleic acid selected from the group consisting of:
   (a) SEQ ID NO: 2564, or a nucleotide sequence having 90% identity thereto;
   (b) a complement of (a); and
   (c) an RNA of (a) or (b), wherein U is substituted for T.

5. A recombinant expression vector comprising the nucleic acid of claim 4 operably linked to a transcription regulatory element.

6. A cell comprising a recombinant expression vector of claim 5.

7. An isolated nucleic acid comprising a nucleotide sequence hybridizable under right stringency conditions to a nucleic acid having a nucleotide sequence selected from the group consisting of:
   (a) SEQ ID NO: 2564;
   (b) a complement of SEQ ID NO: 2564 and; or
   (c) an RNA of (a) or (b), wherein U is substituted for T.

* * * * *

UNITED STATES PATENT AND TRADEMARK OFFICE
CERTIFICATE OF CORRECTION

PATENT NO. : 6,699,703 B1
DATED : March 2, 2004
INVENTOR(S) : Lynn Doucette-Stamm et al.

It is certified that error appears in the above-identified patent and that said Letters Patent is hereby corrected as shown below:

Column 600,
Line 21, reads "right" and should read -- high --; and
Line 25, reads "and;or" should read -- and; --.

Signed and Sealed this

Tenth Day of August, 2004

JON W. DUDAS
*Acting Director of the United States Patent and Trademark Office*